(12) United States Patent
Blaney et al.

(10) Patent No.: US 10,849,975 B2
(45) Date of Patent: Dec. 1, 2020

(54) MULTIVALENT VACCINES FOR RABIES VIRUS AND FILOVIRUSES

(75) Inventors: Joseph E. Blaney, Gettysburg, PA (US); Jason Paragas, Bethesda, MD (US); Peter Jahrling, Gaithersburg, MD (US); Reed Johnson, Frederick, MD (US); Matthias Schnell, Harleysville, PA (US)

(73) Assignees: Thomas Jefferson University, Philadelphia, PA (US); The United States of America, as Represented by the Secretary, Department of Health and Human Services Services, Bethesda, MD (US)

( * ) Notice: Subject to any disclaimer, the term of this patent is extended or adjusted under 35 U.S.C. 154(b) by 181 days.

(21) Appl. No.: 13/983,545

(22) PCT Filed: Feb. 2, 2012

(86) PCT No.: PCT/US2012/023575
§ 371 (c)(1),
(2), (4) Date: Mar. 25, 2014

(87) PCT Pub. No.: WO2012/106490
PCT Pub. Date: Aug. 9, 2012

(65) Prior Publication Data
US 2014/0212434 A1     Jul. 31, 2014

Related U.S. Application Data

(60) Provisional application No. 61/439,046, filed on Feb. 3, 2011.

(51) Int. Cl.
*A61K 39/12* (2006.01)
*A61K 45/06* (2006.01)
*A61K 39/08* (2006.01)
*C12N 7/00* (2006.01)
*C12N 15/86* (2006.01)
*A61K 39/205* (2006.01)
*A61K 39/00* (2006.01)

(52) U.S. Cl.
CPC .............. *A61K 45/06* (2013.01); *A61K 39/08* (2013.01); *A61K 39/12* (2013.01); *A61K 39/205* (2013.01); *C12N 7/00* (2013.01); *C12N 15/86* (2013.01); *A61K 2039/5252* (2013.01); *A61K 2039/5254* (2013.01); *A61K 2039/5256* (2013.01); *A61K 2039/543* (2013.01); *A61K 2039/70* (2013.01); *C12N 2760/14134* (2013.01); *C12N 2760/14234* (2013.01); *C12N 2760/20043* (2013.01); *C12N 2760/20134* (2013.01); *C12N 2760/20143* (2013.01)

(58) Field of Classification Search
CPC ..................................................... A61K 39/12
See application file for complete search history.

(56) References Cited

U.S. PATENT DOCUMENTS

| | | |
|---|---|---|
| 4,945,050 A | 7/1990 | Sanford et al. |
| 5,015,580 A | 5/1991 | Christou et al. |
| 5,149,655 A | 9/1992 | McCabe et al. |
| 5,584,807 A | 12/1996 | McCabe |
| 5,705,385 A | 1/1998 | Bally et al. |
| 5,753,613 A | 5/1998 | Ansell et al. |
| 5,756,122 A | 5/1998 | Thierry et al. |
| 5,785,992 A | 7/1998 | Ansell et al. |
| 5,908,635 A | 6/1999 | Thierry |
| 5,976,567 A | 11/1999 | Wheeler et al. |
| 5,981,501 A | 11/1999 | Wheeler et al. |
| 6,110,745 A | 8/2000 | Zhang et al. |
| 6,200,599 B1 | 3/2001 | Nantz et al. |
| 6,207,456 B1 | 3/2001 | Baru et al. |
| 6,320,017 B1 | 11/2001 | Ansell |
| 6,706,523 B2 | 3/2004 | Fu |
| 6,719,981 B1 | 4/2004 | Mebatsion et al. |
| 6,747,014 B2 | 6/2004 | Teng et al. |
| 6,756,054 B1 | 6/2004 | Miller et al. |
| 6,887,479 B2 | 5/2005 | Mebatsion |
| 7,419,816 B2 | 9/2008 | Fu |
| 7,544,791 B2 | 6/2009 | Fu |
| 2002/0012998 A1 | 1/2002 | Gonda et al. |
| 2002/0160038 A1 | 10/2002 | Kasid et al. |
| 2002/0192274 A1 | 12/2002 | Ponnappa |
| 2002/0192275 A1 | 12/2002 | Zalipsky et al. |
| 2003/0026831 A1 | 2/2003 | Lakkaraju et al. |
| 2003/0031704 A1 | 2/2003 | Huang et al. |

(Continued)

FOREIGN PATENT DOCUMENTS

| | | |
|---|---|---|
| AU | 2003/210303 | 9/2003 |
| EP | 1304160 | 4/2003 |

(Continued)

OTHER PUBLICATIONS

McGettigan, J. P., et al. Jan. 2003, Second-generation rabies virus-based vaccine vectors expressing human immunodeficiency virus type 1 Gag have greatly reduced pathogenicity but are highly immunogenic, J. Virol. 77(1):237-244.*

(Continued)

*Primary Examiner* — Jeffrey S Parkin
(74) *Attorney, Agent, or Firm* — Riverside Law LLP

(57) ABSTRACT

The present invention provides methods and compositions for inducing an immune response that confers dual protection against infections by either or both of a rabies virus and a filovirus, and/or which can be used therapeutically for an existing infection with rabies virus and/or a filovirus to treat at least one symptom thereof and/or to neutralize or clear the infecting agents. In particular, the present invention provides a recombinant rabies virus vector comprising a nucleotide sequence encoding at least one filovirus glycoprotein or an immunogenic fragment thereof, as well as pharmaceutical compositions comprising the vaccine vectors.

26 Claims, 22 Drawing Sheets
Specification includes a Sequence Listing.

(56) References Cited

U.S. PATENT DOCUMENTS

| | | |
|---|---|---|
| 2003/0035829 A1 | 2/2003 | Semple et al. |
| 2003/0072794 A1 | 4/2003 | Boulikas |
| 2003/0108597 A1 | 6/2003 | Chancellor et al. |
| 2003/0129221 A1 | 7/2003 | Semple et al. |
| 2003/0180950 A1 | 9/2003 | Smyth-Templeton |
| 2003/0198664 A1 | 10/2003 | Sullivan et al. |
| 2003/0203865 A1 | 10/2003 | Harvie et al. |
| 2003/0229040 A1 | 12/2003 | Kasid et al. |
| 2005/0037086 A1 | 2/2005 | Tyo et al. |
| 2005/0234232 A1 | 10/2005 | Beigelman et al. |

FOREIGN PATENT DOCUMENTS

| | | |
|---|---|---|
| WO | WO 1995/019799 | 7/1995 |
| WO | WO 1996/040964 | 12/1996 |
| WO | WO 2000/050008 | 8/2000 |
| WO | WO 2001/072283 | 10/2001 |
| WO | WO 2003/057190 | 7/2003 |
| WO | WO 2003/059322 | 7/2003 |
| WO | 2009116982 A2 | 9/2009 |

OTHER PUBLICATIONS

Geisbert, T. W., et al., Jul. 2009, Single-injection vaccine protects nonhuman primates against infection with Marburg virus and three species of Ebola virus, J. Virol. 83(14):7296-7304.*

McGettigan, J. P., et al., Oct. 2003, Functional human immunodeficiency virus type 1 (HIV-1) Gag-Pol or HIV-1 Gag-Pol and Env expressed from a single rhabdovirus-based vaccine vector genome, J. Virol. 77(20):10889-10899.*

Richardson, J. S., et al., Jun. 2010, Recent advances in Ebolavirus vaccine development, Human Vaccines 6(6):439-449.*

Falzarano, D., et al., 2011, Progress in filovirus vaccine development: evaluating the potential for clinical use, Expert Rev. Vaccines 10(1):63-77.*

Hoenen, T., et al., 2012, Current ebola vaccines, Expert Opin. Biol. Ther. 12(7):859-872.*

Messaoudi, I., et al., 2015, Filovirus pathogenesis and immune evasion: Insights from Ebola virus and Marburg virus, Nat. Rev. Microbiol. 13:663-676.*

Blaney et al., "Inactivated or Live-Attenuated Bivalent Vaccines That Confer Protection against Rabies and Ebola Viruses", Joural of Virology, vol. 85, No. 20, pp. 10605-10616 (2011).

McGettigan et al., "Functional Human Immunodeficiency Virus Type 1 (HIV-1) Gag-Pol or HIV-1 Gag-Pol and Env Expressed from a Single Rhabdovirus-Based Vaccine Vector Genome", Journal of Virology, vol. 77, No. 20, pp. 10889-10899 (2003).

McGettigan et al., "Second-Generation Rabies Virus-Based Vaccine Vectors Expressing Human Immunodeficiency Virus Type 1 Gag Have Greatly Reduced Pathogenicity but are Highly Immunogenic", Journal of Virology, vol. 77, No. 1, pp. 237-244 (2003).

Barrett, P. N., Mundt, W., Kistner, O., & Howard, M. K. (2009). "Vero cell platform in vaccine production: moving towards cell culture-based viral vaccines", Expert Rev. Vaccines, 8(5), 607-618. https://doi.org/10.1586/erv.09.19.

Cenna, J., Tan, G. S., Papaneri, A. B., Dietzschold, B., Schnell, M. J., & McGettigan, J. P. (2008), "Immune modulating effect by a phosphoprotein-deleted rabies virus vaccine vector expressing two copies of the rabies virus glycoprotein gene", Vaccine, 26(50), 6405-6414. doi: 10.1016/j.vaccine.2008.08.069 https://www.ncbi.nlm.nih.gov/pubmed/?term,Cenna%2C+et+al.%2C+2008.

Chelbi-Alix, M. K., Vidy, A., El Bougrini, J., & Blondel, D. (2006), "Rabies viral mechanisms to escape the IFN system: the viral protein P interferes with IRF-3, Stat1, and PML nuclear bodies". J. Interferon Cytokine Res., 26(5), 271-280. doi: 10.1089/jir.2006.26.271.

Cleaveland, S., Fevre, E. M., Kaare, M., & Coleman, P. G. (2002), "Estimating human rabies mortality in the United Republic of Tanzania from dog bite injuries". Bull. World Health Organ., 80(4), 304-310. Retrieved from https://www.ncbi.nlm.nih.gov/pubmed/12075367.

Conzelmann, K., Cox, J., Schneider, L., Thiel, H., (1990) "Molecular cloning and complete nucleotide sequence of the attenuated rabies virus SAD B19", Virology. 175, 485-499.

Faul, E. J., Lyles, D. S., & Schnell, M. J. (2009), "Interferon Response and Viral Evasion by Members of the Family Rhabdoviridae", Viruses, 1(3), 832-851. http://doi.org/10.3390/v1030832.

Finke, Stefan, et al., "Replication strategies of rabies virus". Virus Research, vol. 111, Issue 2, 2005, pp. 120-131, https://doi.org/10.1016/j.virusres. (2005).04.004.

Gomme, E. A., Faul, E. J., Flomenberg, P., McGettigan, J. P., & Schnell, M. J. (2010), "Characterization of a single-cycle rabies virus-based vaccine vector", J. Virol., 84(6), 2820-2831. doi: 10.1128/JVI.01870-09 https://www.ncbi.nlm.nih.gov/pmc/articles/PMC2826042/.

Gomme, E. A., Wanjalla, C. N., Wirblich, C., & Schnell, M. J. (2011), "Rabies virus as a research tool and viral vaccine vector", Adv. Virus Res., 79, 139-64. doi: 10.1016/B978-0-12-387040-7.00009-3.

Halder M, Hendriksen C, Cussler K, Balls M., "ECVAM's contributions to the implementation of the Three Rs in the production and quality control of biological", Altern Lab Anim. (Jan.-Feb. 2002);30(1):93-108.

Knobel, D. L., du Toit, J. T., & Bingham, J. (2002), "Development of a bait and baiting system for delivery of oral rabies vaccine to free-ranging African wild dogs (Lycaon pictus)", J. Wildl. Dis., 38(2), 352-362. doi: 10.7589/0090-3558-38.2.352.

Le Gouar, P. J., Vallet, D., David, L., Bermejo, M., Gatti, S., Levrero, F., .Ménard, N. (2009), "How Ebola impacts genetics of Western lowland gorilla populations", PLoS One, 4(12), e8375. doi: 10.1371/journal.pone.0008375 https://www.ncbi.nlm.nih.gov/pmc/articles/PMC2791222/.

McGettigan, J. P., Naper, K., Orenstein, J., Koser, M., McKenna, P. M., & Schnell, M. J. (2003) "Functional human immunodeficiency virus type 1 (HIV-1) Gag-Pol or HIV-1 Gag-Pol and env expressed from a single rhabdovirus-based vaccine vector genome", J. Virol., 77(20), 10889-10899. Retrieved from https://www.ncbi.nlm.nih.gov/pubmed/14512539.

Mebatsion and Conzelmann, "Specific Infection of CD4+ target cells by recombinant rabies virus pseudotypes carrying the HIV-1 envelope spike protein", Proc. National Acad. Sci., USA, vol. 93 pp. 11366-11370, Oct. (1996).

Mebatsion, Teshome et al. "A CXCR4/CD4 Pseudotype Rhabdovirus That Selectively Infects HIV-1 Envelope Protein-Expressing Cells", Cell ,vol. 90 ,Issue 5, p. 841-847 (1997) (https://www.cell.com/cell/fulltext/S0092-8674(00)80349-9?_returnURL=https%3A%2F%2Flinkinghub.elsevier.com%2Fretrieve%2Fpii%2FS0092867400803499%3Fshowall%3Dtrue.

Miyao, T., Takakura, Y., Akiyama, T., Yoneda, F., Sezaki, H., & Hashida, M. (1995), "Stability and pharmacokinetic characteristics of oligonucleotides modified at terminal linkages in mice", Antisense Res. Dev., Summer;5(2), 115-121.

Morenweiser, R. et al., Gene Ther. Oct. 2005;12 Suppl 1:S103-110

Morenweiser, R. (2005). Downstream processing of viral vectors and vaccines. Gene Ther., 12(Suppl), 1. doi: 10.1038/sj.gt.3302624.

Morimoto, K., Shoji, Y., & Inoue, S. (2005), "Characterization of P gene-deficient rabies virus: propagation, pathogenicity and antigenicity", Virus Res., 111(1), 61-67, Apr. 11, 2005 doi: 10.1016/j.virusres.2005.03.011.

Siler, C. A., McGettigan, J. P., Dietzschold, B., Herrine, S. K., Dubuisson, J., Pomerantz, R. J., & Schnell, M. J. (2002), "Live and killed rhabdovirus-based vectors as potential hepatitis C vaccines", Virology, 292(1), 24-34. doi: 10.1006/viro.2001.1212.

Toovey, Stephen, "Preventing rabies with the Verorab® vaccine: 1985-2005, Twenty years of Clinical Experience", (2007), Travel Medicine and Infectious Disease , vol. 5 , Issue 6 , 327-348.

Tordo N, Foumier A, Jallet C, Szelechowski M, Klonjkowski B, Eloit M, "Canine adenovirus based rabies vaccines", Dev Biol (Basel). (2008);131:467-76.

(56) References Cited

OTHER PUBLICATIONS

Vos, A & Neubert, Andreas & Aylan, O & Schuster, P & Pommerening, E & Müller, T & Chai Chivatsi, D. (1999), "An Update on Safety Studies of SAD B19 Rabies Virus Vaccine in Target and Non-target Species. Epidemiology and infection", 123. 165-75; 10.1017/S0950268899002666.

Anon (1993). Report of the forth WHO Consultion on oral immunization of dogs against rabies. unpublished document WHO/RabRes/9342.

Bermejo, M., et al., (2006). Ebola outbreak killed 5000 gorillas. Science, Dec. 2006, vol. 314, 1564.

Ebihara, H., et al., (2006). Molecular determinants of Ebola virus virulence in mice, PLoS Pathog 2, e73, Jul. 2006, vol. 2, Issue 7, 0705-0711.

Faber, M., et al., (2005). A single immunization with a rhabdovirus-based vector expressing severe acute respiratory syndrome coronavirus (SARS-CoV) S protein results in the production of high levels of SARS-CoV-neutralizing antibodies. J Gen Virol 86, 1435-1440.

Faul, E.J., et al., (2008). Interferon-beta expressed by a rabies virus-based HIV-1 vaccine vector serves as a molecular adjuvant and decreases pathogenicity. Virology 382, 226-238.

Geisbert, T.W., et al., (2010). Prospects for immunisation against Marburg and Ebola viruses. Rev Med Virol 20, 344-357.

Lee, et al., (2008a). Structure of the Ebola virus glycoprotein bound to an antibody from a human survivor. Nature 454, 177-182.

Lee, et al., (2008b). Complex of a protective antibody with its Ebola virus GP peptide epitope: unusual features of a V lambda x light chain. J Mol Biol 375, 202-216.

Leroy, et al., (2004). Multiple Ebola virus transmission events and rapid decline of central African wildlife. Science 303, 387-390.

McGettigan, et al., (2003a). Functional human immunodeficiency virus type 1 (HIV-1) Gag-Pol or HIV-1 Gag-Pol and env expressed from a single rhabdovirus-based vaccine vector genome. J Virol 77, No. 20, Oct. 2003, 10889-10899.

McGettigan, et al., (2003b). Second-generation rabies virus-based vaccine vectors expressing human immunodeficiency virus type 1 gag have greatly reduced pathogenicity but are highly immunogenic. J Virol 77, Jan. 2003, No. 1, 237-244.

McKenna, et al., (2004). Immunogenicity study of glycoprotein-deficient rabies virus expressing simian/human immunodeficiency virus SHIV89.6P envelope in a rhesus macaque. J Virol 78, No. 24, Dec. 2004, 13455-13459.

Montagnon, B. J., et al. (1998), "Experience with the Vero cell line", Dev. Biol. Stand., 93(119-23.).

Schnell et al., (2010), "The cell biology of rabies virus: using stealth to reach the brain", Nature Reviews Microbiology vol. 8, pp. 51-61.

Schnell, et al., (1994). Infectious rabies viruses from cloned cDNA. Embo J vol. 13, No. 18, 4195-4203.

Smith, et al., (2006). Rabies virus glycoprotein as a carrier for anthrax protective antigen. Virology, Sep. 2006, 353(2): 344-356.

Snook, et al., (2008). Guanylyl cyclase C-induced immunotherapeutic responses opposing tumor metastases without autoimmunity. J Natl Cancer Inst Jul. 2, 2008, vol. 100, Issue 13, 950-961.

Takakura, Y., et al., (1996), "Uptake characteristics of oligonucleotides in the isolated rat liver perfusion system", Antisense Nucleic Acid Drug Dev., Fall;6(3), 177-183. doi: 10.1089/oli.1.1996.6.177.

Tan, et al.,(2005). Strong cellular and humoral anti-HIV Env immune responses induced by a heterologous rhabdoviral prime-boost approach. Virology 331, 82-93.

Vogel, G. (2006). Ecology. Tracking Ebola's deadly march among wild apes. Science vol. 314, Dec. 8, 2006, 1522-1523.

Vogel, G. (2007). Conservation. Scientists say Ebola has pushed western gorillas to the brink. Science vol. 317, Sep. 14, 2007, 1484.

Vos, et al., (2002). Safety studies of the oral rabies vaccine SAD B19 in striped skunk (*Mephitis mephitis*). J Wildl Dis, vol. 38 (2), 428-431.

Wirblich, et al.,(2011). Rabies virus (RV) glycoprotein expression levels are not critical for pathogenicity of RV. J Virol, Jan. 2011, vol. 85, No. 2, 697-704.

Zhang et al., (2004), Cationic compounds used in lipoplexes and polyplexes for gene delivery J. Control Release, vol. 100:165-180 2.

\* cited by examiner

Ebola (Zaire) genome:

FIG. 1

Takada, A. et al. A system for functional analysis of Ebola virus glycoprotein. PNAS 1997: 197;14764-14769

FIG. 2

A BNSP (derived from RV vaccine strain SAD B19)

3'—[ N ][ P ][ M ][ G ][ L ]—5'

B BNSP333

3'—[ N ][ P ][ M ][ G ³³³ ][ L ]—5'

C BNSP333-GP

3'—[ N ][ Ebola GP ][ P ][ M ][ G ³³³ ][ L ]—5'

D BNSP333-GP$_{GCD}$

3'—[ N ][ Ebola GP ▮][ P ][ M ][ G ³³³ ][ L ]—5'

E BNSPΔG-GP

3'—[ N ][ Ebola GP ][ P ][ M ][ L ]—5'

F BNSPΔG-GP$_{GCD}$

3'—[ N ][ Ebola GP ▮][ P ][ M ][ L ]—5'

FIG. 3

BSR cells

BNSPΔG-GP

FIG. 4A

BSR-RVG cells

BNSPΔG-GP

FIG. 4B

BNSPΔG-GP<sub>GCD</sub>

FIG. 4C

BNSPΔG-GP<sub>GCD</sub>

BNSP333     BNSP333-GP     BNSP333-GP$_{GCD}$

FIG. 6A

Intramuscular

Mean percent change in weight from day 0

Day post infection

- Vehicle
- BNSP
- BNSP333
- BNSP333-GP
- BNSP333-GP(GCD)
- BNSPΔG-GP
- BNSPΔG-GP(GCD)
- INAC-BNSP333-GP
- INAC-BNSP333-GP(GCD)

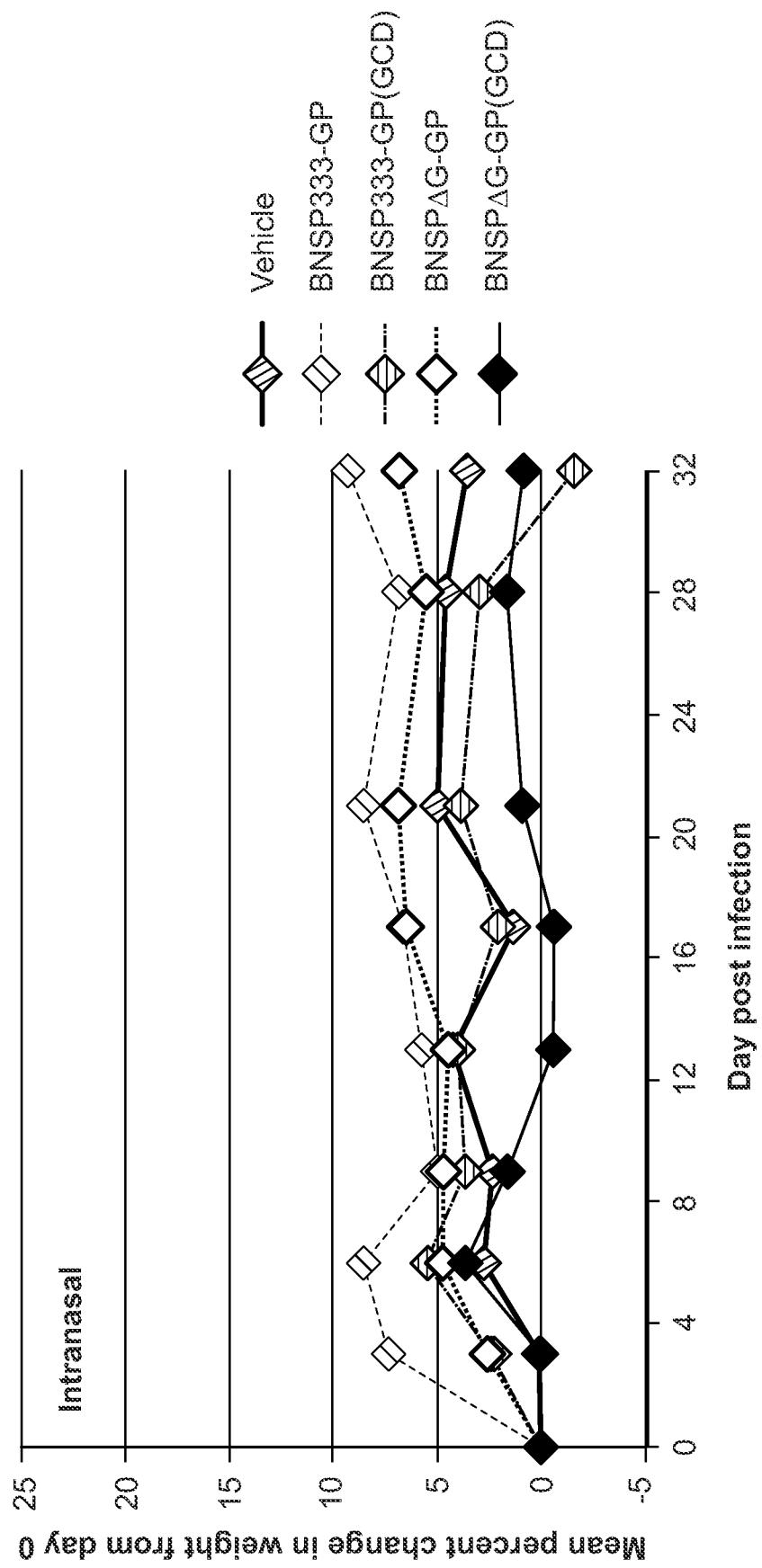

FIG. 7A

EBOV GP ELISA

☐ Pre-RABV Challenge
■ Post-RABV Challenge

Vehicle-Ch.
Vehicle+Ch.
BNSP333
BNSP333-GP
BNSP333-GP(GCD)
BNSPΔG-GP
BNSPΔG-GP(GCD)
INAC-BNSP333-GP(1 dose)
INAC-BNSP333-GP(GCD)(1 dose)
INAC-BNSP333-GP(2 dose)
INAC-BNSP333-GP(GCD)(2 dose)

FIG. 7B

EBOV GP ELISA

☐ Pre-EBOV Challenge
■ Post-EBOV Challenge

Vehicle-Ch.
Vehicle+Ch.
BNSP333
BNSP333-GP
BNSP333-GP(GCD)
BNSPΔG-GP
BNSPΔG-GP(GCD)
INAC-BNSP333-GP(1 dose)
INAC-BNSP333-GP(GCD)(1 dose)
INAC-BNSP333-GP(2 dose)
INAC-BNSP333-GP(GCD)(2 dose)

FIG. 7D RABV G ELISA

□ Pre-EBOV Challenge
■ Post-EBOV Challenge

- Vehicle-Ch.
- Vehicle+Ch.
- BNSP333
- BNSP333-GP
- BNSP333-GP(GCD)
- BNSPΔG-GP
- BNSPΔG-GP(GCD)
- INAC-BNSP333-GP(1 dose)
- INAC-BNSP333-GP(GCD)(1 dose)
- INAC-BNSP333-GP(2 dose)
- INAC-BNSP333-GP(GCD)(2 dose)

FIG. 7C RABV G ELISA

□ Pre-RABV Challenge
■ Post-RABV Challenge

- Vehicle-Ch.
- Vehicle+Ch.
- BNSP333
- BNSP333-GP
- BNSP333-GP(GCD)
- BNSPΔG-GP
- BNSPΔG-GP(GCD)
- INAC-BNSP333-GP(1 dose)
- INAC-BNSP333-GP(GCD)(1 dose)
- INAC-BNSP333-GP(2 dose)
- INAC-BNSP333-GP(GCD)(2 dose)

FIG. 8A

MA-EBOV challenge

BNSPΔG-GP
INAC-BNSP333-GP(2 dose)
INAC-BNSP333-GP$_{GCD}$(1 dose)
INAC-BNSP333-GP$_{GCD}$(2 dose)

BNSP333-GP
BNSP333-GP$_{GCD}$
INAC-BNSP333-GP(1 dose)

BNSPΔG-GP$_{GCD}$

BNSP333

Vehicle

FIG. 8B

RV challenge

BNSP333
BNSP333-GP$_{GCD}$
BNSPΔG-GP
BNSPΔG-GP$_{GCD}$
INAC-BNSP333-GP(1 dose)
INAC-BNSP333-GP$_{GCD}$(1 dose)
INAC-BNSP333-GP$_{GCD}$(2 dose)

INAC-BNSP333-GP(2 dose)

BNSP333-GP

Vehicle

Day post infection

- ◆ No virus challenge
- ◇ Vehicle
- ◇ BNSP333
- ◇ BNSP333-GP
- ◇ BNSP333-GP(GCD)
- ◇ BNSPΔG-GP
- ◇ BNSPΔG-GP(GCD)
- ◇ INAC-BNSP333-GP(1 dose)
- ◇ INAC-BNSP333-GP(GCD)(1 dose)
- ○ INAC-BNSP333-GP(2 dose)
- ○ INAC-BNSP333-GP(GCD)(2 dose)

RV challenge

Day post challenge

Mean percent change in weight

FIG. 14

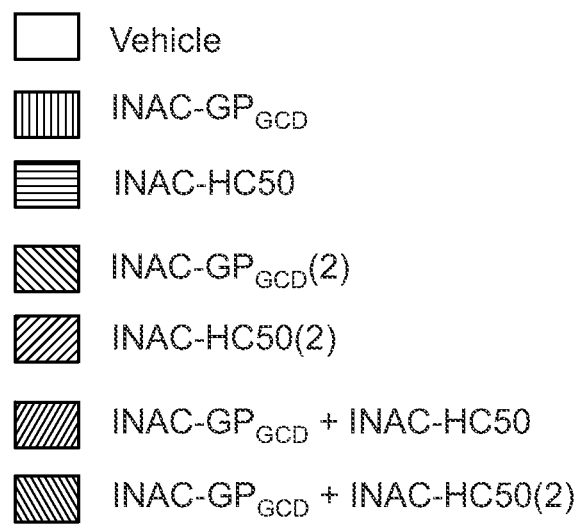
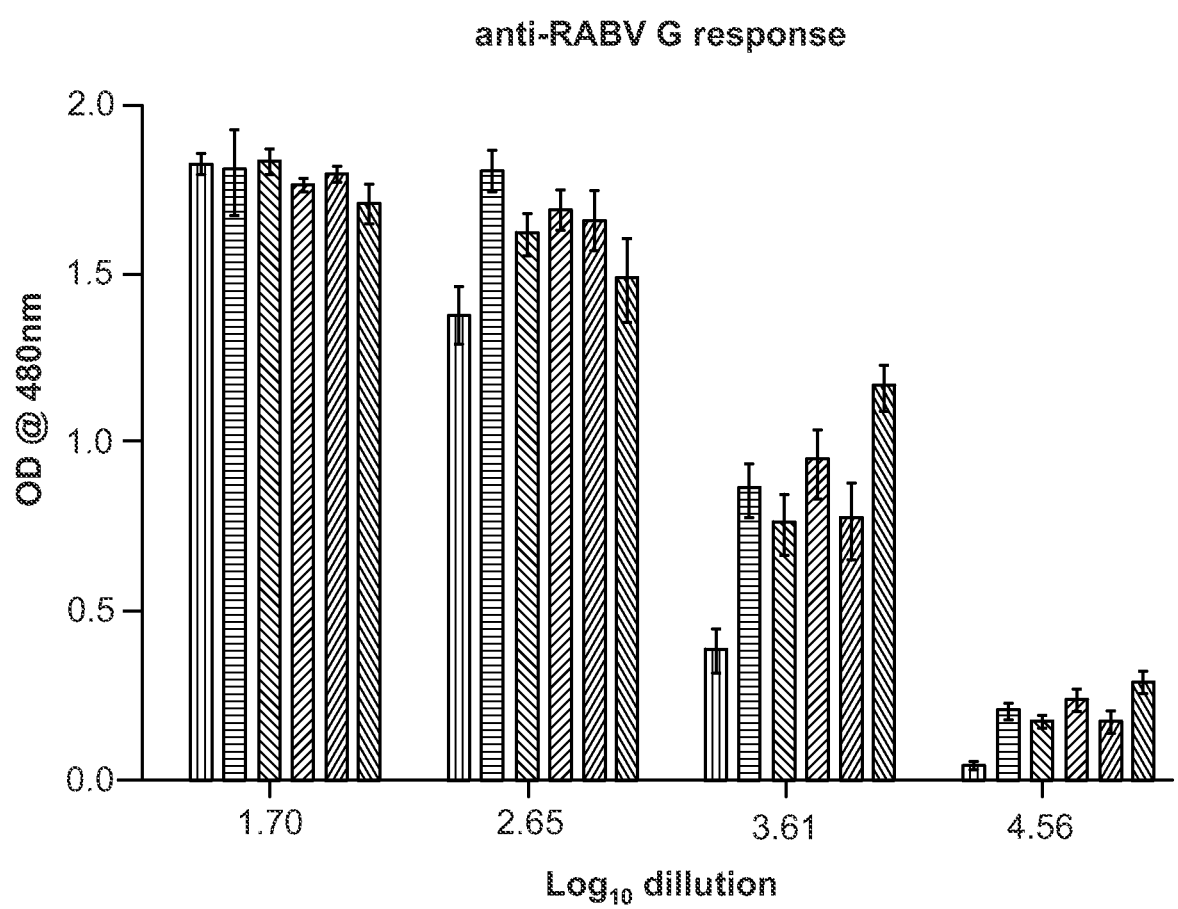
FIG. 15A anti-BoNT response

FIG. 15B

FIG. 16A anti-RABV G response (RVG)

FIG. 16B anti-BoNT response

FIG. 16C anti-EBOV GP response

Legend: Vehicle; INAC-SPBN-HC50; INAC-BNSP333-GP$_{GCD}$; Hc50, then GP$_{GCD}$

MULTIVALENT VACCINES FOR RABIES VIRUS AND FILOVIRUSES

RELATED APPLICATIONS

This application is a 35 U.S.C. § 371 U.S. national entry of International Application PCT/US2012/023575 (WO2012/106490) having an International filing date of Feb. 2, 2012, which claims the benefit of U.S. Provisional Application Ser. No. 61/439,046, filed Feb. 3, 2011 the entire contents of which are hereby incorporated herein by reference.

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

BACKGROUND OF THE INVENTION

1. Field of the Invention

The present invention relates generally to the field of vaccines and to methods and compositions for treating and/or immunizing against viral infections. In particular, the present invention relates to multivalent vaccines as a single therapeutic or immunization agent against infections with one or both of a rabies virus and/or a filovirus, such as Ebolavirus or Marburgvirus.

2. Background

Filoviridae is a family of viruses (e.g., filoviruses or filovirus family) that primarily includes Ebolavirus and Marburgvirus filoviruses and which causes outbreaks of highly lethal hemorrhagic fever in humans and nonhuman primates leading to the deaths of over 24,000 people in Africa each year. The natural reservoir of the filoviruses is not known and currently, there are no available vaccines or effective therapeutic treatments for filovirus infections which are safe and effective.

Filoviruses are single-stranded negative sense RNA viruses having a thread-like appearance which target humans and non-human primates. The genome of Ebolavirus consists of a single strand of negative sense RNA that is approximately 19 kb in length. This RNA contains seven sequentially arranged genes that produce 8 mRNAs upon infection (as depicted in FIG. 1). Ebolavirus virions (as depicted in FIG. 2), like virions of other filoviruses, contain seven proteins: (1) a surface glycoprotein (GP), (2) a nucleoprotein (NP), (3-6) four virion structural proteins (VP40, VP35, VP30, and VP24), and an (7) RNA-dependent RNA polymerase (L). The glycoprotein of Ebolavirus is unlike other filoviruses in that it is encoded in two open reading frames. Transcriptional editing is needed to express the transmembrane form that is incorporated into the virion. The unedited form produces a nonstructural secreted glycoprotein (sGP) that is synthesized in large amounts early during the course of infection. Little is known about the biological functions of these proteins and it is not fully known which antigens significantly contribute to protection (e.g., including a humoral and/or cytotoxic T cell response).

The Marburgvirus is substantially identical structurally to the Ebolavirus, although they elicit different antibodies. The genome of Marburgvirus similarly consists of a single strand of negative sense RNA that is approximately 19.1 kb in length and which encodes a series of polypeptides that correspond in sequence and function to those of Ebolavirus, although the exact intergenic regions are different between the two viruses. Thus, the Marburgvirus consists of seven polypeptides, which are, like Ebolavirus, (1) a surface glycoprotein (GP), (2) a nucleoprotein (NP), (3-6) four virion structural proteins (VP40, VP35, VP30, and VP24), and an (7) RNA-dependent RNA polymerase (L).

The virions of each filovirus tend to be long and filamentious, essentially bacilliform, but often take on a "U" shape, with a length up to 14,000 nm and average diameter of about 80 nm. These viruses consist of a nucleocapsid, surrounded by a cross-striated helical capsid. There is an axial channel in the nucleocapsid, and the whole virion is surrounded by a lipoprotein unit derived from the host cell. In addition, there are 7 nm spikes placed 10 nm apart visible on the surface of the virion. See FIG. 2.

Upon entering an infected cell, filoviruses transcribe their RNA and the viruses replicate in the cytoplasm of the infected cell. Replication is mediated by the synthesis of an antisense positive RNA strand, which is provided as a template for additional viral genomes. As the infection progresses, the cytoplasm of the infected cell develops inclusion bodies which contain viral nucelocapsids, which then become highly structured. The viruses then assemble, and bud off the host cell, obtaining its lipoprotein coat from the outer membrane of the infected cell.

Ebolavirus and Marburgvirus filoviruses cause severe hemorrhagic fever after an incubation period of about four to sixteen days. An infected person typically develops initial symptoms that include sudden fever, chills, intense headaches, anorexia and mylagia. Nausea, vomiting, sore throat, abdominal pain and diarrhea soon develop, followed by severe hemorrhaging, shock, and multi-organ failure between about days five and seven. Death is typical, and occurs between seven and sixteen days.

The Ebolavirus genus is generally recognized as comprising four main species, each of which further comprise a number of different strains. At the genus level, Ebolavirus comprises four species known as Zaire (ZEBOV), Sudan (SEBOV), Cote d'Ivoire (CEBOV), and Reston Ebolavirus (RBOV). A potential fifth species, Bundibugyo (BEBOV), was recently associated with an outbreak of hemorrhagic fever in Uganda in 2007. Since the identification of Zaire EBOV in the 1970's, at least 20 human outbreaks have been reported in Central Africa. While case fatality rates vary between outbreaks and among the EBOV species, ZEBOV has been associated with up to 90% mortality. In addition, outbreaks of lethal EBOV infection have been reported in endemic nonhuman primates (NHPs), including gorillas and chimpanzees. EBOV has also emerged as a significant biodefense concern because of its extreme virulence and ability to induce disease by the aerosol route.

While there are no available vaccines or effective therapeutic treatments for filovirus infections, several strategies have been employed to identify vaccine candidates that confer protection from EBOV. Immunization with the EBOV glycoprotein (GP), which mediates viral attachment and entry, has been shown to confer protection from various EBOV species in NHPs. Delivery of GP by DNA vaccination, virus-like particles, or by expression from recombinant viruses including adenovirus, vesicular stomatitis virus, or paramyxoviruses has been shown to induce humoral and cellular immunity to EBOV, although the exact mechanisms of protective immunity remain incompletely defined. Because of unsuccessful cross-protection studies and the known high amino acid sequence divergence of GP across the EBOV species, a multivalent vaccine may be required to provide protection from all EBOV species.

Recently, cross-protection against Bundibugyo EBOV was demonstrated by DNA/adenovirus prime boost vaccination with Sudan EBOV and ZEBOV indicating the potential for heterologous protection. Taken together, these vaccination strategies suggest that efficient immunization with EBOV GP confers protection from lethal EBOV challenge in rodents and NHPs. As the disease course of EBOV in humans resembles that observed in NHPs, it is possible that human vaccination will be an effective means of disease prevention. Despite the above, obstacles remain which hinder the development of such vaccines, including safety concerns, pre-existing vector immunity, and manufacturing, dosage, or schedule issues. As such, the development of additional vaccine candidates for treating or immunizing against a flavivirus, e.g., Ebolavirus or Marburgvirus, is greatly desired in the art.

SUMMARY OF THE INVENTION

The present invention relates to novel recombinant vaccine contructs that are based on genetically modifying a rabies virus vaccine vector to express one or more filovirus immunogenic polypeptides, e.g., an Ebolavirus or Marburgvirus glycoprotein (GP), such that humoral and/or cellular immune responses are induced against infection by a rabies virus and/or a filovirus upon administering a recombinant vaccine contruct of the invention or a recombinant virion based thereon. Preferably, the rabies virus vaccine vector is attenuated to remove or mitigate to a safe level its capacity for neurological damage. The invention also provides compositions and methods for immunizing against or treating infections by either or both a rabies virus and a filovirus, e.g., Ebolavirus or Marburgvirus. The recombinant vaccine contructs of the invention may be referred to as "bivalent" or "multivalent" because they are as a single construct capable of simultaneous induction of an immune response against two or more viral pathogens, e.g., rabies virus and Ebolavirus. The vaccine constructs of the invention may be used prophylactically, i.e., to induce a humoral and/or cellular immune response as protection against a subsequent infection or challenge by either or both a rabies virus and/or a filovirus, or used therapeutically, i.e., to induce a humoral and/or cellular immune response to aid in neutralizing or clearing a preexisting infection by either or both a rabies virus and a filovirus.

Thus the present invention relates to methods and compositions for use in inducing an immune response that confers dual protection against infections by either or both of a rabies virus and a filovirus, and/or which can be used therapeutically for an existing infection with rabies virus and/or a filovirus to treat at least one symptom thereof and/or to neutralize or clear the infecting agents.

Thus, in one aspect, the present invention provides a recombinant rabies virus vector comprising a nucleotide sequence encoding at least one filovirus glycoprotein or an immunogenic fragment thereof.

In yet another aspect, the present invention entails a multivalent vaccine that is effective to protect against infection with one or both a rabies virus and a filovirus, comprising a recombinant rabies virus vector that expresses at least one filovirus glycoprotein or an immunogenic fragment thereof.

In still another aspect, the present invention provides a vaccine composition that comprises a multivalent vaccine that is effective to protect against infection with one or both a rabies virus and a filovirus, comprising a recombinant rabies virus vector that expresses at least one filovirus glycoprotein or an immunogenic fragment thereof.

In another aspect still, the present invention entails a method of inducing an immune response protective against an infection by one or both of a filovirus and a rabies virus in a subject, comprising administering to the subject a therapeutically effective amount of a multivalent vaccine comprising a recombinant rabies virus vaccine vector that expresses at least one filovirus glycoprotein or an immunogenic fragment thereof.

In a further aspect, the invention provides a method of inducing neutralizing antibodies against a filovirus and/or a rabies virus in a subject infected with or having been exposed to either or both of said viruses, comprising administering to the subject a therapeutically effective amount of a multivalent vaccine comprising a recombinant rabies virus vaccine vector that expresses at least one filovirus glycoprotein or an immunogenic fragment thereof.

In yet a further aspect, the invention involves a method of treating a subject infected with a filovirus and/or a rabies virus, comprising administering to the subject a therapeutically effective amount of a multivalent vaccine comprising a recombinant rabies virus vaccine vector that expresses at least one filovirus glycoprotein or an immunogenic fragment thereof, wherein said vaccine induces an effective immune response against one or both of said viruses.

In certain embodiments, the filovirus glycoprotein encoded by the recombinant rabies vaccine vector used in the different aspects of the invention is an Ebolavirus glycoprotein. The Ebolavirus glycoprotein, in various embodiments and aspect herein, can be a polypeptide comprising the amino acid sequence of SEQ ID NO: 1 (from ZEBOV), SEQ ID NO: 2 (from SEBOV), SEQ ID NO: 3 (from CEBOV), SEQ ID NO: 4 (from REBOV), or SEQ ID NO: 5 (from BEBOV), as provided in Table 1 and elsewhere.

In certain other embodiments, the filovirus glycoprotein encoded by the recombinant rabies vaccine vector used in the different aspects of the invention is a Marburgvirus glycoprotein. The Marburgvirus glycoprotein, in various embodiments and aspect herein, can be a polypeptide comprising the amino acid sequence of SEQ ID NO: 6 (from Marburgvirus strain Musoke), as provided in Table 1 and elsewhere.

In certain other embodiments, the recombinant rabies virus vector used in the various aspects of the invention further expresses one or more additional filovirus proteins or immunogenic fragments thereof. In various embodiments, the additional filovirus proteins can be a protein (an immunogenic fragment thereof) selected from the group consisting of a filovirus nucleoprotein (NP), virion structural protein (e.g., an Ebolavirus VP40, VP35, VP30, or VP24 protein) or a viral replication protein (e.g., an Ebolavirus RNA-dependent RNA polymerase (L)). In various embodiments, the additional filovirus proteins are selected from the group consisting of any one of the Ebolavirus proteins of SEQ ID NOS: 7-36 of Table 2 and as provided herein, or an immunogenic fragment thereof. In various other embodiments, the additional filovirus proteins are selected from the group consisting of any one of the Marburgvirus proteins of SEQ ID NOS: 37-42 of Table 2 and as provided herein.

The invention further contemplates that any filovirus protein expressed by the recombinant rabies virus vaccine vectors used in the various aspects of the invention can be expressed as immunogenic fragments. An immunogenic fragment of a filovirus protein is, for the purposes of this invention, any segment of a filovirus protein this is capable of inducing substantially the same immune response as the full-length counterpart protein. Substantially the same immune response can refer to, for example, where the concentration of antibodies induced against the fragment is about the same, or at least about 75%, or 80%, or 90%, or 95%, or 99% or more the concentration of antibodies induced against the full length filovirus protein tested under the same conditions.

In other embodiments, the recombinant rabies virus vaccine is attenuated, such that its neurovirulence properties have been eliminated or substantially mitigated such that neurological damage typical of the rabies virus is substantially avoided.

In certain embodiments, the recombinant rabies virus vaccine is the live attenuated "SAD B19 RABV" vaccine, which was attenuated by tissue culture passage and has been used as a live oral vaccine for wildlife in Europe for many years (see Conzelmann et al., 1990; Vos et al., 1999; and Vos et al., 2002 identifed under References herein, each of which is incorporated here by reference in their entireties).

In certain other embodiments, the recombinant rabies virus vaccine is derived from SAD B19 RABV by introducing additional genetic changes that results in further attenuation of the virus. For the purpose of the invention, the term "derived" as it refers to a modified nucleic acid molecule (e.g., vaccine vector) relative to a wildtype or other source molecule into which the changes are introduced, where the changes include genetic changes and/or chemical changes, including single nucleotide substitutions (point mutations), deletions, insertions, inversions, multiple point mutations, and chemical changes such as DNA methylation or acetylation. In a particular embodiment, the SAD B19 RABV was derived to form "BNSP" by introducing a novel RABV stop-start transcription signal sequence flanked by unique BsiWI and NheI restriction sites between the nucleoprotein (N) and the phosphoprotein (P) genes for introduction of foreign genes (see FIG. 3 and McGettigan et al., 2003b). In a still further embodiment, the BNSP vector was further derived (and attenuated) by introducing an Arg-->change at amino acid 333 of the RABV G protein (see McGettigan et al., 2003b). The 333 mutation has been shown to greatly attenuate neurovirulence of RABV in adult mice.

In certain other embodiments, the invention provides host cells that can be transfected with the recombinant rabies virus vaccines of the invention for purposes of, including, expressing proteins encoded by the virus vaccines and/or for generating recombinant rabies virions, which can be isolated therefrom and utilized in vaccine compositions in accordance with other aspects and embodiments of the invention. Suitable host cells can include any cell susceptible to being transfected or infected in vitro with a rabies virus vaccine, including any human cell lines or animal cell lines. Such cell lines and their use in expressing proteins and forming rabies virions is well known in the art and described in more detail in, for example, Barrett P N et al., Expert Rev Vaccines. 2009 May; 8(5):607-18; Tordo N et al., Dev Biol (Basel). 2008; 131:467-76; Toovey S. et al., Travel Med Infect Dis. 2007 November; 5(6):327-48; Chelbi-Alix M K, J Interferon Cytokine Res. 2006 May; 26(5):271-80; Morenweiser R. et al., Gene Ther. 2005 October; 12 Suppl 1:S103-10; Morimoto K et al., Virus Res. 2005 July; 111(1):61-7. Epub 2005 April 11; Finke S et al., Virus Res. 2005 August; 111(2):120-31; and Halder M., Altern Lab Anim. 2002 January-February;30(1):93-108; Montagnon BJ et al., Dev Biol Stand. 1998; 93:119-23, each of which are incorporated herein by reference.

It is preferred that the rabies vaccine viruses and the production of any virus virions and their use as vaccines be done in accordance with any necessary national and/or international requirements for health and safety with regard to rabies virus and filoviruses, e.g., in accordance with the requirements of the U.S. Center for Disease Control ("CDC") or the World Health Organization ("WHO").

The vaccine compositions of the invention, in certain embodiments, can include a pharmaceutically acceptable carrier or excipient, as further described below.

In yet another embodiment of the invention, the inventors have specifically constructed the four recombinant rabies virus vaccine vectors of the Examples, which include: (a) BNSP333-GP (a replication-competent, recombinant rabies virus vector vaccine expressing ZEBOV GP of strain Maying a); (b) BNSP333-GP$_{GCD}$ (a replication-competent, recombinant rabies virus vector vaccine expressing the ectodomain and transmembrane domain of ZEBOV GP of strain Maying a fused to the RABV G cytoplasmic domain (GCD); (c) BNSPΔG-GP (a replication-defective, recombinant rabies virus vector vaccine expressing ZEBOV GP of strain Maying a); (d) BNSPΔG-GP$_{GCD}$ (a replication-defective, recombinant rabies virus vector vaccine expressing the ectodomain and transmembrane domain of ZEBOV GP of strain Maying a fused to the RABV G cytoplasmic domain (GCD). Other specific contructs are well within the gambit of the invention and these Examples of specific constructs are not meant to limit the invention in any manner. It will be appreciated further that where a replication-defective rabies vaccine vector is used, such as in (c) and (d) above, cell lines which provide the missing/defective functions in trans may be necessary to propagate the viruses and/or to allow preparation of virions. Such in trans functionalities and cell lines are well known in the art and pertain to the use of the rabies vaccine vectors.

The full nucleotide sequences of these four vaccine constructs of the invention are as follows: BNSP333-GP (SEQ ID NO: 43); BNSP333-GP$_{GCD}$ (SEQ ID NO: 44); BNSPΔG-GP (SEQ ID NO: 45); and BNSPΔG-GP$_{GCD}$ (SEQ ID NO: 46), said sequence of which are provided herein.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1 provides a schematic depiction of the genome of Ebolavirus.

FIG. 2 provides a schematic depiction of an assembled Ebolavirus virion.

FIG. 3 provides a schematic of the virus constructs prepared in accordance with the embodiments of the Examples. Negative sense RNA genomes are illustrated for the parental RABV vaccine constructs, BNSP and BNSP333 (McGettigan et al., 2003a), and four RABV vaccine vectors expressing Zaire Ebolavirus strain Maying a Glycoprotein (GP) with or without RABV Glycoprotein G (ΔG). The 333 mutation results in an Arg→Glu change at amino acid 333 of RABV G, which has been shown to greatly attenuate neurovirulence of RABV vaccine vectors in adult mice (McGettigan et al., 2003a; McGettigan et al., 2003b). ZEBOV GP is expressed authentically or with the RABV G cytoplasmic domain (GCD) fused its ectodomain and transmembrane domain. The GCD is depicted by a black box.

FIGS. 4A-4D provide representative immunofluorescence images demonstrating that ΔG viruses are growth-restricted using a virus spread assay. BSR cells (FIGS. 4A and 4C) or trans-complementing BSR cells expressing RABV G (FIGS. 4B and 4D) were infected at an MOI of 0.001 with BNSPΔG-GP (FIGS. 4A and 4B) or BNSPΔG-GP$_{GCD}$ (FIGS. 4C and 4D). Three days later, cells were fixed and immuno-stained for intracellular RABV nucleoprotein. Representative images are shown at 10× fluorescent microscope magnification.

FIGS. 5A-5C depict the expression of GP by various RABV vaccine constructs in vitro. (FIG. 5A) Western blot analysis of GP expressed by indicated viruses at 24-72 hours. Infected cell lysates were separated by SDS-PAGE and transferred to nitrocellulose membranes. Blots were probed with polyclonal monkey anti-EBOV. (FIG. 5B) Coomassie blue-stained SDS-PAGE gel of purified virus particles with RABV proteins indicated. Western blot probed with anti-EBOV sera or anti-RABV P sera. (FIG. 5C) BSR cells were infected with the indicated viruses and analyzed by dual-label immunogold electron microscopy. RABV G was detected by primary rabbit anti-RABV G followed by secondary anti-rabbit IgG labeled with 15 nm gold particles. ZEBOV GP was detected by primary human anti-GP followed by secondary anti-human IgG labeled with 5 nm gold particles. Magnifications for BNSP333 and BNSP333-GP—150,000×; for BNSP333-GP$_{GCD}$—210,000×.

FIGS. 6A-6C demonstrate that RABV vaccine viruses expressing GP are avirulent in mice after peripheral inoculation. (FIG. 6A) Groups of five BALB/c mice were inoculated 1M with 5×10$^5$ FFU live virus on day 0 or 10 µg inactivated virus on day 0 and 14. Data are representative of two experiments. (FIG. 6B) Groups of 5 SW mice were inoculated with 1×10$^5$ FFU of the indicated viruses. Data are representative of two experiments. (FIG. 6C) Groups of eight BALB/c mice were inoculated IP with 1×10$^6$ FFU of the indicated viruses. Mice inoculated by each route were monitored daily for signs of morbidity and weighed periodically for the indicated time period.

FIGS. 7A-7D demonstrate that RABV vaccines expressing GP induce RABV G- and ZEBOV GP-specific antibodies. Groups of ten BALB/c mice were immunized IM with 5×10$^5$ FFU of indicated live virus or 10 µg of inactivated virus on day 0 (1 dose) or on day 0 and 14 (2 dose) for two independent challenge experiments. Serum was drawn on day 30 post-immunization (blue bars) before RABV challenge (FIGS. 7A and 7C) or MA-EBOV challenge (FIGS. 7B and 7D), pooled, and analyzed by ELISA directed against ZEBOV GP at a 1:200 dilution (FIGS. 7A and 7B) or RABV G at a 1:300 dilution (FIGS. 7C and 7D). Results in 7A, 7C and 7B, 7D are After RABV or MA-EBOV challenge, serum was collected, pooled, and tested in the same manner (red bars). Vehicle–Ch. indicates mice were immunized with vehicle but not challenged. Vehicle+Ch. indicates mice were immunized with vehicle and received indicated challenge virus. No BNSP333-immunized mice survived MA-EBOV challenge.

FIGS. 8A and 8B demonstrate that RABV vaccines expressing GP confer protection from EBOV AND RABV. Two groups of ten BALB/c mice were immunized IM with 5×10$^5$ FFU of indicated live virus or 10 ug of inactivated virus on day 0 (1 dose) or on day 0 and 14 (2 dose). (FIG. 8A) On day 77 post-immunization, groups of ten mice were challenged IP with 1,000 PFU of MA-EBOV. Mice were monitored for morbidity for 21 days. (FIG. 8B) On day 50 post-immunization, groups of ten mice were challenged IM with virulent RABV virus strain CVS-N2c and monitored for morbidity for 21 days.

FIGS. 10A and 10B show evidence of weight loss after challenge with EBOV or RABV. Two groups of ten BALB/c mice were immunized IM with 5×10$^5$ FFU of indicated live virus or 10 ug of inactivated virus on day 0 (1 dose) or on day 0 and 14 (2 dose). (FIG. 10A) On day 77 post-immunization, groups of ten mice were challenged IP with 1,000 PFU of MA-EBOV. Mice were weighed daily for nine days and every other day until day 21. (FIG. 10B) On day 50 post-immunization, groups of ten mice were challenged with virulent RABV virus strain CVS-N2C and weighed daily for 21 days.

(FIG. 11A) Vero cells were infected with indicated viruses at an MOI of 5. (FIG. 11B) BSR-G cells (a BHK cell derivative that expresses RABV G) were infected at an MOI of 0.01. Infected monolayers were incubated at 37° C. for indicated time, and samples were removed at indicated times post-infection. Virus concentrations were determined by viral focus assay. Dashed line indicated limit of detection.

FIG. 14 is a graph showing replication of RABV vaccine viruses expressing GP in suckling mouse brain assayed by qPCR. Five-day-old Swiss Webster mice were inoculated i.c. with 1×10$^5$ FFU of the indicated virus. On days 1, 3, 5, 6, 7, 9, 14, and 21, three mice per group were sacrificed, brain homogenates were generated, and viral cDNA was produced. The level of viral genomic RNA was determined by a RABV nucleoprotein-specific quantitative RT-PCR assay.

FIGS. 15A-15C show the analysis of co-administration of two inactivated vaccines: RABV-GP and a RABV virus expressing the HC50E30 domain of botulinum neurotoxin (BoNT). Groups of five mice were immunized i.m. once (day 0) or twice (day 0 and 14) with the indicated viruses. Groups receiving 2 immunizations are labeled (2). The viruses used are inactivated BNSP333-GP$_{GCD}$ labeled as INAC-GP$_{GCD}$ and SPBN-HC50E30 labeled as INAC-HC50. Single virus doses were administered at 10 ug, while the combined virus groups, INAC-GP$_{GCD}$+INAC-HC50 and INAC-GP$_{GCD}$+INAC-HC50(2) were administered at 20 ug (10 ug of each virus). On day 42, all mice were bled and serum was assayed by ELISA against (FIG. 15A) RABV G, (FIG. 15B) BoNT HC50, and (FIG. 15C) ZEBOV GP.

FIGS. 16A-16C show the induction of GP-specific antibody response in the presence of pre-existing RABV immunity. Groups of five mice were immunized once on day 0 with vehicle, 10 ug inactivated SPBN-HC50E30, or 10 ug inactivated BNSP333-GP$_{GCD}$. A fourth group was immunized with 10 ug SPBN-HC50E30 on day 0 followed by 10 ug inactivated BNSP333-GP$_{GCD}$ on day 28. At least four weeks after immunization, serum was assayed by ELISA against (FIG. 16A) RABV G, (FIG. 16B) BoNT HC50, and (FIG. 16C) ZEBOV GP.

DETAILED DESCRIPTION OF THE INVENTION

Figure 6C:
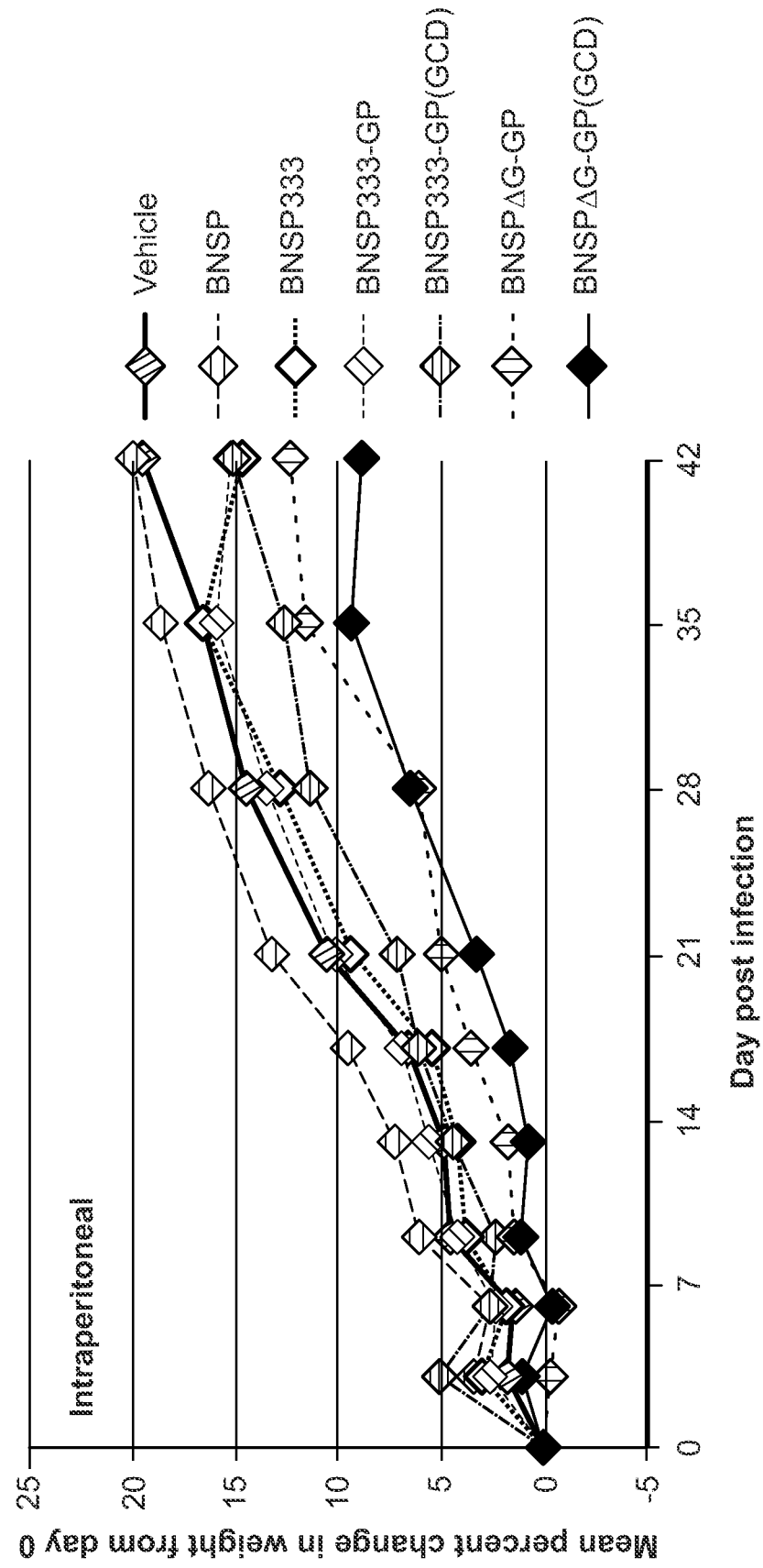

The present invention may be understood more readily by reference to the following detailed description of preferred embodiments of the invention and the Examples included therein. Before the present methods and techniques are disclosed and described, it is to be understood that this invention is not limited to specific methods and compositions, as such may, of course, vary. It is also to be understood that the terminology used herein is for the purpose of describing particular embodiments only and is not intended to be limiting. Unless defined otherwise, all technical and scientific terms used herein have the meaning commonly understood by one of ordinary skill in the art to which this invention belongs.

As used herein and in the appended claims, the singular forms "a," "and," and "the" include plural reference unless the context clearly dictates otherwise. Thus, for example, reference to "a gene" is a reference to one or more genes and includes equivalents thereof known to those skilled in the art, and so forth.

As used herein, the terms "biological sample" or "patient sample" or "test sample" or "sample" as used herein, refer to a sample obtained from an organism or from components (e.g., cells) of a subject or patient for the purpose of diagnosis, prognosis, or evaluation of a subject of interest. The sample can be, for example, blood which potentially is at risk of containing infection with Ebolavirus or rabies virus. In certain embodiments, such a sample may be obtained for assessing the presence of antibodies specific for Ebolavirus or a rabies virus following a suspected infection or following the vaccination using a vaccine construct of the invention. The invention contemplates the practice of any necessary safety and/or Governmental-imposed procedures for the handling and processing of any sample suspected of containing an infection with a rabies virus or a filovirus, e.g., Ebolavirus or Marburgvirus.

As used herein, a "subject" includes human, nonhuman primate (e.g., ape or monkey), animal, e.g., horse, donkey, pig, mouse, hamster, monkey, chicken, and insect such as mosquito.

As used herein, the term "specifically binds to" or is "specific for" in the context of antibody/antigen interactions is intended to mean the specific binding of an antibody to a cognate antigen via specific one or more epitopes recognized by the antibody, without substantially binding to molecules that lack such epitopes.

As used herein, the term "treatment" or "treating" includes any process, action, application, therapy, or the like, wherein a subject (or patient), including a human being, is provided with or administered an agent or composition, e.g., a therapeutic vaccine composition, with the aim of improving the subject's condition, directly or indirectly, or slowing the progression of a condition or disorder in the subject (e.g., hemorrhagic fever or bleeding due to Ebolavirus infection), or ameliorating at least one symptom of the disease or disorder under treatment. As used in the context of disease caused by rabies, Ebolavirus or another filovirus, the terms "treat," "treatment," and the like, refer to relief from or alleviation of a pathological process mediated by said viruses.

The term "combination therapy" or "co-therapy" means the administration of two or more therapeutic agents to treat a disease, condition, and/or disorder, e.g., filovirus-induced hemorrhagic fever. Such administration encompasses "co-administration" of two or more therapeutic agents in a substantially simultaneous manner. One therapy can be based on the dual-protective vaccines of the invention. A second therapy can be based on a known therapy for the disorder being treated. For example, alternative anti-virus drugs may be co-administered with the vaccine vectors of the invention. The order of administration of two or more sequentially co-administered therapeutic agents is not limited. The administration of the two or more therapeutic agents may also be administered by different routes, e.g., by a local route (e.g., mucosal delivery of a dual vaccine of the invention) and a systemic route (e.g., parenteral delivery of an anti-rabies or anti-filovirus small molecule inhibitor).

As used herein, the phrases "therapeutically effective amount" and "prophylactically effective amount" refer to an amount that provides a therapeutic benefit in the treatment, prevention, or management of pathological processes mediated by an infection with rabies virus, Ebolavirus or another filovirus, or an overt symptom of pathological processes mediated by rabies or Ebolavirus or another filovirus. The specific amount that is therapeutically effective can be readily determined by ordinary medical practitioner, and may vary depending on factors known in the art, such as, e.g. the type of pathological processes mediated by virus infection, the patient's history and age, the stage of pathological processes mediated by the virus infection, and the administration of other anti-pathological processes mediated by infection.

As used herein, a "pharmaceutical composition" comprises a pharmacologically effective amount of a vaccine construct and a pharmaceutically acceptable carrier. As used herein, "pharmacologically effective amount," "therapeutically effective amount" or simply "effective amount" refers to that amount of a vaccine effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter. Further, the pharmaceutical composition can be designed to enhance targeting cells involved in the underlying virus infection such as dendritic cells, macrophages, hepatocytes, and other parenchymal cells. As used herein, the term "pharmaceutically acceptable" means that the subject item is appropriate for use in a pharmaceutical product.

As used herein, a "vaccine construct" shall refer to a nucleic acid molecule constituting the recombinant rabies virus vector expressing one or more filovirus antigens (e.g., Ebolavirus glycoprotein) of the invention. The invention also contemplates the use of recombinant vaccine "virions" which are produced by the vaccine constructs of the invention when they are introduced into a host cell suscesptible to infection therefrom, and which are then allowed to propagate and form whole virus virions in the cell, which are then obtained and/or purified. A "virion" refers to a complete virus particle resulting from an infection cycle of the recombinant rabies genome in a cell capable of hosting the rabies genome. The "vaccine" or "recombinant vaccines" of the invention encompass both "genetic vaccines," i.e., the vaccine constructs of the invention, and the traditional vaccines, which are the virions themselves. Depending on the recombinant genome of the vaccine construct, the virions can be replication-competent or replication-deficient. Where they are replication-deficient, their propagation in host cells in vitro or in vivo may require a "helper" virus or cell, in which certain replication functions would be provided in trans by either the helper virus or the cell in which the infection is taking place. Vaccine compositions may also include both vaccine constructs as well as the virions themselves. The virions also may be of the "killed virus" type, whereby the virion is chemically treated or otherwise deactivated by some means of deactivation such that the virion has no or minimal ability to replication. Killed virus vaccines generally rely on their surface-presented polypeptides (e.g., the Ebolavirus GP protein) to induce a humoral-based immune response. Typically, a cellular-based immune response does not occur with the killed-virus type vaccines because these virions do not generally access the interior of cells.

As used herein, the term "isolated" or "purified" polypeptide or protein or virion or biologically-active portion or vaccine construct thereof is substantially free of cellular material or other contaminating proteins from the cell or tissue source from which the polypeptide (e.g., Ebolavirus GP) is obtained.

As used herein, "pharmaceutically acceptable carrier" includes any material which, when combined with an active ingredient of a composition, allows the ingredient to retain biological activity and without causing disruptive reactions with the subject's immune system. Examples include, but are not limited to, any of the standard pharmaceutical carriers such as a phosphate buffered saline solution, water, emulsions such as oil/water emulsion, and various types of wetting agents. Exemplary diluents for aerosol or parenteral administration are phosphate buffered saline or normal (0.9%) saline. Compositions comprising such carriers are formulated by well known conventional methods (see, for example, *Remington's Pharmaceutical Sciences*, Chapter 43, 14th Ed., Mack Publishing Col, Easton Pa. 18042, USA). Pharmaceutically acceptable excipients have been amply described in a variety of publications, including, for example, A. Gennaro (2000) "Remington: The Science and Practice of Pharmacy," 20th edition, Lippincott, Williams, & Wilkins; Remington's Pharmaceutical Sciences, 14th Ed. or latest edition, Mack Publishing Col, Easton Pa. 18042, USA; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc. Further discussion is provided herein.

The present invention contemplates that any suitable rabies virus genome or vector can be used to construct the recombinant vaccines of the invention. Thus, the rabies virus genome can be obtained from any suitable strain or isolate of rabies virus, so long as it is or is made to be attenuated. For the purposes of this invention, the term "attenuated," as it pertains to a property of a rabies virus genome of the invention, shall mean that the rabies virus genome or vector is capable of viral attachment, entry, and in some cases, replication in a host cell. However, attenuated rabies virus genomes—as compared to non-attenuated rabies viruses or rabies virus genomes—have substantially or completely lost the property of neurovirulence. In other words, the neurotropic character of the attenuated RVs of the invention preferably have been abolished or substantially abolished such that the RV vectors of the invention are safe for administering to a subject or animal without a substantial concern for neurovirulence effects.

The basic biology of the rabies virus is well-known. Rabies virus is a non-segmented negative-strand RNA virus of the rhabdoviridae family, and which is the causative agent of rabies. Rabies is a disease that can occur in all warm-blooded species. Infection with rabies virus followed by the outbreak of the clinical features in nearly all instances results in death of the infected species. In Europe, the USA and Canada wild life rabies still exists and is an important factor in the cause of most human rabies cases that occur. On the other hand, urban rabies constitutes the major cause of human rabies in developing countries and entire continents, such as Africa.

Rabies virus (RV) virions are composed of two major structural components: a nucleocapsid or ribonucleoprotein (RNP), and an envelope in the form of a bilayer membrane surrounding the RNP core. The infectious component of all Rhabdoviruses is the RNP core which consists of the RNA genome encapsidated by the nucleocapsid (N) protein in combination with two minor proteins, i.e. RNA-dependent RNA-polymerase (L) and phosphoprotein (P). The membrane surrounding the RNP core consists of two proteins: a trans-membrane glycoprotein (G) and a matrix (M) protein located at the inner site of the membrane.

The G protein, also referred to as spike protein, is responsible for cell attachment and membrane fusion in RV and additionally is the main target for the host immune system. The amino acid region at position 330 to 340 (referred to as antigenic site III) of the G protein has been identified to be responsible for the virulence of the virus, in particular the Arg residue at position 333. All RV strains have this virulence determining antigenic site III in common.

Although wild type rabies virus almost always causes a fatal central nervous system (CNS) disease in mammalian species, attenuated form(s) of rabies virus typically do not cause such problems.

Suitable attenuated rabies virus genome or vectors can be found described elsewhere, for example, in U.S. Pat. Nos. 7,544,791; 7,419,816; 6,887,479; 6,719,981; and 6,706,523, each of which are incorporated herein by reference.

In a preferred embodiment, the attenuated rabies virus genome of the invention is based on the replication-competent rabies virus strain SAD B19, which is a RV strain that has been used for oral immunization of wild-life animals in Europe for more than 20 years and which has a good safety record. The nucleotide sequence for SAD B19 is publicly available as Genbank accession No. M31046.1.

The invention also relates to the filovirus polypeptide of interest—and to their associated nucleotide and amino acid sequences—the genes of which are to be incorporated into the attenutated recombinant rabies vectors of the invention. The invention contemplates using any filovirus protein, including any virion surface glycoprotein, nucleoprotein, structural protein or element of replication machinery, which is to be incorporated using standard and well-known techniques in molecular biology into the attenuated rabies virus genomes of the invention. In preferred embodiments, the filovirus proteins are those identified from Ebolavirus (e.g., from any of Zaire Ebolavirus, Sudan Ebolavirus, Cote d'Ivoire Ebolavirus, or Reston Ebolavirus), including any of the seven encoded Ebolavirus proteins, i.e., membrane-anchored glycoprotein (GP), nucleoprotein (NP), an RNA-dependent RNA polymerase (L), and four virion structure proteins (VP24, VP30, VP35, and VP40).

The corresponding nucleotide and amino acid sequences for these Ebolavirus proteins, as well as, corresponding structural and non-structural proteins of Marburgvirus, are readily available in the art and can be easily utilized by the present invention. Accordingly, the following Table 1 provides pertinent information regarding a non-exhaustive listing of publicly available sequences contemplated by the present invention, in particular with respect to Ebolavirus glycoprotein:

TABLE 1

| Filovirus protein | Filovirus Genus | Species (or subtype) | Strain | Genbank No. Nucleotide Sequence(s) | AA SEQ ID NO: |
|---|---|---|---|---|---|
| Glycoprotein (GP) | Ebolavirus | Zaire | Mayinga | AY142960 | SEQ ID NO: 1 |
| Glycoprotein (GP) | Ebolavirus | Sudan | Boniface | FJ968794.1 | SEQ ID NO: 2 |
| Glycoprotein (GP) | Ebolavirus | Cote d'Ivoire | — | FJ217162.1 | SEQ ID NO: 3 |
| Glycoprotein (GP) | Ebolavirus | Reston | Pennsylvania | AF522874.1 | SEQ ID NO: 4 |
| Glycoprotein (GP) | Ebolavirus | Bundibugyo | — | FJ217161.1 | SEQ ID NO: 5 |
| Glycoprotein (GP) | Marburgvirus | Marburg | Musoke | NC_001608.3 | SEQ ID NO: 6 |

The invention further contemplates that the rabies vaccine of the invention can be engineered—using well-known techniques—to express not only an Ebolavirus glycoprotein, but also to express one or more additional filovirus proteins (e.g., additional Ebolavirus or Marburgvirus proteins). In this manner, use of a bivalent or multivalent attenued rabies virus vector is possible in accordance with the invention. Other such proteins may include but are not limited to those in the following Table 2:

TABLE 2

| Filovirus protein | Filovirus Genus | Species (or subtype) | Strain | Genbank No. Nucleotide Sequence(s) | AA SEQ ID NO: |
|---|---|---|---|---|---|
| Nucleoprotein (NP), VP24, VP30, VP35, VP40, and RNA-dependent RNA polymerasae (L) | Ebolavirus | Zaire | Mayinga | AY142960 | NP (SEQ ID NO: 7) VP24 (SEQ ID NO: 8) VP30 (SEQ ID NO: 9) VP35 (SEQ ID NO: 10) VP40 (SEQ ID NO: 11) L (SEQ ID NO: 12) |
| Nucleoprotein (NP), VP24, VP30, VP35, VP40, and RNA-dependent RNA polymerasae (L) | Ebolavirus | Sudan | Boniface | FJ968794.1 | NP (SEQ ID NO: 13) VP24 (SEQ ID NO: 14) VP30 (SEQ ID NO: 15) VP35 (SEQ ID NO: 16) VP40 (SEQ ID NO: 17) L (SEQ ID NO: 18) |
| Nucleoprotein (NP), VP24, VP30, VP35, VP40, and RNA-dependent RNA polymerasae (L) | Ebolavirus | Cote d'Ivoire | — | FJ217162.1 | NP (SEQ ID NO: 19) VP24 (SEQ ID NO: 20) VP30 (SEQ ID NO: 21) VP35 (SEQ ID NO: 22) VP40 (SEQ ID NO: 23) L (SEQ ID NO: 24) |

TABLE 2-continued

| Filovirus protein | Filovirus Genus | Species (or subtype) | Strain | Genbank No. Nucleotide Sequence(s) | AA SEQ ID NO: |
|---|---|---|---|---|---|
| Nucleoprotein (NP), VP24, VP30, VP35, VP40, and RNA-dependent RNA polymerase (L) | Ebolavirus | Reston | Pennsylvania | AF522874.1 | NP (SEQ ID NO: 25) VP24 (SEQ ID NO: 26) VP30 (SEQ ID NO: 27) VP35 (SEQ ID NO: 28) VP40 (SEQ ID NO: 29) L (SEQ ID NO: 30) |
| Nucleoprotein (NP), VP24, VP30, VP35, VP40, and RNA-dependent RNA polymerase (L) | Ebolavirus | Bundibugyo | — | FJ217161.1 | NP (SEQ ID NO: 31) VP24 (SEQ ID NO: 32) VP30 (SEQ ID NO: 33) VP35 (SEQ ID NO: 34) VP40 (SEQ ID NO: 35) L (SEQ ID NO: 36) |
| Nucleoprotein (NP), VP24, VP30, VP35, VP40, and RNA-dependent RNA polymerase (L) | Marburgvirus | Marburg | Musoke | NC_001608.3 | NP (SEQ ID NO: 37) VP24 (SEQ ID NO: 38) VP30 (SEQ ID NO: 39) VP35 (SEQ ID NO: 40) VP40 (SEQ ID NO: 41) L (SEQ ID NO: 42) |

It is understood in the art that certain changes to the nucleotide sequence employed in a genetic construct have little or no bearing on the proteins encoded by the construct. Such changes result either from silent point mutations or point mutations that encode different amino acids that do not appreciably alter the behavior of the encoded protein. It is also understood that portions of the coding region can be eliminated without affecting the ability of the construct to achieve the desired effect, namely induction of a protective immune response against a filovirus challenge. It is further understood in the art that certain advantageous steps can be taken to increase the antigenicity of an encoded protein by modifying its amino acid composition. Such changes in amino acid composition can be introduced by modifying the genetic sequence encoding the protein. It is contemplated that all such modifications and variations of the filovirus glycoprotein genes are equivalents within the scope of the present invention.

Any suitable means, including any appropriate genetic-based or molecular biology-based techniques and the like can be used to construct the recombinant rabies vaccine vectors of the present invention.

In one embodiment, the skilled artisan may first obtain a rabies virus vector suitable for purposes of the invention. Preferably, the rabies virus vectors that are suitable are those that are attenuated, such there are no harmful effects by the rabies virus vector on the central nervous system when used to administered to a subject. Suitable rabies virus vectors can be readily obtained. Such vectors can be modified to enhance the degree of attenuation by known methods. In a preferred embodiment, the present inventors utilized BNSP RABV vaccine vector (FIG. 3), which was derived from SAD B19 vaccine strain, which was attenuated by tissue culture passage and which has been previously used a live oral vaccine for wildfile in Europe.

This particular construct, as discussed in Example 1 herein, was engineered to contain a novel RABV stop-start transcription signal sequence flanked by unique BsiWI and NheI restriction sites between the nucleoprotein (N) and phosphoprotein (P) genes of the rabies virus genome for the introduction of foreign genes. Moreover, to completely remove neurovirulence observed for this construct, a further attenuated derivate ("BNSP333") was generated which contains an Arg-->Glu change at amino acid 333 of RABV G, which has been shown to greatly attenuate neurovirulence of RABV vaccine vectors in adult mice.

In preferred embodiments, also discussed in more detail in the Examples, the inventors constructed four different recombinant rabies virus vaccines based on the BNSP333 attenuated rabies virus vaccine. In this embodiment, two BSNP333 constructs encoding Zaire Ebolavirus strain Maying a GP ("ZEBOV" here and throughout) were generated (see FIG. 3). BNSP33-GP encodes unmodified ZEBOV GP while BNSP333-GP$_{GCD}$ encodes the GP ectodomain and transmembrane domain fused to the rabies virus G cytoplasmic domain (GCD). The GCD construct was generated to maximize the likelihood that efficient incorporation of GP into virions would occur, which may be important for potential inactivated vaccines where surface presentation is important. In addition, two additional constructs were prepared which were identical to those above, however the BNSP333 vector carried a deletion in the rabies G gene. Rabies G protein is responsible for viral attachment and entry and an important mediator of neurovirulence. Thus, deletion of G results in viruses which are severely growth-restricted and require recovery and propagation with "helper" viruses that provide trans-complementing host cells expressing rabies virus G.

In constructing the rabies virus vector constructs of the invention, a desired filovirus immunogenic polypeptide (e.g., Ebolavirus glycoprotein) can be selected and obtained based on publicly available sequences and with the use of well-known molecular biology techniques. For example, one interested in using the rabies virus vaccine to introduce Ebolavirus glycoprotein into a subject may obtain the nucleotide sequence of the glycoprotein (GP) gene from Ebolavirus Zaire strain Maying a by identifying from the above chart Genbank Accession No. AY142960 using readily available public information (e.g., the data site operated by the National Center for Biotechnology Information). A PCR-based strategy could be used to amplify the GP gene from a suitable source of template DNA, also readily obtainable by those of ordinary skill in the art, using oligonucleotide primers designed from the gene sequence itself. Once amplified, standard methods for cloning, sequence verification, expression, and tranfer of the nucleotide sequence to the BSNP333 rabies vector (or any other suitable rabies vector of the invention) could be performed to obtain the desired recombinant rabies virus vector expressing a Ebolavirus Zaire strain Maying a glycoprotein (GP). It will be readily apparent, however, that any work performed using sequences or materials from Ebolavirus or any other filoviruses may need to be performed in Biosafety Level Three (BSL3) or even BSL4 laboratories given the obvious dangers in working and handling filoviruses.

The invention further contemplates introducing more than a single filovirus polypeptide immunogen into the same recombinant rabies virus vector. For example, one could, using similar procedures offered above, as well as any other suitable procedures, prepare two or more nucleotide sequences that encode different filovirus polypeptide immunogens of interest, e.g., where one polypeptide of interest is the Ebolavirus glycoprotein and a second polypeptide of interest is an Ebolavirus NP, GP24, VP30, VP35 or VP40 virion proteins. Thus, the present invention contemplates administering a rabies virus vector that contains and expresses both a single Ebolavirus glycoprotein and another filovirus polypeptide immunogen.

Moreover, two or more different rabies virus vaccine constructs can be combined into single administration or via co-administration, wherein each of the rabies virus vaccines is engineered to express a different filovirus immunogen polypeptide.

It is further contemplated that, where cross-reactivity occurs, i.e., where antibodies or a cytotoxic T-cell response induced in response to one Ebolavirus or filovirus polypeptide can be cross-reactive with the corresponding polypeptide from a different type of Ebolavirus or even a different genus of filovirus, the invention envisions a single vaccine that expresses a single filovirus polypeptide (e.g., ZEBOV GP) that induces an immune response that is cross-reactive against other types of Ebolavirus (e.g., SEBOV, REBOV, BEBOV, or CEBOV) or even other filoviruses (e.g., Marburgvirus). Generally it is known, however, that GP of Ebolavirus does not induce antibodies that are generally cross-reactive with GP of other types of Ebolavirus; thus, the invention also contemplates vaccine compositions that comprise individual recombinant rabies vaccine vectors which express specific GP (or immunogenic fragments thereof) from specific Ebolavirus subtypes or even specific strains so that a single vaccine composition effective against a variety of Ebolavirus agents can be administered.

These and other methods for obtaining and/or preparing the rabies virus vaccine constructs can be found in, for example, *Current Protocols in Molecular Biology*, Ausubel et al. (eds.), John Wiley and Sons, Inc.

The invention further contemplates that host cells transfected by the recombinant rabies virus vectors of the invention can be used to express virus-encoded protein and/or to form recombinant rabies virions. Methods and techniques for maintaining continuous cell cultures for infection by rabies viruses are well known in the art. A cell line can be infected (or transfected) with a recombinant rabies vaccine vector of the invention. The cell lines may be used to express the viral proteins, or they can be used to produce whole rabies virions containing the expressed Ebolavirus or otherwise desired filovirus polypeptide expressed from the recombinant rabies vaccine vector used to infect the cells. Suitable host cells can include any cell suseptible to being transfected or infected in vitro with a rabies virus vaccine, including any human cell lines or animal cell lines. Such cell lines and their use in expressing proteins and forming rabies virions is well known in the art and described in more detail in, for example, Barrett P N et al., Expert Rev Vaccines. 2009 May; 8(5):607-18; Tordo N et al., Dev Biol (Basel). 2008; 131:467-76; Toovey S. et al., Travel Med Infect Dis. 2007 November; 5(6):327-48; Chelbi-Alix M K, J Interferon Cytokine Res. 2006 May; 26(5):271-80; Morenweiser R. et al., Gene Ther. 2005 October; 12 Suppl 1:S103-10; Morimoto K et al., Virus Res. 2005 July; 111(1):61-7. Epub 2005 April 11; Finke S et al., Virus Res. 2005 August; 111(2):120-31; and Halder M., Ahern Lab Anim. 2002 January-February;30(1):93-108; Montagnon B J et al., Dev Biol Stand. 1998; 93:119-23, each of which are incorporated herein by reference.

It is preferred that the rabies vaccine viruses and the production of any virus virions and their use as vaccines be done in accordance with any necessary national and/or international requirements for health and safety with regard to rabies virus and filoviruses, e.g., in accordance with the requirements of the U.S. Center for Disease Control ("CDC") or the World Health Organization ("WHO").

In another aspect of the invention, the recombinant rabies virus vector vaccines of the invention, or recombinant rabies virion vaccines (which express the desired filovirus polypeptide or polypeptides therein or thereon) may be formulated as compositions in accordance with known methods for preparing medicinal formulations and pharmaceutical compositions. The type and components of the pharmaceutical compositions of the invention can depend on the mode of administration, e.g., oral, parenteral or skin.

Pharmaceutical compositions and formulations for oral administration can include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable.

Pharmaceutical compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention can also include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. In general, the formulations are prepared by uniformly and intimately bringing into association the active ingredients with liquid carriers or finely divided solid carriers or both, and then, if necessary, shaping the product.

In certain embodiments, the pharmaceutical compositions of the present invention can incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid, such as a rabies vaccine vector of the invention, and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4' isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

The pharmaceutical compositions of the invention may also include a "pharmaceutical carrier" or "excipient", which for purposes of the invention, is a pharmaceutically acceptable solvent, suspending agent or any other pharmacologically inert vehicle for delivering one or more nucleic acids (e.g., a recombinant rabies virus vector of the invention) or polypeptide or virus virion (e.g., a recombinant rabies virion expressing the one or more filovirus glycoproteins of the invention) to an animal. The excipient may be liquid or solid and is selected, with the planned manner of administration in mind, so as to provide for the desired bulk, consistency, etc., when combined with an active agent of the invention (e.g., rabies vaccine vector, virion, or expressed polypeptides) the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with the active agents of the invention (e.g., rabies vaccine vector, virion, or expressed polypeptides) can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

The pharmaceutical compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing one or more other additional chemotherapeutic agents, for example, anti-viral small molecule drug inhibits some aspect of Ebolavirus entry and/or replication and/or assembly, or which helps to mitigate one or more symptoms of an Ebolavirus infection, or an infection by another filovirus, such as Marburgvirus. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, The Merck Manual of Diagnosis and Therapy, 15th Ed., Berkow et al., eds., 1987, Rahway, N.J., pages 2499-2506 and 46-49, respectively). Other chemotherapeutic agents are also within the scope of this invention. Two or more combined compounds may be used together or sequentially. Such compounds may be administered using a separate administration schedule relative to the administration schedule of the active agents of the invention. The administration schedules may also be the same or have overlap.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies generally within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the vaccines of the invention can be administered in combination with other known agents effective in treatment of pathological processes mediated by Ebolavirus expression or by another filovirus—such as those listed above and others as well. In any event, the administering physician can adjust the amount and timing of vaccine administration on the basis of results observed using standard measures of efficacy known in the art or described herein.

The present invention contemplates any suitable means or method for administering the vaccine compositions of the invention. The skilled artisan will appreciate that the particular means of administration may depend upon whether the vaccine composition comprises recombinant rabies virus virions (e.g., with expressed Ebolavirus glycoprotein presented at virion surface) or whether the vaccine to be administered is a nucleic acid-based vaccine, i.e., where the vaccine comprises a recombinant rabies virus vector of the invention which has been modified to express a filovirus protein (or immunogenic fragment thereof).

In certain embodiments, administration of any of the vaccines of the invention herein may be carried out by, for example, parenteral injection (such as intraperitoneal, subcutaneous, or intramuscular injection), in ovo injection of birds, orally, or by topical application of the virus (typically carried in a pharmaceutical formulation) to an airway surface. Topical application of a vaccine of the invention to an airway surface can be carried out by intranasal administration (e.g., by use of dropper, swab, or inhaler which deposits a pharmaceutical formulation intranasally). Topical application of a vaccine of the invention to an airway surface can also be carried out by inhalation administration, such as by creating respirable particles of a pharmaceutical formulation (including both solid particles and liquid particles) containing the replicon as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation. As noted above, one particular embodiment is subcutaneous injection, and another is intramuscular injection.

When the vaccine of the invention is RNA or DNA (e.g., a recombinant rabies virus vaccine vector expressing a filovirus glycoprotein, e.g., Ebolavirus glycoprotein), the vaccine vector RNA or DNA can be administered directly using techniques such as delivery on gold beads (gene gun), delivery by liposomes, or by direct injection, among other methods known to those of ordinary skill in the art. Any one or more nucleotide constructs described above can be use in any combination effective to elicit an immunogenic response in a subject. Generally, the nucleic acid vaccine administered may be in an amount of about 1-5 ug of nucleic acid per dose and will depend on the subject to be treated, capacity of the subject's immune system to develop the desired immune response, and the degree of protection desired. Precise amounts of the vaccine to be administered may depend on the judgement of the practitioner and may be peculiar to each subject and antigen.

Lipid based microsphere delivery systems can also be used to deliver the vaccines of the invention, in particular, the vaccine vector molecules of the invention.

Optionally, such systems can be modified such that they specifically target specific cells and/or tissues and/or organs of the body, e.g., infection sites. Methods for preparing such systems will be well known to those having ordinary skill in the art. For example, such vector-delivering microspheres can be modified to comprise one or more ligands or targeting moieties which allow the microsphere to bind and/or interact specifically with a receptor or other target on a target cell or tissue.

Accordingly, in one aspect, the present invention provides recombinant rabies vector formulations comprised of a lipid-based carrier system, such as a stabilized nucleic acid-lipid particle, cationic lipid or liposome nucleic acid complexes (i.e., lipoplexes), a liposome, a micelle, a virosome, or a mixture thereof, which optionally may be modified to contain a moiety that enables it to be targeted to one or more cells or tissues of the gastrointestinal tract. In other embodiments, the carrier system is a polymer-based carrier system such as a cationic polymer-nucleic acid complex (i.e., polyplex), which optionally may be modified to contain a moiety that enables it to be targeted to one or more desired cells or tissues. In additional embodiments, the carrier system is a cyclodextrin-based carrier system, such as a cyclodextrin polymer-nucleic acid complex, which optionally may be modified to contain a moiety that enables it to be targeted to one or more desired cells or tissues. In further embodiments, the carrier system is a protein-based carrier system such as a cationic peptide-nucleic acid complex. Nucleic acid-lipid and/or protein-lipid particles and their method of preparation are disclosed in, e.g., U.S. Pat. Nos. 5,753,613; 5,785,992; 5,705,385; 5,976,567; 5,981,501; 6,110,745; and 6,320,017; and PCT Publication No. WO 96/40964, which are all herein incorporated by reference.

The lipoplexes of the invention can include non-cationic lipids used in the formulations of the present invention, which include any of a variety of neutral uncharged, zwitterionic, or anionic lipids capable of producing a stable complex. Such non-cationic lipids can be neutral or negatively charged. Examples of non-cationic lipids include, without limitation, phospholipid-related materials such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipahnitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), and stearoyloleoyl-phosphatidylethanolamine (SOPE).

Non-cationic lipids or sterols such as cholesterol may also be present in such microspheres. Additional nonphosphorous containing lipids include, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkylaryl sulfate polyethyloxylated fatty acid amides, dioctadecyldimethyl ammonium bromide, ceramide, diacyl-phosphatidylcholine, diacylphosphatidylethanolamine, and the like. Other lipids such as lysophosphatidylcholine and lysophosphatidylethanolamine may be present. Non-cationic lipids also include polyethylene glycol (PEG)-based polymers such as PEG 2000, PEG 5000, and polyethylene glycol conjugated to phospholipids or to ceramides (referred to as PEG-Cer), as described in U.S. patent application Ser. No. 08/316,429.

Non-limiting examples of additional lipid-based carrier systems suitable for use in the present invention include lipoplexes (see, e.g., U.S. Patent Publication No. 20030203865; and Zhang et al., *J. Control Release*, 100: 165-180 (2004)), pH-sensitive lipoplexes (see, e.g., U.S. Patent Publication No. 2002/0192275), reversibly masked lipoplexes (see, e.g., U.S. Patent Publication Nos. 2003/0180950), cationic lipid-based compositions (see, e.g., U.S. Pat. No. 6,756,054; and U.S. Patent Publication No. 2005/0234232), cationic liposomes (see, e.g., U.S. Patent Publication Nos. 2003/0229040, 2002/0160038, and 2002/0012998; U.S. Pat. No. 5,908,635; and PCT Publication No. WO 01/72283), anionic liposomes (see, e.g., U.S. Patent Publication No. 2003/0026831), pH-sensitive liposomes (see, e.g., U.S. Patent Publication No. 2002/0192274; and AU 2003/210303), antibody-coated liposomes (see, e.g., U.S. Patent Publication No. 2003/0108597; and PCT Publication No. WO 00/50008), cell-type specific liposomes (see, e.g., U.S. Patent Publication No. 2003/0198664), liposomes containing nucleic acid and peptides (see, e.g., U.S. Pat. No. 6,207,456), liposomes containing lipids derivatized with releasable hydrophilic polymers (see, e.g., U.S. Patent Publication No. 2003/0031704), lipid-entrapped nucleic acid (see, e.g., PCT Publication Nos. WO 03/057190 and WO 03/059322), lipid-encapsulated nucleic acid (see, e.g., U.S. Patent Publication No. 2003/0129221; and U.S. Pat. No. 5,756,122), other liposomal compositions (see, e.g., U.S. Patent Publication Nos. 2003/0035829 and 2003/0072794; and U.S. Pat. No. 6,200,599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 2005/0037086).

In another embodiment, administration may be by accelerated-particle gene delivery.

The technique of accelerated-particle gene delivery is based on the coating of genetic constructions to be delivered into cells onto extremely small carrier particles, which are designed to be small in relation to the cells sought to be transformed by the process. The coated carrier particles are then physically accelerated toward the cells to be transformed such that the carrier particles lodge in the interior of the target cells. This technique can be used either with cells in vitro or in vivo. At some frequency, the DNA which has been previously coated onto the carrier particles is expressed in the target cells. This gene expression technique has been demonstrated to work in procaryotes and eukaryotes, from bacteria and yeasts to higher plants and animals. Thus, the accelerated particle method provides a convenient methodology for delivering genes into the cells of a wide variety of tissue types, and offers the capability of delivering those genes to cells in situ and in vivo without any adverse impact or effect on the treated individual. Therefore, the accelerated particle method is also preferred in that it allows a genetic vaccine construction capable of eliciting an immune response to be directed both to a particular tissue, and to a particular cell layer in a tissue, by varying the delivery site and the force with which the particles are accelerated, respectively. This technique is thus particularly suited for delivery of genes for antigenic proteins into the epidermis.

Thus, with regard to delivery of the recombinant rabies vaccine vectors of the invention, the invention also contemplates that aqueous droplets containing naked vector can be delivered by suitable acceleration techniques into the tissues of the individual sought to be vaccinated. At some frequency, such "naked" vector material will be taken up in the treated tissues.

The general approach of accelerated particle gene transfection technology is described in U.S. Pat. No. 4,945,050. An instrument based on an improved variant of that approach is available commercially from BioRad Laboratories. An alternative approach to an accelerated particle transfection apparatus is disclosed in U.S. Pat. No. 5,015,580 which, while directed to the transfection of soybean plants, describes an apparatus which is equally adaptable for use with mammalian cells and intact whole mammals. U.S. Pat. No. 5,149,655 describes a convenient hand-held version of an accelerated particle gene delivery device. Other such devices can be based on other propulsive sources using, for example, compressed gas as a motive force. A preferred apparatus and method for delivering genetic material in the present invention is described in published PCT patent application PCT/US95/00780 and in U.S. Pat. No. 5,584,807 which will issue on Dec. 17, 1996. Both are incorporated herein by reference.

A "genetic vaccine," i.e., a recombinant rabies vaccine vector (as opposed to a composition of rabies virions, which are also contemplated herein) can be delivered in a non-invasive manner to a variety of susceptible tissue types in order to achieve the desired antigenic response in the individual. Most advantageously, the genetic vaccine can be introduced into the epidermis. Such delivery, it has been found, will produce a systemic humoral immune response, a memory response, and a cytotoxic immune response. When delivering a genetic vaccine to skin cells, it was once thought desirable to remove or perforate the stratum corneum.

To obtain additional effectiveness from this technique, it may also be desirable that the genes be delivered to a mucosal tissue surface, in order to ensure that mucosal, humoral and cellular immune responses are produced in the vaccinated individual. It is envisioned that there are a variety of suitable delivery sites available including any number of sites on the epidermis, peripheral blood cells, i.e. lymphocytes, which could be treated in vitro and placed back into the individual, and a variety of oral, upper respiratory, and genital mucosal surfaces.

The term "transfected" is used herein to refer to cells which have incorporated the delivered foreign genetic vaccine construction (e.g., the recombinant rabies vaccine vectors), whichever delivery technique is used. The term transfection is used in preference to the term "transformation," to avoid the ambiguity inherent in the latter term, which is also used to refer to cellular changes in the process of oncogenesis. The term "infection" pertains to the normal molecular cellular uptake process by which a virus is introduced into a cell. Such cells are sometimes said to be "suspectible" to infection.

In some embodiments, when inducing cellular, humoral, and protective immune responses after genetic vaccination, preferred target cells are epidermal cells, rather than cells of deeper skin layers such as the dermis. Epidermal cells are preferred recipients of genetic vaccines because they are the most accessible cells of the body and may, therefore, be immunized non-invasively. Secondly, in addition to eliciting a humoral immune response, genetically immunized epidermal cells also elicit a cytotoxic immune response that is stronger than that generated in sub-epidermal cells. Delivery to epidermis also has the advantages of being less invasive and delivering to cells which are ultimately sloughed by the body.

The administration of the vaccines of the present invention (e.g., the recombinant rabies virions and/or the recombinant rabies vaccine vectors of the invention) by any of the above-described means can be in accordance with any suitable vaccination schedule, e.g., day 0, one month, four months, and twelve months from day 0. However, generally speaking, the vaccines described herein may also be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. Other examples of suitable immunization schedules include: (i) 0, 1 months and 6 months, (ii) 0, 7 days and 1 month, (iii) 0 and 1 month, (iv) 0 and 6 months, (v) 0, 1 and 2 months, or other schedules sufficient to elicit the desired immune responses expected to confer protective immunity, or reduce disease symptoms, or reduce severity of disease.

The present invention, in other aspects, provides methods for evaluating a sample for the presence of antibodies raised against rabies and/or a filovirus, e.g., an Ebolavirus. The invention contemplates that such methods may be useful, for example, in evaluating whether a tissue sample contains antibodies against Ebolavirus, another filovirus or rabies, which may be useful in detecting whether a person or animal was exposed to such pathogens. Such detection methods may also be useful in monitoring a subject's blood or other tissues for evidence that an immune response has been induced against a vaccine of the invention.

In a further embodiment, the present invention relates to a method of detecting the presence of antibodies against Ebolavirus in a sample. Using standard methodology well known in the art, a diagnostic assay can be constructed by coating on a surface (i.e. a solid support for example, a microtitration plate, a membrane (e.g. nitrocellulose membrane) or a dipstick), all or a unique portion of any of the Ebolavirus proteins described above or any combination thereof, and contacting it with the serum of a person or animal suspected of having Ebolavirus. The presence of a resulting complex formed between the Ebolavirus protein(s) and serum antibodies specific therefor can be detected by any of the known methods common in the art, such as fluorescent antibody spectroscopy or colorimetry. This method of detection can be used, for example, for the diagnosis of Ebolavirus infection and for determining the degree to which an individual has developed virus-specific antibodies after administration of a vaccine.

In yet another embodiment, the present invention relates to methods for detecting the presence of virion proteins from rabies, a filovirus or Ebolavirus in a sample. Antibodies against GP, NP, and the VP proteins could be used for diagnostic assays. Using standard methodology well known in the art, a diagnostics assay can be constructed by coating on a surface (i.e. a solid support, for example, a microtitration plate or a membrane (e.g. nitrocellulose membrane)), antibodies specific for any of the Ebolavirus proteins described above, and contacting it with serum or a tissue sample of a person suspected of having Ebolavirus infection. The presence of a resulting complex formed between the protein or proteins in the serum and antibodies specific therefor can be detected by any of the known methods common in the art, such as fluorescent antibody spectroscopy or colorimetry. This method of detection can be used, for example, for the diagnosis of Ebolavirus infection.

In yet another embodiment, the present invention relates to DNA or nucleotide sequences for use in detecting the presence of rabies virus or filovirus, e.g., Ebolavirus, using the reverse transcription-polymerase chain reaction (RT-PCR) or by some other suitable means for detection of specific nucleotide sequences. The nucleotide sequence of the present invention can be used to design primers which specifically bind to the viral RNA for the purpose of detecting the presence of Ebolavirus or for measuring the amount of Ebolavirus in a sample. The primers can be any length ranging from 7 to 400 nucleotides, preferably at least 10 to 15 nucleotides, or more preferably 18 to 40 nucleotides. Reagents and controls necessary for PCR reactions are well known in the art. The amplified products can then be analyzed for the presence of viral sequences, for example by gel fractionation, with or without hybridization, by radiochemistry, and immunochemistry techniques, or other suitable techniques.

In yet another embodiment, the present invention relates to a diagnostic kit which contains a vaccine composition of the invention, and optionally a means for detecting whether an immune response is induced following the administration of the vaccine, and further, optionally a means for administering the vaccine of the invention, and still further, optionally a set of instructions indicated a procedure for administering the vaccine and evaluating its effectivity on the immune response.

Depending on how the kit is to be operated, the kit may also include one or more additional vaccine compositions of the invention, wherein each vaccine composition comprises a recombinant rabies virus vector expressing a different filovirus protein (or immunogenic fragment thereof), e.g., an Ebolavirus glycoprotein or immunogenic fragment thereof.

It will be appreciated that certain components of the kits will vary depending on what subject is being vaccinated and/or from which samples are to be drawn. Certain subjects can include, for example, human, non-human primate, animal, e.g., horse, donkey, pig, mouse, hamster, monkey, or other mammals, birds. For example, where a rabies vaccine vector is to be administered to a human, the kit may include a skin path, whereas where the administration is to a non-human primate, the kit may include instead a syringe.

In certain embodiments, the kits may also include an immunodetection reagent or label for the detection of the antibodies induced by the vaccination or to detect samples for the presence of rabies or filovirus peptides. Suitable detection reagents are well known in the art as exemplified by radioactive, enzymatic or otherwise chromogenic ligands, which are typically employed in association with the antigen and/or antibody, or in association with a second antibody having specificity for first antibody. Thus, the reaction is detected or quantified by means of detecting or quantifying the label. Immunodetection reagents and processes suitable for application in connection with the novel methods of the present invention are generally well known in the art.

The reagents may also include ancillary agents such as buffering agents and protein stabilizing agents, e.g., polysaccharides and the like. The kit may further include, where necessary, agents for reducing background interference in a test, agents for increasing signal, apparatus for conducting a test, calibration curves and charts, standardization curves and charts, and the like.

In a further embodiment, such a kit can comprise instructions for suitable operational parameters in the form of a label or separate insert.

The following examples are included to demonstrate preferred embodiments of the invention. It should be appreciated by those of skill in the art that the techniques disclosed in the examples which follow represent techniques discovered by the inventors and thought to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

The materials, compositions, and methods described herein are intended to be representative examples of the invention, and it will be understood that the scope of the invention is not limited by the scope of the examples. Those skilled in the art will recognize that the invention may be practiced with variations on the disclosed materials, compositions and methods, and such variations are regarded as within the ambit of the invention.

The collective objective of these Examples was to identify novel vaccine candidates for EBOV with a maximum potential of licensure and utilization. To this end, the rabies virus (RABV) vaccine platform was chosen. This platform would allow rapid development of replication-competent, replication-deficient, and chemically inactivated vaccine candidates to increase the likelihood that an appropriate balance between vaccine immunogenicity and reactogenicity could be achieved.

RABV is a non-segmented, negative strand RNA virus of the rhabdoviridae family. Although wild type RABV almost always causes a fatal CNS disease in mammalian species (Schnell et al., 2010), in its attenuated form, the RABV vaccine does not cause fatal CNS disease (Cenna et al., 2008; Faber et al., 2005; Faul et al., 2009; Faul et al., 2008; McGettigan et al., 2006; McGettigan et al., 2003a; McGettigan et al., 2003b; Siler et al., 2002; Snook et al., 2008; Tan et al., 2005). The RABV vaccine vectors can be generated from a reverse genetics system derived from the live attenuated SAD B19 RABV vaccine that is used for wildlife vaccination in Europe (Vos et al., 1999; Vos et al., 2002). Further attenuated RABV vectored vaccines have been generated by the introduction of mutations in the RABV glycoprotein (G), as well as the deletion of the RABV G that are propagated on trans-complementing cell lines that express RABV G (Gomme et al., 2010; McGettigan et al., 2003b; McKenna et al., 2004). These recombinant viruses have been demonstrated to be growth-deficient or -restricted in vitro and in vivo and are strongly immunogenic (Gomme et al., 2010; McGettigan et al., 2003b; McKenna et al., 2004). Furthermore, beta-propiolactone-mediated inactivation of RABV vectored vaccines has been used to generate killed vaccine candidates that should have optimal safety profiles (Siler et al., 2002; Smith et al., 2006).

The Examples that follow describe the generation of live-attenuated and inactivated RABV vaccines expressing ZEBOV GP and demonstrate their molecular properties, virulence, immunogenicity, and protective efficacy against RABV and EBOV in mice. In addition to the advantages of the RABV vaccine platform described above, it is anticipated that the current advanced state of RABV vaccine safety, production, and distribution may ease the clinical development of these ZEBOV GP vaccines. In addition, RABV causes an estimated 24,000 deaths per year in Africa so a bivalent RABV/EBOV vaccine would be an effective public health tool in Central Africa.

Example 1

Methods and Materials Used Throughout Examples

Ebolavirus Zaire (ZEBOV) GP. As used in these Examples, Reference to ZEBOV GP is based on the full length coding region encoding the Ebolavirus GP beginning at nucleotide 6039 and extending through nucleotide 8068 of the nucleotide sequence identified as Genbank Accession No. AY142960.1 (Ebolavirus subtype Zaire, strain Maying a).

Plasmid Construction. The full length coding region of the Ebolavirus Zaire (ZEBOV) GP was amplified with primers RP777 (GTGTGAATTCCGGAACGTACGCCGCCAC-CATGGGTGTTACAGGAATATTG CA GTTACCTCGT SEQ ID NO: 47) and RP778 (GGAAGCTAGCT-CACTAAAAGAC AAATTTGCATATACAGAATAAAGC SEQ ID NO: 48) and cloned into the BsiWI and NheI sites of a modified BNSP RV vector, which encodes glutamic acid at position 333 of the RABV-glycoprotein (McGettigan et al 2003). The resulting plasmid was designated cBNSP333-GP. A truncated version of GP that contains the ecto- and transmembrane domains but lacks the cytoplasmic tail was amplified with primers RP777 and RP781 (GGAA GCTAGC CTA GTT AAC GCA TAT ACA GAA TAA AGC GAT AAC TGC AA SEQ ID NO: 49), digested with BsiWI and HpaI and ligated to the HpaI-NheI fragment of pSN-VSV-G (Foley et al, 2000), which contains the cytoplasmic tail of the RABV-G. The fusion gene was then digested with BsiWI and NheI and cloned into cBNSP333 to generate cBNSP-GP$_{GCD}$. The G-deleted constructs BNSPΔG-GP and BNSPΔG-GP$_{GCD}$ were generated by digestion of the G-containing parent plasmids BNSP-GP and BNSP-GP$_{GCD}$ with PacI and SmaI and religation of the blunted fragments.

Virus Recovery from cDNA and Propagation. G-containing and G-deficient recombinant RABV were recovered and grown as described previously (Gomme et al., 2011; Wirblich and Schnell, 2010).

Western Blot. BSR cells were infected at a MOI of 2-5 at 34° C. At 24, 48 and 72 h post infection the cells were washed once in PBS and resuspended in lysis buffer (50 mM Tris-HC1 [pH 7.4], 150 mM NaCl, 1% NP-40, 0.1% sodium dodecyl sulfate [SDS], 1× protease inhibitor cocktail [Sigma]) on ice for 30 min. The suspension was transferred to a microcentrifuge tube and spun for 10 min at 16,000 g to remove cell debris. Proteins were separated by SDS-9% polyacrylamide gel electrophoresis (PAGE) and transferred to a nitrocellulose membrane (Whatman, Minnetonka, Minn.). Blots were blocked for 1 h in 5% dry milk powder in TBS [pH 7.4]). After being blocked, blots were washed twice using a 0.05% TBS-Tween 20 solution and incubated overnight at 4° C. with polyclonal monkey anti-EBOV antibody or monoclonal antibody against RABV phosphoprotein. Blots were then washed four times with 0.1% TBS-Tween. Secondary goat anti-human or goat anti-mouse horseradish peroxidase-conjugated antibodies (diluted 1:50,000) (Jackson ImmunoResearch) were added, and blots were incubated for 1 h at RT. Blots were washed four times with 0.1% TBS-Tween and washed once with PBS (pH 7.4). Chemiluminescence analysis using WestPico substrate (PIERCE) was performed as instructed by the vendor.

Electron Microscopy. BSR cells were grown in DMEM (Gibco) supplemented with 5% FBS (Hyclone) and 1% penicillin/streptomycin for 24 h. Monolayers were washed one time with 1×PBS, and then infected with virus at a multiplicity of infection (moi) of 0.1 in cellgro Complete serum-free media (Mediatech). Flasks were incubated at 37 C/5% $CO_2$ for 72-96 hrs. For double immunogold labeling, infected cells were fixed in their respected flasks for ten minutes in 0.1% Paraformaldehyde, in Millonig's Buffer. The cells were incubated with KZ52 Human anti-Ebolavirus GP antibody for three hours, at room temperature. After wash steps with Cellgro Complete Media (Mediatech Inc., Mannassas, Va.), the cells were incubated with Goat anti-Human 5 nm colloidal gold (Ted Pella, Redding, Calif.) for two hours, at room temperature. After wash steps, the cells were incubated with Rabbit anti-Rabies G antibody (Jackson Immuno, West Grove, Pa.) for three hours, at room temperature. After wash steps, the cells were incubated with Goat anti-Rabbit 15 nm colloidal gold, for two hours, at room temperature. After wash steps, the cells were fixed using 2.5% Glutaraldehyde, 2.0% Paraformaldehyde, in Millonig's Sodium Phosphate Buffer (Tousimis Research, Rockville, Md.). After scraping and pelleting, the samples were washed repeatedly in Millonig's Buffer, and incubated for two hours in 1.0% osmium tetroxide, in the same buffer. Following rinsing steps in Ultrapure Water and en bloc staining with 2.0% uranyl acetate, the samples were dehydrated in a series of graded ethanols, and infiltrated and embedded in DER-736 plastic resin. Embedded blocks were sectioned using a Reichert-Jung Ultracut E Ultramicrotome. 50-70 nanometer sections were collected on 200 mesh copper grids, and post-stained with Reynold's Lead Citrate. EM specimens were examined in a FEI Tecnai Spirit Twin transmission electron microscope, operating at 80 kV.

Virus Spread Assay. Spread assays were conducted to analyze the capacity of the G-deleted RABV expressing GP to multiply on trans-complementing BSR-RVG, as well as on wild type BSR cells. The complementing cell lines were induced by removal of doxycycline, followed by infection with the respective RV at an MOI of 0.01. After 2 h, the virus was removed, cells were washed one time in PBS, and either doxycycline-containing or doxycycline-free medium was replenished. After incubation for 72 h at 34° C., cells were fixed with 80% acetone and viral antigen was detected with fluorescein isothiocyanate (FITC)-conjugated anti-RV nucleoprotein (RV—N) monoclonal antibody (Centocor) using a fluorescence microscope.

Mouse Pathogenicity Experiments. All experiments conducted in mice were approved by either the NIAID or Thomas Jefferson University Institutional Animal Care and Use Committee. Mouse pathogenicity experiments were performed in a Biosafety Level 2 vivarium.

For peripheral inoculation, six to eight week old inbred BALB/c or outbred Swiss Webster mice were administered intraperitoneal (IP), intranasal (IN), or intramuscular (1M) injections of live virus or Beta-propriolactone-inactivated virus at concentrations indicated in the Figure Legends. 1M injections were performed by administration of 50 ul into the hind leg muscle (gastrocnemius). Mice were monitored daily for clinical signs and signs of morbidity during the time periods indicated in the Figure Legends. Mice were individually or group-weighed periodically as a measure of health status.

For analysis of viral neurovirulence, litters of ten five-day-old Swiss Webster mouse pups were administered ten ul injections by the intracerebral (IC) route containing serial dilutions of parental and RABV vaccines expressing GP. Mouse pups were monitored daily for clinical signs of encephalitis and moribund mice were humanely euthanized. The number of surviving mice was recorded daily.

Mouse Immunization and Challenge. For RABV challenge experiments, groups of ten BALB/c mice were immunized 1M with vehicle, $5 \times 10^5$ ffu of indicated virus, or 10 µg of inactivated virus on day 0 (1 dose) or on day 0 and 14 (2 dose). On day 30 post-immunization, all mice were bled and serum was isolated for analysis by ELISA as described below. On day 50 post-immunization, ten mice were challenged IM with the highly virulent RABV virus strain CVS-N2c and monitored for signs of encephalitis and morbidity for 21 days. Moribund mice were humanely euthanized. Mouse survival was recorded daily and weights were taken periodically. Virulent RABV challenge was performed in a Biosafety Level 3 vivarium.

For challenge with mouse-adapted EBOV (MA-EBOV) (Bray et al., 1998), groups of ten BALB/c mice were immunized 1M with vehicle, $5 \times 10^5$ FFU of indicated virus, or 10 µg of inactivated virus on day 0 (1 dose) or on day 0 and 14 (2 dose). On day 30 post-immunization, all mice were bled and serum was isolated for analysis by ELISA as described below. On day 77 post-immunization, mice were challenged IP with 1,000 PFU of MA-EBOV and monitored for signs of morbidity for 21 days. Moribund mice were humanely euthanized. Mouse survival was recorded daily and weights were taken periodically. MA-EBOV challenge was performed in a Biosafety Level 4 vivarium at University of Texas Medical Branch in Galveston, Tex.

Antibody Assays. Mouse sera were tested in an indirect ELISA to evaluate humoral responses against EBOV-GP and RABV-G. GP antigen for coating ELISA plates was obtained by harvesting cell supernatant of mouse neuroblastoma cells transiently transfected with expression plasmids encoding amino acids 33-632 of the GP-ectodomain or a truncated version of the ectodomain that lacks the mucin domain (amino acids 312-462). The plasmids (Lee et al., 2008a; Lee et al., 2008b) were generously provided by Dr. E. Ollmann Saphire, Scripps Research Institute, CA, USA). RABV glycoprotein was purified as described previously. Ninety-six-well Maxisorb plates (NUNC) were coated overnight with 200 µl cell culture supernatant or 200 ng purified RABV-G per well, washed three times with PBST (PBS, 0.05% Tween20) and then blocked for 2-3 hrs with PBST containing 5% nonfat dry milk. Plates were then incubated with the test sera diluted 1:200 in PBST at 4° C. The following day the plates were washed three times with PBST and 200 μl goat anti-mouse IgG conjugated to HRP (1:10.000 dilution) were added per well. Two hours later the plates were washed with PBST and developed with Sigma-Fast o-phenylenediamine substrate. The enzymatic reaction was stopped with 3M H2SO4 and absorption was read at 490 nm.

To determine virus neutralizing antibody levels against RABV in sera from immunized mice, a modified Rapid Fluorescent Focus Inhibition Test (RFFIT) was performed. Briefly, RABV strain CVS-11, at a concentration to achieve an MOI of 1 at 24 h post-infection in the negative control, was added to three-fold serial dilutions of sera or WHO standard in cellgro Complete serum free media (Mediatech) in 96 well plates, and the mixtures were incubated at 37° C. for 1 h. Media was removed from 96 well plates of mouse neuroblastoma cells grown in RPMI (Mediatech) supplemented with 10% FBS (Atlanta Biologicals) and 1% penicillin/streptomycin, and the mixtures were transferred to the cell plates. After 24 h incubation at 37° C., cells were fixed with 80% acetone and stained with FITC anti-RV N (Fujirebio Diagnostics Inc). Percent infected cells per well was determined, and international units (IUs) of antibody were calculated based on the WHO standard, where the dilution of WHO standard that results in a $TCID_{50}$ for the challenge virus is equivalent to 2 IUs of neutralizing antibody.

Example 2

Generation of RABV Vaccines Encoding ZEBOV GP

The BNSP RABV vaccine vector (FIG. 3) was derived from the SAD B19 vaccine strain, which was attenuated by tissue culture passage and has been used as a live oral vaccine for wildlife in Europe (Conzelmann et al., 1990; Vos et al., 1999; Vos et al., 2002). The construct was engineered to contain a novel RABV stop-start transcription signal sequence flanked by unique BsiWI and NheI restriction sites between the nucleoprotein (N) and phosphoprotein (P) genes for introduction of foreign genes (McGettigan et al., 2003b). While BNSP is avirulent after peripheral administration in mice, it retains neurovirulence after intracerebral (IC) inoculation. Therefore a further attenuated derivative, BNSP333, was generated which contains an Arg→Glu change at amino acid 333 of the RABV G (McGettigan et al., 2003b). The 333 mutation has been shown to greatly attenuate neurovirulence of previous RABV vaccine vectors in adult mice so BNSP333 was chosen as the parental virus for these studies.

Two BNSP333 constructs encoding ZEBOV strain Maying a GP were generated (FIG. 3). BNSP333-GP encodes unmodified ZEBOV GP while BNSP333-$GP_{CCD}$ encodes the GP ectodomain and transmembrane domain fused to the RABV G cytoplasmic domain (GCD). The GCD construct was generated to maximize the likelihood that efficient incorporation of GP into virions would occur which is critical for potential inactivated vaccines. Finally, two additional constructs were generated by the deletion of the RABV G gene, BNSPΔG-GP and BNSPΔG-$GP_{GCD}$. RABV G is responsible for viral attachment and entry and a critical mediator of neurovirulence (Schnell et al., 2010). Therefore, deletion of G results in viruses, which are severely growth-restricted and require recovery and propagation in trans-complementing BSR cells expressing RABV G.

Infectious virus was readily recovered by transfection of each of the four plasmid constructs utilizing standard methods as described previously (McGettigan et al., 2003b; Schnell et al., 1994). Virus yields for BNSP333-GP and BNSP333-$GP_{GCD}$ exceed $10^8$ FFU/ml, while BNSPΔG-GP and BNSPΔG-$GP_{GCD}$ reached virus concentrations of $10^6$ FFU/ml, which were concentrated to $10^7$ FFU/ml. To evaluate the in vitro replication potential of the AG viruses, virus spread was assessed by monitoring growth in wild type BSR cells and trans-complementing BSR cells expressing RABV G. Cells were infected at a multiplicity of infection of 0.01 with BNSPΔG-GP and BNSPΔG-$GP_{GCD}$. After two days incubation, cells were immuno-stained for expression of RABV N (FIG. 4). As expected, the RABV G-expressing cells supported efficient virus spread with numerous foci of infected cells apparent. In contrast, infection of unmodified BSR cells with BNSPΔG-GP or BNSPΔG-$GP_{GCD}$ resulted in a different pattern of replication. Specifically, single infected cells or an occasional neighboring cell were found to be infected indicating that these viruses were growth-restricted as intended. However, these results indicate some spread of the G-deleted virus, most likely mediated by ZEBOV GP.

Example 3

Expression of ZEBOV GP by Recombinant RABV Vaccines

Figures 5A, 5B, 5C:
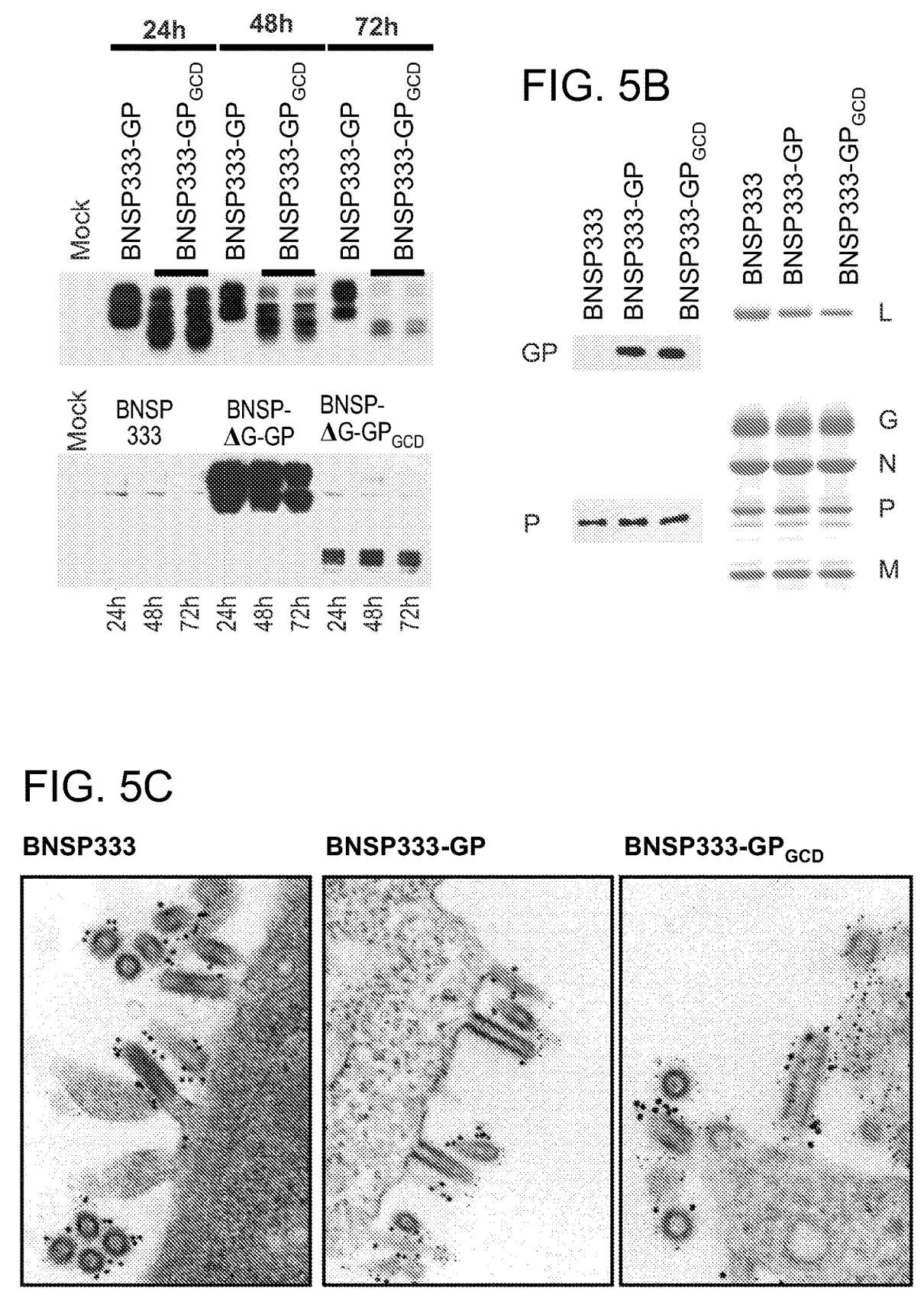

To analyze if ZEBOV GP is efficiently expressed by RABV vectors, BSR cells were infected with an MOI of 2-5 with BNSP333-GP, BNSP333-$GP_{GCD}$ and the G-deleted viruses BNSPΔG-GP, BNSPΔG-$GP_{GCD}$ or BNSP333 as a control. As shown in FIG. 5A, BNSP333-GP, BNSP333-$GP_{GCD}$ and the G-deleted virus, BNSPΔG-GP, expressed a protein in the expected size of ZEBOV GP as early as 24 hours after infection. Interestingly, for the G containing viruses the signal for GP was most prominent after 24 hours and decreased at 72 hours potentially indicating its efficient removal with budding RABV from the infected cell. This phenomenon was not detected for the G-deleted virus BNSPΔG-GP, potentially because of slower growth and release of virus particles. In the case of BNSPΔG-$GP_{GCD}$ we detected only a very weak signal for full-length GP after 48 h but another prominent GP-specific band of around 70 (kilodalton) kd was detected. Whereas the reason for the failure of expression of larger amounts of GP containing the RABV G CD is unknown for this particular virus, the low expression level of GP is reflected by a reduced immune response of this construct (see below and FIG. 7A) indicating that the amount of expressed full-length GP is critical for protection against ZEBOV challenge.

Example 4

Incorporation of ZEBOV into Budding RABV Virions

The utilization of killed (inactivated) virions for a dual RABV/EBOV vaccine requires the incorporation of RABV G as well as ZEBOV GP into budding virions. To analyze incorporation of the ZEBOV GP protein into RV virions, BSR cells were infected with BNSP333, BNSP333-GP and BNSP333-$GP_{GCD}$ and virus was isolated from the supernatants of the infected cells by filtration, concentration followed by purification over 20% sucrose. Viral proteins were separated by SDS-PAGE and detected by Coomassie blue staining (FIG. 5B). The same pattern of the RABV proteins were detected for all three recombinant viruses, but no additional protein of the expected size for ZEBOV GP was detected in the viral particles. The lack of detection of GP may be due to lower incorporation levels or GP running as a more diffuse band then the other RV proteins due its heavy glycosylation. However, analysis of the recombinant virions by Western blot with serum from a ZEBOV infected rhesus monkey detected ZEBOV GP in both BNSP333-GP and BNSP333-GP$_{GCD}$ particles, whereas no signal was detected for the control RABV (BNSP333). No differences in the amount of incorporated GP were detected indicating no advantage of the RV CD for incorporation of ZEBOV GP.

The incorporation of GP into RABV virions was also assessed by electron microscopy (FIG. 5C). BSR cells were infected with BNSP333, BNSP333-GP, and BNSP333-GP$_{GCD}$ and analyzed by dual-label immunogold electron microscopy with anti-RABV G (15 nm gold particles) and anti-ZEBOV GP (5 nm). BNSP333 virions demonstrated characteristic bullet-shaped structures and were only labeled by anti-RABV G as expected. Both BNSP333-GP and BNSP333-GP$_{GCD}$ virions were also found to possess a similar bullet shape. Furthermore, each virus was found to react with anti-RABV G and anti-ZEBOV GP. These results further confirm that the GP is incorporated into the RABV virion and this event is not dependent on the presence of the GCD indicating that inactivated virions may serve as effective antigens for induction of immunity to GP.

Example 5

Pathogenicity of RABV Vaccines Expressing ZEBOV GP in Mice

BNSP333, the parent of the viruses described here is avirulent after peripheral and IC inoculation of adult mice (McGettigan et al., 2003b). To determine if expression of ZEBOV GP resulted in altered virulence phenotypes in mice, we assessed pathogenicity after inoculation by multiple routes (FIG. 6). Groups of adult mice were injected with $1\times10^5$ to $1\times10^6$ FFU of the indicated viruses by the intramuscular (IM), intranasal (IN), or intraperitoneal (IP) route. Mice were monitored daily for four to six weeks for any clinical signs or indications of morbidity. In addition, mice were weighed periodically to assess general health status. No mouse inoculated with BNSP333-GP, BNSP333-GP$_{GCD}$, BNSPΔG-GP, or BNSPΔG-GP$_{GCD}$ developed any clinical signs indicating that expression of ZEBOV GP did not result in any unexpected viral virulence. Furthermore, analysis of the mean percent change in weight showed no differences between groups of mice inoculated with vehicle, BNSP, BNSP-333 or the GP-expressing viruses (FIG. 6).

Neurovirulence was also evaluated for the vaccine candidates by IC injection of highly susceptible suckling mice. Five-day-old suckling mice were inoculated with serial dilutions of BNSP, BNSP-333, BNSP333-GP, and BNSP333-GP$_{GCD}$ and monitored for signs of encephalitis for 21 days. As expected, BNSP and BNSP-333 were lethal as they retain neurovirulence, and BNSP333-GP, and BNSP333-GP$_{GCD}$ shared a similar level of virulence. In contrast to these observations, IC inoculation with BNSPΔG-GP or BNSPΔG-GP$_{GCD}$ with the highest dose possible, $6\times10^4$ FFU, resulted in no clinical signs or lethality. These results indicate that the in vitro growth restriction observed for the ΔG viruses greatly attenuate neurovirulence indicating that they will have an increased safety profile versus the parental RABV vaccine, BNSP-333.

Example 6

Figure 9:
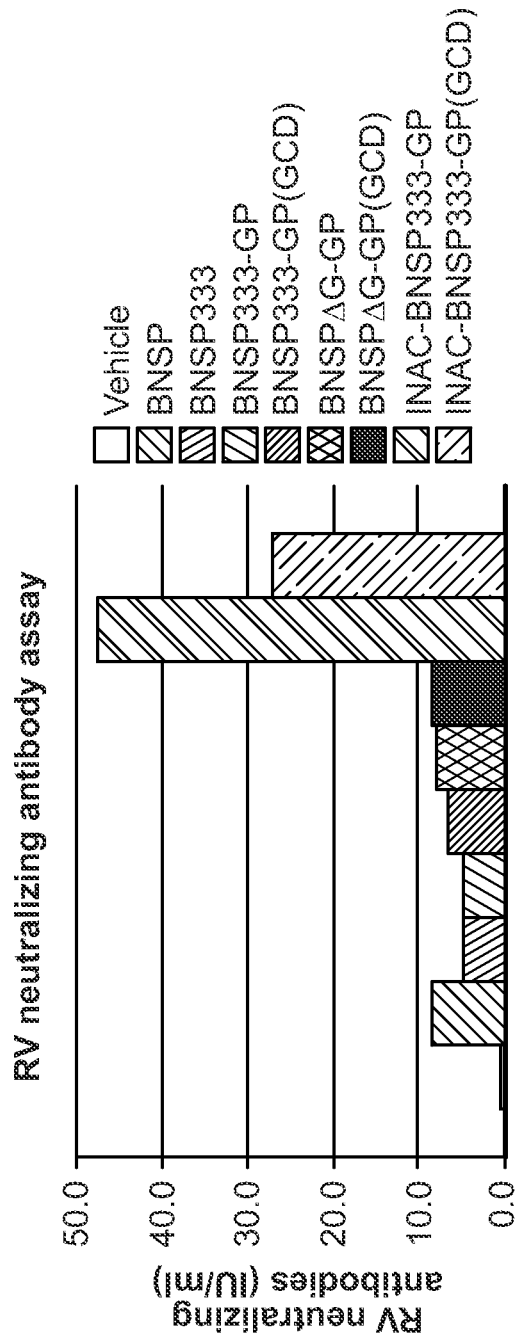
FIG. 9 shows that RABV vaccines expressing GP induce protective levels of RABV G-specific neutralizing antibodies. Groups of five BALB/c mice were immunized IM with 5×10$^5$ FFU of indicated live virus on day 0 or 10 ug of inactivated virus on day 0 and 14 (2 dose). Serum was drawn on day 28 and analyzed by RABV neutralization assay expressed in international units (IU)/ml. 0.5 IU is considered protective by WHO standards.

RABV Vaccines Expressing ZEBOV GP Induce Humoral Immunity to RABV and ZEBOV in Mice To analyze the immunogenicity of the GP-expressing vaccine candidates, groups of ten mice were immunized IM with vehicle or $5\times10^5$ FFU of BNSP, BNSP333, BNSP333-GP, BNSP333-GP$_{GCD}$, BNSPΔG-GP, or BNSPΔG-GP$_{GCD}$). In addition, immunogenicity of inactivated virus preparations generated by the methods used to produce the current inactivated human RABV vaccine was examined. Specifically, virus inactivation was performed by treatment of virus stocks with 1:2,000 beta-propiolactone overnight at 4° C. followed by 30 min incubation at 37° C. Groups of ten mice were immunized with 10 μg of inactivated BNSP333-GP or BNSP333-GP$_{GCD}$ on day 0 (1 dose) or on day 0 and 14 (2 dose). On day 30 post-immunization, serum was isolated from immunized mice and humoral immunity was assessed by ELISAs for RABV G and ZEBOV GP. The results in FIGS. 7A,7C and 7B, 7D (independent experiments of ten mice each that were later challenged with RABV or MA-EBOV) indicate that BNSP333-GP, BNSP333-GP$_{GCD}$, BNSPΔG-GP induced ZEBOV GP-specific antibodies, whereas the strongest immune responses were detected in sera of mice immunized with the killed RABV particles containing GP. BNSPΔG-GP$_{GCD}$ appeared to induce a slightly weaker GP-specific antibody response as measured by ELISA. Interestingly, differences detected for the RABV G specific humoral responses by ELISA were less pronounced but again slightly higher for killed vaccines (FIG. 7C). Sera from mice immunized with the above viruses contained RABV neutralizing antibodies in the range of 5-45 IU indicating that the GP-specific antibody response did not interfere with the development of immunity to RABV G (FIG. 9).

Example 7

RABV Vaccines Expressing ZEBOV GP Confer Protection from RABV and ZEBOV Challenge Based on the strong immunogenicity induced against RABV G and ZEBOV GP, we next examined the ability of immunization to confer protection against virulent RABV and mouse-adapted EBOV (MA-EBOV) challenge (FIG. 8). The groups of mice reported in FIG. 7 were challenged IP with 1,000 PFU of MA-EBOV on day 77 post-immunization or with the highly virulent RABV virus strain CVS-N2c on day 50 post-immunization. All mice were periodically weighed and monitored for clinical signs and indicators of morbidity for 21 days.

Figure 10A:
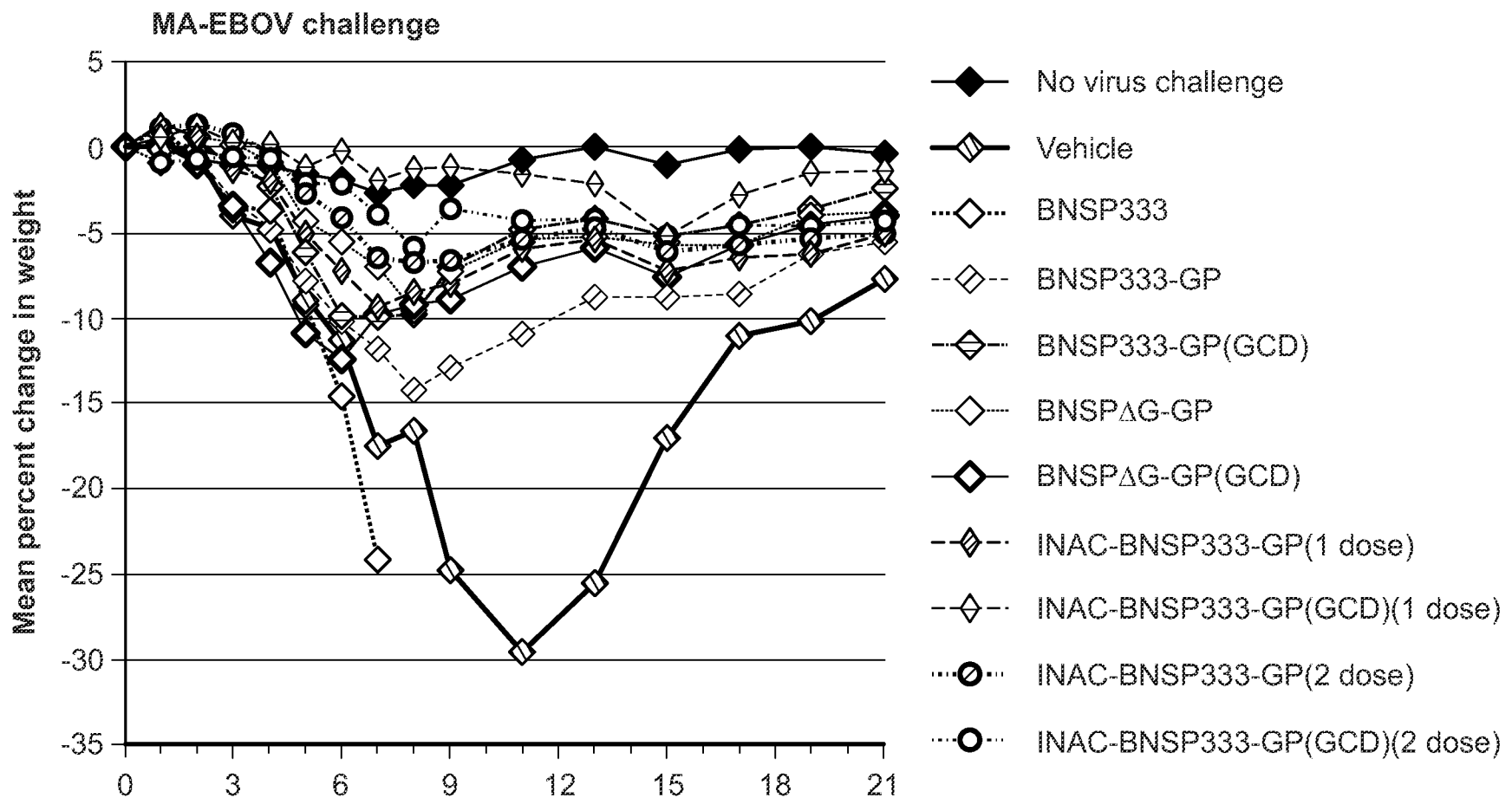

Nine of ten vehicle- and all BNSP333-immunized mice succumbed to lethal MA-EBOV infection. Complete protection from MA-EBOV lethality was conferred by immunization with BNSPΔG-GP, INAC-BNSP333-GP (2 dose), INAC-BNSP333-GP$_{GCD}$ (1 dose), and INAC-BNSP333-GP$_{GCD}$ (2 dose). In addition, BNSP333-GP, BNSP333-GP$_{GCD}$, and INAC-BNSP333-GP (1 dose) conferred 80% protection. BNSPΔG-GP$_{GCD}$ which conferred the weakest level of protection still induced 30% survival. As indicated above, this virus did express only very low amounts of GP (FIG. 3A), and had a weak response as detected by ZEBOV GP-specific ELISA (FIGS. 7A and 7B). Therefore the lower level of protection was not unexpected and correlates with the immunogenicity data. Analysis of weight loss after MA-EBOV challenge, which is an additional indicator of vaccine efficacy, indicates that the inactivated vaccines promoted stronger resistance to EBOV as weight loss was minimal over the course of challenge; particularly for INAC-BNSP333-GP$_{GCD}$ (FIG. 10). We also analyzed the ZEBOV GP specific antibody responses by ELISA after MA-EBOV challenge (FIG. 7B). As expected, the GP-specific antibodies increased after challenge in all surviving mice. Interestingly, the increases were most prominent in the live virus vaccinated groups, which previously had the lowest responses indicating that the high levels of GP-specific antibodies in mice immunized with the killed virions greatly restrict ZEBOV replication.

The results of the virulent RABV challenge were equally promising. Seven of nine vaccine preparations conferred 100% protection (FIG. 8) and INAC-BNSP333-GP (2 dose) conferred 90% protection. BNSP333-GP conferred 60% protection. It should be noted that challenge with $5 \times 10^6$ ffu RABV CVS-N2c is a very stringent model. Analysis of RABV G-specific antibodies after RABV challenge indicated a limited rise in levels. Taken together, these studies demonstrate live and inactivated vaccine candidates confer complete or substantial protection against lethal MA-EBOV and RABV challenge and the mechanism of protection appears to be largely dependent on antibodies directed against EBOV GP or RABV G, respectively.

Discussion of Examples 1-7

Various live and killed RABV vaccines expressing ZEBOV GP have been constructed and their GP expression, safety, immunogenicity, and protective efficacy in mice have been compared. The results indicate that ZEBOV GP is efficiently expressed by RABV vectors in the presence or absence of RABV G. In addition, GP is incorporated into RABV virions and this incorporation is not dependent or apparently enhanced by the addition of the RABV GCD to GP. These results are somewhat surprising because foreign proteins were proposed to require addition of the GCD for RABV incorporation (Mebatsion and Conzelmann, 1996; Mebatsion et al., 1997). However, Siler et al. have shown that the CD of CD4 promoted efficient incorporation of HCV E2 into RABV virions (Siler et al., 2002). However, the successful incorporation of GP into RABV particles permits the use of inactivated virions as a means to vaccinate against ZEBOV. It also indicates that BNSPΔG-GP viruses would have the capability for limited virus spread mediated by GP in the absence of RABV G, which was confirmed by our in vitro findings, although the ΔG viruses were completely avirulent after IC challenge of mice.

To initially determine the immunogenicity of our RABV/EBOV vaccine candidates, the humoral immunity against GP was examined. Somewhat surprisingly, the inactivated vaccine preparations consistently induced higher levels of GP-specific antibodies as measured by ELISA when compared to the live virus vaccines. BNSP333-GP, BNSP333-GP$_{GCD}$, and BNSPΔG-GP induced low but detectable antibody responses, while BNSPΔG-GP$_{GCD}$ induced weaker antibody levels. In contrast, INAC-BNSP333-GP and INAC-BNSP333-GP$_{GCD}$ induced high levels of antibodies by a single vaccination that could be effectively boosted with a second vaccination. The presence of GCD appeared to confer a slight enhancement in induction of antibody levels in the killed vaccine preparations. Importantly, the pre-challenge antibody levels in mice immunized with inactivated vaccines were similar when compared to the level observed after challenge for the single vehicle-immunized mouse that survived MA-EBOV challenge. It is unclear why the inactivated vaccines induce higher levels of antibodies to GP when compared to live virus. One explanation could be that the antigen load is higher in the killed vaccines, and that the live vaccines are so attenuated peripherally that their replication results in little additional antigen load. Alternatively, RABV G may be expressed earlier in the G-containing viruses and interfere with the antibody response to GP. The latter explanation is supported by the fact that such great differences as seen for the anti-GP humoral responses were not detected for the RABV G specific immune response (FIGS. 7C and 7D). Further examination of the immune response to these killed and live vaccine candidates is warranted.

Although humoral immunity when measured by GP-specific ELISA appeared to be low for the live vaccine candidates, each conferred protection from MA-EBOV that appeared to correlate with the antibody levels. BNSP333-GP, BNSP333-GP$_{GCD}$, and BNSPΔG-GP induced 80-100% protection, while BNSPΔG-GP$_{GCD}$ which induced weaker antibody levels conferred 30% protection suggesting that additional mediator(s) of protection may exist. It should be noted that these were single immunizations followed by MA-EBOV challenge on day 77 so the protection model was stringent and likely involved GP-specific antibodies and a T-cell dependent memory immune response as reflected in the increase of GP antibodies after challenge (FIG. 3B). Inactivated vaccines also conferred complete or 80% protection from MA-EBOV. Two indications suggest that the inactivated vaccines conferred an enhanced level of protection from MA-EBOV. First, mice immunized with inactivated vaccine had a lower relative rise in GP-specific antibodies after MA-EBOV challenge when compared to mice immunized by live vaccines. Second, vaccination with inactivated vaccines, particularly BNSP333-GP$_{GCD}$, appeared to result in less weight loss after MA-EBOV challenge which is believed to be a sign of stronger protective immunity. Nearly all vaccines also induced complete protection from virulent RABV challenge and similarly, the ELISA results correlated with the observed level of protection. Interestingly, both BNSPΔG-GP and BNSPΔG-GP$_{GCD}$ induced strong levels of G-specific antibodies and protection from RABV challenge which is presumably mediated by the G present in the virions supplied by the trans-complementing cell line.

As with all vaccines and particularly live viral vaccines, the demonstration of safety and attenuation is paramount. The results in the above Examples indicate that peripheral administration of BNSP333-GP, BNSP333-GP$_{GCD}$, BNSPΔG-GP, and BNSPΔG-GP$_{GCD}$ to over 190 mice resulted in no morbidity or apparent clinical signs demonstrating that these viruses retain an attenuation phenotype. It is important to note that while the ZEBOV Mayinga strain, the source of GP for our RV/EBOV viruses, is avirulent in mice and required passage and genetic adaptation to produce MA-EBOV, the mutations responsible for virulence in mice were localized to EBOV viral protein 24 and nucleoprotein (Ebihara et al., 2006). Therefore, the GP sequence used in the vaccines studied here does have the capability to mediate disease in mice indicating that mice are an appropriate species to evaluate pathogenicity of the RV/EBOV vaccine candidates. Similar to the BNSP333 parent virus, BNSP333-GP and BNSP333-GP$_{GCD}$ retained neurovirulence in suckling mice after IC inoculation although there was no sign of increased neurovirulence mediated by the expression of ZEBOV GP. This level of neurovirulence may preclude the use of these live vaccines in humans based on experience with prior live virus vaccines for neurovirulent viruses. In contrast, BNSPΔG-GP and BNSPΔG-GP$_{GCD}$ were avirulent after IC inoculation and at least 6,000-fold reduced for neurovirulence from BNSP333 as measured by LD$_{50}$. As such, BNSPΔG-GP which conferred 100% protection from RABV and EBOV challenge may warrant consideration for use in humans after further study of its attenuation and immunogenicity.

While the live vaccines described here have potential for use in humans, the most expeditious route to licensure and utilization of an RV/EBOV vaccine would be to pursue inactivated vaccine candidates. RABV inactivated by beta-propiolactone has been used to vaccinate humans since 1978 and has an excellent safety record (Plotkin, 1980). The RABV/EBOV viruses described here were inactivated by the same method as the current human vaccine and were found to be strongly immunogenic and protective after immunization with a single dose of 10 µg. The current human vaccine is administered without adjuvant in a compressed three dose regimen (day 0, 7 and 21-28). Two inactivated RABV vaccines are currently used in the USA, which are manufactured by Novartis Vaccines and Diagnostics (Marburg, Germany) or Sanofi Pasteur (Lyon, France) and several additional manufacturers serve other markets. Based on the efficient replication of BNSP333-GP and BNSP333-GP$_{GCD}$ in tissue culture and the existing manufacturing process and capability of RABV vaccines, production of inactivated RABV/EBOV would appear to be feasible and potentially more simplified than some existing EBOV vaccine candidates (Geisbert et al., 2010). Furthermore, the combination of a desired biodefense vaccine (EBOV) with limited financial incentive for development because of limited market potential with an approved and financially viable vaccine such as RABV vaccine is a unique and potentially important factor in the commercialization of an EBOV vaccine. It is important to note that an inactivated RABV/EBOV vaccine would offer a distinct advantage for use in Africa over existing EBOV vaccine candidates because it would afford protection from two diseases. The World Health organization reports an estimated 24,000 deaths per year in Africa from RABV and this number is believed to be a considerable underestimate (Cleaveland et al., 2002; Knobel et al., 2002; Schnell et al., 2010). Therefore, use of the bivalent vaccines described herein would offer an increased return on investment in public health.

A second intriguing application of these RV vectored EBOV vaccines would be their development for use in threatened NHP populations, which are highly susceptible to lethal EBOV outbreaks. Field research over the past decade has indicated that lethal EBOV outbreaks have affected chimpanzee and particularly western gorilla populations in Gabon and the Democratic Republic of Congo (Bermejo et al., 2006; Le Gouar et al., 2009; Leroy et al., 2004; Vogel, 2006, 2007). In fact, it has been suggested that EBOV is contributing to the endangered status of the western gorilla and that vaccination is needed to protect endemic NHP populations (Vogel, 2007). With the successful history of vaccination of wildlife against RV using dispersed baits containing the SAD B19 vaccine strain (parent virus of the RV/EBOV vaccines described here), one could consider using the live attenuated RV/EBOV vaccines in a similar manner for protection of NHPs in Africa from EBOV. Of note, SAD B19 was safe after a single oral application of $1.5 \times 10^8$ FFU in 10 chimpanzees age 3.5 to 8 years (Anon, 1993). The growth restriction, decreased neurovirulence, and protective efficacy of BNSPΔG-GP suggest that it may be a lead candidate for wildlife vaccination and offer an increased level of safety above the SAD B19 vaccine. The safety, stability, and efficacy of a RV/EBOV vaccine would require exhaustive study in the target NHP species and in other animals that might encounter the vaccine baits. However, the introduction of SAD B19 RV vaccine into Europe and safe dispersal of over 70 million vaccine baits since the 1980's provide a framework for this endeavor. Inactivated RV/EBOV vaccines could also be considered for use in endemic NHPs, and again, would have fewer safety concerns but achieving broad coverage to widely dispersed animals would be challenging. Nevertheless, if conservation authorities determine that vaccination of NHPs against EBOV is a necessary action and appropriate resources are provided; obstacles to the use of live or killed vaccines could be overcome. In addition to the protection of threatened NHPs, vaccination of endemic NHP populations might also offer an additional, critical benefit to humans. The interaction of humans and infected NHPs has been associated with transmission of EBOV to humans and initiation of subsequent outbreaks, so prevention of disease in NHPs may also serve to limit EBOV transmission into the human population.

The Examples described here demonstrate the utility and potential of the RV vaccine vector platform for development of live and killed vaccines against ZEBOV and potentially other hemorrhagic fever viruses or biodefense agents. Presently, the immunogenicity and protective efficacy of the RV/EBOV vaccines require examination in NHPs to determine if these vaccines merit evaluation in humans. Further investigation in mice or NHPs is warranted into the role of humoral and cellular immunity in protection by the various vaccine candidates to understand differences in the induction of immunity by replication-competent, replication-deficient, and inactivated vaccines and correlates of immunity to EBOV. Finally, RV vaccine candidates encoding GP from additional EBOV species and potentially additional hemorrhagic fever viruses will be generated to produce a multivalent, cross-protective vaccine.

Example 8

RABV Vaccine Viruses Expressing ZEBOV GP Replicate to High Virus Titers in Cell Culture Robust replication in appropriate cell culture is critical to the development of a cost-effective vaccination strategy. The replication of the GP expressing RABV viruses in Vero cells (FIG. 11A) which are a cell line currently in use for the production of human vaccines was evaluated. At an MOI of 5, BNSP333-GP and BNSP333-GP$_{GCD}$ reached virus titers of 8.0 and 7.6 Log$_{10}$FFU/ml, respectively, at five days post-infection. Importantly, the expression of ZEBOV GP does not appear to decrease the virus production when the vectored viruses are compared to levels reached by the control RABV viruses, BNSP and BNSP333. These results demonstrate that the RABV viruses expressing GP replicate to levels suitable for consideration of vaccine production with little effort at optimization.

Figure 11A:
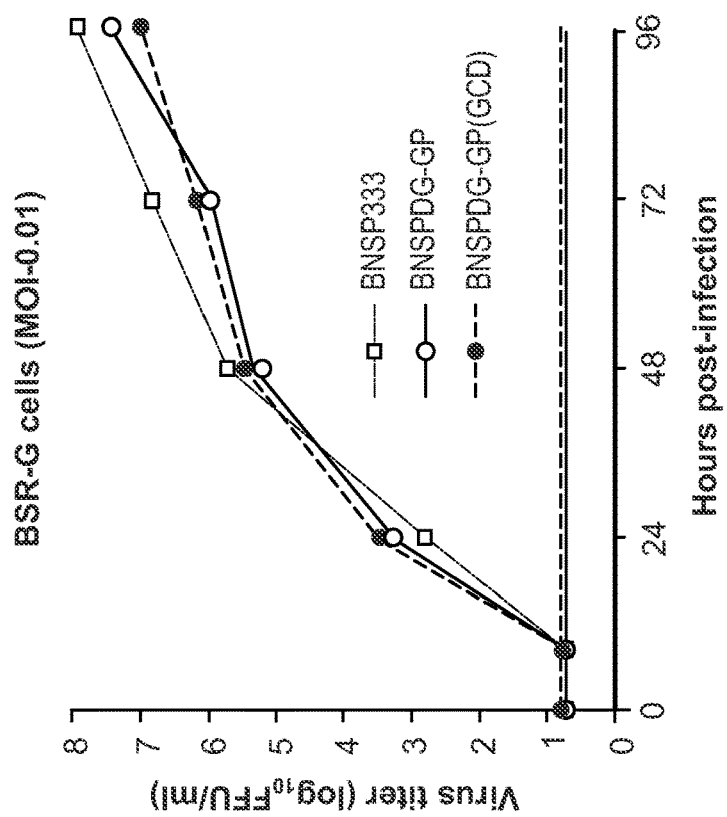
FIGS. 11A and 11B are graphs showing virus yields of vaccine viruses in cell culture.

We also assessed the replication of the G deletion viruses (BNSPΔG-GP and BNSPΔG-GP$_{GCD}$) in (A) Vero cells and (B) BSR-G cells, a BHK cell derivative that expresses RABV G. As expected due to their design as replication-deficient viruses, BNSPΔG-GP and BNSPΔG-GP$_{GCD}$ do not replicate in Vero cells due to their lack of RABV G expression (FIG. 11A). In contrast, BNSPΔG-GP and BNSPΔG-

Figure 11B:
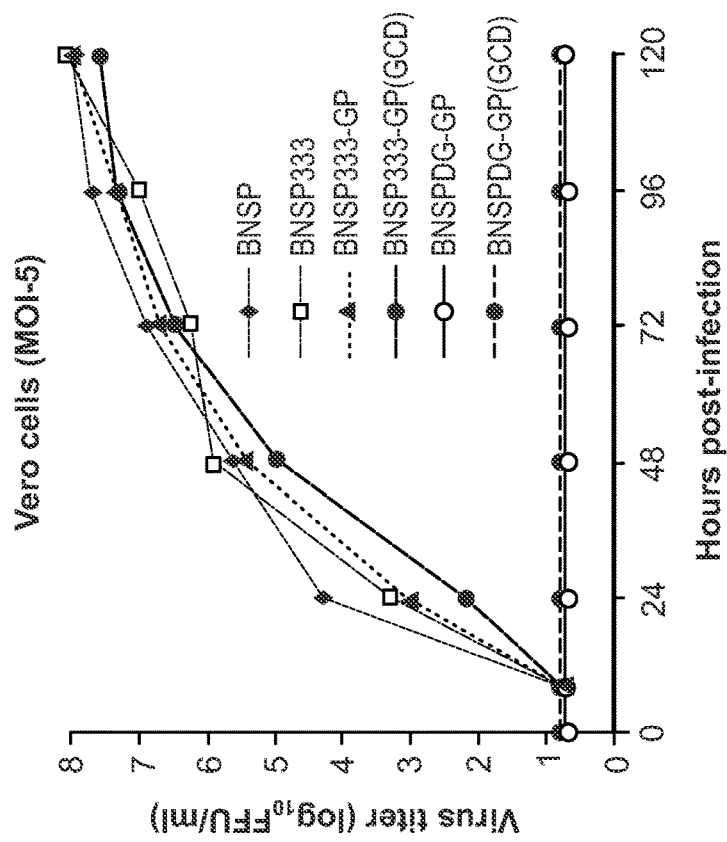

$GP_{GCD}$ reach virus titers of 7.4 and 7.0 $Log_{10}FFU/ml$, respectively, in cells expressing RABV G (FIG. 11B).

In summary, these results indicate that each vaccine candidate described herein replicates efficiently in cell culture with little effort at optimization thus far. As such, the RABV vaccine vectored approach to development of a filovirus vaccine may have cost advantages when compared to competing technologies.

Example 9

Figure 12B:
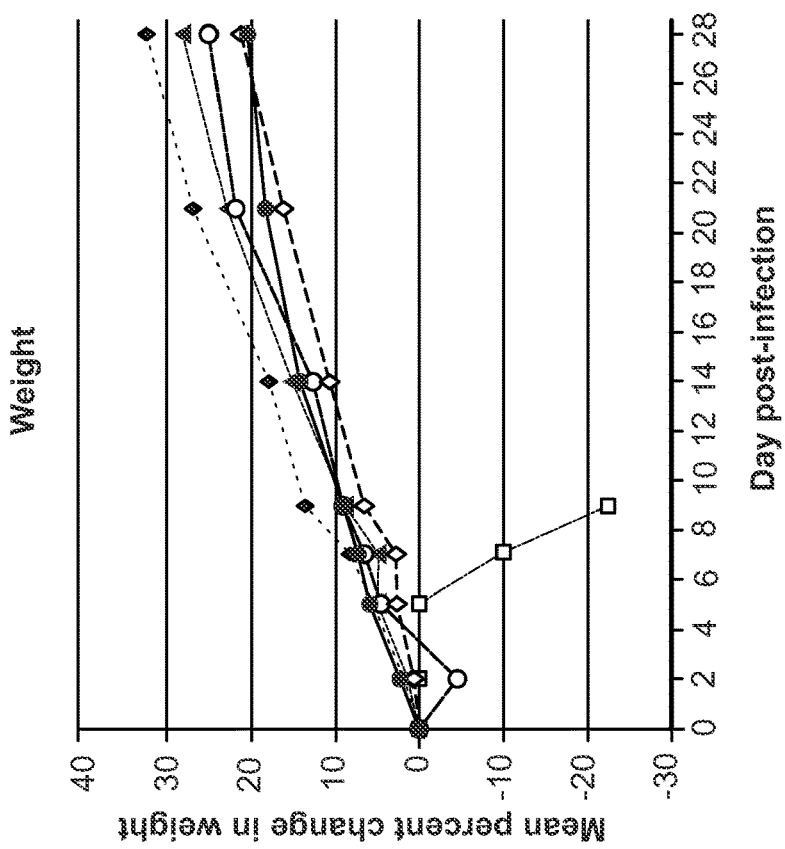
FIGS. 12A and 12B are graphs showing that RABV viruses expressing GP are avirulent after intracerebral (i.c.) inoculation of adult mice. Groups of eight four week-old mice were injected i.c. with 1×10$^5$ FFU of the indicated virus and monitored daily for survival (FIG. 12A) for 28 days. Weights (FIG. 12B) were monitored at indicated times.
Figure 12A:
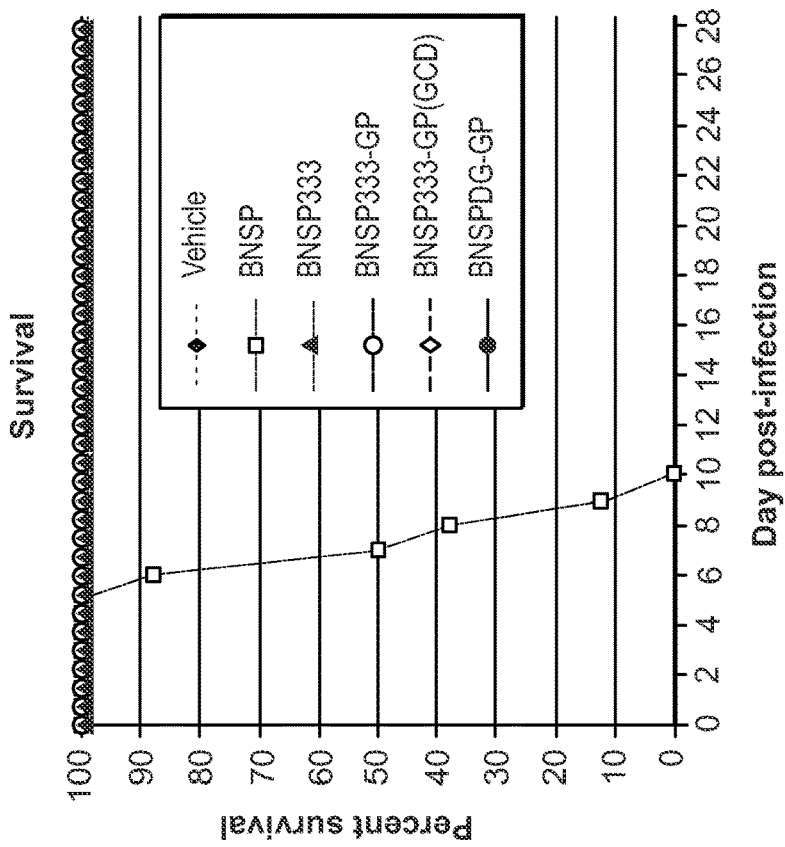

RABV Vaccine Viruses Expressing ZEBOV GP are Avirulent Upon Intracerebral Administration to Adult Mice The recombinant RABV, BNSP, retains neurovirulence upon intracerebral (i.c.) infection of adult mice. BNSP333, the parent virus of the GP-expressing vaccine viruses, is attenuated when administered by i.c. injection. We sought to determine if expression of ZEBOV GP by BNSP333 would modify neurovirulence. Groups of eight four-week-old mice were injected i.c. with $1 \times 10^5$ FFU of the RABV vaccine viruses expressing GP or the G deletion virus, BNSPΔG-GP, and monitored daily for survival and periodically weighed as a measure of overall health. As expected, BNSP was rapidly lethal upon i.c. injection with 100% of mice succumbing by day 10 (FIG. 12A). In contrast, 100% of mice inoculated with BNSP333, BNSP333-GP and BNSP333-$GP_{GCD}$, and BNSPΔG-GP survived infection, and there was no evidence of weight loss in these groups (FIGS. 12A and 12B). These results indicate that in a highly susceptible model of neurovirulence, our RABV-GP vaccine candidates are completely avirulent, further demonstrating their attenuation and safety.

Example 10

Figure 13:
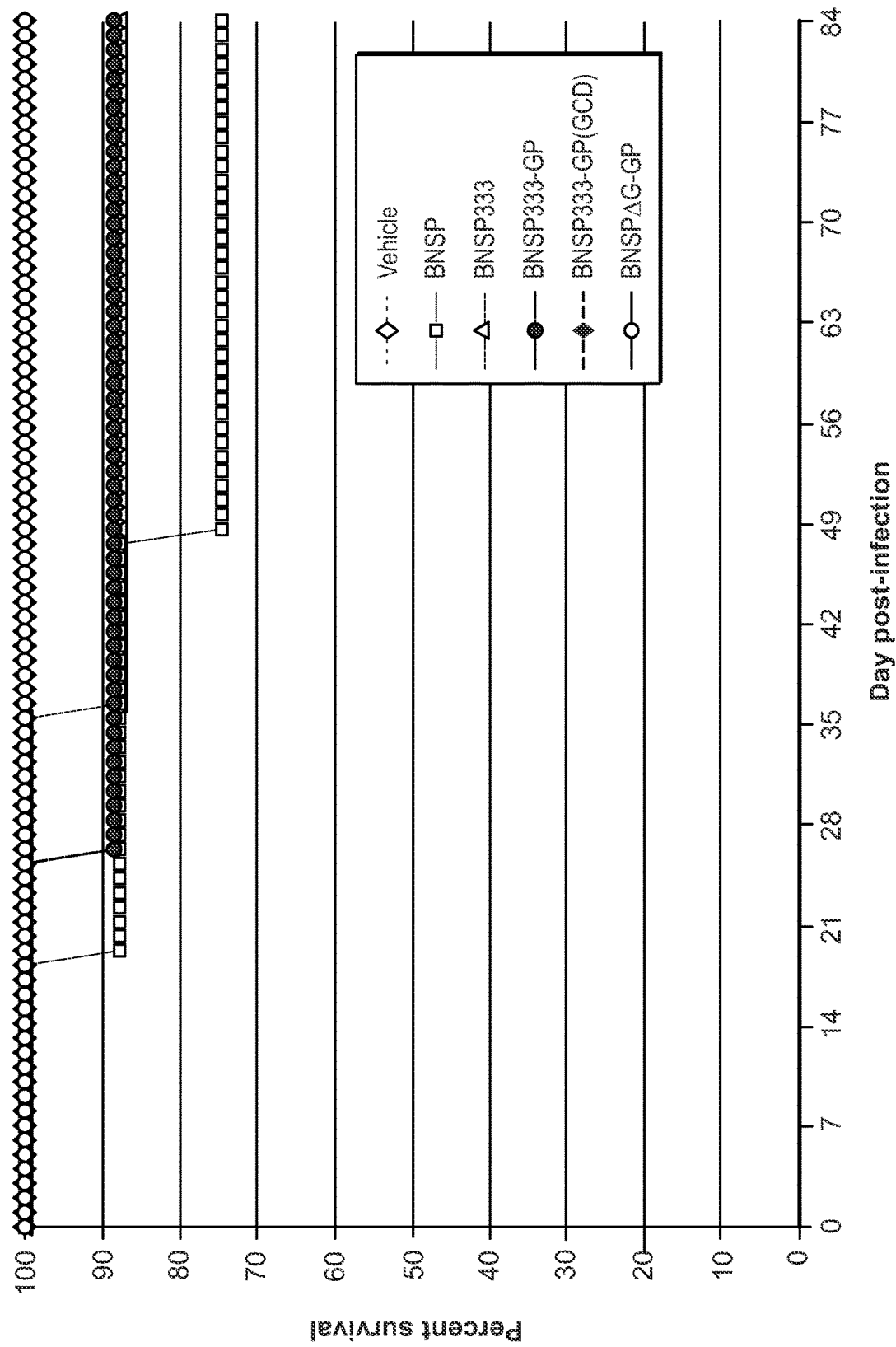
FIG. 13 is a graph showing that addition of GP to RABV does not increase neuroinvasiveness in immunodeficient mice. Groups of 8 4-6 week-old SCID mice were injected i.m. in the hind leg with 1×10$^6$ FFU of the indicated virus and monitored daily for survival for 84 days.

RABV Vaccine Viruses Expressing ZEBOV GP do not have Increased Neuroinvasiveness in Immunodeficient Mice Our results indicated that peripheral injection of RABV vaccine viruses expressing GP (with or without RABV G) by the intramuscular (i.m.), intranasal (i.n.), or intraperitoneal (i.p.) route in immuno-competent mice resulted in no morbidity or moribundity. We next sought to further determine the safety profile of our vaccine candidates by peripheral administration of immunodeficient ICR—SCID mice (FIG. 13). Groups of eight 4-6 week-old ICR—SCID mice were injected i.m. in the hind leg with vehicle or $1 \times 10^6$ FFU of BNSP, BNSP333, BNSP333-GP, BNSP333-$GP_{GCD}$, or BNSPΔG-GP. Mice were monitored daily for signs of infection and survival for 84 days. Results indicated that 2 of 8 and 1 of 8 BNSP- and BNSP333-infected mice succumbed to infection, respectively. Similarly, 1 of 8 mice injected with BNSP333-GP succumbed to infection. No mice in the vehicle, BNSP333-$GP_{GCD}$, or BNSPΔG-GP groups succumbed to infection. These results indicate that GP expression does not increase the virulence of the parent RABV vaccine vector in mice without functional adaptive immunity which is a further indication of the safety of these vaccine candidates.

Example 11

A RABV Vaccine Virus Expressing ZEBOV GP with a Deletion in the RABV G Gene has Reduced Replication in Suckling Mouse Brain Our analysis of neurovirulence in suckling mouse brain indicated that as expected, BNSP and BNSP333 were lethal upon i.c. injection of suckling mice.

Figure 14:
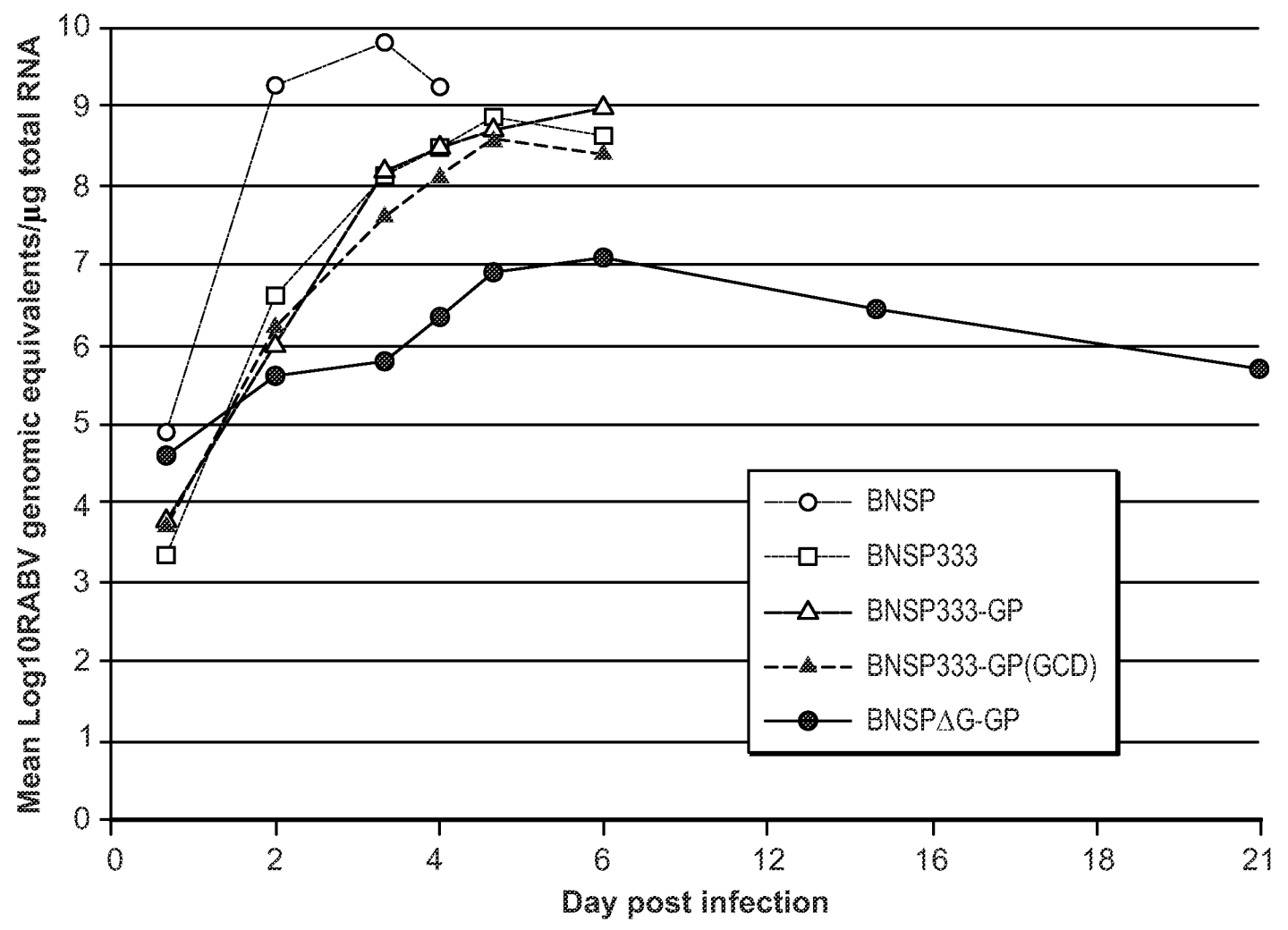

BNSP333-GP and BNSP333-$GP_{GCD}$ retained neurovirulence and were also lethal. In contrast, BNSPΔG-GP was avirulent when injected i.c. with the highest dose available of up to $6 \times 10^4$ FFU. We next sought to determine the viral load of our vaccine candidates, particularly BNSPΔG-GP, in suckling mice injected by the i.c. route. It was of interest to determine if the replication-deficient virus has the capacity to replicate at even a reduced level. To this end, five-day-old Swiss Webster mice were inoculated i.c. with $1 \times 10^5$ FFU of BNSP, BNSP333, BNSP333-GP, BNSP333-$GP_{GCD}$, or BNSPΔG-GP (FIG. 14). On days 1, 3, 5, 6, 7, 9, 14, and 21, three surviving mice per group were sacrificed, brain homogenates were generated, and viral cDNA was produced (Transcriptor high fidelity cDNA synthesis kit, Roche). The level of viral genomic RNA was determined by a quantitative PCR assay targeting RABV nucleoprotein (DyNAmo probe qPCR kit, Thermo Scientific). Viral load was highest in the BNSP group, as expected, peaking at nearly 10.0 $Log_{10}$genomic equivalents/ug of total RNA. Peak viral load of BNSP333, BNSP333-GP and BNSP333-$GP_{GCD}$ were approximately 10-fold reduced and delayed when compared to BNSP. As expected, no mice injected with these viruses survived past day 9. In contrast, mice injected with BNSPΔG-GP survived to study end and reached a peak viral load in the brain at day 9 of approximately 7.0 $Log_{10}$genomic equivalents/ug of total RNA which is approximately 1,000-fold reduced from levels observed for BNSP. These results indicate that although BNSPΔG-GP is avirulent upon i.c. injection of suckling mice, it does retain at least some capacity to replicate and persists to at least day 21.

Example 12

Figure 15B:
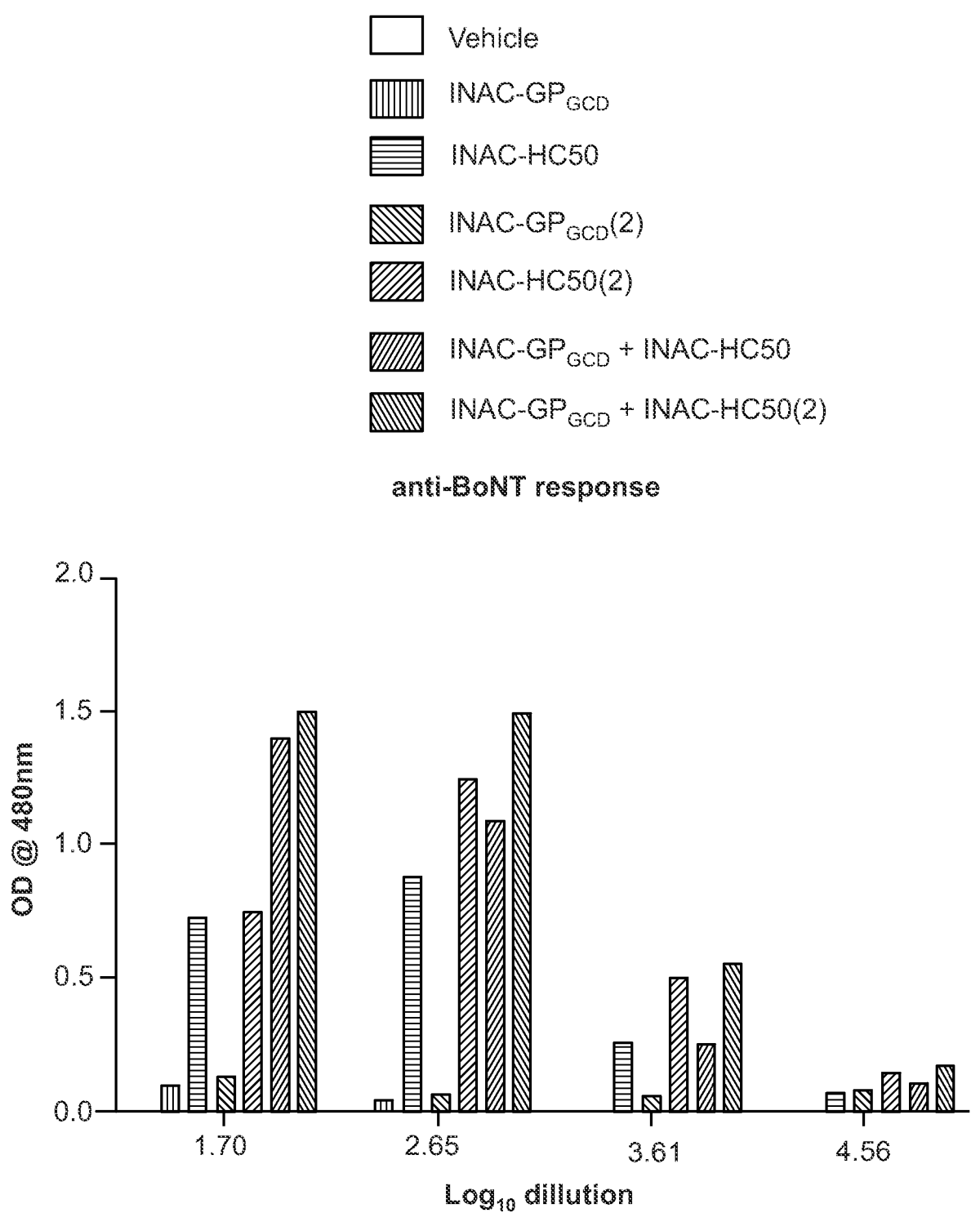
Figure 15C:
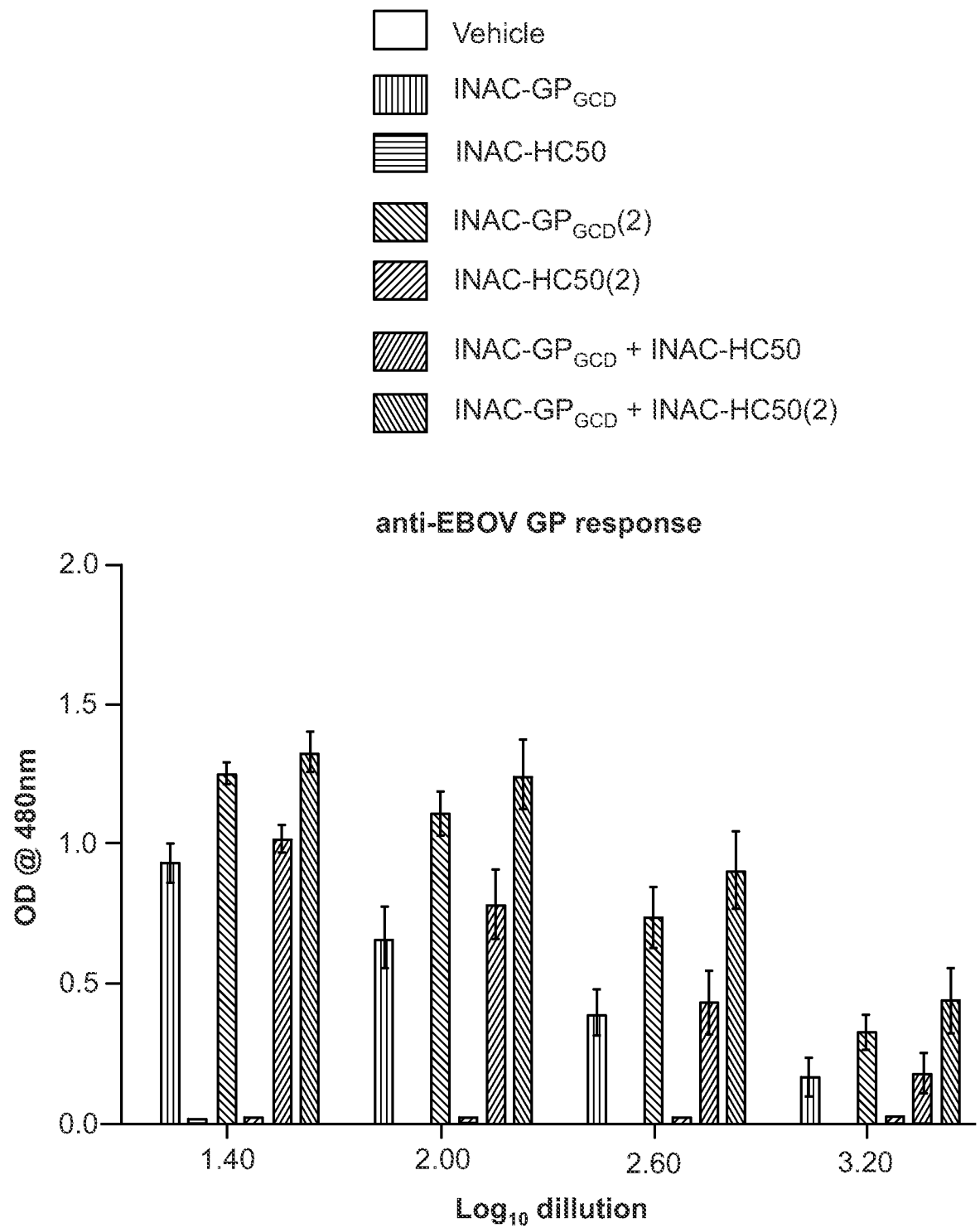

Inactivated RABV Vaccine Viruses Expressing ZEBOV GP can be Combined with an Additional Recombinant RABV Vaccine to Induce a Multivalent Antibody Response We have conclusively demonstrated that RABV vaccine viruses expressing GP effectively induce bivalent RABV-specific and ZEBOV GP-specific antibody responses. We next sought to determine if co-administration with an additional RABV vectored vaccine would result in induction of a multivalent antibody response against three vaccine antigens. As a proof of principle experiment we utilized a previously reported inactivated RABV vectored vaccine which expresses a fragment of the botulinum neurotoxin A (BoNT) termed HC50E30 (Mustafa et al., Vaccine 29:2011 p. 4638) to co-administer with our inactivated RABV virus expressing ZEBOV GP to determine if multivalent antibody responses against RABV G, BoNT, and ZEBOV GP could be induced. The vaccines used in this experiment are inactivated BNSP333-$GP_{GCD}$ labeled as INAC-$GP_{GCD}$ and inactivated SPBN-HC50E30 labeled as INAC-HC50 (FIGS. 15A-15C).

Groups of five mice were immunized i.m. once (day 0) or twice (day 0 and 14) with 10 ug of vehicle or the indicated virus or 20 ug of the combined administrations (10 ug each virus). On day 42, all mice were bled and serum dilutions were assayed by ELISA against (FIG. 15A) RABV G, (FIG. 15B) BoNT HC50, and (FIG. 15C) ZEBOV GP. As indicated in FIG. 15A, each vaccination approach induced strong antibody responses against RABV G as expected since RABV G was present in each immunogen. Either a single dose or two doses of INAC-HC50 induced BoNT-specific antibodies, and interestingly, combined administration with INAC-GP$_{GCD}$ resulted in a stronger BoNT-specific response (FIG. 15B). Finally, analysis of the ZEBOV GP-specific antibody response indicated that single or boosted immunization with INAC-GP$_{GCD}$ induced strong immunity as expected (FIG. 15C). Importantly, co-administration of INAC-GP$_{GCD}$ and INAC-HC50 induced antibody levels that were nearly identical to INAC-GP$_{GCD}$ immunization. These results indicate that a potent multivalent response can be induced by this vaccination approach. Co-immunization with three antigens, RABV G, BoNT, and ZEBOV GP resulted in no decrease in antibody response against each individual immunogen. Considering that successful immunization strategy against the medically relevant filoviruses will likely require multivalent immunization, this proof of principle experiment indicating induction of multivalent immunity further supports the merit of our vaccination strategy.

Example 13

RABV Vaccine Viruses Expressing ZEBOV GP can Induce GP-specific Antibodies in Mice that have Pre-existing Immunity to RABV There is a possibility that some members of the target population for an Ebola vaccine such as lab workers or first responders may be previously vaccinated with the currently approved RABV vaccine and thus have pre-existing immunity to RABV. This pre-existing immunity might interfere with induction of the ZEBOV GP-specific immune response after immunization with RABV-vectored GP vaccine. Therefore, we sought to determine in the mouse model if prior vaccination with RABV vaccine would inhibit the induction of GP-specific antibodies (FIGS. 16A-16C). Groups of five mice were immunized once on day 0 with vehicle, 10 ug inactivated SPBN-HC50E30, or 10 ug inactivated BNSP333-GP$_{GCD}$. A fourth group was immunized with 10 ug inactivated SPBN-HC50E30 on day 0 followed by 10 ug inactivated BNSP333-GP$_{GCD}$ on day 28. At least four weeks after immunization, serum from each group was assayed by ELISA against (FIG. 16A) RABV G, (FIG. 16B) BoNT HC50, and (FIG. 16C) ZEBOV GP. As expected, each vaccination approach induced strong antibody responses against RABV G (FIG. 16A) and vaccination with INAC-SPBN-HC50 or INAC-SPBN-HC50 followed by INAC-BNSP333-GP$_{GCD}$ induced potent BoNT-specific antibodies (FIG. 16B). Interestingly, vaccination with INAC-BNSP333-GP$_{GCD}$ or INAC-SPBN-HC50 followed by INAC-BNSP333-GP$_{GCD}$ induced similar levels of GP-specific antibodies (FIG. 16C). These results indicate that immunization with INAC-BNSP333-GP$_{GCD}$ can induce GP-specific antibodies in the presence of pre-existing RABV immunity. The presence of a potent RABV G-specific antibody response at day 28 prior to immunization with INAC-BNSP333-GP$_{GCD}$ was confirmed (data not shown). The ability to effectively immunize mice in the presence of RABV G-specific antibodies indicates that our vaccination strategy will be effective in previously RABV-vaccinated humans and that boosting with various RABV vectored vaccines will be successful.

Example 14

Live and Inactivated RABV Vaccine Viruses Expressing ZEBOV GP Induce Primary and Memory ZEBOV GP-specific T Cell Responses We have demonstrated that both live and killed RABV vaccines expressing GP are potent inducers of humoral immunity against both RABV G and ZEBOV GP. However, there is evidence from previous studies that T cell mediated immunity may be also critically important for the induction of protective immunity against the filoviruses. Therefore, we determined if our live and killed vaccine candidates induce primary and memory GP-specific T cells using a murine interferon-γ ELISPOT (R and D Systems) with a ZEBOV GP peptide pool as stimulation (FIG. 17).

Figure 17A:
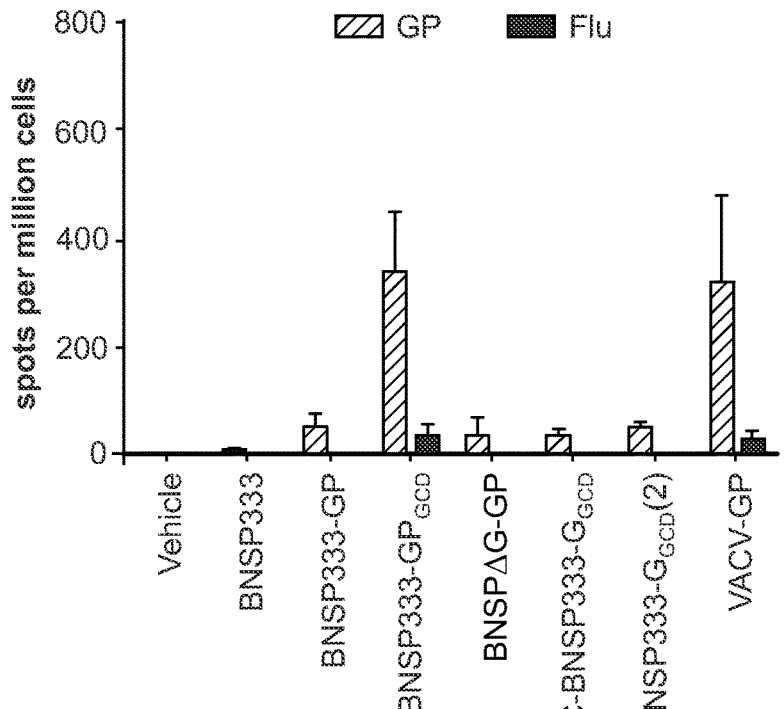
FIGS. 17A and 17B show that live and killed RABV vaccine viruses expressing ZEBOV GP induce (FIG. 17A) primary and (FIG. 17B) memory recall T cell mediated immunity. Groups of ten mice were immunized i.m. with $1\times10^5$ FFU of the live BNSP (RABV viruses) or i.p. with $1\times10^7$ PFU of VACV-GP, a vaccinia virus expressing ZEBOV GP. 10 ug of INAC-BNSP333-GP$_{GCD}$ was administered i.m. to two groups; one immunization or two at day 0 and day 14. For analysis of (FIG. 17A) primary T cell mediated immunity, spleens were removed from four mice per group on day 7 post-immunization. Splenocyte suspensions were generated and used in a murine interferon-γ ELISPOT (R and D Systems) using a ZEBOV GP peptide pool or unrelated Flu control peptide as stimulation. For analysis of (FIG. 17B) memory T cell response, the remaining six mice per group were challenged i.p. with $1\times10^7$ PFU of VACV-GP approximately 4 weeks post-immunization to induce a recall T cell response. Five days later, spleens were removed and ELISPOT was performed as described for the primary response above.
Figure 17B:
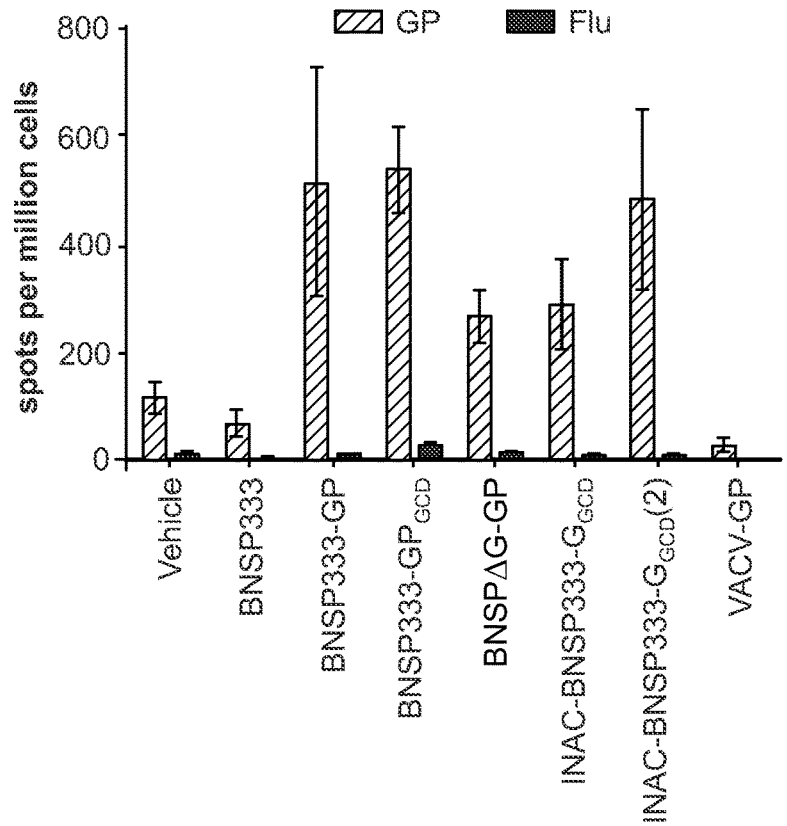

Groups of mice were immunized i.m. with 1×10$^5$ FFU of the live BNSP (RABV viruses) or i.p. with 1×10$^7$ PFU of VACV-GP, a vaccinia virus expressing ZEBOV GP, as a control. Ten ug of INAC-BNSP333-GP$_{GCD}$ was administered i.m. to two groups; one immunization or two at day 0 and day 14. The primary T cell response in splenocytes was assayed at day 7 post-immunization by ELISPOT (FIG. 17A). Each live and inactivated vaccine candidate was found to induce GP-specific interferon-γ-expressing splenocytes above levels observed in the vehicle or BNSP333 control groups. Immunization with live BNSP333-GP$_{GCD}$ resulted in a considerably higher level of interferon-γ-expressing splenocytes similar to VACV-GP immunization. For analysis of the memory T cell response, mice were challenged i.p. with 1×10$^7$ PFU of VACV-GP approximately 4 weeks post-immunization to induce a recall T cell response (FIG. 17B). Five days later, spleens were removed and splenocytes were assayed by ELISPOT. Immunization with BNSP333-GP, BNSP333-GP$_{GCD}$, BNSPΔG-GP, and one or two doses of INAC-BNSP333-GP$_{GCD}$ induced a recall response as detected by the high level of GP-specific, interferon-γ-expressing splenocytes when compared to the vehicle or BNSP333 control groups. Importantly, the replication-deficient virus, BNSPΔG-GP, induced a strong T cell response and two doses of inactivated vaccine induced a T cell response at levels comparable to the live vaccines. These results indicate that both live and killed vaccines induce T cell responses indicating that each of our vaccination strategies induces a potent humoral and cell mediated immune response.

Sequence Information

The sequences appearing in this specification (e.g., in Tables 1 and 2 above) are provided as follows:

SEQ ID NO: 1: Amino acid sequence of Glycoprotein (GP) of Zaire EBOV Mayinga
MGVTGILQLPRDRFKRTSFFLWVIILFQRTFSIPLGVIHNSTLQVSDVDKLVCRDKL

SSTNQLRSVGLNLEGNGVATDVPSATKRWGFRSGVPPKVVNYEAGEWAENCYNLEIK

KPDGSECLPAAPDGIRGFPRCRYVHKVSGTGPCAGDFAFHKEGAFFLYDRLASTVIY

RGTTFAEGVVAFLILPQAKKDFFSSHPLREPVNATEDPSSGYYSTTIRYQATGFGTN

ETEYLFEVDNLTYVQLESRFTPQFLLQLNETIYTSGKRSNTTGKLIWKVNPEIDTTI

GEWAFWETKKNLTRKIRSEELSFTVVSNGAKNISGQSPARTSSDPGTNTTTEDHKIM

ASENSSAMVQVHSQGREAAVSHLTTLATISTSPQSLTTKPGPDNSTHNTPVYKLDIS

EATQVEQHHRRTDNDSTASDTPSATTAAGPPKAENTNTSKSTDFLDPATTTSPQNHS

ETAGNNNTHHQDTGEESASSGKLGLITNTIAGVAGLITGGRRTRREAIVNAQPKCNP

NLHYWTTQDEGAAIGLAWIPYFGPAAEGIYTEGLMHNQDGLICGLRQLANETTQALQ

LFLRATTELRTFSILNRKAIDFLLQRWGGTCHILGPDCCIEPHDWTKNITDKIDQII

HDFVDKTLPDQGDNDNWWTGWRQWIPAGIGVTGVIIAVIALFCICKFVF

SEQ ID NO: 2: Amino acid sequence of Glycoprotein (GP) of Sudan EBOV Boniface
MEGLSLLQLPRDKFRKSSFFVWVIILFQKAFSMPLGVVTNSTLEVTEIDQLVCKDHL

ASTDQLKSVGLNLEGSGVSTDIPSATKRWGFRSGVPPKVFSYEAGEWAENCYNLEIK

KPDGSECLPPPPDGVRGFPRCRYVHKAQGTGPCPGDYAFHKDGAFFLYDRLASTVIY

RGVNFAEGVIAFLILAKPKETFLQSPPIREAVNYTENTSSYYATSYLEYEIENFGAQ

HSTTLFKINNNTFVLLDRPHTPQFLFQLNDTIHLHQQLSNTTGKLIWTLDANINADI

GEWAFWENKKNLSEQLRGEELSFETLSLNETEDDDATSSRTTKGRISDRATRKYSDL

VPKDSPGMVSLHVPEGETTLPSQNSTEGRRVDVNTQETITETTATIIGTNGNNMQIS

TIGTGLSSSQILSSSPTMAPSPETQTSTTYTPKLPVMTTEESTTPPRNSPGSTTEAP

TLTTPENITTAVKTVLPQESTSNGLITSTVTGILGSLGLRKRSRRQVNTRATGKCNP

NLHYWTAQEQHNAAGIAWIPYFGPGAEGIYTEGLMHNQNALVCGLRQLANETTQALQ

LFLRATTELRTYTILNRKAIDFLLRRWGGTCRILGPDCCIEPHDWTKNITDKINQII

HDFIDNPLPNQDNDDNWWTGWRQWIPAGIGITGIIIAIIALLCVCKLLC

SEQ ID NO: 3: Amino acid sequence of Glycoprotein (GP) of Cote d'Ivoire EBOV
MGASGILQLPRERFRKTSFFVWVIILFHKVFSIPLGVVHNNTLQVSDIDKFVCRDKL

SSTSQLKSVGLNLEGNGVATDVPTATKRWGFRAGVPPKVVNCEAGEWAENCYNLAIK

KVDGSECLPEAPEGVRDFPRCRYVHKVSGTGPCPGGLAFHKEGAFFLYDRLASTIIY

RGTTFAEGVIAFLILPKARKDFFQSPPLHEPANMTTDPSSYYHTTTINYVVDNFGTN

TTEFLFQVDHLTYVQLEARFTPQFLVLLNETIYSDNRRSNTTGKLIWKINPTVDTSM

GEWAFWENKKNFTKTLSSEELSFVPVPETQNQVLDTTATVSPPISAHNHAAEDHKEL

VSEDSTPVVQMQNIKGKDTMPTTVTGVPTTTPSPFPINARNTDHTKSFIGLEGPQED

HSTTQPAKTTSQPTNSTESTTLNPTSEPSSRGTGPSSPTVPNTTESHAELGKTTPTT

LPEQHTAASAIPRAVHPDELSGPGFLTNTIRGVTNLLTGSRRKRRDVTPNTQPKCNP

NLHYWTALDEGAAIGLAWIPYFGPAAEGIYTEGIMENQNGLICGLRQLANETTQALQ

LFLRATTELRTFSILNRKAIDFLLQRWGGTCHILGPDCCIEPQDWTKNITDKIDQII

HDFVDNNLPNQNDGSNWWTGWKQWVPAGIGITGVIIAIIALLCICKFML

SEQ ID NO: 4: Amino acid sequence of Glycoprotein (GP) of Reston EBOV Pennsylvania
MGSGYQLLQLPRERFRKTSFLVWVIILFQRAISMPLGIVTNSTLKATEIDQLVCRDK

LSSTSQLKSVGLNLEGNGIATDVPSATKRWGFRSGVPPKVVSYEAGEWAENCYNLEI

KKSDGSECLPLPPDGVRGFPRCRYVHKVQGTGPCPGDLAFHKNGAFFLYDRLASTVI

YRGTTFAEGVVAFLILSEPKKHFWKATPAHEPVNTTDDSTSYYMTLTLSYEMSNFGG

NESNTLFKVDNHTYVQLDRPHTPQFLVQLNETLRRNNRLSNTGRLTWTLDPKIEPD

VGEWAFWETKKNFSQQLHGENLHFQIPSTHTNNSSDQSPAGTVQGKISYHPPANNSE

LVPTDSPPVVSVLTAGRTEEMSTQGLTNGETITGFTANPMTTTIAPSPTMTSEVDNN

VPSEQPNNTASIEDSPPSASNETIYHSEMDPIQGSNNSAQSPQTKTTPAPTTSPMTQ

DPQETANSSKPGTSPGSAAGPSQPGLTINTVSKVADSLSPTRKQKRSVRQNTANKCN

-continued

PDLYYWTAVDEGAAVGLAWIPYFGPAAEGIYIEGVMHNQNGLICGLRQLANETTQAL

QLFLRATTELRTYSLLNRKAIDFLLQRWGGTCRILGPSCCIEPHDWTKNITDEINQI

KHDFIDNPLPDHGDDLNLWTGWRQWIPAGIGIIGVIIAIIALLCICKILC

SEQ ID NO: 5: Amino acid sequence of Glycoprotein (GP) of Bundibugyo EBOV
MVTSGILQLPRERFRKTSFFVWVIILFHKVFPIPLGVVHNNTLQVSDIDKLVCRDKL

SSTSQLKSVGLNLEGNGVATDVPTATKRWGFRAGVPPKVVNYEAGEWAENCYNLDIK

KADGSECLPEAPEGVRGFPRCRYVHKVSGTGPCPEGYAFHKEGAFFLYDRLASTIIY

RSTTFSEGVVAFLILPETKKDFFQSPPLHEPANMTTDPSSYYHTVTLNYVADNFGTN

MTNFLFQVDHLTYVQLEPRFTPQFLVQLNETIYTNGRRSNTTGTLIWKVNPTVDTGV

GEWAFWENKKNFTKTLSSEELSVIFVPRAQDPGSNQKTKVTPTSFANNQTSKNHEDL

VPEDPASVVQVRDLQRENTVPTPPPDTVPTTLIPDTMEEQTTSHYEPPNISRNHQER

NNTAHPETLANNPPDNTTPSTPPQDGERTSSHTTPSPRPVPTSTIHPTTRETHIPTT

MTTSHDTDSNRPNPIDISESTEPGPLTNTTRGAANLLTGSRRTRREITLRTQAKCNP

NLHYWTTQDEGAAIGLAWIPYFGPAAEGIYTEGIMHNQNGLICGLRQLANETTQALQ

LFLRATTELRTFSILNRKAIDFLLQRWGGTCHILGPDCCIEPHDWTKNITDKIDQII

HDFIDKPLPDQTDNDNWWTGWRQWVPAGIGITGVIIAVIALLCICKFLL

SEQ ID NO: 6: Amino acid sequence of Glycoprotein (GP) of Marburgvirus strain
Musoke
MKTTCFLISLILIQGTKNLPILEIASNNQPQNVDSVCSGTLQKTEDVHLMGFTLSGQ

KVADSPLEASKRWAFRTGVPPKNVEYTEGEEAKTCYNISVTDPSGKSLLLDPPTNIR

DYPKCKTIHHIQGQNPHAQGIALHLWGAFFLYDRIASTTMYRGKVFTEGNIAAMIVN

KTVHKMIFSRQGQGYRHMNLTSTNKYWTSSNGTQTNDTGCFGALQEYNSTKNQTCAP

SKIPPPLPTARPEIKLTSTPTDATKLNTTDPSSDDEDLATSGSGSGEREPHTTSDAV

TKQGLSSTMPPTPSPQPSTPQQGGNNTNHSQDAVTELDKNNTTAQPSMPPHNTTTIS

TNNTSKHNFSTLSAPLQNTTNDNTQSTITENEQTSAPSITTLPPTGNPTTAKSTSSK

KGPATTAPNTTNEHFTSPPPTPSSTAQHLVYFRRKRSILWREGDMFPFLDGLINAPI

DFDPVPNTKTIFDESSSSGASAEEDQHASPNISLTLSYFPNINENTAYSGENENDCD

AELRIWSVQEDDLAAGLSWIPFFGPGIEGLYTAVLIKNQNNLVCRLRRLANQTAKSL

ELLLRVTTEERTFSLINRHAIDFLLTRWGGTCKVLGPDCCIGIEDLSKNISEQIDQI

KKDEQKEGTGWGLGGKWWTSDWGVLTNLGILLLLSIAVLIALSCICRIFTKYIG

SEQ ID NO: 7: Amino acid sequence of NP of Zaire EBOV Mayinga
MDSRPQKIWMAPSLTESDMDYHKILTAGLSVQQGIVRQRVIPVYQVNNLEEICQLII

QAFEAGVDFQESADSFLLMLCLHHAYQGDYKLFLESGAVKYLEGHGFRFEVKKRDGV

KRLEELLPAVSSGKNIKRTLAAMPEEETTEANAGQFLSFASLFLPKLVVGEKACLEK

VQRQIQVHAEQGLIQYPTAWQSVGHMMVIFRLMRTNFLIKFLLIHQGMHMVAGHDAN

DAVISNSVAQARFSGLLIVKTVLDHILQKTERGVRLHPLARTAKVKNEVNSFKAALS

SLAKHGEYAPFARLLNLSGVNNLEHGLFPQLSAIALGVATAHGSTLAGVNVGEQYQQ

LREAATEAEKQLQQYAESRELDHLGLDDQEKKILMNFHQKKNEISFQQTNAMVTLRK

ERLAKLTEAITAASLPKTSGHYDDDDDIPFPGPINDDDNPGHQDDDPTDSQDTTIPD

VVVDPDDGSYGEYQSYSENGMNAPDDLVLFDLDEDDEDTKPVPNRSTKGGQQKNSQK

GQHIEGRQTQSRPIQNVPGPHRTIHHASAPLTDNDRRNEPSGSTSPRMLTPINEEAD

PLDDADDETSSLPPLESDDEEQDRDGTSNRTPTVAPPAPVYRDHSEKKELPQDEQQD

QDHTQEARNQDSDNTQSEHSFEEMYRHILRSQGPFDAVLYYHMMKDEPVVFSTSDGK

EYTYPDSLEEEYPPWLTEKEAMNEENRFVTLDGQQFYWPVMNHKNKFMAILQHHQ

SEQ ID NO: 8: Amino acid sequence of VP24 of Zaire EBOV Mayinga
MAKATGRYNLISPKKDLEKGVVLSDLCNFLVSQTIQGWKVYWAGIEFDVTHKGMALL

HRLKTNDFAPAWSMTRNLFPHLFQNPNSTIESPLWALRVILAAGIQDQLIDQSLIEP

LAGALGLISDWLLTTNTNHFNMRTQRVKEQLSLKMLSLIRSNILKFINKLDALHVVN

YNGLLSSIEIGTQNHTIIITRTNMGFLVELQEPDKSAMNRMKPGPAKFSLLHESTLK

AFTQGSSTRMQSLILEFNSSLAI

SEQ ID NO: 9: Amino acid sequence of VP30 of Zaire EBOV Mayinga
MEASYERGRPRAARQHSRDGHDHHVRARSSSRENYRGEYRQSRSASQVRVPTVFHKK

RVEPLTVPPAPKDICPTLKKGFLCDSSFCKKDHQLESLTDRELLLLIARKTCGSVEQ

QLNITAPKDSRLANPTADDFQQEEGPKITLLTLIKTAEHWARQDIRTIEDSKLRALL

TLCAVMTRKFSKSQLSLLCETHLRREGLGQDQAEPVLEVYQRLHSDKGGSFEAALWQ

QWDRQSLIMFITAFLNIALQLPCESSAVVVSGLRTLVPQSDNEEASTNPGTCSWSDE

GTP

SEQ ID NO: 10: Amino acid sequence of VP35 of Zaire EBOV Mayinga
MTTRTKGRGHTAATTQNDRMPGPELSGWISEQLMTGRIPVSDIFCDIENNPGLCYAS

QMQQTKPNPKTRNSQTQTDPICNHSFEEVVQTLASLATVVQQQTIASESLEQRITSL

ENGLKPVYDMAKTISSLNRVCAEMVAKYDLLVMTTGRATATAAATEAYWAEHGQPPP

GPSLYEESAIRGKIESRDETVPQSVREAFNNLNSTTSLTEENFGKPDISAKDLRNIM

YDHLPGFGTAFHQLVQVICKLGKDSNSLDIIHAEFQASLAEGDSPQCALIQITKRVP

IFQDAAPPVIHIRSRGDIPRACQKSLRPVPPSPKIDRGWVCVFQLQDGKTLGLKI

SEQ ID NO: 11: Amino acid sequence of VP40 of Zaire EBOV Mayinga
MRRVILPTAPPEYMEAIYPVRSNSTIARGGNSNTGFLTPESVNGDTPSNPLRPIADD

TIDHASHTPGSVSSAFILEAMVNVISGPKVLMKQIPIWLPLGVADQKTYSFDSTTAA

IMLASYTITHFGKATNPLVRVNRLGPGIPDHPLRLLRIGNQAFLQEFVLPPVQLPQY

FTFDLTALKLITQPLPAATWTDDTPTGSNGALRPGISFHPKLRPILLPNKSGKKGNS

ADLTSPEKIQAIMTSLQDFKIVPIDPTKNIMGIEVPETLVHKLTGKKVTSKNGQPII

PVLLPKYIGLDPVAPGDLTMVITQDCDTCHSPASLPAVIEK

SEQ ID NO: 12: Amino acid sequence of L of Zaire EBOV Mayinga
MATQHTQYPDARLSSPIVLDQCDLVTRACGLYSSYSLNPQLRNCKLPKHIYRLKYDV

TVTKFLSDVPVATLPIDFIVPVLLKALSGNGFCPVEPRCQQFLDEIIKYTMQDALFL

KYYLKNVGAQEDCVDEHFQEKILSSIQGNEFLHQMFFWYDLAILTRRGRLNRGNSRS

TWFVHDDLIDILGYGDYVFWKIPISMLPLNTQGIPHAAMDWYQASVFKEAVQGHTHI

VSVSTADVLIMCKDLITCRFNTTLISKIAEIEDPVCSDYPNFKIVSMLYQSGDYLLS

ILGSDGYKIIKFLEPLCLAKIQLCSKYTERKGRFLTQMHLAVNHTLEEITEMRALKP

SQAQKIREFHRTLIRLEMTPQQLCELFSIQKHWGHPVLHSETAIQKVKKHATVLKAL

RPIVIFETYCVFKYSIAKHYFDSQGSWYSVTSDRNLTPGLNSYIKRNQFPPLPMIKE

LLWEFYHLDHPPLFSTKIISDLSIFIKDRATAVERTCWDAVFEPNVLGYNPPHKFST

KRVPEQFLEQENFSIENVLSYAQKLEYLLPQYRNFSFSLKEKELNVGRTFGKLPYPT

RNVQTLCEALLADGLAKAFPSNMMVVTEREQKESLLHQASWHHTSDDFGEHATVRGS

SFVTDLEKYNLAFRYEFTAPFIEYCNRCYGVKNVFNWMHYTIPQCYMHVSDYYNPPH

NLTLENRDNPPEGPSSYRGHMGGIEGLQQKLWTSISCAQISLVEIKTGFKLRSAVMG

-continued

DNQCITVLSVFPLETDADEQEQSAEDNAARVAASLAKVTSACGIFLKPDETFVHSGF

IYFGKKQYLNGVQLPQSLKTATRMAPLSDAIFDDLQGTLASIGTAFERSISETRHIF

PCRITAAFHTFFSVRILQYHHLGFNKGFDLGQLTLGKPLDFGTISLALAVPQVLGGL

SFLNPEKCFYRNLGDPVTSGLFQLKTYLRMIEMDDLFLPLIAKNPGNCTAIDFVLNP

SGLNVPGSQDLTSFLRQIVRRTITLSAKNKLINTLFHASADFEDEMVCKWLLSSTPV

MSRFAADIFSRTPSGKRLQILGYLEGTRTLLASKIINNNTETPVLDRLRKITLQRWS

LWFSYLDHCDNILAEALTQITCTVDLAQILREYSWAHILEGRPLIGATLPCMIEQFK

VFWLKPYEQCPQCSNAKQPGGKPFVSVAVKKHIVSAWPNASRISWTIGDGIPYIGSR

TEDKIGQPAIKPKCPSAALREAIELASRLTWVTQGSSNSDLLIKPFLEARVNLSVQE

ILQMTPSHYSGNIVHRYNDQYSPHSFMANRMSNSATRLIVSTNTLGEFSGGGQSARD

SNIIFQNVINYAVALFDIKFRNTEATDIQYNRAHLHLTKCCTREVPAQYLTYTSTLD

LDLTRYRENELIYDSNPLKGGLNCNISFDNPFFQGKRLNIIEDDLIRLPHLSGWELA

KTIMQSIISDSNNSSTDPISSGETRSFTTHFLTYPKIGLLYSFGAFVSYYLGNTILR

TKKLTLDNFLYYLTTQIHNLPHRSLRILKPTFKHASVMSRLMSIDPHFSIYIGGAAG

DRGLSDAARLFLRTSISSFLTFVKEWIINRGTIVPLWIVYPLEGQNPTPVNNFLYQI

VELLVHDSSRQQAFKTTISDHVHPHDNLVYTCKSTASNFFHASLAYWRSRHRNSNRK

YLARDSSTGSSTNNSDGHIERSQEQTTRDPHDGTERNLVLQMSHEIKRTTIPQENTH

QGPSFQSFLSDSACGTANPKLNFDRSRHNVKFQDHNSASKREGHQIISHRLVLPFFT

LSQGTRQLTSSNESQTQDEISKYLRQLRSVIDTTVYCRFTGIVSSMHYKLDEVLWEI

ESFKSAVTLAEGEGAGALLLIQKYQVKTLFFNTLATESSIESEIVSGMTTPRMLLPV

MSKFHNDQIEIILNNSASQITDITNPTWFKDQRARLPKQVEVITMDAETTENINRSK

LYEAVYKLILHHIDPSVLKAVVLKVFLSDTEGMLWLNDNLAPFFATGYLIKPITSSA

RSSEWYLCLTNFLSTTRKMPHQNHLSCKQVILTALQLQIQRSPYWLSHLTQYADCEL

HLSYIRLGFPSLEKVLYHRYNLVDSKRGPLVSITQHLAHLRAEIRELTNDYNQQRQS

RTQTYHFIRTAKGRITKLVNDYLKFFLIVQALKHNGTWQAEFKKLPELISVCNRFYH

IRDCNCEERFLVQTLYLHRMQDSEVKLIERLTGLLSLFPDGLYRFD

SEQ ID NO: 13: Amino acid sequence of NP of Sudan EBOV Boniface
MDKRVRGSWALGGQSEVDLDYHKILTAGLSVQQGIVRQRVIPVYVVNDLEGICQHII

QAFEAGVDFQDNADSFLLLLCLHHAYQGDHRLFLKSDAVQYLEGHGFRFEVREKENV

HRLDELLPNVTGGKNLRRTLAAMPEEETTEANAGQFLSFASLFLPKLVVGEKACLEK

VQRQIQVHAEQGLIQYPTSWQSVGHMMVIFRLMRTNFLIKFLLIHQGMHMVAGHDAN

DTVISNSVAQARFSGLLIVKTVLDHILQKTDLGVRLHPLARTAKVKNEVSSFKAALG

SLAKHGEYAPFARLLNLSGVNNLEHGLYPQLSAIALGVATAHGSTLAGVNVGEQYQQ

LREAATEAEKQLQQYAETRELDNLGLDEQEKKILMSFHQKKNEISFQQTNAMVTLRK

ERLAKLTEAITTASKIKVGDRYPDDNDIPFPGPIYDDTHPNPSDDNPDDSRDTTIPG

GVVDPYDDESNNYPDYEDSAEGTTGDLDLFNLDDDDDSRPGPPDRGQNKERAARTY

GLQDPTLDGAKKVPELTPGSHQPGNLHITKSGSNTNQPQGNMSSTLHSMTPIQEESE

PDDQKDNDDESLTSLDSEGDEDGESISEENTPTVAPPAPVYKDTGVDTNQQNGPSST

VDSQGSESEALPINSKKSSALEETYYHLLKTQGPFEAINYYHLMSDEPIAFSTESGK

EYIFPDSLEEAYPPWLSEKEALEKENRYLVIDGQQFLWPVMSLQDKFLAVLQHD

SEQ ID NO: 14: Amino acid sequence of VP24 of Sudan EBOV Boniface
MAKATGRYNLVTPKRELEQGVVFSDLCNFLVTPTVQGWKVYWAGLEFDVNQKGITLL

NRLKVNDFAPAWAMTRNLFPHLFKNQQSEVQTPIWALRVILAAGILDQLMDHSLIEP

LSGALNLIADWLLTTSTNHFNMRTQRVKDQLSMRMLSLIRSNIINFINKLETLHVVN

YKGLLSSVEIGTPSYAIIITRTNMGYLVEVQEPDKSAMDIRHPGPVKFSLLHESTLK

PVATSKPSSITSLIMEFNSSLAI

SEQ ID NO: 15: Amino acid sequence of VP30 of Sudan EBOV Boniface
MERGRERGRSRSSRADQQNSTGPQFRTRSISRDKTTTDYRSSRSTSQVRVPTVFHKK

GTGTLTVPPAPKDICPTLRKGFLCDSNFCKKDHQLESLTDRELLLLIARKTCGSTDS

SLNIAAPKDLRLANPTADDFKQDGSPKLTLKLLVETAEFWANQNINEVDDAKLRALL

TLSAVLVRKFSKSQLSQLCESHLRRENLGQDQAESVLEVYQRLHSDKGGAFEAALWQ

QWDRQSLTMFISAFLHVALQLSCESSTVVISGLRLLAPPSVNEGLPPAPGEYTWSED

STT

SEQ ID NO: 16: Amino acid sequence of VP35 of Sudan EBOV Boniface
MQQDKTYRHHGPEVSGWFSEQLMTGKIPLTEVFVDVETKPSPTPITIISKNPKTTRK

SDKQVQTDDASSLLTEEVKTAINSVISAVRRQTNAIESLESRIANLEASLKPVQDMA

KTISSLNRSCAEMVAKYDLLVMTTGRATATAAATEAYWNEHGQAPPGPSLYEDDAIK

AKLKDPNGKVPESVKQAYTNLDSTSALNEENFGRPYISAKDLKEIIYDHLPGFGTAF

HQLVQVICKIGKDNNILDIIHAEFQASLAEGDSPQCALIQITKRIPTFQDASPPIVH

IKSRGDIPKACQKSLRPVPPSPKIDRGWVCIFQFQDGKTLGLKI

SEQ ID NO: 17: Amino acid sequence of VP40 of Sudan EBOV Boniface
MRRVTVPTAPPAYADIGYPMSMLPIKSSRAVSGIQQKQEVLPGMDTPSNSMRPVADD

NIDHTSHTPNGVASAFILEATVNVISGPKVLMKQIPIWLPLGIADQKTYSFDSTTAA

IMLASYTITHFGKANNPLVRVNRLGQGIPDHPLRLLRMGNQAFLQEFVLPPVQLPQY

FTFDLTALKLVTQPLPAATWTDETPSNLSGALRPGLSFHPKLRPVLLPGKTGKKGHV

SDLTAPDKIQTIVNLMQDFKIVPIDPAKSIIGIEVPELLVHKLTGKKMSQKNGQPII

PVLLPKYIGLDPISPGDLTMVITPDYDDCHSPASCSYLSEK

SEQ ID NO: 18: Amino acid sequence of L of Sudan EBOV Boniface
MMATQHTQYPDARLSSPIVLDQCDLVTRACGLYSEYSLNPKLRTCRLPKHIYRLKYD

AIVLRFISDVPVATIPIDYIAPMLINVLADSKNAPLEPPCLSFLDEIVNYTVQDAAF

LNYYMNQIKTQEGVITDQLKQNIRRVIHKNRYLSALFFWHDLSILTRRGRMNRGNVR

STWFVTNEVVDILGYGDYIFWKIPIALLPMNTANVPHASTDWYQPNIFKEAIQGHTH

IISVSTAEVLIMCKDLVTSRFNTLLIAELARLEDPVSADYPLVDDIQSLYNAGDYLL

SILGSEGYKIIKYLEPLCLAKIQLCSQYTERKGRFLTQMHLAVIQTLRELLLNRGLK

KSQLSKIREFHQLLLRLRSTPQQLCELFSIQKHWGHPVLHSEKAIQKVKNHATVLKA

LRPIIISETYCVFKYSVAKHFFDSQGTWYSVISDRCLTPGLNSYIRRNQFPPLPMIK

DLLWEFYHLDHPPLFSTKIISDLSIFIKDRATAVEQTCWDAVFEPNVLGYSPPYRFN

TKRVPEQFLEQEDFSIESVLQYAQELRYLLPQNRNFSFSLKEKELNVGRTFGKLPYL

TRNVQTLCEALLADGLAKAFPSNMMVVTEREQKESLLHQASWHHTSDDFGEHATVRG

SSFVTDLEKYNLAFRYEFTAPFIKYCNQCYGVRNVFDWMHFLIPQCYMHVSDYYNPP

HNVTLENREYPPEGPSAYRGHLGGIEGLQQKLWTSISCAQISLVEIKTGFKLRSAVM

GDNQCITVLSVFPLESSPNEQERCAEDNAARVAASLAKVTSACGIFLKPDETFVHSG

FIYFGKKQYLNGIQLPQSLKTAARMAPLSDAIFDDLQGTLASIGTAFERSISETRHI

```
LPCRVAAAFHTYFSVRILQHHHLGFHKGSDLGQLAINKPLDFGTIALSLAVPQVLGG

LSFLNPEKCLYRNLGDPVTSGLFQLKHYLSMVGMSDIFHALVAKSPGNCSAIDFVLN

PGGLNVPGSQDLTSFLRQIVRRSITLSARNKLINTLFHASADLEDELVCKWLLSSTP

VMSRFAADIFSRTPSGKRLQILGYLEGTRTLLASRMISNNAETPILERLRKITLQRW

NLWFSYLDHCDSALMEAIQPIRCTVDIAQILREYSWAHILDGRQLIGATLPCIPEQF

QTTWLKPYEQCVECSSTNNSSPYVSVALKRNVVSAWPDASRLGWTIGDGIPYIGSRT

EDKIGQPAIKPRCPSAALREAIELTSRLTWVTQGSANSDQLIRPFLEARVNLSVQEI

LQMTPSHYSGNIVHRYNDQYSPHSFMANRMSNTATRLMVSTNTLGEFSGGGQAARDS

NIIFQNVINFAVALYDIRFRNTCTSSIQYHRAHIHLTDCCTREVPAQYLTYTTTLNL

DLSKYRNNELIYDSEPLRGGLNCNLSIDSPLMKGPRLNIIEDDLIRLPHLSGWELAK

TVLQSIISDSSNSSTDPISSGETRSFTTHFLTYPKIGLLYSFGALISFYLGNTILCT

KKIGLTEFLYYLQNQIHNLSHRSLRIFKPTFRHSSVMSRLMDIDPNFSIYIGGTAGD

RGLSDAARLFLRIAISTFLSFVEEWVIFRKANIPLWVVYPLEGQRPDPPGEFLNRVK

SLIVGIEDDKNKGSILSRSEEKGSSNLVYNCKSTASNFFHASLAYWRGRHRPKKTIG

ATKATTAPHIILPLGNSDRPPGLDLNQSNDTFIPTRIKQIVQGDSRNDRTTTTRLPP

KSRSTPTSATEPPTKIYEGSTTYRGKSTDTHLDEGHNAKEFPFNPHRLVVPFFKLTK

DGEYSIEPSPEESRSNIKGLLQHLRTMVDTTIYCRFTGIVSSMHYKLDEVLWEYNKF

ESAVTLAEGEGSGALLLIQKYGVKKLFLNTLATEHSIESEVISGYTTPRMLLSVMPR

THRGELEVILNNSASQITDITHRDWFSNQKNRIPNDVDIITMDAETTENLDRSRLYE

AVYTIICNHINPKTLKVVILKVFLSDLDGMCWINNYLAPMFGSGYLIKPITSSARSS

EWYLCLSNLLSTLRTTQHQTQANCLHVVQCALQQQVQRGSYWLSHLTKYTTSRLHNS

YIAFGFPSLEKVLYHRYNLVDSRNGPLVSITRHLALLQTEIRELVTDYNQLRQSRTQ

TYHFIKTSKGRITKLVNDYLRFELVIRALKNNSTWHHELYLLPELIGVCHRFNHTRN

CTCSERFLVQTLYLHRMSDAEIKLMDRLTSLVNMFPEGFRSSSV

SEQ ID NO: 19: Amino acid sequence of NP of Cote d'Ivoire EBOV
MESRAHKAWMTHTASGFETDYHKILTAGLSVQQGIVRQRVIQVHQVTNLEEICQLII

QAFEAGVDFQESADSFLLMLCLHHAYQGDYKQFLESNAVKYLEGHGFRFEVRKKEGV

KRLEELLPAASSGKSIRRTLAAMPEEETTEANAGQFLSFASLFLPKLVVGEKACLEK

VQRQIQVHSEQGLIQYPTAWQSVGHMMVIFRLMRTNFLIKFLLIHQGMHMVAGHDAN

DAVIANSVAQARFSGLLIVKTVLDHILQKTEHGVRLHPLARTAKVKNEVNSFKAALS

SLAQHGEYAPFARLLNLSGVNNLEHGLFPQLSAIALGVATAHGSTLAGVNVGEQYQQ

LREAATEAEKQLQKYAESRELDHLGLDDQEKKILKDFHQKKNEISFQQTTAMVTLRK

ERLAKLTEAITSTSLLKTGKQYDDDNDIPFPGPINDNENSEQQDDDPTDSQDTTIPD

IIVDPDDGRYNNYGDYPSETANAPEDLVLFDLEDGDEDDHRPSSSSENNNKHSLTGT

DSNKTSNWNRNPTNMPKKDSTQNNDNPAQRAQEYARDNIQDTPTPHRALTPISEETG

SNGHNEDDIDSIPPLESDEENNTETTITTTKNTTAPPAPVYRSNSEKEPLPQEKSQK

QPNQVSGSENTDNKPHSEQSVEEMYRHILQTQGPFDAILYYYMMTEEPIVFSTSDGK

EYVYPDSLEGEHPPWLSEKEALNEDNRFITMDDQQFYWPVMNHRNKFMAILQHHK

SEQ ID NO: 20: Amino acid sequence of VP24 of Cote d'Ivoire EBOV
MAKATGRYNLISPKKDLEKGLVLNDLCTLSVAQTVQGWKVTWAGIEFDVTQKGMALL

HRLKTSDFAPAWSMTRNLFPHLFQNPNSTIESPLWALRVILAAGIQDQLIDQSLIEP

LAGALGLIADWLLTTGTNHFQMRTQQAKEQLSLKMLSLVRSNILKFINQLDALHVVN
```

-continued

YNGLLSSIEIGTKSHTIIITRTNMGFLVELQEPDKSAMNTRKPGPVKFSLLHESTLK

TLAKKPATQMQALILEFNSSLAI

SEQ ID NO: 21: Amino acid sequence of VP30 of Cote d'Ivoire EBOV
MEVVHERGRSRISRQNTRDGPSHLVRARSSSRASYRSEYHTPRSASQIRVPTVFHRK

KTDLLTVPPAPKDVCPTLKKGFLCDSNFCKKDHQLESLTDRELLLLIARKTCGSTEQ

QLSIVAPKDSRLANPIAEDFQQKDGPKVTLSMLIETAEYWSKQDIKNIDDSRLRALL

TLCAVMTRKFSKSQLSLLCESHLRREGLGQDQSESVLEVYQRLHSDKGGNFEAALWQ

QWDRQSLIMFITAFLNIALQLPCESSSVVISGLRMLIPQSEATEVVTPSETCTWSEG

GSSH

SEQ ID NO: 22: Amino acid sequence of VP35 of Cote d'Ivoire EBOV
MISTRAAAINDPSLPIRNQCTRGPELSGWISEQLMTGKIPVHEIFNDTEPHISSGSD

CLPRPKNTAPRTRNTQTQTDPVCNHNFEDVTQALTSLTNVIQKQALNLESLEQRIID

LENGLKPMYDMAKVISALNRSCAEMVAKYDLLVMTTGRATATAAATEAYWEEHGQPP

PGPSLYEESAIRGKINKQEDKVPKEVQEAFRNLDSTSSLTEENFGKPDISAKDLRDI

MYDHLPGFGTAFHQLVQVICKLGKDNSALDIIHAEFQASLAEGDSPQCALIQITKRI

PIFQDATPPTIHIRSRGDIPRACQKSLRPVPPSPKIDRGWVCIFQLQDGKTLGLKI

SEQ ID NO: 23: Amino acid sequence of VP40 of Cote d'Ivoire EBOV
MRRIILPTAPPEYMEAVYPMRTMNSGADNTASGPNYTTTGVMTNDTPSNSLRPVADD

NIDHPSHTPNSVASAFILEAMVNVISGPKVLMKQIPIWLPLGVSDQKTYSFDSTTAA

IMLASYTITHFGKTSNPLVRINRLGPIPDHPLRLLRIGNQAFLQEFVLPPVQLPQY

FTFDLTALKLITQPLPAATWTDETPAVSTGTLRPGISFHPKLRPILLPGRAGKKGSN

SDLTSPDKIQAIMNFLQDLKIVPIDPTKNIMGIEVPELLVHRLTGKKTTTKNGQPII

PILLPKYIGLDPLSQGDLTMVITQDCDSCHSPASLPPVNEK

SEQ ID NO: 24: Amino acid sequence of L of Cote d'Ivoire EBOV
MATQHTQYPDARLSSPIVLDQCDLVTRACGLYSAYSLNPQLKNCRLPKHIYRLKYDT

TVTEFLSDVPVATLPADFLVPTFLRTLSGNGSCPIDPKCSQFLEEIVNYTLQDIRFL

NYYLNRAGVHNDHVDRDFGQKIRNLICDNEVLHQMFHWYDLAILARRGRLNRGNNRS

TWFASDNLVDILGYGDYIFWKIPLSLLPVDTQGLPHAAKDWYHESVFKEAIQGHTHI

VSISTADVLIMCKDIITCRFNTLLIAAVANLEDSVHSDYPLPETVSDLYKAGDYLIS

LLGSEGYKVIKFLEPLCLAKIQLCSNYTERKGRFLTQMHLAVNHTLEELTGSRELRP

QQIRKVREFHQMLINLKATPQQLCELFSVQKHWGHPVLHSEKAIQKVKKHATVIKAL

RPIIIFETYCVFKYSIAKHYFDSQGTWYSVTSDRCLTPGLSSYIKRNQFPPLPMIKE

LLWEFYHLDHPPLFSTKVISDLSIFIKDRATAVEKTCWDAVFEPNVLGYNPPNKFAT

KRVPEQFLEQENFSIESVLHYAQRLEYLLPEYRNFSFSLKEKELNIGRAFGKLPYPT

RNVQTLCEALLADGLAKAFPSNMMVVTEREQKESLLHQASWHHTSDDFGENATVRGS

SFVTDLEKYNLAFRYEFTAPPFIEYCNRCYGVRNLFNWMHYTIPQCYIHVSDYYNPPH

GVSLENRENPPEGPSSYRGHLGGIEGLQQKLWTSISCAQISLVEIKTGFKLRSAVMG

DNQCITVLSVFPLETESSEQELSSEDNAARVAASLAKVTSACGIFLKPDETFVHSGF

IYFGKKQYLNGVQLPQSLKTATRIAPLSDAIFDDLQGTLASIGTAFERSISETRHVV

PCRVAAAFHTFFSVRILQYHHLGFNKGTDLGQLSLSKPLDFGTITLALAVPQVLGGL

SFLNPEKCFYRNLGDPVTSGLFQLKTYLQMIHMDDLFLPLIAKNPGNCSAIDFVLNP

SGLNVPGSQDLTSFLRQIVRRTITLSAKNKLINTLFHSSADLEDEMVCKWLLSSTPV

MSRFAADIFSRTPSGKRLQILGYLEGTRTLLASKIINHNTETPILDRLRKITLQRWS

-continued

LWFSYLDHCDQVLADALTQITCTVDLAQILREYTWAHILEGRQLIGATLPCILEQLN

VIWLKPYEHCPKCAKSANPKGEPFVSIAIKKHVVSAWPDQSRLSWTIGDGIPYIGSR

TEDKIGQPAIKPKCPSAALREAIELTSRLTWVTQGGANSDLLVKPFIEARVNLSVQE

ILQMTPSHYSGNIVHRYNDQYSPHSFMANRMSNSATRLVVSTNTLGEFSGGGQSARD

SNIIFQNVINFAVALFDLRFRNVATSSIQHHRAHLHLSKCCTREVPAQYLVYTSTLP

LDLTRYRDNELIYDDNPLRGGLNCNLSFDNPLFKGQRLNIIEEDLIRLPYLSGWELA

KTVIQSIISDSNNSSTDPISSGETRSFTTHFLTYPKIGLLYSFGALISYYLGNTIIR

TKKLTLNNFIYYLATQIHNLPHRSLRILKPTLKHASVISRLISIDSHFSIYIGGTAG

DRGLSDAARLFLRTAITVFLQFVRKWIVERKTAIPLWVIYPLEGQSPSPINSFLHHV

IALLQHESSHDHVCAAEAHSRVETFDNLVYMCKSTASNFFHASLAYWRSRSKNQDKR

EMTKILSLTQTEKKNSFGYTAHPESTAVLGSLQTSLAPPPSADEATYDRKNKVLKAS

RPGKYSQNTTKAPPNQTSCRDVSPNITGTDGCPSANEGSNSNNNNLVSHRIVLPFFT

LSHNYNERPSIRKSEGTTEIVRLTRQLRAIPDTTIYCRFTGIVSSMHYKLDEVLWEF

DNFKSAITLAEGEGSGALLLLQKYKVETLFFNTLATEHSIEAEIISGITTPRMLLPI

MSRFHGGQIKVTLNNSASQITDITNPSWLADQKSRIPKQVEIITMDAETTENINRSK

LYEAVQQLIVSHIDPNALKVVVLKVFLSDIDGILWLNDNLTPLFGLGYLIKPITSSP

KSSEWYLCLSNLLSTSRRLPHQSHTTCMHVIQTALQLQIQRSSYWLSHLVQYANHNL

HLDYINLGFPSLERVLYHRYNLVDSQKGPLTSIVQHLAHLQTEIRELVNDYNQQRQS

RTQTYHFIKTIKGRITKLVNDYLKFFLIIQALKHNCTWQEELRALPDLISVCTRFYH

TRNCSCENRFLVQTLYLSRMQDSEIKLIDRLTGLLSLCPNGFFR

SEQ ID NO: 25: Amino acid sequence of NP of Reston EBOV Pennsylvania
MDRGTRRIWVSQNQGDTDLDYHKILTAGLTVQQGIVRQKIISVYLVDNLEAMCQLVI

QAFEAGIDFQENADSFLLMLCLHHAYQGDYKLFLESNAVQYLEGHGFKFELRKKDGV

NRLEELLPAATSGKNIRRTLAALPEEETTEANAGQFLSFASLFLPKLVVGEKACLEK

VQRQIQVHAEQGLIQYPTAWQSVGHMMVIFRLMRTNFLIKYLLIHQGMHMVAGHDAN

DAVIANSVAQARFSGLLIVKTVLDHILQKTDQGVRLHPLARTAKVRNEVNAFKAALS

SLAKHGEYAPFARLLNLSGVNNLEHGLYPQLSAIALGVATAHGSTLAGVNVGEQYQQ

LREAATEAEKQLQQYAESRELDSLGLDDQERRILMNFHQKKNEISFQQTNAMVTLRK

ERLAKLTEAITLASRPNLGSRQDDGNEIPFPGPISNNPDQDHLEDDPRDSRDTIIPN

GAIDPEDGDFENYNGYHDDEVGTAGDLVLFDLDDHEDDNKAFEPQDSSPQSQREIER

ERLIHPPPGNNKDDNRASDNNQQSADSEEQGGQYNWHRGPERTTANRRLSPVHEEDT

LMDQGDDDPSSLPPLESDDDDASSSQQDPDYTAVAPPAPVYRSAEAHEPPHKSSNEP

AETSQLNEDPDIGQSKSMQKLEETYHHLLRTQGPFEAINYYHMMKDEPVIFSTDDGK

EYTYPDSLEEAYPPWLTEKERLDKENRYIYINNQQFFWPVMSPRDKFLAILQHHQ

SEQ ID NO: 26: Amino acid sequence of VP24 of Reston EBOV Pennsylvania
MAKATGRYNLVPPKKDMEKGVIFSDLCNFLITQTLQGWKVYWAGIEFDVSQKGMALL

TRLKTNDFAPAWAMTRNLFPHLFQNPNSVIQSPIWALRVILAAGLQDQLLDHSLVEP

LTGALGLISDWLLTTTSTHFNLRTRSVKDQLSLRMLSLIRSNILQFINKLDALHVVN

YNGLLSSIEIGTSTHTIIITRTNMGFLVEVQEPDKSAMNSKRPGPVKFSLLHESAFK

PFTRVPQSGMQSLIMEFNSLLAI

SEQ ID NO: 27: Amino acid sequence of VP30 of Reston EBOV Pennsylvania
MEHSRERGRSSNMRHNSREPYENPSRSRSLSRDPNQVDRRQPRSASQIRVPNLFHRK

KTDALIVPPAPKDICPTLKKGFLCDSKFCKKDHQLDSLNDHELLLLIARRTCGIIES

NSQITSPKDMRLANPTAEDFSQGNSPKLTLAVLLQIAEHWATRDLRQIEDSKLRALL

TLCAVLTRKFSKSQLGLLCETHLRHEGLGQDQADSVLEVYQRLHSDKGGNFEAALWQ

QWDRQSLIMFISAFLNIALQIPCESSSVVVSGLATLYPAQDNSTPSEATNDTTWSST

VE

SEQ ID NO: 28: Amino acid sequence of VP35 of Reston EBOV Pennsylvania
MYNNKLKVCSGPETTGWISEQLMTGKIPVTDIFIDIDNKPDQMEVRLKPSSRSSTRT

CTSSSQTEVNYVPLLKKVEDTLTMLVNATSRQNAAIEALENRLSTLESSLKPIQDMG

KVISSLNRSCAEMVAKYDLLVMTTGRATSTAAAVDAYWKEHKQPPPGPALYEENALK

GKIDDPNSYVPDAVQEAYKNLDSTSTLTEENFGKPYISAKDLKEIMYDHLPGFGTAF

HQLVQVICKIGKDNNLLDTIHAEFQASLADGDSPQCALIQITKRVPIFQDVPPPIIH

IRSRGDIPRACQKSLRPAPPSPKIDRGWVCLFKMQDGKTLGLKI

SEQ ID NO: 29: Amino acid sequence of VP40 of Reston EBOV Pennsylvania
MRRGVLPTAPPAYNDIAYPMSILPTRPSVIVNETKSDVLAVPGADVPSNSMRPVADD

NIDHSSHTPSGVASAFILEATVNVISGTKVLMKQIPIWLPLGVADQKIYSFDSTTAA

IMLASYTVTHFGKISNPLVRVNRLGPGIPDHPLRLLRLGNQAFLQEFVLPPVQLPQY

FTFDLTALKLITQPLPAATWTDETPAGAVNALRPGLSLHPKLRPILLPGKTGKKGHA

SDLTSPDKIQTIMNAIPDLKIVPIDPTKNIVGIEVPELLVQRLTGKKPQPKNGQPII

PVLLPKYVGLDPISPGDLTMVITQDCDSCHSPASHPYHMDKQNSYQ

SEQ ID NO: 30: Amino acid sequence of L of Reston EBOV Pennsylvania
MATQHTQYPDARLSSPIVLDQCDLVTRACGLYSSYSLNPQLRQCKLPKHIYRLKFDT

IVSKFLSDTPVATLPIDYLVPILLRSLTGHGDRPLTPTCNQFLDEIINYTLHDAAFL

DYYLKATGAQDHLTNIATREKLKNEILNNDYVHQLFFWHDLSILARRGRLNRGNNRS

TWFVHDEFIDILGYGDYIFWKIPLSLLPVTIDGVPHAATDWYQPTLFKESILGHSQI

LSVSTAEILIMCKDIITCRFNTSLIASIAKLEDVDVSDYPDPSDILKIYNAGDYVIS

ILGSEGYKIIKYLEPLCLAKIQLCSKFTERKGRFLTQMHLSVINDLRELISNRRLKD

YQQEKIRDFHKILLQLQLSPQQFCELFSVQKHWGHPILHSEKAIQKVKRHATILKAL

RPNVIFETYCVFKYNIAKHYFDSQGTWYSVISDRNLTPGLNSFIKRNHFPSLPMIKD

LLWEFYHLNHPPLFSTKVISDLSIFIKDRATAVEQTCWDAVFEPNVLGYNPPNKFST

KRVPEQFLEQEDFSIESVLNYAQELHYLLPQNRNFSFSLKEKELNIGRTFGKLPYLT

RNVQTLCEALLADGLAKAFPSNMMVVTEREQKESLLHQASWHHTSDDFGENATVRGS

SFVTDLEKYNLAFRYEFTAPFIEYCNHCYGVRNVFNWMHYLIPQCYMHVSDYYNPPH

NVNLSNREYPPEGPSSYRGHLGGIEGLQQKLWTSISCAQISLVEIKTGFKLRSAVMG

DNQCITVLSVFPPLKTDPEEQEQSAEDNAARVAASLAKVTSACGIFLKPDETFVHSGF

IYFGKKQYLNGVQLPQSLKTAARMAPLSDAIFDDLQGTLASIGTAFERAISETRHIL

PCRIVAAFHTYFAVRILQYHHLGFNKGIDLGQLSLSKPLDYGTITLTLAVPQVLGGL

SFLNPEKCFYRNFGDPVTSGLFQLRVYLEMVNMKDLFCPLISKNPGNCSAIDFVLNP

SGLNVPGSQDLTSFLRQIVRRSITLTARNKLINTLFHASADLEDEMVCKWLLSSNPV

MSRFAADIFSRTPSGKRLQILGYLEGTRTLLASKIINNNSETPVLDKLRKITLQRWN

LWFSYLDHCDQLLADALQKISCTVDLAQILREYTWSHILEGRSLIGATLPCMVEQFK

VKWLGQYEPCPECLNKKGSNAYVSVAVKDQVVSAWPNTSRISWTIGSGVPYIGSRTE

DKIGQPAIKPRCPSSALKEAIELASRLTWVTQGGSNSEQLIRPFLEARVNLSVSEVL

QMTPSHYSGNIVHRYNDQYSPHSFMANRMSNTATRLIVSTNTLGEFSGGGQAARDSN

IIFQNVINLAVALYDIRFRNTNTSDIRHNRAHLHLTECCTKEVPAQYLTYTSALNLD

LSRYRDNELIYDSNPLKGGLNCNLTIDSPLVKGPRLNMIEDDLLRFPHLSGWELAKT

VVQSIISDNSNSSTDPISSGETRSFTTHFLTYPQIGLLYSFGAVLCFYLGNTILWTK

KLDYEQFLYYLHNQLHNLPHRALRVFKPTFKHASVMSRLMEIDSNFSIYIGGTSGDR

GLSDAARLFLRTAIASFLQFLKSWIIDRQKTIPLWIVYPLEGQQPESINEFLHKILG

LLKQGPKSIPKEVSIQNDGHLDLAENNYVYNSKSTASNFFHASLAYWRSRKSRKTQD

HNDFSRGDGTLTEPVRKFSSNHQSDEKYYNVTCGKSPKPQERKDFSQYRLSNNGQTM

SNHRKKGKFHKWNPCKMLMESQRGTVLTEGDYFQNNTPPTDDVSSPHRLILPFFKLG

NHNHAHDQDAQELMNQNIKQYLHQLRSMLDTTIYCRFTGIVSSMHYKLDEVLLEYNS

FDSAITLAEGEGSGALLLLQKYSTRLLFLNTLATEHSIESEVVSGFSTPRMLLPIMQ

KVHEGQVTVILNNSASQITDITSSMWLSNQKYNLPCQVEIIMMDAETTENLNRSQLY

RAVYNLILDHIDPQYLKVVVLKVFLSDIEGILWINDYLAPLFGAGYLIKPITSSARS

SEWYLCLSNLISTNRRSAHQTHKACLGVIRDALQAQVQRGVYWLSHIAQYATKNLHC

EYIGLGFPSLEKVLYHRYNLVDTGLGPLSSVIRHLTNLQAEIRDLVLDYNLMRESRT

QTYHFIKTAKGRITKLVNDFLKFSLIVQALKNNSSWYTELKKLPEVINVCNRFYHTH

NCECQEKFFVQTLYLQRLRDAEIKLIERLTGLMRFYPEGLIYSNHT

SEQ ID NO: 31: Amino acid sequence of NP of Bundibugyo EBOV
MDPRPIRTWMMHNTSEVEADYHKILTAGLSVQQGIVRQRIIPVYQISNLEEVCQLII

QAFEAGVDFQDSADSFLLMLCLHHAYQGDYKQFLESNAVKYLEGHGFRFEMKKKEGV

KRLEELLPAASSGKNIKRTLAAMPEEETTEANAGQFLSFASLFLPKLVVGEKACLEK

VQRQIQVHAEQGLIQYPTSWQSVGHMMVIFRLMRTNFLIKFLLIHQGMHMVAGHDAN

DAVIANSVAQARFSGLLIVKTVLDHILQKTEHGVRLHPLARTAKVKNEVSSFKAALA

SLAQHGEYAPFARLLNLSGVNNLEHGLFPQLSAIALGVATAHGSTLAGVNVGEQYQQ

LREAATEAEKQLQKYAESRELDHLGLDDQEKKILKDFHQKKNEISFQQTTAMVTLRK

ERLAKLTEAITSTSILKTGRRYDDDNDIPFPGPINDNENSGQNDDDPTDSQDTTIPD

VIIDPNDGGYNNYSDYANDAASAPDDLVLFDLEDEDDADNPAQNTPEKNDRPATTKL

RNGQDQDGNQGETASPRVAPNQYRDKPMPQVQDRSENHDQTLQTQSRVLTPISEEAD

PSDHNDGDNESIPPLESDDEGSTDTTAAETKPATAPPAPVYRSISVDDSVPSENIPA

QSNQTNNEDNVRNNAQSEQSIAEMYQHILKTQGPFDAILYYHMMKEEPIIFSTSDGK

EYTYPDSLEDEYPPWLSEKEAMNEDNRFITMDGQQFYWPVMNHRNKFMAILQHHR

SEQ ID NO: 32: Amino acid sequence of VP24 of Bundibugyo EBOV
MAKATGRYNLVSPKKDLERGLVLSDLCTFLVDQTIQGWRVTWVGIEFDIAQKGMALL

HRLKTADFAPAWSMTRNLFPHLFQNSNSTIESPLWALRVILAAGIQDQLIDQSLVEP

LAGALSLVSDWLLTTNTNHFQMRTQHAKEQLSLKMLSLVRSNILKFISQLDALHVVN

YNGLLSSIEIGTRNHTIIITRTNMGFLVELQEPDKSAMNQKKPGPVKFSLLHESTFK

ALIKKPATKMQALILEFNSSLAI

SEQ ID NO: 33: Amino acid sequence of VP30 of Bundibugyo EBOV
MDSFHERGRSRTIRQSARDGPSHQVRTRSSSRDSHRSEYHTPRSSSQVRVPTVFHRK

RTDSLTVPPAPKDICPTLRKGFLCDSNFCKKDHQLESLTDRELLLLIARKTCGSLEQ

QLNITAPKDTRLANPIADDFQQKDGPKITLLTLLETAEYWSKQDIKGIDDSRLRALL

-continued

TLCAVMTRKFSKSQLSLLCESHLRREGLGQDQSESVLEVYQRLHSDKGGNFEAALWQ

QWDRQSLIMFITAFLNIALQLPCESSSVVISGLRLLVPQSEDTETSTYTETRAWSEE

GGPH

SEQ ID NO: 34: Amino acid sequence of VP35 of Bundibugyo EBOV
MTSNRARVTYNPPPTTTGTRSCGPELSGWISEQLMTGKIPITDIFNEIETLPSISPS

IHSKIKTPSVQTRSVQTQTDPNCNHDFAEVVKMLTSLTLVVQKQTLATESLEQRITD

LEGSLKPVSEITKIVSALNRSCAEMVAKYDLLVMTTGRATATAAATEAYWAEHGRPP

PGPSLYEEDAIRTKIGKQGDMVPKEVQEAFRNLDSTALLTEENFGKPDISAKDLRNI

MYDHLPGFGTAFHQLVQVICKLGKDNSSLDVIHAEFQASLAEGDSPQCALIQITKRI

PIFQDAAPPVIHIRSRGDIPKACQKSLRPVPPSPKIDRGWVCIFQLQDGKTLGLKI

SEQ ID NO: 35: Amino acid sequence of VP40 of Bundibugyo EBOV
MRRAILPTAPPEYIEAVYPMRTVSTSINSTASGPNFPAPDVMMSDTPSNSLRPIADD

NIDHPSHTPTSVSSAFILEAMVNVISGPKVLMKQIPIWLPLGVADQKTYSFDSTTAA

IMLASYTITHFGKTSNPLVRINRLGPGIPDHPLRLLRIGNQAFLQEFVLPPVQLPQY

FTFDLTALKLITQPLPAATWTDDTPTGPTGILRPGISFHPKLRPILLPGKTGKRGSS

SDLTSPDKIQAIMNFLQDLKLVPIDPAKNIMGIEVPELLVHRLTGKKITTKNGQPII

PILLPKYIGMDPISQGDLTMVITQDCDTCHSPASLPPVSEK

SEQ ID NO: 36: Amino acid sequence of L of Bundibugyo EBOV
MATQHTQYPDARLSSPIVLDQCDLVTRACGLYSSYSLNPQLKNCRLPKHIYRLKFDA

TVTKFLSDVPIVTLPIDYLTPLLLRTLSGEGLCPVEPKCSQFLDEIVSYVLQDARFL

RYYFRHVGVHDDNVGKNFEPKIKALIYDNEFLQQLFYWYDLAILTRRGRLNRGNNRS

TWFANDDLIDILGYGDYIFWKIPLSLLSLNTEGIPHAAKDWYHASIFKEAVQGHTHI

VSVSTADVLIMCKDIITCRFNTTLIAALANLEDSICSDYPQPETISNLYKAGDYLIS

ILGSEGYKVIKFLEPLCLAKIQLCSNYTERKGRFLTQMHLAVNHTLEELIEGRGLKS

QQDWKMREFHRILVNLKSTPQQLCELFSVQKHWGHPVLHSEKAIQKVKKHATVIKAL

RPVIIFETYCVFKYSIAKHYFDSQGSWYSVISDKHLTPGLHSYIKRNQFPPLPMIKD

LLWEFYHLDHPPLFSTKIISDLSIFIKDRATAVEKTCWDAVFEPNVLGYSPPNKFST

KRVPEQFLEQENFSIDSVLTYAQRLDYLLPQYRNFSFSLKEKELNVGRAFGKLPYPT

RNVQTLCEALLADGLAKAFPSNMMVVTEREQKESLLHQASWHHTSDDFGENATVRGS

SFVTDLEKYNLAFRYEFTAPFIEYCNRCYGVKNLFNWMHYTIPQCYIHVSDYYNPPH

GVSLENREDPPEGPSSYRGHLGGIEGLQQKLWTSISCAQISLVEIKTGFKLRSAVMG

DNQCITVLSVFPLETDSNEQEHSSEDNAARVAASLAKVTSACGIFLKPDETFVHSGF

IYFGKKQYLNGVQLPQSLKTATRIAPLSDAIFDDLQGTLASIGTAFERSISETRHVY

PCRVVAAFHTFFSVRILQYHHLGFNKGTDLGQLSLSKPLDFGTITLALAVPQVLGGL

SFLNPEKCFYRNLGDPVTSGLFQLRTYLQMINMDDLFLPLIAKNPGNCSAIDFVLNP

SGLNVPGSQDLTSFLRQIVRRTITLSAKNKLINTLFHSSADLEDEMVCKWLLSSTPV

MSRFAADIFSRTPSGKRLQILGYLEGTRTLLASKVINNNAETPILDRLRKITLQRWS

LWFSYLDHCDQVLADALIKVSCTVDLAQILREYTWAHILEGRQLIGATLPCMLEQFN

VFWLKSYEQCPKCAKSRNPKGEPFVSIAIKKQVVSAWPNQSRLNWTIGDGVPYIGSR

TEDKIGQPAIKPKCPSAALREAIELTSRLTWVTQGGANSDLLVKPFVEARVNLSVQE

ILQMTPSHYSGNIVHRYNDQYSPHSFMANRMSNSATRLVVSTNTLGEFSGGGQSARD

SNIIFQNVINFSVALFDLRFRNTETSSIQHNRAHLHLSQCCTREVPAQYLTYTSTLS

-continued

LDLTRYRENELIYDNNPLKGGLNCNLSFDNPLFKGQRLNIIEEDLIRFPHLSGWELA

KTIIQSIISDSNNSSTDPISSGETRSFTTHFLTYPKVGLLYSFGAIVSYYLGNTIIR

TKKLDLSHFMYYLTTQIHNLPHRSLRILKPTFKHVSVISRLMSIDPHFSIYIGGTAG

DRGLSDATRLFLRVAISSFLQFIKKWIVEYKTAIPLWVIYPLEGQNPDPINSFLHLI

IALLQNESPQNNIQFQEDRNNQQLSDNLVYMCKSTASNFFHASLAYWRSRHKGRPKN

RSTEEQTVKPIPYDNFHSVKCASNPPSIPKSKSGTQGSSAFFEKLEYDKERELPTAS

TPAEQSKTYIKALSSRIYHGKTPSNAAKDDSTTSKGCDSKEENAVQASHRIVLPFFT

LSQNDYRTPSAKKSEYITEITKLIRQLKAIPDTTVYCRFTGVVSSMHYKLDEVLWEF

DSFKTAVTLAEGEGSGALLLLQKYKVRTIFFNTLATEHSIEAEIVSGTTTPRMLLPV

MAKLHDDQINVILNNSASQVTDITNPAWFTDQKSRIPTQVEIMTMDAETTENINRSK

LYEAIQQLIVSHIDTRVLKIVIIKVFLSDIEGLLWLNDHLAPLFGSGYLIKPITSSP

KSSEWYLCLSNFLSASRRRPHQGHATCMQVIQTALRLQVQRSSYWLSHLVQYADINL

HLSYVNLGFPSLEKVLYHRYNLVDSRKGPLVSILYHLTHLQAEIRELVCDYNQQRQS

RTQTYHFIKTTKGRITKLVNDYLKFYLVVQALKHNCLWQEELRTLPDLINVCNRFYH

IRDCSCEDRFLIQTLYLTRMQDSEAKLMERLTGFLGLYPNGINA

SEQ ID NO: 37: Amino acid sequence of NP of Marburgvirus strain Musoke
MDLHSLLELGTKPTAPHVRNKKVILFDTNHQVSICNQIIDAINSGIDLGDLLEGGLL

TLCVEHYYNSDKDKFNTSPIAKYLRDAGYEFDVIKNADATRFLDVIPNEPHYSPLIL

ALKTLESTESQRGRIGLFLSFCSLFLPKLVVGDRASIEKALRQVTVHQEQGIVTYPN

HWLTTGHMKVIFGILRSSFILKFVLIHQGVNLVTGHDAYDSIISNSVGQTRFSGLLI

VKTVLEFILQKTDSGVTLHPLVRTSKVKNEVASFKQALSNLARHGEYAPFARVLNLS

GINNLEHGLYPQLSAIALGVATAHGSTLAGVNVGEQYQQLREAAHDAEVKLQRRHEH

QEIQAIAEDDEERKILEQFHLQKTEITHSQTLAVLSQKREKLARLAAEIENNIVEDQ

GFKQSQNRVSQSFLNDPTPVEVTVQARPMNRPTALPPPVDDKIEHESTEDSSSSSSF

VDLNDPFALLNEDEDTLDDSVMIPGTTSREFQGIPEPPRQSQDLNNSQGKQEDESTN

PIKKQFLRYQELPPVQEDDESEYTTDSQESIDQPGSDNEQGVDLPPPPLYAQEKRQD

PIQHPAANPQDPFGSIGDVNGDILEPIRSPSSPSAPQEDTRMREAYELSPDFTNDED

NQQNWPQRVVTKKGRTFLYPNDLLQTNPPESLITALVEEYQNPVSAKELQADWPDMS

FDERRHVAMNL

SEQ ID NO: 38: Amino acid sequence of VP24 of Marburgvirus strain Musoke
MAELSTRYNLPANVTENSINLDLNSTARWIKEPSVGGWTVKWGNFVFHIPNTGMTLL

HHLKSNFVVPEWQQTRNLFSHLFKNPKSTIIEPFLALRILLGVALKDQELQQSLIPG

FRSIVHMLSEWLLLEVTSAIHISPNLLGIYLTSDMFKILMAGVKNFFNKMFTLHVVN

DHGKPSSIEIKLTGQQIIITRVNMGFLVEVRRIDIEPCCGETVLSESVVFGLVAEAV

LREHSQMEKGQPLNLTQYMNSKIAI

SEQ ID NO: 39: Amino acid sequence of VP30 of Marburgvirus strain Musoke
MQQPRGRSRTRNHQVTPTIYHETQLPSKPHYTNYHPRARSMSSTRSSAESSPTNHIP

RARPPSTFNLSKPPPPPKDMCRNMKIGLPCADPTCNRDHDLDNLTNRELLLLMARKM

LPNTDKTFRSPQDCGSPSLSKGLSKDKQEQTKDVLTLENLGHILSYLHRSEIGKLDE

TSLRAALSLTCAGIRKTNRSLINTMTELHMNHENLPQDQNGVIKQTYTGIHLDKGGQ

FEAALWQGWDKRSISLFVQAALYVMNNIPCESSISVQASYDHFILPQSQGKGQ

SEQ ID NO: 40: Amino acid sequence of VP35 of Marburgvirus strain Musoke
MWDSSYMQQVSEGLMTGKVPIDQVFGANPLEKLYKRRKPKGTVGLQCSPCLMSKATS

TDDIIWDQLIVKRTLADLLIPINRQISDIQSTLSEVTTRVHEIERQLHEITPVLKMG

RTLEAISKGMSEMLAKYDHLVISTGRTTAPAAAFDAYLNEHGVPPPQPAIFKDLGVA

QQACSKGTMVKNATTDAADKMSKVLELSEETFSKPNLSAKDLALLLFTHLPGNNTPF

HILAQVLSKIAYKSGKSGAFLDAFHQILSEGENAQAALTRLSRTFDAFLGVVPPVIR

VKNFQTVPRPCQKSLRAVPPNPTIDKGWVCVYSSEQGETRALKI

SEQ ID NO: 41: Amino acid sequence of VP40 of Marburgvirus strain Musoke
MASSSNYNTYMQYLNPPPYADHGANQLIPADQLSNQQG ITPNYVGDLNLDDQFKGNV

CHAFTLEAIIDISAYNERTVKGVPAWLPLGIMSNFEYPLAHTVAALLTGSYTITQFT

HNGQKFVRVNRLGTGIPAHPLRMLREGNQAFIQNMVIPRNFSTNQFTYNLTNLVLSV

QKLPDDAWRPSKDKLIGNTMHPAVSIHPNLPPIVLPTVKKQAYRQHKNPNNGPLLAI

SGILHQLRVEKVPEKTSLFRISLPADMFSVKEGMMKKRGENSPVVYFQAPENFPLNG

FNNRQVVLAYANPTLSAV

SEQ ID NO: 42: Amino acid sequence of L of Marburgvirus strain Musoke
MQHPTQYPDARLSSPIILDQCDLLARSLGLYSHYSHNPKLRNCRIPHHIYRLRNSTA

LKTFLQNCSILTVPFHSIWDHILTSIQYDAINHVDDFKYLLPSELVKYANWDNEFLK

AYLNKILGLDHVFSASARSQCEDFSPKENPYYWGMLLLVHLSQLARRIKGQRGSLRS

NWKFIGTDLELFGIADFVIFKVPVKTIIRNAVSLQASKPGLRIWYRDQNLTPYLCDD

EFIVSVASYECFIMIKDVFIERYNTWEICARAWLEDSDGADYPPLDVLGELYNQGDQ

IIAMYLEDGFKLIKHLEPLCVSCIQTHGIFTPRKYWFQSQMIKSYYDELHDLNLKLQ

ISDNKAECAQNFIKTIVQAKLTPQQYCELFSLQKHWGHPVLYNDVALDKVKKHAQST

KILKPKVMFETFCVFKFIVAKNHYHSQGSWYKTTHDLHLTPYLRQHIVSNSFPSQAE

IYQHLWEWYFVEHEPLFSTKIISDLSIFIKDRATAVNQECWDSVFDRSVLGYNPPVR

FQSKRVPEQFLGQADFSLNQILEFAEKLEYLAPSYRNFSFSLKEKELNIGRTFGKLP

YRVRNVQTLAEALLADGLAKAFPSNMMVVTEREQKEALLHQASWHHNSASIGENAIV

RGASFVTDLEKYNLAFRYEFTRHFIDYCNRCYGVKNLFDWMHFLIPLCYMHVSDFYS

PPHCVTEDNRNNPPDCANAYHYHLGGIEGLQQKLWTCISCAQITLVELKTKLKLKSS

VMGDNQCITTLSLFPIDAPNDYQENEAELNAARVAVELAITTGYSGIFLKPEETFVH

SGFIYFGKKQYLNGVQLPQSLKTMARCGPLSDSIFDDLQGSLASIGTSFERGTSETR

HIFPSRWIASFHSMLAINLLNQNHLGFPLGFNIDISCFKKPLTFSEKLIALITPQVL

GGLSFLNPEKLFYRNISDPLTSGLFQLKNALEFLEKEELFYILISKKPGLADASDFV

MNPLGLNVPGSKEIITFLRQTVRENITITSQNRIINSLFHIGSDLEDQRVCEWLLSS

NPVMSRFAADIFSRTPSGKRLQVLGYLEGTRTLLASRTISLTTEGTMLMKLRELTRN

RWKSWFSYIDALDDDLSESLEKFTCTVDVANFLRAYSWSDVLKGKRLIGATLPCLLE

QFEVKWINLSEDLREQFNLSSDSKSTINLLPYDCKELRLEGSNDTELNYVSCALDRK

VVQKHPSVNRLAWTIGNRAPYIGSRTEDKIGYPPLRVNCPSAALKEAIEMVSRLLWV

TQGTADREKLLIPLLNSRVNLDYQTVLNFLPTHYSGNIVHRYNDQYGQHSFMANRMS

NTSTRAIISTNTLGKYAGGGQAAIDSNIIFQNTINLGVAVLDIALSLAKLSSASNVT

FRLMLNKCCTRHVPSEYLYFDKPLDVDLNKYMDNELVYDNDPLCSGIKGRLGRVSRS

TLTLSLNVSDIGSYDFPTIAAWTLGETIVGSIFSDESSQSTDPISSGCTKTFVTHFL

VYPVESIFYAFGANLIVESLSLSRIKSIKNLSDLTFLISSTIRNLSHRSLRILQSTF

-continued

RHELVLTRLAHHIPLISLMLGGSAGEKSSSDAVRLFLTASYQNFINNFSCLMKKGQS

SLPVWLYFPSEGQQLKPILKILQRLSDLLSPDKIQKRKILADTCCPIGSFWVYPSKS

TRTNHYYASLNYWRDKANKVKNTPFSHLINCSFPEFSSHTSSVSSNQQVTNSKYIVY

PENITEINARTRLINYGSTALQGMDTKMPLSEQNLVENCRPSEGIRFKDNQKITKHD

QRCEREESSPQQMFPEDNMQTPAHIHSSSPFQILIKSLDAHEDFDASKIILNSEINN

LNLTEYTLNTKLLTTPTRTEILDTSPLQSSRYSSTSRERSLLSREQASYLYVDCSNI

PSISLDPGFRSMSDQNQVQMLINTYKRDLHACFDSNQFCRFTGVVSSMHYKLYDLLP

PGKLKKAICLAEGEGSGARLLLKWKETDYLFFNTLATDSQQEAEILSGRVIPRMLYN

IDRLSALLESRRLILNNLTIQITDITNPLWLDSVIQYLPEDSDILTMDAETTKDETR

EQLYKTIVNIWTRTSPNIPKISIIKVFLLDYEGTLFLMKNAIQYYGQVQLKKPYSSN

AKNSEWYLCCGKRRIQRLQIDFSDQVGIFLICKAMSRQRQAIPYWLKHIEKNYPASL

HEFFLTLGFPSLESSFCHRYTIPFSEGKALFHKVQSYVRQGKQHLHSLMLDYENNSP

LLDLRNHFICSLRGKITKYYNDILKLNLVIKAVEKGKNWSQLVEILPNMHSVCIVHV

DHECSGCEKRLLLKLDFIRNTKIAEQKLLNRVIGYILFFPFGLFKSGSLRA

SEQ ID NO: 43: Nucleotide sequence of the BNSP333-GP vaccine vector of the Examples
ACGCTTAACAACCAGATCAAAGAAAAAACAGACATTGTCAATTGCAAAGCAAAAATGTAACACCCCTAC

AATGGATGCCGACAAGATTGTATTCAAAGTCAATAATCAGGTGGTCTCTTTGAAGCCTGAGATTATCGT

GGATCAATATGAGTACAAGTACCCTGCCATCAAAGATTTGAAAAAGCCCTGTATAACCCTAGGAAAGGC

TCCCGATTTAAATAAAGCATACAAGTCAGTTTTGTCAGGCATGAGCGCCGCCAAACTTAATCCTGACGA

TGTATGTTCCTATTTGGCAGCGGCAATGCAGTTTTTTGAGGGGACATGTCCGGAAGACTGGACCAGCTA

TGGAATTGTGATTGCACGAAAAGGAGATAAGATCACCCCAGGTTCTCTGGTGGAGATAAAACGTACTGA

TGTAGAAGGGAATTGGGCTCTGACAGGAGGCATGGAACTGACAAGAGACCCCACTGTCCCTGAGCATGC

GTCCTTAGTCGGTCTTCTCTTGAGTCTGTATAGGTTGAGCAAAATATCCGGGCAAAACACTGGTAACTA

TAAGACAAACATTGCAGACAGGATAGAGCAGATTTTTGAGACAGCCCCTTTTGTTAAAATCGTGGAACA

CCATACTCTAATGACAACTCACAAaATGTGTGCTAATTGGAGTACTATACCAAACTTCAGATTTTTGGC

CGGAACCTATGACATGTTTTTCTCCCGGATTGAGCATCTATATTCAGCAATCAGAGTGGGCACAGTTGT

CACTGCTTATGAAGACTGTTCAGGACTGGTATCATTTACTGGGTTCATAAAACAAATCAATCTCACCGC

TAGAGAGGCAATACTATATTTCTTCCACAAGAACTTTGAGGAAGAGATAAGAAGAATGTTTGAGCCAGG

GCAGGAGACAGCTGTTCCTCACTCTTATTTCATCCACTTCCGTTCACTAGGCTTGAGTGGGAAATCTCC

TTATTCATCAAATGCTGTTGGTCACGTGTTCAATCTCATTCACTTTGTAGGATGCTATATGGGTCAAGT

CAGATCCCTAAATGCAACGGTTATTGCTGCATGTGCTCCTCATGAAATGTCTGTTCTAGGGGGCTATCT

GGGAGAGGAATTCTTCGGGAAAGGGACATTTGAAAGAAGATTCTTCAGAGATGAGAAAGAACTTCAAGA

ATACGAGGCGGCTGAACTGACAAAGACTGACGTAGCACTGGCAGATGATGGAACTGTCAACTCTGACGA

CGAGGACTACTTTTCAGGTGAAACCAGAAGTCCGGAGGCTGTTTATACTCGAATCATGATGAATGGAGG

TCGACTAAAGAGATCTCACATACGGAGATATGTCTCAGTCAGTTCCAATCATCAAGCCCGTCCAAACTC

ATTCGCCGAGTTTCTAAACAAGACATATTCGAGTGACTCATAAcatgaaaaaaactaacacccctcccg tacgCCGCCACCatgGGTGTTACAGGAATATTGCAGTTACCTCGTGATCGATTCAAGAGGACATCATTC

TTTCTTTGGGTAATTATCCTTTTCCAAAGAACATTTTCCATCCCACTTGGAGTCATCCACAATAGCACA

TTACAGGTTAGTGATGTCGACAAACTAGTTTGTCGTGACAAACTGTCATCCACAAATCAATTGAGATCA

GTTGGACTGAATCTCGAAGGGAATGGAGTGGCAACTGACGTGCCATCTGCAACTAAAAGATGGGGCTTC

AGGTCCGGTGTCCCACCAAAGGTGGTCAATTATGAAGCTGGTGAATGGGCTGAAAACTGCTACAATCTT

-continued

```
GAAATCAAAAAACCTGACGGGAGTGAGTGTCTACCAGCAGCGCCAGACGGGATTCGGGGCTTCCCCCGG

TGCCGGTATGTGCACAAAGTATCAGGAACGGGACCGTGTGCCGGAGACTTTGCCTTCCATAAAGAGGGT

GCTTTCTTCCTGTATGATCGACTTGCTTCCACAGTTATCTACCGAGGAACGACTTTCGCTGAAGGTGTC

GTTGCATTTCTGATACTGCCCCAAGCTAAGAAGGACTTCTTCAGCTCACACCCCTTGAGAGAGCCGGTC

AATGCAACGGAGGACCCGTCTAGTGGCTACTATTCTACCACAATTAGATATCAGGCTACCGGTTTTGGA

ACCAATGAGACAGAGTACTTGTTCGAGGTTGACAATTTGACCTACGTCCAACTTGAATCAAGATTCACA

CCACAGTTTCTGCTCCAGCTGAATGAGACAATATATACAAGTGGGAAAAGGAGCAATACCACGGGAAAA

CTAATTTGGAAGGtCAACCCCGAAATTGATACAACAATCGGGGAGTGGGCCTTCTGGGAAacTAAAAAA

AACCTCACTAGAAAAaTTCGCAGTGAAGAGTTgTCTTTCACAGTTGTATCAAACAGAGCCAAAAACATC

AGTGGTCAGAGTCCGGCGCGAACTTCTTCCGACCCAGGGACCAACACAACAACTGAAGACCACAAAATC

ATGGCTTCAGAAAATTCCTCTGCAATGGTTCAAGTGCACAGTCAAGGAAGGGAAGCTGCAGTGTCGCAT

CTGACAACCCCTGCCACAATCTCCACGAGTCTTCAACCCCCCACAACCAAACCAGGTCCGGACAACAGC

ACCCACAATACACCCGTGTATAAACTTGACATCTCTGAGGCAACTCAAGTTGAACAACATCACCGCAGA

ACAGACAACGACAGCACAGCcTCCGACACTCCcTCTGCCACGACcGCAGCCGGACCCCCAAAAGCAGAG

AACACCAACACGAGCAAGAGCACTGACTTCCTGGACCCCGCCACCACAACAAGTCCCCAAAACCACAGC

GAGACCGCTGGCAACAACAACACTCATCACCAAGATACCGGAGAAGAGAGTGCCAGCAGCGGGAAGCTA

GGCTTAATTACCAATACTATTGCTGGAGTCGCAGGACTGATCACAGGCGGGAGAAGAACTCGAAGAGAA

GCAATTGTCAATGCTCAACCCAAATGCAACCCTAATTTACATTACTGGACTACTCAGGATGAAGGTGCT

GCAATCGGACTGGCCTGGATACCATATTTCGGGCCAGCAGCCGAGGGAATTTACATAGAGGGGCTAATG

CACAATCAAGATGGTTTAATCTGTGGGTTGAGACAGCTGGCCAACGAGACGACTCAAGCTCTTCAACTG

TTCCTGAGAGCCACAACTGAGCTACGCACCTTTTCAATCCTCAACCGTAAGGCAATTGATTTCTTGCTG

CAGCGATGGGGCGGCACATGCCACATTCTGGGACCGGACTGCTGTATCGAACCACATGATTGGACCAAG

AACATAACAGACAAAATTGATCAGATTATTCATGATTTTGTTGATAAAACCCTTCCGGACCAGGGGGAC

AATGACAATTGGTGGACAGGATGGAGACAATGGATACCGGCAGGTATTGGAGTTACAGGCGTTGTAATT

GCAGTTATCGCTTTATTCTGTATATGCAAATTTGTCTTTTAGGAGCTAGCCATGAAAAAAACTAACACC

CCTCCTTTCGAACCATCCCAAACATGAGCAAGATCTTTGTCAATCCTAGTGCTATTAGAGCCGGTCTGG

CCGATCTTGAGATGGCTGAAGAAACTGTTGATCTGATCAATAGAAATATCGAAGACAATCAGGCTCATC

TCCAAGGGGAACCCATAGAGGTGGACAATCTCCCTGAGGATATGGGCGACTTCACCTGGATGATGGAA

AATCGCCCAACCATGGTGAGATAGCCAAGGTGGGAGAAGGCAAGTATCGAGAGGACTTTCAGATGGATG

AAGGAGAGGATCCTAGCTTCCTGTTCCAGTCATACCTGGAAAATGTTGGAGTCCAAATAGTCAGACAAA

TGAGGTCAGGAGAGAGATTTCTCAAGATATGGTCACAGACCGTAGAAGAGATTATATCCTATGTCGCGG

TCAACTTTCCCAACCCTCCAGGAAAGTCTTCAGAGGATAAATCAACCCAGACTACTGGCCGAGAGCTCA

AGAAGGAGACAACACCCACTCCTTCTCAGAGAGAAAGCCAATCATCGAAAGCCAGGATGGCGGCTCAAA

TTGCTTCTGGCCCTCCAGCCCTTGAATGGTCGGCTACCAATGAAGAGGATGATCTATCAGTGGAGGCTG

AGATCGCTCACCAGATTGCAGAAAGTTTCTCCAAAAAATATAAGTTTCCCTCTCGATCCTCAGGGATAC

TCTTGTATAATTTTGAGCAATTGAAAATGAACCTTGATGATATAGTTAAAGAGGCAAAAAATGTACCAG

GTGTGACCCGTTTAGCCCATGACGGGTCCAAACTCCCCCTAAGATGTGTACTGGGATGGGTCGCTTTGG

CCAACTCTAAGAAATTCCAGTTGTTAGTCGAATCCGACAAGCTGAGTAAAATCATGCAAGATGACTTGA

ATCGCTATACATCTTGCTAACCGAACCTCTCCCCTCAGTCCCTCTAGACAATAAAATCCGAGATGTCCC

AAAGTCAACATGAAAAAAACAGGCAACACCACTGATAAAATGAACCTCCTACGTAAGATAGTGAAAAAC

CGCAGGGACGAGGACACTCAAAAATCCTCTCCCGCGTCAGCCCCTCTGGATGACGATGACTTGTGGCTT
```

-continued

```
CCACCCCCTGAATACGTCCCGCTGAAAGAACTTACAGGCAAGAAGAACATGAGGAACTTTTGTATCAAC

GGAAGGGTTAAAGTGTGTAGCCCGAATGGTTACTCGTTCAGGATCCTGCGGCACATTCTGAAATCATTC

GACGAGATATATTCTGGGAATCATAGGATGATCGGGTTAGTCAAAGTGGTTATTGGACTGGCTTTGTCA

GGATCTCCAGTCCCTGAGGGCCTGAACTGGGTATACAAATTGAGGAGAACCTTTATCTTCCAGTGGGCT

GATTCCAGGGGCCCTCTTGAAGGGGAGGAGTTGGAATACTCTCAGGAGATCACTTGGGATGATGATACT

GAGTTCGTCGGATTGCAAATAAGAGTGATTGCAAAACAGTGTCATATCCAGGGCAGAGTCTGGTGTATC

AACATGAACCCGAGAGCATGTCAACTATGGTCTGACATGTCTCTTCAGACACAAAGGTCCGAAGAGGAC

AAAGATTCCTCTCTGCTTCTAGAATAATCAGATTATATCCCGCAAATTTATCACTTGTTTACCTCTGGA

GGAGAGAACATATGGGCTCAACTCCAACCCTTGGGAGCAATATAACAAAAAACATGTTATGGTGCCATT

AAACCGCTGCATTTCATCAAAGTCAAGTTGATTACCTTTACATTTTGATCCTCTTGGATGTGAAAAAAA

CTATTAACATCCCTCAAAAGACcccgggAAAGATGGTTCCTCAGGCTCTCCTGTTTGTACCCCTTCTGG

TTTTTCCATTGTGTTTTGGGAAATTCCCTATTTACACGATACCAGACAAGCTTGGTCCCTGGAGTCCGA

TTGACATACATCACCTCAGCTGCCCAAACAATTTGGTAGTGGAGGACGAAGGATGCACCAACCTGTCAG

GGTTCTCCTACATGGAACTTAAAGTTGGATACATCTTAGCCATAAAAGTGAACGGGTTCACTTGCACAG

GCGTTGTGACGGAGGCTGAAACCTACACTAACTTCGTTGGTTATGTCACAACCACGTTCAAAAGAAAGC

ATTTCCGCCCAACACCAGATGCATGTAGAGCCGCGTACAACTGGAAGATGGCCGGTGACCCCAGATATG

AAGAGTCTCTACACAATCCGTACCCTGACTACCGCTGGCTTCGAACTGTAAAAACCACCAAGGAGTCTC

TCGTTATCATATCTCCAAGTGTGGCAGATTTGGACCCATATGACAGATCCCTTCACTCGAGGGTCTTCC

CTAGCGGGAAGTGCTCAGGAGTAGCGGTGTCTTCTACCTACTGCTCCACTAACCACGATTACACCATTT

GGATGCCCGAGAATCCGAGACTAGGGATGTCTTGTGACATTTTTACCAATAGTAGAGGGAAGAGAGCAT

CCAAAGGGAGTGAGACTTGCGGCTTTGTAGATGAAAGAGGCCTATATAAGTCTTTAAAAGGAGCATGCA

AACTCAAGTTATGTGGAGTTCTAGGACTTAGACTTATGGATGGAACATGGGTCTCGATGCAAACATCAA

ATGAAACCAAATGGTGCCCTCCCGATAAGTTGGTGAACCTGCACGACTTTCGCTCAGACGAAATTGAGC

ACCTTGTTGTAGAGGAGTTGGTCAGGAAGAGAGAGGAGTGTCTGGATGCACTAGAGTCCATCATGACAA

CCAAGTCAGTGAGTTTCAGACGTCTCAGTCATTTAAGAAAACTTGTCCCTGGGTTTGGAAAAGCATATA

CCATATTCAACAAGACCTTGATGGAAGCCGATGCTCACTACAAGTCAGTCgagACTTGGAATGAGATCC

TCCCTTCAAAAGGGTGTTTAAGAGTTGGGGGGAGGTGTCATCCTCATGTGAACGGGGTGTTTTTCAATG

GTATAATATTAGGACCTGACGGCAATGTCTTAATCCCAGAGATGCAATCATCCCTCCTCCAGCAACATA

TGGAGTTGTTGGAATCCTCGGTTATCCCCCTTGTGCACCCCCTGGCAGACCCGTCTACCGTTTTCAAGG

ACGGTGACGAGGCTGAGGATTTTGTTGAAGTTCACCTTCCCGATGTGCACAATCAGGTCTCAGGAGTTG

ACTTGGGTCTCCCGAACTGGGGGAAGTATGTATTACTGAGTGCAGGGGCCCTGACTGCCTTGATGTTGA

TAATTTTCCTGATGACATGTTGTAGAAGAGTCAATCGATCAGAACCTACGCAACACAATCTCAGAGGGA

CAGGGAGGGAGGTGTCAGTCACTCCCCAAAGCGGGAAGATCATATCTTCATGGGAATCACACAAGAGTG

GGGGTGAGACCAGACTGTAAttaattaaCGTCCTTTCAACGATCCAAGTCcatgaaaaaaactaacacc cctcccgtacctagcTTATAAAGTGCTGGGTCATCTAAGCTTTTCAGTCGAGAAAAAAACATTAGATCA

GAAGAACAACTGGCAACACTTCTCAACCTGAGACTTACTTCAAGATGCTCGATCCTGGAGAGGTCTATG

ATGACCCTATTGACCCAATCGAGTTAGAGGCTGAACCCAGAGGAACCCCCATTGTCCCCAACATCTTGA

GGAACTCTGACTACAATCTCAACTCTCCTTTGATAGAAGATCCTGCTAGACTAATGTTAGAATGGTTAA

AAACAGGGAATAGACCTTATCGGATGACTCTAACAGACAATTGCTCCAGGTCTTTCAGAGTTTTGAAAG

ATTATTTCAAGAAGGTAGATTTGGGTTCTCTCAAGGTGGCGGAATGGCTGCACAGTCAATGATTTCTC

TCTGGTTATATGGTGCCCACTCTGAATCCAACAGGAGCCGGAGATGTATAACAGACTTGGCCCATTTCT
```

-continued

```
ATTCCAAGTCGTCCCCCATAGAGAAGCTGTTGAATCTCACGCTAGGAAATAGAGGGCTGAGAATCCCCC
CAGAGGGAGTGTTAAGTTGCCTTGAGAGGGTTGATTATGATAATGCATTTGGAAGGTATCTTGCCAACA
CGTATTCCTCTTACTTGTTCTTCCATGTAATCACCTTATACATGAACGCCCTAGACTGGGATGAAGAAA
AGACCATCCTAGCATTATGGAAAGATTTAACCTCAGTGGACATCGGGAAGGACTTGGTAAAGTTCAAAG
ACCAAATATGGGGACTGCTGATCGTGACAAAGGACTTTGTTTACTCCCAAAGTTCCAATTGTCTTTTTG
ACAGAAACTACACACTTATGCTAAAAGATCTTTTCTTGTCTCGCTTCAACTCCTTAATGGTCTTGCTCT
CTCCCCCAGAGCCCCGATACTCAGATGACTTGATATCTCAACTATGCCAGCTGTACATTGCTGGGGATC
AAGTCTTGTCTATGTGTGGAAACTCCGGCTATGAAGTCATCAAAATATTGGAGCCATATGTCGTGAATA
GTTTAGTCCAGAGAGCAGAAAAGTTTAGGCCTCTCATTCATTCCTTGGGAGACTTTCCTGTATTTATAA
AAGACAAGGTAAGTCAACTTGAAGAGACGTTCGGTCCCTGTGCAAGAAGGTTCTTTAGGGCTCTGGATC
AATTCGACAACATACATGACTTGGTTTTTGTGTTTGGCTGTTACAGGCATTGGGGGCACCCATATATAG
ATTATCGAAAGGGTCTGTCAAAACTATATGATCAGGTTCACCTTAAAAAAATGATAGATAAGTCCTACC
AGGAGTGCTTAGCAAGCGACCTAGCCAGGAGGATCCTTAGATGGGGTTTTGATAAGTACTCCAAGTGGT
ATCTGGATTCAAGATTCCTAGCCCGAGACCACCCCTTGACTCCTTATATCAAAACCCAAACATGGCCAC
CCAAACATATTGTAGACTTGGTGGGGATACATGGCACAAGCTCCCGATCACGCAGATCTTTGAGATTC
CTGAATCAATGGATCCGTCAGAAATATTGGATGACAAATCACATTCTTTCACCAGAACGAGACTAGCTT
CTTGGCTGTCAGAAAACCGAGGGGGGCCTGTTCCTAGCGAAAAAGTTATTATCACGGCCCTGTCTAAGC
CGCCTGTCAATCCCCGAGAGTTTCTGAGGTCTATAGACCTCGGAGGATTGCCAGATGAAGACTTGATAA
TTGGCCTCAAGCCAAAGGAACGGGAATTGAAGATTGAAGGTCGATTCTTTGCTCTAATGTCATGGAATC
TAAGATTGTATTTTGTCATCACTGAAAAACTCTTGGCCAACTACATCTTGCCACTTTTTGACGCGCTGA
CTATGACAGACAACCTGAACAAGGTGTTTAAAAAGCTGATCGACAGGGTCACCGGGCAAGGGCTTTTGG
ACTATTCAAGGGTCACATATGCATTTCACCTGGACTATGAAAAGTGGAACAACCATCAAAGATTAGAGT
CAACAGAGGATGTATTTTCTGTCCTAGATCAAGTGTTTGGATTGAAGAGAGTGTTTTCTAGAACACACG
AGTTTTTTCAAAAGGCCTGGATCTATTATTCAGACAGATCAGACCTCATCGGGTTACGGGAGGATCAAA
TATACTGCTTAGATGCGTCCAACGGCCCAACCTGTTGGAATGGCCAGGATGGCGGGCTAGAAGGCTTAC
GGCAGAAGGGCTGGAGTCTAGTCAGCTTATTGATGATAGATAGAGAATCTCAAATCAGGAACACAAGAA
CCAAAATACTAGCTCAAGGAGACAACCAGGTTTTATGTCCGACATACATGTTGTCGCCAGGGCTATCTC
AAGAGGGGCTCCTCTATGAATTGGAGAGAATATCAAGGAATGCACTTTCGATATACAGAGCCGTCGAGG
AAGGGGCATCTAAGCTAGGGCTGATCATCAAGAAAGAAGAGACCATGTGTAGTTATGACTTCCTCATCT
ATGGAAAAACCCCTTTGTTTAGAGGTAACATATTGGTGCCTGAGTCCAAAAGATGGGCCAGAGTCTCTT
GCGTCTCTAATGACCAAATAGTCAACCTCGCCAATATAATGTCGACAGTGTCCACCAATGCGCTAACAG
TGGCACAACACTCTCAATCTTTGATCAAACCGATGAGGGATTTTCTGCTCATGTCAGTACAGGCAGTCT
TTCACTACCTGCTATTTAGCCCAATCTTAAAGGGAAGAGTTTACAAGATTCTGAGCGCTGAAGGGGAGA
GCTTTCTCCTAGCCATGTCAAGGATAATCTATCTAGATCCTTCTTTGGGAGGGATATCTGGAATGTCCC
TCGGAAGATTCCATATACGACAGTTCTCAGACCCTGTCTCTGAAGGGTTATCCTTCTGGAGAGAGATCT
GGTTAAGCTCCCAAGAGTCCTGGATTCACGCGTTGTGTCAAGAGGCTGGAAACCCAGATCTTGGAGAGA
GAACACTCGAGAGCTTCACTCGCCTTCTAGAAGATCCGACCACCTTAAATATCAGAGGAGGGGCCAGTC
CTACCATTCTACTCAAGGATGCAATCAGAAAGGCTTTATATGACGAGGTGGACAAGGTGGAAAATTCAG
AGTTTCGAGAGGCAATCCTGTTGTCCAAGACCCATAGAGATAATTTTATACTCTTCTTAATATCTGTTG
AGCCTCTGTTTCCTCGATTTCTCAGTGAGCTATTCAGTTCGTCTTTTTTGGGAATCCCCGAGTCAATCA
TTGGATTGATACAAAACTCCCGAACGATAAGAAGGCAGTTTAGAAAGAGTCTCTCAAAAACTTTAGAAG
```

-continued

```
AATCCTTCTACAACTCAGAGATCCACGGGATTAGTCGGATGACCCAGACACCTCAGAGGGTTGGGGGGG
TGTGGCCTTGCTCTTCAGAGAGGGCAGATCTACTTAGGGAGATCTCTTGGGGAAGAAAAGTGGTAGGCA
CGACAGTTCCTCACCCTTCTGAGATGTTGGGATTACTTCCCAAGTCCTCTATTTCTTGCACTTGTGGAG
CAACAGGAGGAGGCAATCCTAGAGTTTCTGTATCAGTACTCCCGTCCTTTGATCAGTCATTTTTTTCAC
GAGGCCCCCTAAAGGGATACTTGGGCTCGTCCACCTCTATGTCGACCCAGCTATTCCATGCATGGGAAA
AAGTCACTAATGTTCATGTGGTGAAGAGAGCTCTATCGTTAAAAGAATCTATAAACTGGTTCATTACTA
GAGATTCCAACTTGGCTCAAGCTCTAATTAGGAACATTATGTCTCTGACAGGCCCTGATTTCCCTCTAG
AGGAGGCCCCTGTCTTCAAAAGGACGGGGTCAGCCTTGCATAGGTTCAAGTCTGCCAGATACAGCGAAG
GAGGGTATTCTTCTGTCTGCCCGAACCTCCTCTCTCATATTTCTGTTAGTACAGACACCATGTCTGATT
TGACCCAAGACGGGAAGAACTACGATTTCATGTTCCAGCCATTGATGCTTTATGCACAGACATGGACAT
CAGAGCTGGTACAGAGAGACACAAGGCTAAGAGACTCTACGTTTCATTGGCACCTCCGATGCAACAGGT
GTGTGAGACCCATTGACGACGTGACCCTGGAGACCTCTCAGATCTTCGAGTTTCCGGATGTGTCGAAAA
GAATATCCAGAATGGTTTCTGGGGCTGTGCCTCACTTCCAGAGGCTTCCCGATATCCGTCTGAGACCAG
GAGATTTTGAATCTCTAAGCGGTAGAGAAAAGTCTCACCATATCGGATCAGCTCAGGGGCTCTTATACT
CAATCTTAGTGGCAATTCACGACTCAGGATACAATGATGGAACCATCTTCCCTGTCAACATATACGGCA
AGGTTTCCCCTAGAGACTATTTGAGAGGGCTCGCAAGGGAGTATTGATAGGATCCTCGATTTGCTTCT
TGACAAGAATGACAAATATCAATATTAATAGACCTCTTGAATTGGTCTCAGGGGTAATCTCATATATTC
TCCTGAGGCTAGATAACCATCCCTCCTTGTACATAATGCTCAGAGAACCGTCTCTTAGAGGAGAGATAT
TTTCTATCCCTCAGAAAATCCCCGCCGCTTATCCAACCACTATGAAAGAAGGCAACAGATCAATCTTGT
GTTATCTCCAACATGTGCTACGCTATGAGCGAGAGATAATCACGGCGTCTCCAGAGAATGACTGGCTAT
GGATCTTTTCAGACTTTAGAAGTGCCAAAATGACGTACCTATCCCTCATTACTTACCAGTCTCATCTTC
TACTCCAGAGGGTTGAGAGAAACCTATCTAAGAGTATGAGAGATAACCTGCGACAATTGAGTTCTTTGA
TGAGGCAGGTGCTGGGCGGGCACGGAGAAGATACCTTAGAGTCAGACGACAACATTCAACGACTGCTAA
AAGACTCTTTACGAAGGACAAGATGGGTGGATCAAGAGGTGCGCCATGCAGCTAGAACCATGACTGGAG
ATTACAGCCCCAACAAGAAGGTGTCCCGTAAGGTAGGATGTTCAGAATGGGTCTGCTCTGCTCAACAGG
TTGCAGTCTCTACCTCAGCAAACCCGGCCCCTGTCTCGGAGCTTGACATAAGGGCCCTCTCTAAGAGGT
TCCAGAACCCTTTGATCTCGGGCTTGAGAGTGGTTCAGTGGGCAACCGGTGCTCATTATAAGCTTAAGC
CTATTCTAGATGATCTCAATGTTTTCCCATCTCTCTGCCTTGTAGTTGGGGACGGGTCAGGGGGATAT
CAAGGGCAGTCCTCAACATGTTTCCAGATGCCAAGCTTGTGTTCAACAGTCTTTTAGAGGTGAATGACC
TGATGGCTTCCGGAACACATCCACTGCCTCCTTCAGCAATCATGAGGGGAGGAAATGATATCGTCTCCA
GAGTGATAGATCTTGACTCAATCTGGGAAAAACCGTCCGACTTGAGAAACTTGGCAACCTGGAAATACT
TCCAGTCAGTCCAAAAGCAGGTCAACATGTCCTATGACCTCATTATTTGCGATGCAGAAGTTACTGACA
TTGCATCTATCAACCGGATCACCCTGTTAATGTCCGATTTTGCATTGTCTATAGATGGACCACTCTATT
TGGTCTTCAAAACTTATGGGACTATGCTAGTAAATCCAAACTACAAGGCTATTCAACACCTGTCAAGAG
CGTTCCCCTCGGTCACAGGGTTTATCACCCAAGTAACTTCGTCTTTTTCATCTGAGCTCTACCTCCGAT
TCTCCAAACGAGGGAAGTTTTTCAGAGATGCTGAGTACTTGACCTCTTCCACCCTTCGAGAAATGAGCC
TTGTGTTATTCAATTGTAGCAGCCCCAAGAGTGAGATGCAGAGAGCTCGTTCCTTGAACTATCAGGATC
TTGTGAGAGGATTTCCTGAAGAAATCATATCAAATCCTTACAATGAGATGATCATAACTCTGATTGACA
GTGATGTAGAATCTTTTCTAGTCCACAAGATGGTTGATGATCTTGAGTTACAGAGGGGAACTCTGTCTA
AAGTGGCTATCATTATAGCCATCATGATAGTTTTCTCCAACAGAGTCTTCAACGTTTCCAAACCCCTAA
CTGACCCCTCGTTCTATCCACCGTCTGATCCCAAAATCCTGAGGCACTTCAACATATGTTGCAGTACTA
```

-continued

```
TGATGTATCTATCTACTGCTTTAGGTGACGTCCCTAGCTTCGCAAGACTTCACGACCTGTATAACAGAC

CTATAACTTATTACTTCAGAAAGCAAGTCATTCGAGGGAACGTTTATCTATCTTGGAGTTGGTCCAACG

ACACCTCAGTGTTCAAAAGGGTAGCCTGTAATTCTAGCCTGAGTCTGTCATCTCACTGGATCAGGTTGA

TTTACAAGATAGTGAAGACTACCAGACTCGTTGGCAGCATCAAGGATCTATCCAGAGAAGTGGAAAGAC

ACCTTCATAGGTACAACAGGTGGATCACCCTAGAGGATATCAGATCTAGATCATCCCTACTAGACTACA

GTTGCCTGTGAACCGGATACTCCTGGAAGCCTGCCCATGCTAAGACTCTTGTGTGATGTATCTTGAAAA

AAACAAGATCCTAAATCTGAACCTTTGGTTGTTTGATTGTTTTTCTCAttttttgttgttttatttgttaa gcgt
```

SEQ ID NO: 44: Nucleotide sequence of the BNSP333-GP$_{GCD}$ vaccine vector of the Examples

```
ACGCTTAACAACCAGATCAAAGAAAAAACAGACATTGTCAATTGCAAAGCAAAAATGTAACACCCCTAC

AATGGATGCCGACAAGATTGTATTCAAAGTCAATAATCAGGTGGTCTCTTTGAAGCCTGAGATTATCGT

GGATCAATATGAGTACAAGTACCCTGCCATCAAAGATTTGAAAAAGCCCTGTATAACCCTAGGAAAGGC

TCCCGATTTAAATAAAGCATACAAGTCAGTTTTGTCAGGCATGAGCGCCGCCAAACTTAATCCTGACGA

TGTATGTTCCTATTTGGCAGCGGCAATGCAGTTTTTTGAGGGGACATGTCCGGAAGACTGGACCAGCTA

TGGAATTGTGATTGCACGAAAAGGAGATAAGATCACCCCAGGTTCTCTGGTGGAGATAAAACGTACTGA

TGTAGAAGGGAATTGGGCTCTGACAGGAGGCATGGAACTGACAAGAGACCCCACTGTCCCTGAGCATGC

GTCCTTAGTCGGTCTTCTCTTGAGTCTGTATAGGTTGAGCAAAATATCCGGGCAAAACACTGGTAACTA

TAAGACAAACATTGCAGACAGGATAGAGCAGATTTTTGAGACAGCCCCTTTTGTTAAAATCGTGGAACA

CCATACTCTAATGACAACTCACAAaATGTGTGCTAATTGGAGTACTATACCAAACTTCAGATTTTTGGC

CGGAACCTATGACATGTTTTTCTCCCGGATTGAGCATCTATATTCAGCAATCAGAGTGGGCACAGTTGT

CACTGCTTATGAAGACTGTTCAGGACTGGTATCATTTACTGGGTTCATAAAACAAATCAATCTCACCGC

TAGAGAGGCAATACTATATTTCTTCCACAAGAACTTTGAGGAAGAGATAAGAAGAATGTTTGAGCCAGG

GCAGGAGACAGCTGTTCCTCACTCTTATTTCATCCACTTCCGTTCACTAGGCTTGAGTGGGAAATCTCC

TTATTCATCAAATGCTGTTGGTCACGTGTTCAATCTCATTCACTTTGTAGGATGCTATATGGGTCAAGT

CAGATCCCTAAATGCAACGGTTATTGCTGCATGTGCTCCTCATGAAATGTCTGTTCTAGGGGCTATCT

GGGAGAGGAATTCTTCGGGAAAGGGACATTTGAAAGAAGATTCTTCAGAGATGAGAAAGAACTTCAAGA

ATACGAGGCGGCTGAACTGACAAAGACTGACGTAGCACTGGCAGATGATGGAACTGTCAACTCTGACGA

CGAGGACTACTTTTCAGGTGAAACCAGAAGTCCGGAGGCTGTTTATACTCGAATCATGATGAATGGAGG

TCGACTAAAGAGATCTCACATACGGAGATATGTCTCAGTCAGTTCCAATCATCAAGCCCGTCCAAACTC

ATTCGCCGAGTTTCTAAACAAGACATATTCGAGTGACTCATAAcatgaaaaaaactaacacccctcccG

TACGCCGCCACCatgGGTGTTACAGGAATATTGCAGTTACCTCGTGATCGATTCAAGAGGACATCATTC

TTTCTTTGGGTAATTATCCTTTTCCAAAGAACATTTTCCATCCCACTTGGAGTCATCCACAATAGCACA

TTACAGGTTAGTGATGTCGACAAACTAGTTTGTCGTGACAAACTGTCATCCACAAATCAATTGAGATCA

GTTGGACTGAATCTCGAAGGGAATGGAGTGGCAACTGACGTGCCATCTGCAACTAAAAGATGGGCTTC

AGGTCCGGTGTCCCACCAAAGGTGGTCAATTATGAAGCTGGTGAATGGGCTGAAAACTGCTACAATCTT

GAAATCAAAAAACCTGACGGGAGTGAGTGTCTACCAGCAGCGCCAGACGGGATTCGGGGCTTCCCCCGG

TGCCGGTATGTGCACAAAGTATCAGGAACGGGACCGTGTGCCGGAGACTTTGCCTTCCATAAAGAGGGT

GCTTTCTTCCTGTATGATCGACTTGCTTCCACAGTTATCTACCGAGGAACGACTTTCGCTGAAGGTGTC

GTTGCATTTCTGATACTGCCCCAAGCTAAGAAGGACTTCTTCAGCTCACACCCCTTGAGAGAGCCGGTC

AATGCAACGGAGGACCCGTCTAGTGGCTACTATTCTACCACAATTAGATATCAGGCTACCGGTTTTGGA

ACCAATGAGACAGAGTACTTGTTCGAGGTTGACAATTTGACCTACGTCCAACTTGAATCAAGATTCACA
```

-continued

```
CCACAGTTTCTGCTCCAGCTGAATGAGACAATATATACAAGTGGGAAAAGGAGCAATACCACGGGAAAA
CTAATTTGGAAGGtCAACCCCGAAATTGATACAACAATCGGGGAGTGGGCCTTCTGGGAAacTAAAAAA
AACCTCACTAGAAAAaTTCGCAGTGAAGAGTTgTCTTTCACAGTTGTATCAAACAGAGCCAAAAACATC
AGTGGTCAGAGTCCGGCGCGAACTTCTTCCGACCCAGGGACCAACACAACAACTGAAGACCACAAAATC
ATGGCTTCAGAAAATTCCTCTGCAATGGTTCAAGTGCACAGTCAAGGAAGGGAAGCTGCAGTGTCGCAT
CTGACAACCCCTGCCACAATCTCCACGAGTCTTCAACCCCCCACAACCAAACCAGGTCCGGACAACAGC
ACCCACAATACACCCGTGTATAAACTTGACATCTCTGAGGCAACTCAAGTTGAACAACATCACCGCAGA
ACAGACAACGACAGCACAGCcTCCGACACTCCcTCTGCCACGACcGCAGCCGGACCCCCAAAAGCAGAG
AACACCAACACGAGCAAGAGCACTGACTTCCTGGACCCCGCCACCACAACAAGTCCCCAAAACCACAGC
GAGACCGCTGGCAACAACAACACTCATCACCAAGATACCGGAGAAGAGAGTGCCAGCAGCGGGAAGCTA
GGCTTAATTACCAATACTATTGCTGGAGTCGCAGGACTGATCACAGGCGGGAGAAGAACTCGAAGAGAA
GCAATTGTCAATGCTCAACCCAAATGCAACCCTAATTTACATTACTGGACTACTCAGGATGAAGGTGCT
GCAATCGGACTGGCCTGGATACCATATTTCGGGCCAGCAGCCGAGGGAATTTACATAGAGGGGCTAATG
CACAATCAAGATGGTTTAATCTGTGGGTTGAGACAGCTGGCCAACGAGACGACTCAAGCTCTTCAACTG
TTCCTGAGAGCCACAACTGAGCTACGCACCTTTTCAATCCTCAACCGTAAGGCAATTGATTTCTTGCTG
CAGCGATGGGGCGGCACATGCCACATTCTGGGACCGGACTGCTGTATCGAACCACATGATTGGACCAAG
AACATAACAGACAAAATTGATCAGATTATTCATGATTTTGTTGATAAAACCCTTCCGGACCAGGGGGAC
AATGACAATTGGTGGACAGGATGGAGACAATGGATACCGGCAGGTATTGGAGTTACAGGCGTTGTAATT
GCAGTTATCGCTTTATTCTGTATATGCgttaacAGAAGAGTCAATCGATCAGAACCTACGCAACACAAT
CTCAGAGGGACAGGGAGGGAGGTGTCAGTCACTCCCCAAAGCGGGAAGATCATATCTTCATGGGAATCA
CACAAGAGTGGGGGTGAGACCAGACTGTAAgCTAGCCATGAAAAAAACTAACACCCCTCCTTTCGAACC
ATCCCAAACATGAGCAAGATCTTTGTCAATCCTAGTGCTATTAGAGCCGGTCTGGCCGATCTTGAGATG
GCTGAAGAAACTGTTGATCTGATCAATAGAAATATCGAAGACAATCAGGCTCATCTCCAAGGGGAACCC
ATAGAGGTGGACAATCTCCCTGAGGATATGGGGCGACTTCACCTGGATGATGGAAAATCGCCCAACCAT
GGTGAGATAGCCAAGGTGGGAGAAGGCAAGTATCGAGAGGACTTTCAGATGGATGAAGGAGAGGATCCT
AGCTTCCTGTTCCAGTCATACCTGGAAAATGTTGGAGTCCAAATAGTCAGACAAATGAGGTCAGGAGAG
AGATTTCTCAAGATATGGTCACAGACCGTAGAAGAGATTATATCCTATGTCGCGGTCAACTTTCCCAAC
CCTCCAGGAAAGTCTTCAGAGGATAAATCAACCCAGACTACTGGCCGAGAGCTCAAGAAGGAGACAACA
CCCACTCCTTCTCAGAGAGAAAGCCAATCATCGAAAGCCAGGATGGCGGCTCAAATTGCTTCTGGCCCT
CCAGCCCTTGAATGGTCGGCTACCAATGAAGAGGATGATCTATCAGTGGAGGCTGAGATCGCTCACCAG
ATTGCAGAAAGTTTCTCCAAAAAATATAAGTTTCCCTCTCGATCCTCAGGGATACTCTTGTATAATTTT
GAGCAATTGAAAATGAACCTTGATGATATAGTTAAAGAGGCAAAAAATGTACCAGGTGTGACCCGTTTA
GCCCATGACGGGTCCAAACTCCCCCTAAGATGTGTACTGGGATGGGTCGCTTTGGCCAACTCTAAGAAA
TTCCAGTTGTTAGTCGAATCCGACAAGCTGAGTAAAATCATGCAAGATGACTTGAATCGCTATACATCT
TGCTAACCGAACCTCTCCCCTCAGTCCCTCTAGACAATAAAATCCGAGATGTCCCAAAGTCAACATGAA
AAAAACAGGCAACACCACTGATAAAATGAACCTCCTACGTAAGATAGTGAAAAACCGCAGGGACGAGGA
CACTCAAAAATCCTCTCCCGCGTCAGCCCCTCTGGATGACGATGACTTGTGGCTTCCACCCCCTGAATA
CGTCCCGCTGAAAGAACTTACAGGCAAGAAGAACATGAGGAACTTTTGTATCAACGGAAGGGTTAAAGT
GTGTAGCCCGAATGGTTACTCGTTCAGGATCCTGCGGCACATTCTGAAATCATTCGACGAGATATATTC
TGGGAATCATAGGATGATCGGGTTAGTCAAAGTGGTTATTGGACTGGCTTTGTCAGGATCTCCAGTCCC
TGAGGGCCTGAACTGGGTATACAAATTGAGGAGAACCTTTATCTTCCAGTGGGCTGATTCCAGGGGCCC
```

-continued

```
TCTTGAAGGGGAGGAGTTGGAATACTCTCAGGAGATCACTTGGGATGATGATACTGAGTTCGTCGGATT
GCAAATAAGAGTGATTGCAAAACAGTGTCATATCCAGGGCAGAGTCTGGTGTATCAACATGAACCCGAG
AGCATGTCAACTATGGTCTGACATGTCTCTTCAGACACAAAGGTCCGAAGAGGACAAAGATTCCTCTCT
GCTTCTAGAATAATCAGATTATATCCCGCAAATTTATCACTTGTTTACCTCTGGAGGAGAGAACATATG
GGCTCAACTCCAACCCTTGGGAGCAATATAACAAAAAACATGTTATGGTGCCATTAAACCGCTGCATTT
CATCAAAGTCAAGTTGATTACCTTTACATTTTGATCCTCTTGGATGTGAAAAAAACTATTAACATCCCT
CAAAAGACcccgggAAAGATGGTTCCTCAGGCTCTCCTGTTTGTACCCCTTCTGGTTTTTCCATTGTGT
TTTGGGAAATTCCCTATTTACACGATACCAGACAAGCTTGGTCCCTGGAGTCCGATTGACATACATCAC
CTCAGCTGCCCAAACAATTTGGTAGTGGAGGACGAAGGATGCACCAACCTGTCAGGGTTCTCCTACATG
GAACTTAAAGTTGGATACATCTTAGCCATAAAAGTGAACGGGTTCACTTGCACAGGCGTTGTGACGGAG
GCTGAAACCTACACTAACTTCGTTGGTTATGTCACAACCACGTTCAAAAGAAAGCATTTCCGCCCAACA
CCAGATGCATGTAGAGCCGCGTACAACTGGAAGATGGCCGGTGACCCCAGATATGAAGAGTCTCTACAC
AATCCGTACCCTGACTACCGCTGGCTTCGAACTGTAAAAACCACCAAGGAGTCTCTCGTTATCATATCT
CCAAGTGTGGCAGATTTGGACCCATATGACAGATCCCTTCACTCGAGGGTCTTCCCTAGCGGGAAGTGC
TCAGGAGTAGCGGTGTCTTCTACCTACTGCTCCACTAACCACGATTACACCATTTGGATGCCCGAGAAT
CCGAGACTAGGGATGTCTTGTGACATTTTTACCAATAGTAGAGGGAAGAGAGCATCCAAAGGGAGTGAG
ACTTGCGGCTTTGTAGATGAAAGAGGCCTATATAAGTCTTTAAAAGGAGCATGCAAACTCAAGTTATGT
GGAGTTCTAGGACTTAGACTTATGGATGGAACATGGGTCTCGATGCAAACATCAAATGAAACCAAATGG
TGCCCTCCCGATAAGTTGGTGAACCTGCACGACTTTCGCTCAGACGAAATTGAGCACCTTGTTGTAGAG
GAGTTGGTCAGGAAGAGAGAGGAGTGTCTGGATGCACTAGAGTCCATCATGACAACCAAGTCAGTGAGT
TTCAGACGTCTCAGTCATTTAAGAAAACTTGTCCCTGGGTTTGGAAAAGCATATACCATATTCAACAAG
ACCTTGATGGAAGCCGATGCTCACTACAAGTCAGTCgagACTTGGaatGAGATCCTCCCTTCAAAAGGG
TGTTTAAGAGTTGGGGGAGGTGTCATCCTCATGTGAACGGGGTGTTTTTCAATGGTATAATATTAGGA
CCTGACGGCAATGTCTTAATCCCAGAGATGCAATCATCCCTCCTCCAGCAACATATGGAGTTGTTGGAA
TCCTCGGTTATCCCCCTTGTGCACCCCCTGGCAGACCCGTCTACCGTTTTCAAGGACGGTGACGAGGCT
GAGGATTTTGTTGAAGTTCACCTTCCCGATGTGCACAATCAGGTCTCAGGAGTTGACTTGGGTCTCCCG
AACTGGGGGAAGTATGTATTACTGAGTGCAGGGGCCCTGACTGCCTTGATGTTGATAATTTTCCTGATG
ACATGTTGTAGAAGAGTCAATCGATCAGAACCTACGCAACACAATCTCAGAGGGACAGGGAGGGAGGTG
TCAGTCACTCCCCAAAGCGGGAAGATCATATCTTCATGGGAATCACACAAGAGTGGGGGTGAGACCAGA
CTGTAAttaattaaCGTCCTTTCAACGATCCAAGTCcatgaaaaaaactaacacccctcccgtacctag
cTTATAAAGTGCTGGGTCATCTAAGCTTTTCAGTCGAGAAAAAAACATTAGATCAGAAGAACAACTGGC
AACACTTCTCAACCTGAGACTTACTTCAAGATGCTCGATCCTGGAGAGGTCTATGATGACCCTATTGAC
CCAATCGAGTTAGAGGCTGAACCCAGAGGAACCCCCATTGTCCCCAACATCTTGAGGAACTCTGACTAC
AATCTCAACTCTCCTTTGATAGAAGATCCTGCTAGACTAATGTTAGAATGGTTAAAAACAGGGAATAGA
CCTTATCGGATGACTCTAACAGACAATTGCTCCAGGTCTTTCAGAGTTTTGAAAGATTATTTCAAGAAG
GTAGATTTGGGTTCTCTCAAGGTGGGCGGAATGGCTGCACAGTCAATGATTTCTCTCTGGTTATATGGT
GCCCACTCTGAATCCAACAGGAGCCGGAGATGTATAACAGACTTGGCCCATTTCTATTCCAAGTCGTCC
CCCATAGAGAAGCTGTTGAATCTCACGCTAGGAAATAGAGGGCTGAGAATCCCCCCAGAGGGAGTGTTA
AGTTGCCTTGAGAGGGTTGATTATGATAATGCATTTGGAAGGTATCTTGCCAACACGTATTCCTCTTAC
TTGTTCTTCCATGTAATCACCTTATACATGAACGCCCTAGACTGGGATGAAGAAAAGACCATCCTAGCA
TTATGGAAAGATTTAACCTCAGTGGACATCGGGAAGGACTTGGTAAAGTTCAAAGACCAAATATGGGGA
```

-continued
CTGCTGATCGTGACAAAGGACTTTGTTTACTCCCAAAGTTCCAATTGTCTTTTTGACAGAAACTACACA

CTTATGCTAAAAGATCTXTTCTTGTCTCGCTTCAACTCCTTAATGGTCTTGCTCTCTCCCCCAGAGCCC

CGATACTCAGATGACTTGATATCTCAACTATGCCAGCTGTACATTGCTGGGGATCAAGTCTTGTCTATG

TGTGGAAACTCCGGCTATGAAGTCATCAAAATATTGGAGCCATATGTCGTGAATAGTTTAGTCCAGAGA

GCAGAAAAGTTTAGGCCTCTCATTCATTCCTTGGGAGACTTTCCTGTATTTATAAAAGACAAGGTAAGT

CAACTTGAAGAGACGTTCGGTCCCTGTGCAAGAAGGTTCTTTAGGGCTCTGGATCAATTCGACAACATA

CATGACTTGGTTTTTGTGTTTGGCTGTTACAGGCATTGGGGGCACCCATATATAGATTATCGAAAGGGT

CTGTCAAAACTATATGATCAGGTTCACCTTAAAAAAATGATAGATAAGTCCTACCAGGAGTGCTTAGCA

AGCGACCTAGCCAGGAGGATCCTTAGATGGGGTTTTGATAAGTACTCCAAGTGGTATCTGGATTCAAGA

TTCCTAGCCCGAGACCACCCCTTGACTCCTTATATCAAAACCCAAACATGGCCACCCAAACATATTGTA

GACTTGGTGGGGATACATGGCACAAGCTCCCGATCACGCAGATCTTTGAGATTCCTGAATCAATGGAT

CCGTCAGAAATATTGGATGACAAATCACATTCTTTCACCAGAACGAGACTAGCTTCTTGGCTGTCAGAA

AACCGAGGGGGCCTGTTCCTAGCGAAAAAGTTATTATCACGGCCCTGTCTAAGCCGCCTGTCAATCCC

CGAGAGTTTCTGAGGTCTATAGACCTCGGAGGATTGCCAGATGAAGACTTGATAATTGGCCTCAAGCCA

AAGGAACGGGAATTGAAGATTGAAGGTCGATTCTTTGCTCTAATGTCATGGAATCTAAGATTGTATTTT

GTCATCACTGAAAAACTCTTGGCCAACTACATCTTGCCACTTTTTGACGCGCTGACTATGACAGACAAC

CTGAACAAGGTGTTTAAAAAGCTGATCGACAGGGTCACCGGGCAAGGGCTTTTGGACTATTCAAGGGTC

ACATATGCATTTCACCTGGACTATGAAAAGTGGAACAACCATCAAAGATTAGAGTCAACAGAGGATGTA

TTTTCTGTCCTAGATCAAGTGTTTGGATTGAAGAGAGTGTTTTCTAGAACACACGAGTTTTTTCAAAAG

GCCTGGATCTATTATTCAGACAGATCAGACCTCATCGGGTTACGGGAGGATCAAATATACTGCTTAGAT

GCGTCCAACGGCCCAACCTGTTGGAATGGCCAGGATGGCGGGCTAGAAGGCTTACGGCAGAAGGGCTGG

AGTCTAGTCAGCTTATTGATGATAGATAGAGAATCTCAAATCAGGAACACAAGAACCAAAATACTAGCT

CAAGGAGACAACCAGGTTTTATGTCCGACATACATGTTGTCGCCAGGGCTATCTCAAGAGGGGCTCCTC

TATGAATTGGAGAGAATATCAAGGAATGCACTTTCGATATACAGAGCCGTCGAGGAAGGGGCATCTAAG

CTAGGGCTGATCATCAAGAAAGAAGAGACCATGTGTAGTTATGACTTCCTCATCTATGGAAAAACCCCT

TTGTTTAGAGGTAACATATTGGTGCCTGAGTCCAAAAGATGGGCCAGAGTCTCTTGCGTCTCTAATGAC

CAAATAGTCAACCTCGCCAATATAATGTCGACAGTGTCCACCAATGCGCTAACAGTGGCACAACACTCT

CAATCTTTGATCAAACCGATGAGGGATTTTCTGCTCATGTCAGTACAGGCAGTCTTTCACTACCTGCTA

TTTAGCCCAATCTTAAAGGGAAGAGTTTACAAGATTCTGAGCGCTGAAGGGGAGAGCTTTCTCCTAGCC

ATGTCAAGGATAATCTATCTAGATCCTTCTTTGGGAGGGATATCTGGAATGTCCCTCGGAAGATTCCAT

ATACGACAGTTCTCAGACCCTGTCTCTGAAGGGTTATCCTTCTGGAGAGAGATCGGTTAAGCTCCCAA

GAGTCCTGGATTCACGCGTTGTGTCAAGAGGCTGGAAACCCAGATCTTGGAGAGAGAACACTCGAGAGC

TTCACTCGCCTTCTAGAAGATCCGACCACCTTAAATATCAGAGGAGGGGCCAGTCCTACCATTCTACTC

AAGGATGCAATCAGAAAGGCTTTATATGACGAGGTGGACAAGGTGGAAAATTCAGAGTTTCGAGAGGCA

ATCCTGTTGTCCAAGACCCATAGAGATAATTTTATACTCTTCTTAATATCTGTTGAGCCTCTGTTTCCT

CGATTTCTCAGTGAGCTATTCAGTTCGTCTTTTTTGGGAATCCCCGAGTCAATCATTGGATTGATACAA

AACTCCCGAACGATAAGAAGGCAGTTTAGAAAGAGTCTCTCAAAAACTTTAGAAGAATCCTTCTACAAC

TCAGAGATCCACGGGATTAGTCGGATGACCCAGACACCTCAGAGGGTTGGGGGGGTGTGGCCTTGCTCT

TCAGAGAGGGCAGATCTACTTAGGGAGATCTCTTGGGGAAGAAAAGTGGTAGGCACGACAGTTCCTCAC

CCTTCTGAGATGTTGGGATTACTTCCCAAGTCCTCTATTTCTTGCACTTGTGGAGCAACAGGAGGAGGC

AATCCTAGAGTTTCTGTATCAGTACTCCCGTCCTTTGATCAGTCATTTTTTTCACGAGGCCCCCTAAAG

-continued

```
GGATACTTGGGCTCGTCCACCTCTATGTCGACCCAGCTATTCCATGCATGGGAAAAAGTCACTAATGTT
CATGTGGTGAAGAGAGCTCTATCGTTAAAAGAATCTATAAACTGGTTCATTACTAGAGATTCCAACTTG
GCTCAAGCTCTAATTAGGAACATTATGTCTCTGACAGGCCCTGATTTCCCTCTAGAGGAGGCCCCTGTC
TTCAAAAGGACGGGGTCAGCCTTGCATAGGTTCAAGTCTGCCAGATACAGCGAAGGAGGGTATTCTTCT
GTCTGCCCGAACCTCCTCTCTCATATTTCTGTTAGTACAGACACCATGTCTGATTTGACCCAAGACGGG
AAGAACTACGATTTCATGTTCCAGCCATTGATGCTTTATGCACAGACATGGACATCAGAGCTGGTACAG
AGAGACACAAGGCTAAGAGACTCTACGTTTCATTGGCACCTCCGATGCAACAGGTGTGTGAGACCCATT
GACGACGTGACCCTGGAGACCTCTCAGATCTTCGAGTTTCCGGATGTGTCGAAAAGAATATCCAGAATG
GTTTCTGGGGCTGTGCCTCACTTCCAGAGGCTTCCCGATATCCGTCTGAGACCAGGAGATTTTGAATCT
CTAAGCGGTAGAGAAAAGTCTCACCATATCGGATCAGCTCAGGGGCTCTTATACTCAATCTTAGTGGCA
ATTCACGACTCAGGATACAATGATGGAACCATCTTCCCTGTCAACATATACGGCAAGGTTTCCCCTAGA
GACTATTTGAGAGGGCTCGCAAGGGGAGTATTGATAGGATCCTCGATTTGCTTCTTGACAAGAATGACA
AATATCAATATTAATAGACCTCTTGAATTGGTCTCAGGGGTAATCTCATATATTCTCCTGAGGCTAGAT
AACCATCCCTCCTTGTACATAATGCTCAGAGAACCGTCTCTTAGAGGAGAGATATTTTCTATCCCTCAG
AAAATCCCCGCCGCTTATCCAACCACTATGAAAGAAGGCAACAGATCAATCTTGTGTTATCTCCAACAT
GTGCTACGCTATGAGCGAGAGATAATCACGGCGTCTCCAGAGAATGACTGGCTATGGATCTTTTCAGAC
TTTAGAAGTGCCAAAATGACGTACCTATCCCTCATTACTTACCAGTCTCATCTTCTACTCCAGAGGGTT
GAGAGAAACCTATCTAAGAGTATGAGAGATAACCTGCGACAATTGAGTTCTTTGATGAGGCAGGTGCTG
GGCGGGCACGGAGAAGATACCTTAGAGTCAGACGACAACATTCAACGACTGCTAAAAGACTCTTTACGA
AGGACAAGATGGGTGGATCAAGAGGTGCGCCATGCAGCTAGAACCATGACTGGAGATTACAGCCCCAAC
AAGAAGGTGTCCCGTAAGGTAGGATGTTCAGAATGGGTCTGCTCTGCTCAACAGGTTGCAGTCTCTACC
TCAGCAAACCCGGCCCCTGTCTCGGAGCTTGACATAAGGGCCCTCTCTAAGAGGTTCCAGAACCCTTTG
ATCTCGGGCTTGAGAGTGGTTCAGTGGGCAACCGGTGCTCATTATAAGCTTAAGCCTATTCTAGATGAT
CTCAATGTTTTCCCATCTCTCTGCCTTGTAGTTGGGGACGGGTCAGGGGGATATCAAGGGCAGTCCTC
AACATGTTTCCAGATGCCAAGCTTGTGTTCAACAGTCTTTTAGAGGTGAATGACCTGATGGCTTCCGGA
ACACATCCACTGCCTCCTTCAGCAATCATGAGGGGAGGAAATGATATCGTCTCCAGAGTGATAGATCTT
GACTCAATCTGGGAAAAACCGTCCGACTTGAGAAACTTGGCAACCTGGAAATACTTCCAGTCAGTCCAA
AAGCAGGTCAACATGTCCTATGACCTCATTATTTGCGATGCAGAAGTTACTGACATTGCATCTATCAAC
CGGATCACCCTGTTAATGTCCGATTTTGCATTGTCTATAGATGGACCACTCTATTTGGTCTTCAAAACT
TATGGGACTATGCTAGTAAATCCAAACTACAAGGCTATTCAACACCTGTCAAGAGCGTTCCCCTCGGTC
ACAGGGTTTATCACCCAAGTAACTTCGTCTTTTTCATCTGAGCTCTACCTCCGATTCTCCAAACGAGGG
AAGTTTTTCAGAGATGCTGAGTACTTGACCTCTTCCACCCTTCGAGAAATGAGCCTTGTGTTATTCAAT
TGTAGCAGCCCCAAGAGTGAGATGCAGAGAGCTCGTTCCTTGAACTATCAGGATCTTGTGAGAGGATTT
CCTGAAGAAATCATATCAAATCCTTACAATGAGATGATCATAACTCTGATTGACAGTGATGTAGAATCT
TTTCTAGTCCACAAGATGGTTGATGATCTTGAGTTACAGAGGGGAACTCTGTCTAAAGTGGCTATCATT
ATAGCCATCATGATAGTTTTCTCCAACAGAGTCTTCAACGTTTCCAAACCCCTAACTGACCCCTCGTTC
TATCCACCGTCTGATCCCAAAATCCTGAGGCACTTCAACATATGTTGCAGTACTATGATGTATCTATCT
ACTGCTTTAGGTGACGTCCCTAGCTTCGCAAGACTTCACGACCTGTATAACAGACCTATAACTTATTAC
TTCAGAAAGCAAGTCATTCGAGGGAACGTTTATCTATCTTGGAGTTGGTCCAACGACACCTCAGTGTTC
AAAAGGGTAGCCTGTAATTCTAGCCTGAGTCTGTCATCTCACTGGATCAGGTTGATTTACAAGATAGTG
AAGACTACCAGACTCGTTGGCAGCATCAAGGATCTATCCAGAGAAGTGGAAAGACACCTTCATAGGTAC
```

-continued

AACAGGTGGATCACCCTAGAGGATATCAGATCTAGATCATCCCTACTAGACTACAGTTGCCTGTGAACC

GGATACTCCTGGAAGCCTGCCCATGCTAAGACTCTTGTGTGATGTATCTTGAAAAAAACAAGATCCTAA

ATCTGAACCTTTGGTTGTTTGATTGTTTTTCTCAttttttgttgtttatttgttaagcgt

SEQ ID NO: 45: Nucleotide sequence of the BNSPΔG-GP vaccine vector of the Examples
ACGCTTAACAACCAGATCAAAGAAAAAAC -continued

```
CTGACAACCCCTGCCACAATCTCCACGAGTCTTCAACCCCCCACAACCAAACCAGGTCCGGACAACAGC
ACCCACAATACACCCGTGTATAAACTTGACATCTCTGAGGCAACTCAAGTTGAACAACATCACCGCAGA
ACAGACAACGACAGCACAGCcTCCGACACTCCcTCTGCCACGACcGCAGCCGGACCCCCAAAAGCAGAG
AACACCAACACGAGCAAGAGCACTGACTTCCTGGACCCCGCCACCACAACAAGTCCCCAAAACCACAGC
GAGACCGCTGGCAACAACAACACTCATCACCAAGATACCGGAGAAGAGAGTGCCAGCAGCGGGAAGCTA
GGCTTAATTACCAATACTATTGCTGGAGTCGCAGGACTGATCACAGGCGGGAGAAGAACTCGAAGAGAA
GCAATTGTCAATGCTCAACCCAAATGCAACCCTAATTTACATTACTGGACTACTCAGGATGAAGGTGCT
GCAATCGGACTGGCCTGGATACCATATTTCGGGCCAGCAGCCGAGGGAATTTACATAGAGGGGCTAATG
CACAATCAAGATGGTTTAATCTGTGGGTTGAGACAGCTGGCCAACGAGACGACTCAAGCTCTTCAACTG
TTCCTGAGAGCCACAACTGAGCTACGCACCTTTTCAATCCTCAACCGTAAGGCAATTGATTTCTTGCTG
CAGCGATGGGCGGCACATGCCACATTCTGGGACCGGACTGCTGTATCGAACCACATGATTGGACCAAG
AACATAACAGACAAAATTGATCAGATTATTCATGATTTTGTTGATAAAACCCTTCCGGACCAGGGGAC
AATGACAATTGGTGGACAGGATGGAGACAATGGATACCGGCAGGTATTGGAGTTACAGGCGTTGTAATT
GCAGTTATCGCTTTATTCTGTATATGCAAATTTGTCTTTTAGGAGCTAGCCATGAAAAAAACTAACACC
CCTCCTTTCGAACCATCCCAAACATGAGCAAGATCTTTGTCAATCCTAGTGCTATTAGAGCCGGTCTGG
CCGATCTTGAGATGGCTGAAGAAACTGTTGATCTGATCAATAGAAATATCGAAGACAATCAGGCTCATC
TCCAAGGGGAACCCATAGAGGTGGACAATCTCCCTGAGGATATGGGCGACTTCACCTGGATGATGGAA
AATCGCCCAACCATGGTGAGATAGCCAAGGTGGGAGAAGGCAAGTATCGAGAGGACTTTCAGATGGATG
AAGGAGAGGATCCTAGCTTCCTGTTCCAGTCATACCTGGAAAATGTTGGAGTCCAAATAGTCAGACAAA
TGAGGTCAGGAGAGAGATTTCTCAAGATATGGTCACAGACCGTAGAAGAGATTATATCCTATGTCGCGG
TCAACTTTCCCAACCCTCCAGGAAAGTCTTCAGAGGATAAATCAACCCAGACTACTGGCCGAGAGCTCA
AGAAGGAGACAACACCCACTCCTTCTCAGAGAGAAAGCCAATCATCGAAAGCCAGGATGGCGGCTCAAA
TTGCTTCTGGCCCTCCAGCCCTTGAATGGTCGGCTACCAATGAAGAGGATGATCTATCAGTGGAGGCTG
AGATCGCTCACCAGATTGCAGAAAGTTTCTCCAAAAAATATAAGTTTCCCTCTCGATCCTCAGGGATAC
TCTTGTATAATTTTGAGCAATTGAAAATGAACCTTGATGATATAGTTAAAGAGGCAAAAAATGTACCAG
GTGTGACCCGTTTAGCCCATGACGGGTCCAAACTCCCCCTAAGATGTGTACTGGGATGGGTCGCTTTGG
CCAACTCTAAGAAATTCCAGTTGTTAGTCGAATCCGACAAGCTGAGTAAAATCATGCAAGATGACTTGA
ATCGCTATACATCTTGCTAACCGAACCTCTCCCCTCAGTCCCTCTAGACAATAAAATCCGAGATGTCCC
AAAGTCAACATGAAAAAAACAGGCAACACCACTGATAAAATGAACCTCCTACGTAAGATAGTGAAAAAC
CGCAGGGACGAGGACACTCAAAAATCCTCTCCCGCGTCAGCCCCTCTGGATGACGATGACTTGTGGCTT
CCACCCCCTGAATACGTCCCGCTGAAAGAACTTACAGGCAAGAAGAACATGAGGAACTTTTGTATCAAC
GGAAGGGTTAAAGTGTGTAGCCCGAATGGTTACTCGTTCAGGATCCTGCGGCACATTCTGAAATCATTC
GACGAGATATATTCTGGGAATCATAGGATGATCGGGTTAGTCAAAGTGGTTATTGGACTGGCTTTGTCA
GGATCTCCAGTCCCTGAGGGCCTGAACTGGGTATACAAATTGAGGAGAACCTTTATCTTCCAGTGGGCT
GATTCCAGGGGCCCTCTTGAAGGGAGGAGTTGGAATACTCTCAGGAGATCACTTGGGATGATGATACT
GAGTTCGTCGGATTGCAAATAAGAGTGATTGCAAAACAGTGTCATATCCAGGGCAGAGTCTGGTGTATC
AACATGAACCCGAGAGCATGTCAACTATGGTCTGACATGTCTCTTCAGACACAAAGGTCCGAAGAGGAC
AAAGATTCCTCTCTGCTTCTAGAATAATCAGATTATATCCCGCAAATTTATCACTTGTTTACCTCTGGA
GGGAGAGAACATATGGGCTCAACTCCAACCCTTGGGAGCAATATAACAAAAAACATGTTATGGTGCCATT
AAACCGCTGCATTTCATCAAAGTCAAGTTGATTACCTTTACATTTTGATCCTCTTGGATGTGAAAAAA
CTATTAACATCCCTCAAAAGACccctaaCGTCCTTTCAACGATCCAAGTCcatgaaaaaaactaacacc
```

-continued cctcccgtacctagcTTATAAAGTGCTGGGTCATCTAAGCTTTTCAGTCGAGAAAAAACATTAGATCA

GAAGAACAACTGGCAACACTTCTCAACCTGAGACTTACTTCAAGATGCTCGATCCTGGAGAGGTCTATG

ATGACCCTATTGACCCAATCGAGTTAGAGGCTGAACCCAGAGGAACCCCCATTGTCCCCAACATCTTGA

GGAACTCTGACTACAATCTCAACTCTCCTTTGATAGAAGATCCTGCTAGACTAATGTTAGAATGGTTAA

AAACAGGGAATAGACCTTATCGGATGACTCTAACAGACAATTGCTCCAGGTCTTTCAGAGTTTTGAAAG

ATTATTTCAAGAAGGTAGATTTGGGTTCTCTCAAGGTGGGCGGAATGGCTGCACAGTCAATGATTTCTC

TCTGGTTATATGGTGCCCACTCTGAATCCAACAGGAGCCGGAGATGTATAACAGACTTGGCCCATTTCT

ATTCCAAGTCGTCCCCCATAGAGAAGCTGTTGAATCTCACGCTAGGAAATAGAGGGCTGAGAATCCCCC

CAGAGGGAGTGTTAAGTTGCCTTGAGAGGGTTGATTATGATAATGCATTTGGAAGGTATCTTGCCAACA

CGTATTCCTCTTACTTGTTCTTCCATGTAATCACCTTATACATGAACGCCCTAGACTGGGATGAAGAAA

AGACCATCCTAGCATTATGGAAAGATTTAACCTCAGTGGACATCGGGAAGGACTTGGTAAAGTTCAAAG

ACCAAATATGGGGACTGCTGATCGTGACAAAGGACTTTGTTTACTCCCAAAGTTCCAATTGTCTTTTTG

ACAGAAACTACACACTTATGCTAAAAGATCTTTTCTTGTCTCGCTTCAACTCCTTAATGGTCTTGCTCT

CTCCCCCAGAGCCCCGATACTCAGATGACTTGATATCTCAACTATGCCAGCTGTACATTGCTGGGGATC

AAGTCTTGTCTATGTGTGGAAACTCCGGCTATGAAGTCATCAAAATATTGGAGCCATATGTCGTGAATA

GTTTAGTCCAGAGAGCAGAAAAGTTTAGGCCTCTCATTCATTCCTTGGGAGACTTTCCTGTATTTATAA

AAGACAAGGTAAGTCAACTTGAAGAGACGTTCGGTCCCTGTGCAAGAAGGTTCTTTAGGGCTCTGGATC

AATTCGACAACATACATGACTTGGTTTTTGTGTTTGGCTGTTACAGGCATTGGGGGCACCCATATATAG

ATTATCGAAAGGGTCTGTCAAAACTATATGATCAGGTTCACCTTAAAAAAATGATAGATAAGTCCTACC

AGGAGTGCTTAGCAAGCGACCTAGCCAGGAGGATCCTTAGATGGGGTTTTGATAAGTACTCCAAGTGGT

ATCTGGATTCAAGATTCCTAGCCCGAGACCACCCCTTGACTCCTTATATCAAAACCCAAACATGGCCAC

CCAAACATATTGTAGACTTGGTGGGGATACATGGCACAAGCTCCCGATCACGCAGATCTTTGAGATTC

CTGAATCAATGGATCCGTCAGAAATATTGGATGACAAATCACATTCTTTCACCAGAACGAGACTAGCTT

CTTGGCTGTCAGAAAACCGAGGGGGGCCTGTTCCTAGCGAAAAAGTTATTATCACGGCCCTGTCTAAGC

CGCCTGTCAATCCCCGAGAGTTTCTGAGGTCTATAGACCTCGGAGGATTGCCAGATGAAGACTTGATAA

TTGGCCTCAAGCCAAAGGAACGGGAATTGAAGATTGAAGGTCGATTCTTTGCTCTAATGTCATGGAATC

TAAGATTGTATTTTGTCATCACTGAAAAACTCTTGGCCAACTACATCTTGCCACTTTTTGACGCGCTGA

CTATGACAGACAACCTGAACAAGGTGTTTAAAAAGCTGATCGACAGGGTCACCGGGCAAGGGCTTTTGG

ACTATTCAAGGGTCACATATGCATTTCACCTGGACTATGAAAAGTGGAACAACCATCAAAGATTAGAGT

CAACAGAGGATGTATTTTCTGTCCTAGATCAAGTGTTTGGATTGAAGAGAGTGTTTTCTAGAACACACG

AGTTTTTTCAAAAGGCCTGGATCTATTATTCAGACAGATCAGACCTCATCGGGTTACGGGAGGATCAAA

TATACTGCTTAGATGCGTCCAACGGCCCAACCTGTTGGAATGGCCAGGATGGCGGGCTAGAAGGCTTAC

GGCAGAAGGGCTGGAGTCTAGTCAGCTTATTGATGATAGATAGAGAATCTCAAATCAGGAACACAAGAA

CCAAAATACTAGCTCAAGGAGACAACCAGGTTTTATGTCCGACATACATGTTGTCGCCAGGGCTATCTC

AAGAGGGGCTCCTCTATGAATTGGAGAGAATATCAAGGAATGCACTTTCGATATACAGAGCCGTCGAGG

AAGGGGCATCTAAGCTAGGGCTGATCATCAAGAAAGAAGAGACCATGTGTAGTTATGACTTCCTCATCT

ATGGAAAAACCCCTTTGTTTAGAGGTAACATATTGGTGCCTGAGTCCAAAAGATGGGCCAGAGTCTCTT

GCGTCTCTAATGACCAAATAGTCAACCTCGCCAATATAATGTCGACAGTGTCCACCAATGCGCTAACAG

TGGCACAACACTCTCAATCTTTGATCAAACCGATGAGGGATTTTCTGCTCATGTCAGTACAGGCAGTCT

TTCACTACCTGCTATTTAGCCCAATCTTAAAGGGAAGAGTTTACAAGATTCTGAGCGCTGAAGGGGAGA

GCTTTCTCCTAGCCATGTCAAGGATAATCTATCTAGATCCTTCTTTGGGAGGGATATCTGGAATGTCCC

-continued

```
TCGGAAGATTCCATATACGACAGTTCTCAGACCCTGTCTCTGAAGGGTTATCCTTCTGGAGAGAGATCT

GGTTAAGCTCCCAAGAGTCCTGGATTCACGCGTTGTGTCAAGAGGCTGGAAACCCAGATCTTGGAGAGA

GAACACTCGAGAGCTTCACTCGCCTTCTAGAAGATCCGACCACCTTAAATATCAGAGGAGGGGCCAGTC

CTACCATTCTACTCAAGGATGCAATCAGAAAGGCTTTATATGACGAGGTGGACAAGGTGGAAAATTCAG

AGTTTCGAGAGGCAATCCTGTTGTCCAAGACCCATAGAGATAATTTTATACTCTTCTTAATATCTGTTG

AGCCTCTGTTTCCTCGATTTCTCAGTGAGCTATTCAGTTCGTCTTTTTTGGGAATCCCCGAGTCAATCA

TTGGATTGATACAAAACTCCCGAACGATAAGAAGGCAGTTTAGAAAGAGTCTCTCAAAAACTTTAGAAG

AATCCTTCTACAACTCAGAGATCCACGGGATTAGTCGGATGACCCAGACACCTCAGAGGGTTGGGGGGG

TGTGGCCTTGCTCTTCAGAGAGGGCAGATCTACTTAGGGAGATCTCTTGGGGAAGAAAAGTGGTAGGCA

CGACAGTTCCTCACCCTTCTGAGATGTTGGGATTACTTCCCAAGTCCTCTATTTCTTGCACTTGTGGAG

CAACAGGAGGAGGCAATCCTAGAGTTTCTGTATCAGTACTCCCGTCCTTTGATCAGTCATTTTTTTCAC

GAGGCCCCCTAAAGGGATACTTGGGCTCGTCCACCTCTATGTCGACCCAGCTATTCCATGCATGGGAAA

AAGTCACTAATGTTCATGTGGTGAAGAGAGCTCTATCGTTAAAAGAATCTATAAACTGGTTCATTACTA

GAGATTCCAACTTGGCTCAAGCTCTAATTAGGAACATTATGTCTCTGACAGGCCCTGATTTCCCTCTAG

AGGAGGCCCCTGTCTTCAAAAGGACGGGGTCAGCCTTGCATAGGTTCAAGTCTGCCAGATACAGCGAAG

GAGGGTATTCTTCTGTCTGCCCGAACCTCCTCTCTCATATTTCTGTTAGTACAGACACCATGTCTGATT

TGACCCAAGACGGGAAGAACTACGATTTCATGTTCCAGCCATTGATGCTTTATGCACAGACATGGACAT

CAGAGCTGGTACAGAGAGACACAAGGCTAAGAGACTCTACGTTTCATTGGCACCTCCGATGCAACAGGT

GTGTGAGACCCATTGACGACGTGACCCTGGAGACCCTCTCAGATCTTCGAGTTTCCGGATGTGTCGAAAA

GAATATCCAGAATGGTTTCTGGGGCTGTGCCTCACTTCCAGAGGCTTCCCGATATCCGTCTGAGACCAG

GAGATTTTGAATCTCTAAGCGGTAGAGAAAAGTCTCACCATATCGGATCAGCTCAGGGGCTCTTATACT

CAATCTTAGTGGCAATTCACGACTCAGGATACAATGATGGAACCATCTTCCCTGTCAACATATACGGCA

AGGTTTCCCCTAGAGACTATTTGAGAGGGCTCGCAAGGGGAGTATTGATAGGATCCTCGATTTGCTTCT

TGACAAGAATGACAAATATCAATATTAATAGACCTCTTGAATTGGTCTCAGGGGTAATCTCATATATTC

TCCTGAGGCTAGATAACCATCCCTCCTTGTACATAATGCTCAGAGAACCGTCTCTTAGAGGAGAGATAT

TTTCTATCCCTCAGAAAATCCCCGCCGCTTATCCAACCACTATGAAAGAAGGCAACAGATCAATCTTGT

GTTATCTCCAACATGTGCTACGCTATGAGCGAGAGATAATCACGGCGTCTCCAGAGAATGACTGGCTAT

GGATCTTTTCAGACTTTAGAAGTGCCAAAATGACGTACCTATCCCTCATTACTTACCAGTCTCATCTTC

TACTCCAGAGGGTTGAGAGAAACCTATCTAAGAGTATGAGAGATAACCTGCGACAATTGAGTTCTTTGA

TGAGGCAGGTGCTGGGCGGGCACGGAGAAGATACCTTAGAGTCAGACGACAACATTCAACGACTGCTAA

AAGACTCTTTACGAAGGACAAGATGGGTGGATCAAGAGGTGCGCCATGCAGCTAGAACCATGACTGGAG

ATTACAGCCCCAACAAGAAGGTGTCCCGTAAGGTAGGATGTTCAGAATGGGTCTGCTCTGCTCAACAGG

TTGCAGTCTCTACCTCAGCAAACCCGGCCCCTGTCTCGGAGCTTGACATAAGGGCCCTCTCTAAGAGGT

TCCAGAACCCTTTGATCTCGGGCTTGAGAGTGGTTCAGTGGGCAACCGGTGCTCATTATAAGCTTAAGC

CTATTCTAGATGATCTCAATGTTTTCCCATCTCTCTGCCTTGTAGTTGGGGACGGGTCAGGGGGGATAT

CAAGGGCAGTCCTCAACATGTTTCCAGATGCCAAGCTTGTGTTCAACAGTCTTTTAGAGGTGAATGACC

TGATGGCTTCCGGAACACATCCACTGCCTCCTTCAGCAATCATGAGGGGAGGAAATGATATCGTCTCCA

GAGTGATAGATCTTGACTCAATCTGGGAAAAACCGTCCGACTTGAGAAACTTGGCAACCTGGAAATACT

TCCAGTCAGTCCAAAAGCAGGTCAACATGTCCTATGACCTCATTATTTGCGATGCAGAAGTTACTGACA

TTGCATCTATCAACCGGATCACCCTGTTAATGTCCGATTTTGCATTGTCTATAGATGGACCACTCTATT

TGGTCTTCAAAACTTATGGGACTATGCTAGTAAATCCAAACTACAAGGCTATTCAACACCTGTCAAGAG
```

-continued

CGTTCCCCTCGGTCACAGGGTTTATCACCCAAGTAACTTCGTCTTTTTCATCTGAGCTCTACCTCCGAT

TCTCCAAACGAGGGAAGTTTTTCAGAGATGCTGAGTACTTGACCTCTTCCACCCTTCGAGAAATGAGCC

TTGTGTTATTCAATTGTAGCAGCCCCAAGAGTGAGATGCAGAGAGCTCGTTCCTTGAACTATCAGGATC

TTGTGAGAGGATTTCCTGAAGAAATCATATCAAATCCTTACAATGAGATGATCATAACTCTGATTGACA

GTGATGTAGAATCTTTTCTAGTCCACAAGATGGTTGATGATCTTGAGTTACAGAGGGGAACTCTGTCTA

AAGTGGCTATCATTATAGCCATCATGATAGTTTTCTCCAACAGAGTCTTCAACGTTTCCAAACCCCTAA

CTGACCCCTCGTTCTATCCACCGTCTGATCCCAAAATCCTGAGGCACTTCAACATATGTTGCAGTACTA

TGATGTATCTATCTACTGCTTTAGGTGACGTCCCTAGCTTCGCAAGACTTCACGACCTGTATAACAGAC

CTATAACTTATTACTTCAGAAAGCAAGTCATTCGAGGGAACGTTTATCTATCTTGGAGTTGGTCCAACG

ACACCTCAGTGTTCAAAAGGGTAGCCTGTAATTCTAGCCTGAGTCTGTCATCTCACTGGATCAGGTTGA

TTTACAAGATAGTGAAGACTACCAGACTCGTTGGCAGCATCAAGGATCTATCCAGAGAAGTGGAAAGAC

ACCTTCATAGGTACAACAGGTGGATCACCCTAGAGGATATCAGATCTAGATCATCCCTACTAGACTACA

GTTGCCTGTGAACCGGATACTCCTGGAAGCCTGCCCATGCTAAGACTCTTGTGTGATGTATCTTGAAAA

AAACAAGATCCTAAATCTGAACCTTTGGTTGTTTGATTGTTTTTCTCAttttttgttgtttatttgttaa gcgt

SEQ ID NO: 46: Nucleotide sequence of the BNSPΔG-GP$_{GCD}$ vaccine vector of the Examples

ACGCTTAACAACCAGATCAAAGAAAAAACAGACATTGTCAATTGCAAAGCAAAAATGTAACACCCCTAC

AATGGATGCCGACAAGATTGTATTCAAAGTCAATAATCAGGTGGTCTCTTTGAAGCCTGAGATTATCGT

GGATCAATATGAGTACAAGTACCCTGCCATCAAAGATTTGAAAAAGCCCTGTATAACCCTAGGAAAGGC

TCCCGATTTAAATAAAGCATACAAGTCAGTTTTGTCAGGCATGAGCGCCGCCAAACTTAATCCTGACGA

TGTATGTTCCTATTTGGCAGCGGCAATGCAGTTTTTTGAGGGGACATGTCCGGAAGACTGGACCAGCTA

TGGAATTGTGATTGCACGAAAAGGAGATAAGATCACCCCAGGTTCTCTGGTGGAGATAAAACGTACTGA

TGTAGAAGGGAATTGGGCTCTGACAGGAGGCATGGAACTGACAAGAGACCCCACTGTCCCTGAGCATGC

GTCCTTAGTCGGTCTTCTCTTGAGTCTGTATAGGTTGAGCAAAATATCCGGGCAAACACTGGTAACTA

TAAGACAAACATTGCAGACAGGATAGAGCAGATTTTTGAGACAGCCCCTTTTGTTAAAATCGTGGAACA

CCATACTCTAATGACAACTCACAAaATGTGTGCTAATTGGAGTACTATACCAAACTTCAGATTTTTGGC

CGGAACCTATGACATGTTTTTCTCCCGGATTGAGCATCTATATTCAGCAATCAGAGTGGGCACAGTTGT

CACTGCTTATGAAGACTGTTCAGGACTGGTATCATTTACTGGGTTCATAAAACAAATCAATCTCACCGC

TAGAGAGGCAATACTATATTTCTTCCACAAGAACTTTGAGGAAGAGATAAGAAGAATGTTTGAGCCAGG

GCAGGAGACAGCTGTTCCTCACTCTTATTTCATCCACTTCCGTTCACTAGGCTTGAGTGGGAAATCTCC

TTATTCATCAAATGCTGTTGGTCACGTGTTCAATCTCATTCACTTTGTAGGATGCTATATGGGTCAAGT

CAGATCCCTAAATGCAACGGTTATTGCTGCATGTGCTCCTCATGAAATGTCTGTTCTAGGGGGCTATCT

GGGAGAGGAATTCTTCGGGAAAGGGACATTTGAAAGAAGATTCTTCAGAGATGAGAAAGAACTTCAAGA

ATACGAGGCGGCTGAACTGACAAAGACTGACGTAGCACTGGCAGATGATGGAACTGTCAACTCTGACGA

CGAGGACTACTTTTCAGGTGAAACCAGAAGTCCGGAGGCTGTTTATACTCGAATCATGATGAATGGAGG

TCGACTAAAGAGATCTCACATACGGAGATATGTCTCAGTCAGTTCCAATCATCAAGCCCGTCCAAACTC

ATTCGCCGAGTTTCTAAACAAGACATATTCGAGTGACTCATAAcatgaaaaaaactaacaccccctcccG

TACGCCGCCACCatgGGTGTTACAGGAATATTGCAGTTACCTCGTGATCGATTCAAGAGGACATCATTC

TTTCTTTGGGTAATTATCCTTTTCCAAAGAACATTTTCCATCCCACTTGGAGTCATCCACAATAGCACA

TTACAGGTTAGTGATGTCGACAAACTAGTTTGTCGTGACAAACTGTCATCCACAAATCAATTGAGATCA

GTTGGACTGAATCTCGAAGGGAATGGAGTGGCAACTGACGTGCCATCTGCAACTAAAAGATGGGGCTTC

```
AGGTCCGGTGTCCCACCAAAGGTGGTCAATTATGAAGCTGGTGAATGGGCTGAAAACTGCTACAATCTT
GAAATCAAAAAACCTGACGGGAGTGAGTGTCTACCAGCAGCGCCAGACGGGATTCGGGGCTTCCCCCGG
TGCCGGTATGTGCACAAAGTATCAGGAACGGGACCGTGTGCCGGAGACTTTGCCTTCCATAAAGAGGGT
GCTTTCTTCCTGTATGATCGACTTGCTTCCACAGTTATCTACCGAGGAACGACTTTCGCTGAAGGTGTC
GTTGCATTTCTGATACTGCCCCAAGCTAAGAAGGACTTCTTCAGCTCACACCCCTTGAGAGAGCCGGTC
AATGCAACGGAGGACCCGTCTAGTGGCTACTATTCTACCACAATTAGATATCAGGCTACCGGTTTTGGA
ACCAATGAGACAGAGTACTTGTTCGAGGTTGACAATTTGACCTACGTCCAACTTGAATCAAGATTCACA
CCACAGTTTCTGCTCCAGCTGAATGAGACAATATATACAAGTGGGAAAAGGAGCAATACCACGGGAAAA
CTAATTTGGAAGGtCAACCCCGAAATTGATACAACAATCGGGGAGTGGGCCTTCTGGGAAacTAAAAAA
AACCTCACTAGAAAAaTTCGCAGTGAAGAGTTgTCTTTCACAGTTGTATCAAACAGAGCCAAAAACATC
AGTGGTCAGAGTCCGGCGCGAACTTCTTCCGACCCAGGGACCAACACAACAACTGAAGACCACAAAATC
ATGGCTTCAGAAAATTCCTCTGCAATGGTTCAAGTGCACAGTCAAGGAAGGGAAGCTGCAGTGTCGCAT
CTGACAACCCCTGCCACAATCTCCACGAGTCTTCAACCCCCCACAACCAAACCAGGTCCGGACAACAGC
ACCCACAATACACCCGTGTATAAACTTGACATCTCTGAGGCAACTCAAGTTGAACAACATCACCGCAGA
ACAGACAACGACAGCACAGCcTCCGACACTCCcTCTGCCACGACcGCAGCCGGACCCCCAAAAGCAGAG
AACACCAACACGAGCAAGAGCACTGACTTCCTGGACCCCGCCACCACAACAAGTCCCCAAAACCACAGC
GAGACCGCTGGCAACAACAACACTCATCACCAAGATACCGGAGAAGAGAGTGCCAGCAGCGGGAAGCTA
GGCTTAATTACCAATACTATTGCTGGAGTCGCAGGACTGATCACAGGCGGGAGAAGAACTCGAAGAGAA
GCAATTGTCAATGCTCAACCCAAATGCAACCCTAATTTACATTACTGGACTACTCAGGATGAAGGTGCT
GCAATCGGACTGGCCTGGATACCATATTTCGGGCCAGCAGCCGAGGGAATTTACATAGAGGGGCTAATG
CACAATCAAGATGGTTTAATCTGTGGGTTGAGACAGCTGGCCAACGAGACGACTCAAGCTCTTCAACTG
TTCCTGAGAGCCACAACTGAGCTACGCACCTTTTCAATCCTCAACCGTAAGGCAATTGATTTCTTGCTG
CAGCGATGGGCGGCACATGCCACATTCTGGGACCGGACTGCTGTATCGAACCACATGATTGGACCAAG
AACATAACAGACAAAATTGATCAGATTATTCATGATTTTGTTGATAAAACCCTTCCGGACCAGGGGAC
AATGACAATTGGTGGACAGGATGGAGACAATGGATACCGGCAGGTATTGGAGTTACAGGCGTTGTAATT
GCAGTTATCGCTTTATTCTGTATATGCgttaacAGAAGAGTCAATCGATCAGAACCTACGCAACACAAT
CTCAGAGGGACAGGGAGGGAGGTGTCAGTCACTCCCCAAAGCGGGAAGATCATATCTTCATGGGAATCA
CACAAGAGTGGGGGTGAGACCAGACTGTAAgCTAGCCATGAAAAAAACTAACACCCCTCCTTTCGAACC
ATCCCAAACATGAGCAAGATCTTTGTCAATCCTAGTGCTATTAGAGCCGGTCTGGCCGATCTTGAGATG
GCTGAAGAAACTGTTGATCTGATCAATAGAAATATCGAAGACAATCAGGCTCATCTCCAAGGGGAACCC
ATAGAGGTGGACAATCTCCCTGAGGATATGGGGCGACTTCACCTGGATGATGGAAAATCGCCCAACCAT
GGTGAGATAGCCAAGGTGGGAGAAGGCAAGTATCGAGAGGACTTTCAGATGGATGAAGGAGAGGATCCT
AGCTTCCTGTTCCAGTCATACCTGGAAAATGTTGGAGTCCAAATAGTCAGACAAATGAGGTCAGGAGAG
AGATTTCTCAAGATATGGTCACAGACCGTAGAAGAGATTATATCCTATGTCGCGGTCAACTTTCCCAAC
CCTCCAGGAAAGTCTTCAGAGGATAAATCAACCCAGACTACTGGCCGAGAGCTCAAGAAGGAGACAACA
CCCACTCCTTCTCAGAGAGAAAGCCAATCATCGAAAGCCAGGATGGCGGCTCAAATTGCTTCTGGCCCT
CCAGCCCTTGAATGGTCGGCTACCAATGAAGAGGATGATCTATCAGTGGAGGCTGAGATCGCTCACCAG
ATTGCAGAAAGTTTCTCCAAAAAATATAAGTTTCCCTCTCGATCCTCAGGGATACTCTTGTATAATTTT
GAGCAATTGAAAATGAACCTTGATGATATAGTTAAAGAGGCAAAAAATGTACCAGGTGTGACCCGTTTA
GCCCATGACGGGTCCAAACTCCCCCTAAGATGTGTACTGGGATGGGTCGCTTTGGCCAACTCTAAGAAA
TTCCAGTTGTTAGTCGAATCCGACAAGCTGAGTAAAATCATGCAAGATGACTTGAATCGCTATACATCT
```

```
TGCTAACCGAACCTCTCCCCTCAGTCCCTCTAGACAATAAAATCCGAGATGTCCCAAAGTCAACATGAA

AAAAACAGGCAACACCACTGATAAAATGAACCTCCTACGTAAGATAGTGAAAAACCGCAGGGACGAGGA

CACTCAAAAATCCTCTCCCGCGTCAGCCCCTCTGGATGACGATGACTTGTGGCTTCCACCCCCTGAATA

CGTCCCGCTGAAAGAACTTACAGGCAAGAAGAACATGAGGAACTTTTGTATCAACGGAAGGGTTAAAGT

GTGTAGCCCGAATGGTTACTCGTTCAGGATCCTGCGGCACATTCTGAAATCATTCGACGAGATATATTC

TGGGAATCATAGGATGATCGGGTTAGTCAAAGTGGTTATTGGACTGGCTTTGTCAGGATCTCCAGTCCC

TGAGGGCCTGAACTGGGTATACAAATTGAGGAGAACCTTTATCTTCCAGTGGGCTGATTCCAGGGCCC

TCTTGAAGGGGAGGAGTTGGAATACTCTCAGGAGATCACTTGGGATGATGATACTGAGTTCGTCGGATT

GCAAATAAGAGTGATTGCAAAACAGTGTCATATCCAGGGCAGAGTCTGGTGTATCAACATGAACCCGAG

AGCATGTCAACTATGGTCTGACATGTCTCTTCAGACACAAAGGTCCGAAGAGGACAAAGATTCCTCTCT

GCTTCTAGAATAATCAGATTATATCCCGCAAATTTATCACTTGTTTACCTCTGGAGGAGAGAACATATG

GGCTCAACTCCAACCCTTGGGAGCAATATAACAAAAAACATGTTATGGTGCCATTAAACCGCTGCATTT

CATCAAAGTCAAGTTGATTACCTTTACATTTTGATCCTCTTGGATGTGAAAAAAACTATTAACATCCCT

CAAAAGACccctaaCGTCCTTTCAACGATCCAAGTCcatgaaaaaaactaacacccctcccgtacctag cTTATAAAGTGCTGGGTCATCTAAGCTTTTCAGTCGAGAAAAAAACATTAGATCAGAAGAACAACTGGC

AACACTTCTCAACCTGAGACTTACTTCAAGATGCTCGATCCTGGAGAGGTCTATGATGACCCTATTGAC

CCAATCGAGTTAGAGGCTGAACCCAGAGGAACCCCCATTGTCCCCAACATCTTGAGGAACTCTGACTAC

AATCTCAACTCTCCTTTGATAGAAGATCCTGCTAGACTAATGTTAGAATGGTTAAAAACAGGGAATAGA

CCTTATCGGATGACTCTAACAGACAATTGCTCCAGGTCTTTCAGAGTTTTGAAAGATTATTTCAAGAAG

GTAGATTTGGGTTCTCTCAAGGTGGGCGGAATGGCTGCACAGTCAATGATTTCTCTCTGGTTATATGGT

GCCCACTCTGAATCCAACAGGAGCCGGAGATGTATAACAGACTTGGCCCATTTCTATTCCAAGTCGTCC

CCCATAGAGAAGCTGTTGAATCTCACGCTAGGAAATAGAGGGCTGAGAATCCCCCCAGAGGGAGTGTTA

AGTTGCCTTGAGAGGGTTGATTATGATAATGCATTTGGAAGGTATCTTGCCAACACGTATTCCTCTTAC

TTGTTCTTCCATGTAATCACCTTATACATGAACGCCCTAGACTGGGATGAAGAAAAGACCATCCTAGCA

TTATGGAAAGATTTAACCTCAGTGGACATCGGGAAGGACTTGGTAAAGTTCAAAGACCAAATATGGGA

CTGCTGATCGTGACAAAGGACTTTGTTTACTCCCAAAGTTCCAATTGTCTTTTTGACAGAAACTACACA

CTTATGCTAAAAGATCTTTTCTTGTCTCGCTTCAACTCCTTAATGGTCTTGCTCTCTCCCCAGAGCCC

CGATACTCAGATGACTTGATATCTCAACTATGCCAGCTGTACATTGCTGGGGATCAAGTCTTGTCTATG

TGTGGAAACTCCGGCTATGAAGTCATCAAAATATTGGAGCCATATGTCGTGAATAGTTTAGTCCAGAGA

GCAGAAAAGTTTAGGCCTCTCATTCATTCCTTGGGAGACTTTCCTGTATTTATAAAAGACAAGGTAAGT

CAACTTGAAGAGACGTTCGGTCCCTGTGCAAGAAGGTTCTTTAGGGCTCTGGATCAATTCGACAACATA

CATGACTTGGTTTTTGTGTTTGGCTGTTACAGGCATTGGGGGCACCCATATATAGATTATCGAAAGGGT

CTGTCAAAACTATATGATCAGGTTCACCTTAAAAAAATGATAGATAAGTCCTACCAGGAGTGCTTAGCA

AGCGACCTAGCCAGGAGGATCCTTAGATGGGGTTTTGATAAGTACTCCAAGTGGTATCTGGATTCAAGA

TTCCTAGCCCGAGACCACCCCTTGACTCCTTATATCAAAACCCAAACATGGCCACCCAAACATATTGTA

GACTTGGTGGGGATACATGGCACAAGCTCCCGATCACGCAGATCTTTGAGATTCCTGAATCAATGGAT

CCGTCAGAAATATTGGATGACAAATCACATTCTTTCACCAGAACGAGACTAGCTTCTTGGCTGTCAGAA

AACCGAGGGGGCCTGTTCCTAGCGAAAAAGTrATrATCACGGCCCTGTCTAAGCCGCCTGTCAATCCC

CGAGAGTTTCTGAGGTCTATAGACCTCGGAGGATTGCCAGATGAAGACTTGATAATTGGCCTCAAGCCA

AAGGAACGGAATTGAAGATTGAAGGTCGATTCTTTGCTCTAATGTCATGGAATCTAAGATTGTATTTT

GTCATCACTGAAAAACTCTTGGCCAACTACATCTTGCCACTTTTTGACGCGCTGACTATGACAGACAAC
```

-continued

```
CTGAACAAGGTGTTTAAAAAGCTGATCGACAGGGTCACCGGGCAAGGGCTTTTGGACTATTCAAGGGTC

ACATATGCATTTCACCTGGACTATGAAAAGTGGAACAACCATCAAAGATTAGAGTCAACAGAGGATGTA

TTTTCTGTCCTAGATCAAGTGTTTGGATTGAAGAGAGTGTTTTCTAGAACACACGAGTTTTTTCAAAAG

GCCTGGATCTATTATTCAGACAGATCAGACCTCATCGGGTTACGGGAGGATCAAATATACTGCTTAGAT

GCGTCCAACGGCCCAACCTGTTGGAATGGCCAGGATGGCGGGCTAGAAGGCTTACGGCAGAAGGGCTGG

AGTCTAGTCAGCTTATTGATGATAGATAGAGAATCTCAAATCAGGAACACAAGAACCAAAATACTAGCT

CAAGGAGACAACCAGGTTTTATGTCCGACATACATGTTGTCGCCAGGGCTATCTCAAGAGGGGCTCCTC

TATGAATTGGAGAGAATATCAAGGAATGCACTTTCGATATACAGAGCCGTCGAGGAAGGGGCATCTAAG

CTAGGGCTGATCATCAAGAAAGAAGAGACCATGTGTAGTTATGACTTCCTCATCTATGGAAAAACCCCT

TTGTTTAGAGGTAACATATTGGTGCCTGAGTCCAAAAGATGGGCCAGAGTCTCTTGCGTCTCTAATGAC

CAAATAGTCAACCTCGCCAATATAATGTCGACAGTGTCCACCAATGCGCTAACAGTGGCACAACACTCT

CAATCTTTGATCAAACCGATGAGGGATTTTCTGCTCATGTCAGTACAGGCAGTCTTTCACTACCTGCTA

TTTAGCCCAATCTTAAAGGGAAGAGTTTACAAGATTCTGAGCGCTGAAGGGGAGAGCTTTCTCCTAGCC

ATGTCAAGGATAATCTATCTAGATCCTTCTTTGGGAGGGATATCTGGAATGTCCCTCGGAAGATTCCAT

ATACGACAGTTCTCAGACCCTGTCTCTGAAGGGTTATCCTTCTGGAGAGAGATCTGGTTAAGCTCCCAA

GAGTCCTGGATTCACGCGTTGTGTCAAGAGGCTGGAAACCCAGATCTTGGAGAGAGAACACTCGAGAGC

TTCACTCGCCTTCTAGAAGATCCGACCACCTTAAATATCAGAGGAGGGGCCAGTCCTACCATTCTACTC

AAGGATGCAATCAGAAAGGCTTTATATGACGAGGTGGACAAGGTGGAAAATTCAGAGTTTCGAGAGGCA

ATCCTGTTGTCCAAGACCCATAGAGATAATTTTATACTCTTCTTAATATCTGTTGAGCCTCTGTTTCCT

CGATTTCTCAGTGAGCTATTCAGTTCGTCTTTTTTGGGAATCCCCGAGTCAATCATTGGATTGATACAA

AACTCCCGAACGATAAGAAGGCAGTTTAGAAAGAGTCTCTCAAAAACTTTAGAAGAATCCTTCTACAAC

TCAGAGATCCACGGGATTAGTCGGATGACCCAGACACCTCAGAGGGTTGGGGGGGTGTGGCCTTGCTCT

TCAGAGAGGGCAGATCTACTTAGGGAGATCTCTTGGGGAAGAAAAGTGGTAGGCACGACAGTTCCTCAC

CCTTCTGAGATGTTGGGATTACTTCCCAAGTCCTCTATTTCTTGCACTTGTGGAGCAACAGGAGGAGGC

AATCCTAGAGTTTCTGTATCAGTACTCCCGTCCTTTGATCAGTCATTTTTTTCACGAGGCCCCCTAAAG

GGATACTTGGGCTCGTCCACCTCTATGTCGACCCAGCTATTCCATGCATGGGAAAAAGTCACTAATGTT

CATGTGGTGAAGAGAGCTCTATCGTTAAAAGAATCTATAAACTGGTTCATTACTAGAGATTCCAACTTG

GCTCAAGCTCTAATTAGGAACATTATGTCTCTGACAGGCCCTGATTTCCCTCTAGAGGAGGCCCCTGTC

TTCAAAAGGACGGGGTCAGCCTTGCATAGGTTCAAGTCTGCCAGATACAGCGAAGGAGGGTATTCTTCT

GTCTGCCCGAACCTCCTCTCTCATATTTCTGTTAGTACAGACACCATGTCTGATTTGACCCAAGACGGG

AAGAACTACGATTTCATGTTCCAGCCATTGATGCTTTATGCACAGACATGGACATCAGAGCTGGTACAG

AGAGACACAAGGCTAAGAGACTCTACGTTTCATTGGCACCTCCGATGCAACAGGTGTGTGAGACCCATT

GACGACGTGACCCTGGAGACCTCTCAGATCTTCGAGTTTCCGGATGTGTCGAAAAGAATATCCAGAATG

GTTTCTGGGGCTGTGCCTCACTTCCAGAGGCTTCCCGATATCCGTCTGAGACCAGGAGATTTTGAATCT

CTAAGCGGTAGAGAAAAGTCTCACCATATCGGATCAGCTCAGGGGCTCTTATACTCAATCTTAGTGGCA

ATTCACGACTCAGGATACAATGATGGAACCATCTTCCCTGTCAACATATACGGCAAGGTTTCCCCTAGA

GACTATTTGAGAGGGCTCGCAAGGGGAGTATTGATAGGATCCTCGATTTGCTTCTTGACAAGAATGACA

AATATCAATATTAATAGACCTCTTGAATTGGTCTCAGGGGTAATCTCATATATTCTCCTGAGGCTAGAT

AACCATCCCTCCTTGTACATAATGCTCAGAGAACCGTCTCTTAGAGGAGAGATATTTTCTATCCCTCAG

AAAATCCCCGCCGCTTATCCAACCACTATGAAAGAAGGCAACAGATCAATCTTGTGTTATCTCCAACAT

GTGCTACGCTATGAGCGAGAGATAATCACGGCGTCTCCAGAGAATGACTGGCTATGGATCTTTTCAGAC
```

-continued
```
TTTAGAAGTGCCAAAATGACGTACCTATCCCTCATTACTTACCAGTCTCATCTTCTACTCCAGAGGGTT

GAGAGAAACCTATCTAAGAGTATGAGAGATAACCTGCGACAATTGAGTTCTTTGATGAGGCAGGTGCTG

GGCGGGCACGGAGAAGATACCTTAGAGTCAGACGACAACATTCAACGACTGCTAAAAGACTCTTTACGA

AGGACAAGATGGGTGGATCAAGAGGTGCGCCATGCAGCTAGAACCATGACTGGAGATTACAGCCCCAAC

AAGAAGGTGTCCCGTAAGGTAGGATGTTCAGAATGGGTCTGCTCTGCTCAACAGGTTGCAGTCTCTACC

TCAGCAAACCCGGCCCCTGTCTCGGAGCTTGACATAAGGGCCCTCTCTAAGAGGTTCCAGAACCCTTTG

ATCTCGGGCTTGAGAGTGGTTCAGTGGGCAACCGGTGCTCATTATAAGCTTAAGCCTATTCTAGATGAT

CTCAATGTTTTCCCATCTCTCTGCCTTGTAGTTGGGGACGGGTCAGGGGGGATATCAAGGGCAGTCCTC

AACATGTTTCCAGATGCCAAGCTTGTGTTCAACAGTCTTTTAGAGGTGAATGACCTGATGGCTTCCGGA

ACACATCCACTGCCTCCTTCAGCAATCATGAGGGGAGGAAATGATATCGTCTCCAGAGTGATAGATCTT

GACTCAATCTGGGAAAAACCGTCCGACTTGAGAAACTTGGCAACCTGGAAATACTTCCAGTCAGTCCAA

AAGCAGGTCAACATGTCCTATGACCTCATTATTTGCGATGCAGAAGTTACTGACATTGCATCTATCAAC

CGGATCACCCTGTTAATGTCCGATTTTGCATTGTCTATAGATGGACCACTCTATTTGGTCTTCAAAACT

TATGGGACTATGCTAGTAAATCCAAACTACAAGGCTATTCAACACCTGTCAAGAGCGTTCCCCTCGGTC

ACAGGGTTTATCACCCAAGTAACTTCGTCTTTTTCATCTGAGCTCTACCTCCGATTCTCCAAACGAGGG

AAGTTTTTCAGAGATGCTGAGTACTTGACCTCTTCCACCCTTCGAGAAATGAGCCTTGTGTTATTCAAT

TGTAGCAGCCCCAAGAGTGAGATGCAGAGAGCTCGTTCCTTGAACTATCAGGATCTTGTGAGAGGATTT

CCTGAAGAAATCATATCAAATCCTTACAATGAGATGATCATAACTCTGATTGACAGTGATGTAGAATCT

TTTCTAGTCCACAAGATGGTTGATGATCTTGAGTTACAGAGGGGAACTCTGTCTAAAGTGGCTATCATT

ATAGCCATCATGATAGTTTTCTCCAACAGAGTCTTCAACGTTTCCAAACCCCTAACTGACCCCTCGTTC

TATCCACCGTCTGATCCCAAAATCCTGAGGCACTTCAACATATGTTGCAGTACTATGATGTATCTATCT

ACTGCTTTAGGTGACGTCCCTAGCTTCGCAAGACTTCACGACCTGTATAACAGACCTATAACTTATTAC

TTCAGAAAGCAAGTCATTCGAGGGAACGTTTATCTATCTTGGAGTTGGTCCAACGACACCTCAGTGTTC

AAAAGGGTAGCCTGTAATTCTAGCCTGAGTCTGTCATCTCACTGGATCAGGTTGATTTACAAGATAGTG

AAGACTACCAGACTCGTTGGCAGCATCAAGGATCTATCCAGAGAAGTGGAAAGACACCTTCATAGGTAC

AACAGGTGGATCACCCTAGAGGATATCAGATCTAGATCATCCCTACTAGACTACAGTTGCCTGTGAACC

GGATACTCCTGGAAGCCTGCCCATGCTAAGACTCTTGTGTGATGTATCTTGAAAAAAACAAGATCCTAA

ATCTGAACCTTTGGTTGTTTGATTGTTTTTCTCAttttttgttgtttatttgttaagcgt
```

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

REFERENCES

All documents cited in this list of References, and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

What is claimed is:

1. A composition comprising a therapeutically effective amount of a recombinant multivalent rabies virus vector comprising a nucleotide sequence encoding at least one filovirus glycoprotein which is incorporated into the rabies virus virion, wherein the rabies virus genome is attenuated and, wherein the therapeutically effective amount of said recombinant multivalent rabies virus vector is an amount sufficient to induce an immune response that is protective against a rabies virus infection and a filovirus infection and that includes neutralizing antibodies to the rabies virus and the filovirus.

2. The composition of claim 1, wherein the at least one filovirus glycoprotein is Ebolavirus glycoprotein.

3. The composition of claim 1, wherein the at least one filovirus is Zaire Ebolavirus (ZEBOV), Sudan Ebolavirus (SEBOV), Cote d'Ivoire Ebolavirus (CEBOV), Reston Ebolavirus (REBOV), Bundibugyo Ebolavirus (BEBOV), or Marburgvirus.

4. The composition of claim 1, wherein the glycoprotein comprises the amino acid sequence of SEQ ID NO: 1 (from ZEBOV), SEQ ID NO: 2 (from SEBOV), SEQ ID NO: 3 (from CEBOV), SEQ ID NO: 4 (from REBOV), SEQ ID NO: 5 (from BEBOV), or SEQ ID NO: 6 (from Marburgvirus).

5. The composition of claim 1, wherein the rabies virus vector is derived from the live attenuated SAD B19 RABV vaccine.

6. The composition according to claim 1, wherein the rabies virus genome further expresses one or more additional filovirus proteins.

7. The composition according to claim 6, wherein the one or more filovirus proteins are selected from the group consisting of a nucleoprotein (NP), VP40, VP35, VP30, VP24, and an RNA-dependent RNA polymerase (L) from an Ebolavirus or Marburgvirus.

8. A multivalent immunogenic composition, comprising a therapeutically effective amount of a recombinant rabies virus vector that expresses at least one filovirus glycoprotein which is incorporated into the rabies virus virion, wherein the rabies virus genome is attenuated and, wherein the therapeutically effective amount of said multivalent immunogenic composition is an amount sufficient to induce an immune response that is protective against a rabies virus infection and a filovirus infection and that includes neutralizing antibodies to the rabies virus and the filovirus.

9. The multivalent immunogenic composition according to claim 8, wherein the at least one filovirus glycoprotein is Ebola glycoprotein.

10. The multivalent immunogenic composition according to claim 8, wherein the at least one filovirus is ZEBOV, SEBOV, CEBOV, REBOV, BEBOV or Marburgvirus.

11. The multivalent immunogenic composition according to claim 8, wherein the Ebola glycoprotein comprises the amino acid sequence of SEQ ID NO: 1 (from ZEBOV), SEQ ID NO: 2 (from SEBOV), SEQ ID NO: 3 (from CEBOV), SEQ ID NO: 4 (from REBOV), SEQ ID NO: 5 (from BEBOV), or SEQ ID NO: 6 (from Marburgvirus).

12. The multivalent immunogenic composition according to claim 8, wherein the rabies virus genome is derived from the live attenuated SAD B19 RABV vaccine.

13. A pharmaceutical composition comprising the composition of claim 1 and a pharmaceutically acceptable carrier.

14. The pharmaceutical composition according to claim 13, further comprising at least one additional therapeutic agent.

15. The multivalent immunogenic composition according to claim 8, wherein the rabies virus genome further expresses one or more additional filovirus proteins.

16. The multivalent immunogenic composition according to claim 15, wherein the one or more filovirus proteins are selected from the group consisting of a nucleoprotein (NP), VP40, VP35, VP30, VP24, and an RNA-dependent RNA polymerase (L) from an Ebolavirus or Marburgvirus.

17. The multivalent immunogenic composition according to claim 15, wherein the one or more additional filovirus proteins is a structural or nonstructural protein from a Marburgvirus.

18. A pharmaceutical composition comprising one or more multivalent immunogenic compositions according to claim 8 and a pharmaceutically acceptable carrier.

19. The pharmaceutical composition according to claim 18, further comprising at least one additional therapeutic agent.

20. The pharmaceutical composition according to claim 19, wherein the therapeutic agent is an anti-viral drug, and anti-viral antibody, an immunostimulatory agent, or an adjuvant.

21. The composition according to claim 6, wherein the one or more additional filovirus proteins is a structural or nonstructural protein from a Marburgvirus.

22. A method of treating a subject infected with a filovirus and/or a rabies virus, comprising administering to the subject a therapeutically effective amount of the composition of claim 1, wherein the composition is effective at treating the subject.

23. A method of treating a subject infected with a filovirus and/or a rabies virus, comprising administering to the subject a therapeutically effective amount of the composition of claim 8, wherein the composition is effective at treating the subject.

24. A method of inducing an immune response protective against a filovirus and a rabies virus in a subject, the method comprising administering to the subject the composition of claim 1.

25. A method of inducing neutralizing antibodies against a filovirus and a rabies virus in a subject, comprising administering to the subject the composition of claim 1, wherein the composition is effective at inducing neutralizing antibodies against the filovirus and the rabies virus.

26. A method of inducing neutralizing antibodies against a Filovirus and a rabies virus in a subject, comprising administering to the subject the composition of claim 9, wherein the composition is effective at inducing neutralizing antibodies against the Filovirus and the rabies virus.

* * * * *

SEQUENCE LISTING

<160> NUMBER OF SEQ ID NOS: 49

<210> SEQ ID NO 1
<211> LENGTH: 676
<212> TYPE: PRT
<213> ORGANISM: Zaire ebolavirus

<400> SEQUENCE: 1

```
Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
        355                 360                 365
```

Ala Thr Ile Ser Thr Ser Pro Gln Ser Leu Thr Thr Lys Pro Gly Pro
    370                 375                 380

Asp Asn Ser Thr His Asn Thr Pro Val Tyr Lys Leu Asp Ile Ser Glu
385                 390                 395                 400

Ala Thr Gln Val Glu Gln His Arg Arg Thr Asp Asn Asp Ser Thr
            405                 410                 415

Ala Ser Asp Thr Pro Ser Ala Thr Thr Ala Ala Gly Pro Pro Lys Ala
            420                 425                 430

Glu Asn Thr Asn Thr Ser Lys Ser Thr Asp Phe Leu Asp Pro Ala Thr
            435                 440                 445

Thr Thr Ser Pro Gln Asn His Ser Glu Thr Ala Gly Asn Asn Asn Thr
    450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Thr
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675

<210> SEQ ID NO 2
<211> LENGTH: 676
<212> TYPE: PRT
<213> ORGANISM: Sudan ebolavirus

<400> SEQUENCE: 2

Met Glu Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
                20                  25                  30

Met Pro Leu Gly Val Val Thr Asn Ser Thr Leu Glu Val Thr Glu Ile
            35                  40                  45

Asp Gln Leu Val Cys Lys Asp His Leu Ala Ser Thr Asp Gln Leu Lys
        50                  55                  60

-continued

```
Ser Val Gly Leu Asn Leu Glu Gly Ser Gly Val Ser Thr Asp Ile Pro
 65                  70                  75                  80

Ser Ala Thr Lys Arg Trp Gly Phe Arg Ser Gly Val Pro Pro Lys Val
                 85                  90                  95

Phe Ser Tyr Glu Ala Gly Glu Trp Ala Glu Asn Cys Tyr Asn Leu Glu
                100                 105                 110

Ile Lys Lys Pro Asp Gly Ser Glu Cys Leu Pro Pro Pro Asp Gly
                115                 120                 125

Val Arg Gly Phe Pro Arg Cys Arg Tyr Val His Lys Ala Gln Gly Thr
            130                 135                 140

Gly Pro Cys Pro Gly Asp Tyr Ala Phe His Lys Asp Gly Ala Phe Phe
145                 150                 155                 160

Leu Tyr Asp Arg Leu Ala Ser Thr Val Ile Tyr Arg Gly Val Asn Phe
                165                 170                 175

Ala Glu Gly Val Ile Ala Phe Leu Ile Leu Ala Lys Pro Lys Glu Thr
            180                 185                 190

Phe Leu Gln Ser Pro Pro Ile Arg Glu Ala Val Asn Tyr Thr Glu Asn
            195                 200                 205

Thr Ser Ser Tyr Tyr Ala Thr Ser Tyr Leu Glu Tyr Glu Ile Glu Asn
210                 215                 220

Phe Gly Ala Gln His Ser Thr Thr Leu Phe Lys Ile Asn Asn Asn Thr
225                 230                 235                 240

Phe Val Leu Leu Asp Arg Pro His Thr Pro Gln Phe Leu Phe Gln Leu
                245                 250                 255

Asn Asp Thr Ile His Leu His Gln Gln Leu Ser Asn Thr Thr Gly Lys
            260                 265                 270

Leu Ile Trp Thr Leu Asp Ala Asn Ile Asn Ala Asp Ile Gly Glu Trp
            275                 280                 285

Ala Phe Trp Glu Asn Lys Lys Asn Leu Ser Glu Gln Leu Arg Gly Glu
            290                 295                 300

Glu Leu Ser Phe Glu Thr Leu Ser Leu Asn Glu Thr Glu Asp Asp Asp
305                 310                 315                 320

Ala Thr Ser Ser Arg Thr Thr Lys Gly Arg Ile Ser Asp Arg Ala Thr
                325                 330                 335

Arg Lys Tyr Ser Asp Leu Val Pro Lys Asp Ser Pro Gly Met Val Ser
                340                 345                 350

Leu His Val Pro Glu Gly Glu Thr Thr Leu Pro Ser Gln Asn Ser Thr
            355                 360                 365

Glu Gly Arg Arg Val Asp Val Asn Thr Gln Glu Thr Ile Thr Glu Thr
            370                 375                 380

Thr Ala Thr Ile Ile Gly Thr Asn Gly Asn Asn Met Gln Ile Ser Thr
385                 390                 395                 400

Ile Gly Thr Gly Leu Ser Ser Ser Gln Ile Leu Ser Ser Ser Pro Thr
                405                 410                 415

Met Ala Pro Ser Pro Glu Thr Gln Thr Ser Thr Thr Tyr Thr Pro Lys
                420                 425                 430

Leu Pro Val Met Thr Thr Glu Glu Ser Thr Thr Pro Pro Arg Asn Ser
            435                 440                 445

Pro Gly Ser Thr Thr Glu Ala Pro Thr Leu Thr Thr Pro Glu Asn Ile
            450                 455                 460

Thr Thr Ala Val Lys Thr Val Leu Pro Gln Glu Ser Thr Ser Asn Gly
465                 470                 475                 480
```

```
Leu Ile Thr Ser Thr Val Thr Gly Ile Leu Gly Ser Leu Gly Leu Arg
                485                 490                 495

Lys Arg Ser Arg Arg Gln Val Asn Thr Arg Ala Thr Gly Lys Cys Asn
            500                 505                 510

Pro Asn Leu His Tyr Trp Thr Ala Gln Glu Gln His Asn Ala Ala Gly
            515                 520                 525

Ile Ala Trp Ile Pro Tyr Phe Gly Pro Gly Ala Glu Gly Ile Tyr Thr
            530                 535                 540

Glu Gly Leu Met His Asn Gln Asn Ala Leu Val Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Tyr Thr Ile Leu Asn Arg Lys Ala Ile Asp Phe
            580                 585                 590

Leu Leu Arg Arg Trp Gly Gly Thr Cys Arg Ile Leu Gly Pro Asp Cys
            595                 600                 605

Cys Ile Glu Pro His Asp Trp Thr Lys Asn Ile Thr Asp Lys Ile Asn
            610                 615                 620

Gln Ile Ile His Asp Phe Ile Asp Asn Pro Leu Pro Asn Gln Asp Asn
625                 630                 635                 640

Asp Asp Asn Trp Trp Thr Gly Trp Arg Gln Trp Ile Pro Ala Gly Ile
                645                 650                 655

Gly Ile Thr Gly Ile Ile Ala Ile Ile Ala Leu Leu Cys Val Cys
            660                 665                 670

Lys Leu Leu Cys
        675

<210> SEQ ID NO 3
<211> LENGTH: 676
<212> TYPE: PRT
<213> ORGANISM: Cote d'Ivoire ebolavirus

<400> SEQUENCE: 3

Met Gly Ala Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Ser
            20                  25                  30

Ile Pro Leu Gly Val Val His Asn Asn Thr Leu Gln Val Ser Asp Ile
            35                  40                  45

Asp Lys Phe Val Cys Arg Asp Lys Leu Ser Ser Thr Ser Gln Leu Lys
    50                  55                  60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Cys Glu Ala Gly Glu Trp Ala Glu Asn Cys Tyr Asn Leu Ala
            100                 105                 110

Ile Lys Lys Val Asp Gly Ser Glu Cys Leu Pro Glu Ala Pro Glu Gly
            115                 120                 125

Val Arg Asp Phe Pro Arg Cys Arg Tyr Val His Lys Val Ser Gly Thr
            130                 135                 140

Gly Pro Cys Pro Gly Gly Leu Ala Phe His Lys Glu Gly Ala Phe Phe
145                 150                 155                 160

Leu Tyr Asp Arg Leu Ala Ser Thr Ile Ile Tyr Arg Gly Thr Thr Phe
                165                 170                 175
```

```
Ala Glu Gly Val Ile Ala Phe Leu Ile Leu Pro Lys Ala Arg Lys Asp
            180                 185                 190

Phe Phe Gln Ser Pro Pro Leu His Glu Pro Ala Asn Met Thr Thr Asp
            195                 200             205

Pro Ser Ser Tyr Tyr His Thr Thr Ile Asn Tyr Val Val Asp Asn
210                     215                 220

Phe Gly Thr Asn Thr Thr Glu Phe Leu Phe Gln Val Asp His Leu Thr
225                 230              235                     240

Tyr Val Gln Leu Glu Ala Arg Phe Thr Pro Gln Phe Leu Val Leu Leu
            245                 250                 255

Asn Glu Thr Ile Tyr Ser Asp Asn Arg Arg Ser Asn Thr Thr Gly Lys
            260                 265             270

Leu Ile Trp Lys Ile Asn Pro Thr Val Asp Thr Ser Met Gly Glu Trp
            275                 280              285

Ala Phe Trp Glu Asn Lys Lys Asn Phe Thr Lys Thr Leu Ser Ser Glu
            290              295              300

Glu Leu Ser Phe Val Pro Val Pro Glu Thr Gln Asn Gln Val Leu Asp
305                 310                 315                 320

Thr Thr Ala Thr Val Ser Pro Pro Ile Ser Ala His Asn His Ala Ala
                325                 330                 335

Glu Asp His Lys Glu Leu Val Ser Glu Asp Ser Thr Pro Val Val Gln
            340                 345                 350

Met Gln Asn Ile Lys Gly Lys Asp Thr Met Pro Thr Thr Val Thr Gly
            355                 360                 365

Val Pro Thr Thr Thr Pro Ser Pro Phe Pro Ile Asn Ala Arg Asn Thr
    370                 375                 380

Asp His Thr Lys Ser Phe Ile Gly Leu Glu Gly Pro Gln Glu Asp His
385                 390                 395                 400

Ser Thr Thr Gln Pro Ala Lys Thr Thr Ser Gln Pro Thr Asn Ser Thr
                405                 410                 415

Glu Ser Thr Thr Leu Asn Pro Thr Ser Glu Pro Ser Ser Arg Gly Thr
            420                 425                 430

Gly Pro Ser Ser Pro Thr Val Pro Asn Thr Thr Glu Ser His Ala Glu
            435                 440                 445

Leu Gly Lys Thr Thr Pro Thr Thr Leu Pro Glu Gln His Thr Ala Ala
            450                 455                 460

Ser Ala Ile Pro Arg Ala Val His Pro Asp Glu Leu Ser Gly Pro Gly
465                 470                 475                 480

Phe Leu Thr Asn Thr Ile Arg Gly Val Thr Asn Leu Leu Thr Gly Ser
                485                 490                 495

Arg Arg Lys Arg Arg Asp Val Thr Pro Asn Thr Gln Pro Lys Cys Asn
            500                 505                 510

Pro Asn Leu His Tyr Trp Thr Ala Leu Asp Glu Gly Ala Ala Ile Gly
            515                 520                 525

Leu Ala Trp Ile Pro Tyr Phe Gly Pro Ala Ala Glu Gly Ile Tyr Thr
            530                 535                 540

Glu Gly Ile Met Glu Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590
```

-continued

```
Leu Leu Gln Arg Trp Gly Gly Thr Cys His Ile Leu Gly Pro Asp Cys
            595                 600                 605

Cys Ile Glu Pro Gln Asp Trp Thr Lys Asn Ile Thr Asp Lys Ile Asp
610                 615                 620

Gln Ile Ile His Asp Phe Val Asp Asn Asn Leu Pro Asn Gln Asn Asp
625                 630                 635                 640

Gly Ser Asn Trp Trp Thr Gly Trp Lys Gln Trp Val Pro Ala Gly Ile
            645                 650                 655

Gly Ile Thr Gly Val Ile Ile Ala Ile Ala Leu Leu Cys Ile Cys
            660                 665                 670

Lys Phe Met Leu
            675

<210> SEQ ID NO 4
<211> LENGTH: 677
<212> TYPE: PRT
<213> ORGANISM: Reston ebolavirus

<400> SEQUENCE: 4

Met Gly Ser Gly Tyr Gln Leu Leu Gln Leu Pro Arg Glu Arg Phe Arg
1               5                   10                  15

Lys Thr Ser Phe Leu Val Trp Val Ile Ile Leu Phe Gln Arg Ala Ile
                20                  25                  30

Ser Met Pro Leu Gly Ile Val Thr Asn Ser Thr Leu Lys Ala Thr Glu
            35                  40                  45

Ile Asp Gln Leu Val Cys Arg Asp Lys Leu Ser Ser Thr Ser Gln Leu
50                  55                  60

Lys Ser Val Gly Leu Asn Leu Glu Gly Asn Gly Ile Ala Thr Asp Val
65                  70                  75                  80

Pro Ser Ala Thr Lys Arg Trp Gly Phe Arg Ser Gly Val Pro Pro Lys
                85                  90                  95

Val Val Ser Tyr Glu Ala Gly Glu Trp Ala Glu Asn Cys Tyr Asn Leu
            100                 105                 110

Glu Ile Lys Lys Ser Asp Gly Ser Glu Cys Leu Pro Leu Pro Pro Asp
        115                 120                 125

Gly Val Arg Gly Phe Pro Arg Cys Arg Tyr Val His Lys Val Gln Gly
    130                 135                 140

Thr Gly Pro Cys Pro Gly Asp Leu Ala Phe His Lys Asn Gly Ala Phe
145                 150                 155                 160

Phe Leu Tyr Asp Arg Leu Ala Ser Thr Val Ile Tyr Arg Gly Thr Thr
                165                 170                 175

Phe Ala Glu Gly Val Val Ala Phe Leu Ile Leu Ser Glu Pro Lys Lys
            180                 185                 190

His Phe Trp Lys Ala Thr Pro Ala His Glu Pro Val Asn Thr Thr Asp
        195                 200                 205

Asp Ser Thr Ser Tyr Tyr Met Thr Leu Thr Leu Ser Tyr Glu Met Ser
    210                 215                 220

Asn Phe Gly Gly Asn Glu Ser Asn Thr Leu Phe Lys Val Asp Asn His
225                 230                 235                 240

Thr Tyr Val Gln Leu Asp Arg Pro His Thr Pro Gln Phe Leu Val Gln
                245                 250                 255

Leu Asn Glu Thr Leu Arg Arg Asn Asn Arg Leu Ser Asn Ser Thr Gly
            260                 265                 270

Arg Leu Thr Trp Thr Leu Asp Pro Lys Ile Glu Pro Asp Val Gly Glu
        275                 280                 285
```

Trp Ala Phe Trp Glu Thr Lys Lys Asn Phe Ser Gln Gln Leu His Gly
            290                 295                 300

Glu Asn Leu His Phe Gln Ile Pro Ser Thr His Thr Asn Asn Ser Ser
305                 310                 315                 320

Asp Gln Ser Pro Ala Gly Thr Val Gln Gly Lys Ile Ser Tyr His Pro
                325                 330                 335

Pro Ala Asn Asn Ser Glu Leu Val Pro Thr Asp Ser Pro Pro Val Val
            340                 345                 350

Ser Val Leu Thr Ala Gly Arg Thr Glu Glu Met Ser Thr Gln Gly Leu
        355                 360                 365

Thr Asn Gly Glu Thr Ile Thr Gly Phe Thr Ala Asn Pro Met Thr Thr
370                 375                 380

Thr Ile Ala Pro Ser Pro Thr Met Thr Ser Glu Val Asp Asn Asn Val
385                 390                 395                 400

Pro Ser Glu Gln Pro Asn Asn Thr Ala Ser Ile Glu Asp Ser Pro Pro
                405                 410                 415

Ser Ala Ser Asn Glu Thr Ile Tyr His Ser Glu Met Asp Pro Ile Gln
                420                 425                 430

Gly Ser Asn Asn Ser Ala Gln Ser Pro Gln Thr Lys Thr Thr Pro Ala
            435                 440                 445

Pro Thr Thr Ser Pro Met Thr Gln Asp Pro Gln Glu Thr Ala Asn Ser
        450                 455                 460

Ser Lys Pro Gly Thr Ser Pro Gly Ser Ala Ala Gly Pro Ser Gln Pro
465                 470                 475                 480

Gly Leu Thr Ile Asn Thr Val Ser Lys Val Ala Asp Ser Leu Ser Pro
                485                 490                 495

Thr Arg Lys Gln Lys Arg Ser Val Arg Gln Asn Thr Ala Asn Lys Cys
            500                 505                 510

Asn Pro Asp Leu Tyr Tyr Trp Thr Ala Val Asp Glu Gly Ala Ala Val
        515                 520                 525

Gly Leu Ala Trp Ile Pro Tyr Phe Gly Pro Ala Ala Glu Gly Ile Tyr
    530                 535                 540

Ile Glu Gly Val Met His Asn Gln Asn Gly Leu Ile Cys Gly Leu Arg
545                 550                 555                 560

Gln Leu Ala Asn Glu Thr Thr Gln Ala Leu Gln Leu Phe Leu Arg Ala
                565                 570                 575

Thr Thr Glu Leu Arg Thr Tyr Ser Leu Leu Asn Arg Lys Ala Ile Asp
            580                 585                 590

Phe Leu Leu Gln Arg Trp Gly Gly Thr Cys Arg Ile Leu Gly Pro Ser
        595                 600                 605

Cys Cys Ile Glu Pro His Asp Trp Thr Lys Asn Ile Thr Asp Glu Ile
610                 615                 620

Asn Gln Ile Lys His Asp Phe Ile Asp Asn Pro Leu Pro Asp His Gly
625                 630                 635                 640

Asp Asp Leu Asn Leu Trp Thr Gly Trp Arg Gln Trp Ile Pro Ala Gly
                645                 650                 655

Ile Gly Ile Ile Gly Val Ile Ile Ala Ile Ala Leu Leu Cys Ile
            660                 665                 670

Cys Lys Ile Leu Cys
        675

<210> SEQ ID NO 5
<211> LENGTH: 676

<212> TYPE: PRT
<213> ORGANISM: Bundibugyo ebolavirus

<400> SEQUENCE: 5

```
Met Val Thr Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Pro
            20                  25                  30

Ile Pro Leu Gly Val Val His Asn Asn Thr Leu Gln Val Ser Asp Ile
        35                  40                  45

Asp Lys Leu Val Cys Arg Asp Lys Leu Ser Ser Thr Ser Gln Leu Lys
    50                  55                  60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Tyr Glu Ala Gly Glu Trp Ala Glu Asn Cys Tyr Asn Leu Asp
            100                 105                 110

Ile Lys Lys Ala Asp Gly Ser Glu Cys Leu Pro Glu Ala Pro Glu Gly
        115                 120                 125

Val Arg Gly Phe Pro Arg Cys Arg Tyr Val His Lys Val Ser Gly Thr
    130                 135                 140

Gly Pro Cys Pro Glu Gly Tyr Ala Phe His Lys Glu Gly Ala Phe Phe
145                 150                 155                 160

Leu Tyr Asp Arg Leu Ala Ser Thr Ile Ile Tyr Arg Ser Thr Thr Phe
                165                 170                 175

Ser Glu Gly Val Val Ala Phe Leu Ile Leu Pro Glu Thr Lys Lys Asp
            180                 185                 190

Phe Phe Gln Ser Pro Pro Leu His Glu Pro Ala Asn Met Thr Thr Asp
        195                 200                 205

Pro Ser Ser Tyr Tyr His Thr Val Thr Leu Asn Tyr Val Ala Asp Asn
    210                 215                 220

Phe Gly Thr Asn Met Thr Asn Phe Leu Phe Gln Val Asp His Leu Thr
225                 230                 235                 240

Tyr Val Gln Leu Glu Pro Arg Phe Thr Pro Gln Phe Leu Val Gln Leu
                245                 250                 255

Asn Glu Thr Ile Tyr Thr Asn Gly Arg Arg Ser Asn Thr Thr Gly Thr
            260                 265                 270

Leu Ile Trp Lys Val Asn Pro Thr Val Asp Thr Gly Val Gly Glu Trp
        275                 280                 285

Ala Phe Trp Glu Asn Lys Lys Asn Phe Thr Lys Thr Leu Ser Ser Glu
    290                 295                 300

Glu Leu Ser Val Ile Phe Val Pro Arg Ala Gln Asp Pro Gly Ser Asn
305                 310                 315                 320

Gln Lys Thr Lys Val Thr Pro Thr Ser Phe Ala Asn Asn Gln Thr Ser
                325                 330                 335

Lys Asn His Glu Asp Leu Val Pro Glu Asp Pro Ala Ser Val Val Gln
            340                 345                 350

Val Arg Asp Leu Gln Arg Glu Asn Thr Val Pro Thr Pro Pro Pro Asp
        355                 360                 365

Thr Val Pro Thr Thr Leu Ile Pro Asp Thr Met Glu Glu Gln Thr Thr
    370                 375                 380

Ser His Tyr Glu Pro Pro Asn Ile Ser Arg Asn His Gln Glu Arg Asn
385                 390                 395                 400
```

Asn Thr Ala His Pro Glu Thr Leu Ala Asn Asn Pro Pro Asp Asn Thr
                405                 410                 415

Thr Pro Ser Thr Pro Pro Gln Asp Gly Glu Arg Thr Ser Ser His Thr
            420                 425                 430

Thr Pro Ser Pro Arg Pro Val Pro Thr Ser Thr Ile His Pro Thr Thr
        435                 440                 445

Arg Glu Thr His Ile Pro Thr Thr Met Thr Thr Ser His Asp Thr Asp
    450                 455                 460

Ser Asn Arg Pro Asn Pro Ile Asp Ile Ser Glu Ser Thr Glu Pro Gly
465                 470                 475                 480

Pro Leu Thr Asn Thr Thr Arg Gly Ala Ala Asn Leu Leu Thr Gly Ser
                485                 490                 495

Arg Arg Thr Arg Arg Glu Ile Thr Leu Arg Thr Gln Ala Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Thr
    530                 535                 540

Glu Gly Ile Met His Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Ile Asp Lys Pro Leu Pro Asp Gln Thr Asp
625                 630                 635                 640

Asn Asp Asn Trp Trp Thr Gly Trp Arg Gln Trp Val Pro Ala Gly Ile
                645                 650                 655

Gly Ile Thr Gly Val Ile Ile Ala Val Ile Ala Leu Leu Cys Ile Cys
            660                 665                 670

Lys Phe Leu Leu
        675

<210> SEQ ID NO 6
<211> LENGTH: 681
<212> TYPE: PRT
<213> ORGANISM: Lake Victoria marburgvirus

<400> SEQUENCE: 6

Met Lys Thr Thr Cys Phe Leu Ile Ser Leu Ile Leu Ile Gln Gly Thr
1               5                   10                  15

Lys Asn Leu Pro Ile Leu Glu Ile Ala Ser Asn Asn Gln Pro Gln Asn
                20                  25                  30

Val Asp Ser Val Cys Ser Gly Thr Leu Gln Lys Thr Glu Asp Val His
            35                  40                  45

Leu Met Gly Phe Thr Leu Ser Gly Gln Lys Val Ala Asp Ser Pro Leu
    50                  55                  60

Glu Ala Ser Lys Arg Trp Ala Phe Arg Thr Gly Val Pro Pro Lys Asn
65                  70                  75                  80

Val Glu Tyr Thr Glu Gly Glu Glu Ala Lys Thr Cys Tyr Asn Ile Ser

-continued

```
                85                  90                  95
Val Thr Asp Pro Ser Gly Lys Ser Leu Leu Asp Pro Thr Asn
               100                 105                 110
Ile Arg Asp Tyr Pro Lys Cys Lys Thr Ile His His Ile Gln Gly Gln
               115                 120                 125
Asn Pro His Ala Gln Gly Ile Ala Leu His Leu Trp Gly Ala Phe Phe
       130                 135                 140
Leu Tyr Asp Arg Ile Ala Ser Thr Thr Met Tyr Arg Gly Lys Val Phe
145                 150                 155                 160
Thr Glu Gly Asn Ile Ala Ala Met Ile Val Asn Lys Thr Val His Lys
                   165                 170                 175
Met Ile Phe Ser Arg Gln Gly Gln Gly Tyr Arg His Met Asn Leu Thr
               180                 185                 190
Ser Thr Asn Lys Tyr Trp Thr Ser Ser Asn Gly Thr Gln Thr Asn Asp
           195                 200                 205
Thr Gly Cys Phe Gly Ala Leu Gln Glu Tyr Asn Ser Thr Lys Asn Gln
       210                 215                 220
Thr Cys Ala Pro Ser Lys Ile Pro Pro Leu Pro Thr Ala Arg Pro
225                 230                 235                 240
Glu Ile Lys Leu Thr Ser Pro Thr Asp Ala Thr Lys Leu Asn Thr
                   245                 250                 255
Thr Asp Pro Ser Ser Asp Asp Glu Asp Leu Ala Thr Ser Gly Ser Gly
               260                 265                 270
Ser Gly Glu Arg Glu Pro His Thr Thr Ser Asp Ala Val Thr Lys Gln
           275                 280                 285
Gly Leu Ser Ser Thr Met Pro Pro Thr Pro Ser Pro Gln Pro Ser Thr
       290                 295                 300
Pro Gln Gln Gly Gly Asn Asn Thr Asn His Ser Gln Asp Ala Val Thr
305                 310                 315                 320
Glu Leu Asp Lys Asn Asn Thr Thr Ala Gln Pro Ser Met Pro Pro His
                   325                 330                 335
Asn Thr Thr Thr Ile Ser Thr Asn Asn Thr Ser Lys His Asn Phe Ser
               340                 345                 350
Thr Leu Ser Ala Pro Leu Gln Asn Thr Thr Asn Asp Asn Thr Gln Ser
           355                 360                 365
Thr Ile Thr Glu Asn Glu Gln Thr Ser Ala Pro Ser Ile Thr Thr Leu
       370                 375                 380
Pro Pro Thr Gly Asn Pro Thr Thr Ala Lys Ser Thr Ser Ser Lys Lys
385                 390                 395                 400
Gly Pro Ala Thr Thr Ala Pro Asn Thr Asn Glu His Phe Thr Ser
                   405                 410                 415
Pro Pro Pro Thr Pro Ser Ser Thr Ala Gln His Leu Val Tyr Phe Arg
               420                 425                 430
Arg Lys Arg Ser Ile Leu Trp Arg Glu Gly Asp Met Phe Pro Phe Leu
           435                 440                 445
Asp Gly Leu Ile Asn Ala Pro Ile Asp Phe Asp Pro Val Pro Asn Thr
       450                 455                 460
Lys Thr Ile Phe Asp Glu Ser Ser Ser Gly Ala Ser Ala Glu Glu
465                 470                 475                 480
Asp Gln His Ala Ser Pro Asn Ile Ser Leu Thr Leu Ser Tyr Phe Pro
                   485                 490                 495
Asn Ile Asn Glu Asn Thr Ala Tyr Ser Gly Glu Asn Glu Asn Asp Cys
               500                 505                 510
```

```
Asp Ala Glu Leu Arg Ile Trp Ser Val Gln Glu Asp Leu Ala Ala
        515                 520                 525

Gly Leu Ser Trp Ile Pro Phe Phe Gly Pro Gly Ile Glu Gly Leu Tyr
        530                 535                 540

Thr Ala Val Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Arg Val
        565                 570                 575

Thr Thr Glu Glu Arg Thr Phe Ser Leu Ile Asn Arg His Ala Ile Asp
        580                 585                 590

Phe Leu Leu Thr Arg Trp Gly Gly Thr Cys Lys Val Leu Gly Pro Asp
        595                 600                 605

Cys Cys Ile Gly Ile Glu Asp Leu Ser Lys Asn Ile Ser Glu Gln Ile
        610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
        645                 650                 655

Ile Leu Leu Leu Leu Ser Ile Ala Val Leu Ile Ala Leu Ser Cys Ile
        660                 665                 670

Cys Arg Ile Phe Thr Lys Tyr Ile Gly
        675                 680

<210> SEQ ID NO 7
<211> LENGTH: 739
<212> TYPE: PRT
<213> ORGANISM: Zaire ebolavirus

<400> SEQUENCE: 7

Met Asp Ser Arg Pro Gln Lys Ile Trp Met Ala Pro Ser Leu Thr Glu
1               5                   10                  15

Ser Asp Met Asp Tyr His Lys Ile Leu Thr Ala Gly Leu Ser Val Gln
                20                  25                  30

Gln Gly Ile Val Arg Gln Arg Val Ile Pro Val Tyr Gln Val Asn Asn
            35                  40                  45

Leu Glu Glu Ile Cys Gln Leu Ile Ile Gln Ala Phe Glu Ala Gly Val
        50                  55                  60

Asp Phe Gln Glu Ser Ala Asp Ser Phe Leu Leu Met Leu Cys Leu His
65                  70                  75                  80

His Ala Tyr Gln Gly Asp Tyr Lys Leu Phe Leu Glu Ser Gly Ala Val
                85                  90                  95

Lys Tyr Leu Glu Gly His Gly Phe Arg Phe Glu Val Lys Lys Arg Asp
            100                 105                 110

Gly Val Lys Arg Leu Glu Glu Leu Pro Ala Val Ser Ser Gly Lys
        115                 120                 125

Asn Ile Lys Arg Thr Leu Ala Ala Met Pro Glu Glu Thr Thr Glu
        130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ala Trp Gln
            180                 185                 190

Ser Val Gly His Met Met Val Ile Phe Arg Leu Met Arg Thr Asn Phe
```

```
            195                 200                 205
Leu Ile Lys Phe Leu Leu Ile His Gln Gly Met His Met Val Ala Gly
210                 215                 220

His Asp Ala Asn Asp Ala Val Ile Ser Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu Arg Gly Val Arg Leu His Pro Leu Ala Arg Thr Ala Lys
                260                 265                 270

Val Lys Asn Glu Val Asn Ser Phe Lys Ala Ala Leu Ser Ser Leu Ala
                275                 280                 285

Lys His Gly Glu Tyr Ala Pro Phe Ala Arg Leu Leu Asn Leu Ser Gly
                290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
                340                 345                 350

Gln Leu Gln Gln Tyr Ala Glu Ser Arg Glu Leu Asp His Leu Gly Leu
                355                 360                 365

Asp Asp Gln Glu Lys Lys Ile Leu Met Asn Phe His Gln Lys Lys Asn
370                 375                 380

Glu Ile Ser Phe Gln Gln Thr Asn Ala Met Val Thr Leu Arg Lys Glu
385                 390                 395                 400

Arg Leu Ala Lys Leu Thr Glu Ala Ile Thr Ala Ala Ser Leu Pro Lys
                405                 410                 415

Thr Ser Gly His Tyr Asp Asp Asp Asp Ile Pro Phe Pro Gly Pro
                420                 425                 430

Ile Asn Asp Asp Asn Pro Gly His Gln Asp Asp Pro Thr Asp
                435                 440                 445

Ser Gln Asp Thr Thr Ile Pro Asp Val Val Asp Pro Asp Gly
                450                 455                 460

Ser Tyr Gly Glu Tyr Gln Ser Tyr Ser Glu Asn Gly Met Asn Ala Pro
465                 470                 475                 480

Asp Asp Leu Val Leu Phe Asp Leu Asp Glu Asp Asp Glu Asp Thr Lys
                485                 490                 495

Pro Val Pro Asn Arg Ser Thr Lys Gly Gly Gln Gln Lys Asn Ser Gln
                500                 505                 510

Lys Gly Gln His Ile Glu Gly Arg Gln Thr Gln Ser Arg Pro Ile Gln
                515                 520                 525

Asn Val Pro Gly Pro His Arg Thr Ile His His Ser Ala Pro Leu
                530                 535                 540

Thr Asp Asn Asp Arg Arg Asn Glu Pro Ser Gly Ser Thr Ser Pro Arg
545                 550                 555                 560

Met Leu Thr Pro Ile Asn Glu Glu Ala Asp Pro Leu Asp Asp Ala Asp
                565                 570                 575

Asp Glu Thr Ser Ser Leu Pro Pro Leu Glu Ser Asp Asp Glu Glu Gln
                580                 585                 590

Asp Arg Asp Gly Thr Ser Asn Arg Thr Pro Thr Val Ala Pro Pro Ala
                595                 600                 605

Pro Val Tyr Arg Asp His Ser Glu Lys Lys Glu Leu Pro Gln Asp Glu
                610                 615                 620
```

```
Gln Gln Asp Gln Asp His Thr Gln Glu Ala Arg Asn Gln Asp Ser Asp
625                 630                 635                 640

Asn Thr Gln Ser Glu His Ser Phe Glu Glu Met Tyr Arg His Ile Leu
            645                 650                 655

Arg Ser Gln Gly Pro Phe Asp Ala Val Leu Tyr Tyr His Met Met Lys
        660                 665                 670

Asp Glu Pro Val Val Phe Ser Thr Ser Asp Gly Lys Glu Tyr Thr Tyr
    675                 680                 685

Pro Asp Ser Leu Glu Glu Tyr Pro Pro Trp Leu Thr Glu Lys Glu
690                 695                 700

Ala Met Asn Glu Glu Asn Arg Phe Val Thr Leu Asp Gly Gln Gln Phe
705                 710                 715                 720

Tyr Trp Pro Val Met Asn His Lys Asn Lys Phe Met Ala Ile Leu Gln
                725                 730                 735

His His Gln

<210> SEQ ID NO 8
<211> LENGTH: 251
<212> TYPE: PRT
<213> ORGANISM: Zaire ebolavirus

<400> SEQUENCE: 8

Met Ala Lys Ala Thr Gly Arg Tyr Asn Leu Ile Ser Pro Lys Lys Asp
1               5                   10                  15

Leu Glu Lys Gly Val Val Leu Ser Asp Leu Cys Asn Phe Leu Val Ser
            20                  25                  30

Gln Thr Ile Gln Gly Trp Lys Val Tyr Trp Ala Gly Ile Glu Phe Asp
        35                  40                  45

Val Thr His Lys Gly Met Ala Leu Leu His Arg Leu Lys Thr Asn Asp
    50                  55                  60

Phe Ala Pro Ala Trp Ser Met Thr Arg Asn Leu Phe Pro His Leu Phe
65                  70                  75                  80

Gln Asn Pro Asn Ser Thr Ile Glu Ser Pro Leu Trp Ala Leu Arg Val
                85                  90                  95

Ile Leu Ala Ala Gly Ile Gln Asp Gln Leu Ile Asp Gln Ser Leu Ile
            100                 105                 110

Glu Pro Leu Ala Gly Ala Leu Gly Leu Ile Ser Asp Trp Leu Leu Thr
        115                 120                 125

Thr Asn Thr Asn His Phe Asn Met Arg Thr Gln Arg Val Lys Glu Gln
    130                 135                 140

Leu Ser Leu Lys Met Leu Ser Leu Ile Arg Ser Asn Ile Leu Lys Phe
145                 150                 155                 160

Ile Asn Lys Leu Asp Ala Leu His Val Val Asn Tyr Asn Gly Leu Leu
                165                 170                 175

Ser Ser Ile Glu Ile Gly Thr Gln Asn His Thr Ile Ile Thr Arg
            180                 185                 190

Thr Asn Met Gly Phe Leu Val Glu Leu Gln Glu Pro Asp Lys Ser Ala
        195                 200                 205

Met Asn Arg Met Lys Pro Gly Pro Ala Lys Phe Ser Leu Leu His Glu
    210                 215                 220

Ser Thr Leu Lys Ala Phe Thr Gln Gly Ser Ser Thr Arg Met Gln Ser
225                 230                 235                 240

Leu Ile Leu Glu Phe Asn Ser Ser Leu Ala Ile
                245                 250
```

<210> SEQ ID NO 9
<211> LENGTH: 288
<212> TYPE: PRT
<213> ORGANISM: Zaire ebolavirus

<400> SEQUENCE: 9

Met Glu Ala Ser Tyr Glu Arg Gly Arg Pro Arg Ala Ala Arg Gln His
1               5                   10                  15

Ser Arg Asp Gly His Asp His Val Arg Ala Arg Ser Ser Ser Arg
            20                  25                  30

Glu Asn Tyr Arg Gly Tyr Arg Gln Ser Arg Ser Ala Ser Gln Val
        35                  40                  45

Arg Val Pro Thr Val Phe His Lys Lys Arg Val Glu Pro Leu Thr Val
    50                  55                  60

Pro Pro Ala Pro Lys Asp Ile Cys Pro Thr Leu Lys Lys Gly Phe Leu
65                  70                  75                  80

Cys Asp Ser Ser Phe Cys Lys Lys Asp His Gln Leu Glu Ser Leu Thr
                85                  90                  95

Asp Arg Glu Leu Leu Leu Leu Ile Ala Arg Lys Thr Cys Gly Ser Val
            100                 105                 110

Glu Gln Gln Leu Asn Ile Thr Ala Pro Lys Asp Ser Arg Leu Ala Asn
        115                 120                 125

Pro Thr Ala Asp Asp Phe Gln Gln Glu Glu Gly Pro Lys Ile Thr Leu
    130                 135                 140

Leu Thr Leu Ile Lys Thr Ala Glu His Trp Ala Arg Gln Asp Ile Arg
145                 150                 155                 160

Thr Ile Glu Asp Ser Lys Leu Arg Ala Leu Leu Thr Leu Cys Ala Val
                165                 170                 175

Met Thr Arg Lys Phe Ser Lys Ser Gln Leu Ser Leu Leu Cys Glu Thr
            180                 185                 190

His Leu Arg Arg Glu Gly Leu Gly Gln Asp Gln Ala Glu Pro Val Leu
        195                 200                 205

Glu Val Tyr Gln Arg Leu His Ser Asp Lys Gly Gly Ser Phe Glu Ala
    210                 215                 220

Ala Leu Trp Gln Gln Trp Asp Arg Gln Ser Leu Ile Met Phe Ile Thr
225                 230                 235                 240

Ala Phe Leu Asn Ile Ala Leu Gln Leu Pro Cys Glu Ser Ser Ala Val
                245                 250                 255

Val Val Ser Gly Leu Arg Thr Leu Val Pro Gln Ser Asp Asn Glu Glu
            260                 265                 270

Ala Ser Thr Asn Pro Gly Thr Cys Ser Trp Ser Asp Glu Gly Thr Pro
        275                 280                 285

<210> SEQ ID NO 10
<211> LENGTH: 340
<212> TYPE: PRT
<213> ORGANISM: Zaire ebolavirus

<400> SEQUENCE: 10

Met Thr Thr Arg Thr Lys Gly Arg Gly His Thr Ala Ala Thr Thr Gln
1               5                   10                  15

Asn Asp Arg Met Pro Gly Pro Glu Leu Ser Gly Trp Ile Ser Glu Gln
            20                  25                  30

Leu Met Thr Gly Arg Ile Pro Val Ser Asp Ile Phe Cys Asp Ile Glu
        35                  40                  45

Asn Asn Pro Gly Leu Cys Tyr Ala Ser Gln Met Gln Gln Thr Lys Pro
         50                  55                  60

Asn Pro Lys Thr Arg Asn Ser Gln Thr Gln Thr Asp Pro Ile Cys Asn
 65                  70                  75                  80

His Ser Phe Glu Glu Val Val Gln Thr Leu Ala Ser Leu Ala Thr Val
                 85                  90                  95

Val Gln Gln Gln Thr Ile Ala Ser Glu Ser Leu Glu Gln Arg Ile Thr
                100                 105                 110

Ser Leu Glu Asn Gly Leu Lys Pro Val Tyr Asp Met Ala Lys Thr Ile
            115                 120                 125

Ser Ser Leu Asn Arg Val Cys Ala Glu Met Val Ala Lys Tyr Asp Leu
        130                 135                 140

Leu Val Met Thr Thr Gly Arg Ala Thr Ala Thr Ala Ala Ala Thr Glu
145                 150                 155                 160

Ala Tyr Trp Ala Glu His Gly Gln Pro Pro Pro Gly Pro Ser Leu Tyr
                165                 170                 175

Glu Glu Ser Ala Ile Arg Gly Lys Ile Glu Ser Arg Asp Glu Thr Val
            180                 185                 190

Pro Gln Ser Val Arg Glu Ala Phe Asn Asn Leu Asn Ser Thr Thr Ser
        195                 200                 205

Leu Thr Glu Glu Asn Phe Gly Lys Pro Asp Ile Ser Ala Lys Asp Leu
210                 215                 220

Arg Asn Ile Met Tyr Asp His Leu Pro Gly Phe Gly Thr Ala Phe His
225                 230                 235                 240

Gln Leu Val Gln Val Ile Cys Lys Leu Gly Lys Asp Ser Asn Ser Leu
                245                 250                 255

Asp Ile Ile His Ala Glu Phe Gln Ala Ser Leu Ala Glu Gly Asp Ser
            260                 265                 270

Pro Gln Cys Ala Leu Ile Gln Ile Thr Lys Arg Val Pro Ile Phe Gln
        275                 280                 285

Asp Ala Ala Pro Pro Val Ile His Ile Arg Ser Arg Gly Asp Ile Pro
290                 295                 300

Arg Ala Cys Gln Lys Ser Leu Arg Pro Val Pro Pro Ser Pro Lys Ile
305                 310                 315                 320

Asp Arg Gly Trp Val Cys Val Phe Gln Leu Gln Asp Gly Lys Thr Leu
                325                 330                 335

Gly Leu Lys Ile
            340

<210> SEQ ID NO 11
<211> LENGTH: 326
<212> TYPE: PRT
<213> ORGANISM: Zaire ebolavirus

<400> SEQUENCE: 11

Met Arg Arg Val Ile Leu Pro Thr Ala Pro Pro Glu Tyr Met Glu Ala
1                5                  10                  15

Ile Tyr Pro Val Arg Ser Asn Ser Thr Ile Ala Arg Gly Gly Asn Ser
                20                  25                  30

Asn Thr Gly Phe Leu Thr Pro Glu Ser Val Asn Gly Asp Thr Pro Ser
            35                  40                  45

Asn Pro Leu Arg Pro Ile Ala Asp Asp Thr Ile Asp His Ala Ser His
        50                  55                  60

Thr Pro Gly Ser Val Ser Ser Ala Phe Ile Leu Glu Ala Met Val Asn

```
                65                  70                  75                  80
Val Ile Ser Gly Pro Lys Val Leu Met Lys Gln Ile Pro Ile Trp Leu
                    85                  90                  95

Pro Leu Gly Val Ala Asp Gln Lys Thr Tyr Ser Phe Asp Ser Thr Thr
                100                 105                 110

Ala Ala Ile Met Leu Ala Ser Tyr Thr Ile Thr His Phe Gly Lys Ala
                115                 120                 125

Thr Asn Pro Leu Val Arg Val Asn Arg Leu Gly Pro Gly Ile Pro Asp
            130                 135                 140

His Pro Leu Arg Leu Leu Arg Ile Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Ile Thr Gln Pro Leu Pro Ala Ala Thr Trp Thr
                180                 185                 190

Asp Asp Thr Pro Thr Gly Ser Asn Gly Ala Leu Arg Pro Gly Ile Ser
            195                 200                 205

Phe His Pro Lys Leu Arg Pro Ile Leu Leu Pro Asn Lys Ser Gly Lys
            210                 215                 220

Lys Gly Asn Ser Ala Asp Leu Thr Ser Pro Glu Lys Ile Gln Ala Ile
225                 230                 235                 240

Met Thr Ser Leu Gln Asp Phe Lys Ile Val Pro Ile Asp Pro Thr Lys
                245                 250                 255

Asn Ile Met Gly Ile Glu Val Pro Glu Thr Leu Val His Lys Leu Thr
                260                 265                 270

Gly Lys Lys Val Thr Ser Lys Asn Gly Gln Pro Ile Ile Pro Val Leu
            275                 280                 285

Leu Pro Lys Tyr Ile Gly Leu Asp Pro Val Ala Pro Gly Asp Leu Thr
            290                 295                 300

Met Val Ile Thr Gln Asp Cys Asp Thr Cys His Ser Pro Ala Ser Leu
305                 310                 315                 320

Pro Ala Val Ile Glu Lys
                325

<210> SEQ ID NO 12
<211> LENGTH: 2212
<212> TYPE: PRT
<213> ORGANISM: Zaire ebolavirus

<400> SEQUENCE: 12

Met Ala Thr Gln His Thr Gln Tyr Pro Asp Ala Arg Leu Ser Ser Pro
1               5                   10                  15

Ile Val Leu Asp Gln Cys Asp Leu Val Thr Arg Ala Cys Gly Leu Tyr
                20                  25                  30

Ser Ser Tyr Ser Leu Asn Pro Gln Leu Arg Asn Cys Lys Leu Pro Lys
            35                  40                  45

His Ile Tyr Arg Leu Lys Tyr Asp Val Thr Val Thr Lys Phe Leu Ser
        50                  55                  60

Asp Val Pro Val Ala Thr Leu Pro Ile Asp Phe Ile Val Pro Val Leu
65                  70                  75                  80

Leu Lys Ala Leu Ser Gly Asn Gly Phe Cys Pro Val Glu Pro Arg Cys
                85                  90                  95

Gln Gln Phe Leu Asp Glu Ile Ile Lys Tyr Thr Met Gln Asp Ala Leu
                100                 105                 110
```

```
Phe Leu Lys Tyr Tyr Leu Lys Asn Val Gly Ala Gln Glu Asp Cys Val
            115                 120                 125

Asp Glu His Phe Gln Glu Lys Ile Leu Ser Ser Ile Gln Gly Asn Glu
        130                 135                 140

Phe Leu His Gln Met Phe Phe Trp Tyr Asp Leu Ala Ile Leu Thr Arg
145                 150                 155                 160

Arg Gly Arg Leu Asn Arg Gly Asn Ser Arg Ser Thr Trp Phe Val His
                165                 170                 175

Asp Asp Leu Ile Asp Ile Leu Gly Tyr Gly Asp Tyr Val Phe Trp Lys
            180                 185                 190

Ile Pro Ile Ser Met Leu Pro Leu Asn Thr Gln Gly Ile Pro His Ala
        195                 200                 205

Ala Met Asp Trp Tyr Gln Ala Ser Val Phe Lys Glu Ala Val Gln Gly
    210                 215                 220

His Thr His Ile Val Ser Val Ser Thr Ala Asp Val Leu Ile Met Cys
225                 230                 235                 240

Lys Asp Leu Ile Thr Cys Arg Phe Asn Thr Thr Leu Ile Ser Lys Ile
                245                 250                 255

Ala Glu Ile Glu Asp Pro Val Cys Ser Asp Tyr Pro Asn Phe Lys Ile
            260                 265                 270

Val Ser Met Leu Tyr Gln Ser Gly Asp Tyr Leu Leu Ser Ile Leu Gly
        275                 280                 285

Ser Asp Gly Tyr Lys Ile Ile Lys Phe Leu Glu Pro Leu Cys Leu Ala
    290                 295                 300

Lys Ile Gln Leu Cys Ser Lys Tyr Thr Glu Arg Lys Gly Arg Phe Leu
305                 310                 315                 320

Thr Gln Met His Leu Ala Val Asn His Thr Leu Glu Glu Ile Thr Glu
                325                 330                 335

Met Arg Ala Leu Lys Pro Ser Gln Ala Gln Lys Ile Arg Glu Phe His
            340                 345                 350

Arg Thr Leu Ile Arg Leu Glu Met Thr Pro Gln Leu Cys Glu Leu
        355                 360                 365

Phe Ser Ile Gln Lys His Trp Gly His Pro Val Leu His Ser Glu Thr
370                 375                 380

Ala Ile Gln Lys Val Lys Lys His Ala Thr Val Leu Lys Ala Leu Arg
385                 390                 395                 400

Pro Ile Val Ile Phe Glu Thr Tyr Cys Val Phe Lys Tyr Ser Ile Ala
                405                 410                 415

Lys His Tyr Phe Asp Ser Gln Gly Ser Trp Tyr Ser Val Thr Ser Asp
            420                 425                 430

Arg Asn Leu Thr Pro Gly Leu Asn Ser Tyr Ile Lys Arg Asn Gln Phe
        435                 440                 445

Pro Pro Leu Pro Met Ile Lys Glu Leu Leu Trp Glu Phe Tyr His Leu
    450                 455                 460

Asp His Pro Pro Leu Phe Ser Thr Lys Ile Ile Ser Asp Leu Ser Ile
465                 470                 475                 480

Phe Ile Lys Asp Arg Ala Thr Ala Val Glu Arg Thr Cys Trp Asp Ala
                485                 490                 495

Val Phe Glu Pro Asn Val Leu Gly Tyr Asn Pro His Lys Phe Ser
            500                 505                 510

Thr Lys Arg Val Pro Glu Gln Phe Leu Glu Gln Glu Asn Phe Ser Ile
        515                 520                 525

Glu Asn Val Leu Ser Tyr Ala Gln Lys Leu Glu Tyr Leu Leu Pro Gln
```

```
              530               535               540
Tyr Arg Asn Phe Ser Phe Ser Leu Lys Glu Lys Glu Leu Asn Val Gly
545               550               555               560

Arg Thr Phe Gly Lys Leu Pro Tyr Pro Thr Arg Asn Val Gln Thr Leu
                  565               570               575

Cys Glu Ala Leu Leu Ala Asp Gly Leu Ala Lys Ala Phe Pro Ser Asn
                  580               585               590

Met Met Val Val Thr Glu Arg Glu Gln Lys Glu Ser Leu Leu His Gln
                  595               600               605

Ala Ser Trp His His Thr Ser Asp Asp Phe Gly Glu His Ala Thr Val
                  610               615               620

Arg Gly Ser Ser Phe Val Thr Asp Leu Glu Lys Tyr Asn Leu Ala Phe
625               630               635               640

Arg Tyr Glu Phe Thr Ala Pro Phe Ile Glu Tyr Cys Asn Arg Cys Tyr
                  645               650               655

Gly Val Lys Asn Val Phe Asn Trp Met His Tyr Thr Ile Pro Gln Cys
                  660               665               670

Tyr Met His Val Ser Asp Tyr Tyr Asn Pro Pro His Asn Leu Thr Leu
                  675               680               685

Glu Asn Arg Asp Asn Pro Pro Glu Gly Pro Ser Ser Tyr Arg Gly His
                  690               695               700

Met Gly Gly Ile Glu Gly Leu Gln Gln Lys Leu Trp Thr Ser Ile Ser
705               710               715               720

Cys Ala Gln Ile Ser Leu Val Glu Ile Lys Thr Gly Phe Lys Leu Arg
                  725               730               735

Ser Ala Val Met Gly Asp Asn Gln Cys Ile Thr Val Leu Ser Val Phe
                  740               745               750

Pro Leu Glu Thr Asp Ala Asp Glu Gln Glu Gln Ser Ala Glu Asp Asn
                  755               760               765

Ala Ala Arg Val Ala Ala Ser Leu Ala Lys Val Thr Ser Ala Cys Gly
                  770               775               780

Ile Phe Leu Lys Pro Asp Glu Thr Phe Val His Ser Gly Phe Ile Tyr
785               790               795               800

Phe Gly Lys Lys Gln Tyr Leu Asn Gly Val Gln Leu Pro Gln Ser Leu
                  805               810               815

Lys Thr Ala Thr Arg Met Ala Pro Leu Ser Asp Ala Ile Phe Asp Asp
                  820               825               830

Leu Gln Gly Thr Leu Ala Ser Ile Gly Thr Ala Phe Glu Arg Ser Ile
                  835               840               845

Ser Glu Thr Arg His Ile Phe Pro Cys Arg Ile Thr Ala Ala Phe His
850               855               860

Thr Phe Phe Ser Val Arg Ile Leu Gln Tyr His His Leu Gly Phe Asn
865               870               875               880

Lys Gly Phe Asp Leu Gly Gln Leu Thr Leu Gly Lys Pro Leu Asp Phe
                  885               890               895

Gly Thr Ile Ser Leu Ala Leu Ala Val Pro Gln Val Leu Gly Gly Leu
                  900               905               910

Ser Phe Leu Asn Pro Glu Lys Cys Phe Tyr Arg Asn Leu Gly Asp Pro
                  915               920               925

Val Thr Ser Gly Leu Phe Gln Leu Lys Thr Tyr Leu Arg Met Ile Glu
                  930               935               940

Met Asp Asp Leu Phe Leu Pro Leu Ile Ala Lys Asn Pro Gly Asn Cys
945               950               955               960
```

-continued

```
Thr Ala Ile Asp Phe Val Leu Asn Pro Ser Gly Leu Asn Val Pro Gly
            965                 970                 975

Ser Gln Asp Leu Thr Ser Phe Leu Arg Gln Ile Val Arg Arg Thr Ile
        980                 985                 990

Thr Leu Ser Ala Lys Asn Lys Leu Ile Asn Thr Leu Phe His Ala Ser
    995                 1000                1005

Ala Asp Phe Glu Asp Glu Met Val Cys Lys Trp Leu Leu Ser Ser
    1010                1015                1020

Thr Pro Val Met Ser Arg Phe Ala Ala Asp Ile Phe Ser Arg Thr
    1025                1030                1035

Pro Ser Gly Lys Arg Leu Gln Ile Leu Gly Tyr Leu Glu Gly Thr
    1040                1045                1050

Arg Thr Leu Leu Ala Ser Lys Ile Ile Asn Asn Thr Glu Thr
    1055                1060                1065

Pro Val Leu Asp Arg Leu Arg Lys Ile Thr Leu Gln Arg Trp Ser
    1070                1075                1080

Leu Trp Phe Ser Tyr Leu Asp His Cys Asp Asn Ile Leu Ala Glu
    1085                1090                1095

Ala Leu Thr Gln Ile Thr Cys Thr Val Asp Leu Ala Gln Ile Leu
    1100                1105                1110

Arg Glu Tyr Ser Trp Ala His Ile Leu Glu Gly Arg Pro Leu Ile
    1115                1120                1125

Gly Ala Thr Leu Pro Cys Met Ile Glu Gln Phe Lys Val Phe Trp
    1130                1135                1140

Leu Lys Pro Tyr Glu Gln Cys Pro Gln Cys Ser Asn Ala Lys Gln
    1145                1150                1155

Pro Gly Gly Lys Pro Phe Val Ser Val Ala Val Lys Lys His Ile
    1160                1165                1170

Val Ser Ala Trp Pro Asn Ala Ser Arg Ile Ser Trp Thr Ile Gly
    1175                1180                1185

Asp Gly Ile Pro Tyr Ile Gly Ser Arg Thr Glu Asp Lys Ile Gly
    1190                1195                1200

Gln Pro Ala Ile Lys Pro Lys Cys Pro Ser Ala Ala Leu Arg Glu
    1205                1210                1215

Ala Ile Glu Leu Ala Ser Arg Leu Thr Trp Val Thr Gln Gly Ser
    1220                1225                1230

Ser Asn Ser Asp Leu Leu Ile Lys Pro Phe Leu Glu Ala Arg Val
    1235                1240                1245

Asn Leu Ser Val Gln Glu Ile Leu Gln Met Thr Pro Ser His Tyr
    1250                1255                1260

Ser Gly Asn Ile Val His Arg Tyr Asn Asp Gln Tyr Ser Pro His
    1265                1270                1275

Ser Phe Met Ala Asn Arg Met Ser Asn Ser Ala Thr Arg Leu Ile
    1280                1285                1290

Val Ser Thr Asn Thr Leu Gly Glu Phe Ser Gly Gly Gly Gln Ser
    1295                1300                1305

Ala Arg Asp Ser Asn Ile Ile Phe Gln Asn Val Ile Asn Tyr Ala
    1310                1315                1320

Val Ala Leu Phe Asp Ile Lys Phe Arg Asn Thr Glu Ala Thr Asp
    1325                1330                1335

Ile Gln Tyr Asn Arg Ala His Leu His Leu Thr Lys Cys Cys Thr
    1340                1345                1350
```

```
Arg Glu Val Pro Ala Gln Tyr Leu Thr Tyr Thr Ser Thr Leu Asp
    1355                1360                1365
Leu Asp Leu Thr Arg Tyr Arg Glu Asn Glu Leu Ile Tyr Asp Ser
    1370                1375                1380
Asn Pro Leu Lys Gly Gly Leu Asn Cys Asn Ile Ser Phe Asp Asn
    1385                1390                1395
Pro Phe Phe Gln Gly Lys Arg Leu Asn Ile Ile Glu Asp Asp Leu
    1400                1405                1410
Ile Arg Leu Pro His Leu Ser Gly Trp Glu Leu Ala Lys Thr Ile
    1415                1420                1425
Met Gln Ser Ile Ile Ser Asp Ser Asn Asn Ser Ser Thr Asp Pro
    1430                1435                1440
Ile Ser Ser Gly Glu Thr Arg Ser Phe Thr Thr His Phe Leu Thr
    1445                1450                1455
Tyr Pro Lys Ile Gly Leu Leu Tyr Ser Phe Gly Ala Phe Val Ser
    1460                1465                1470
Tyr Tyr Leu Gly Asn Thr Ile Leu Arg Thr Lys Lys Leu Thr Leu
    1475                1480                1485
Asp Asn Phe Leu Tyr Tyr Leu Thr Thr Gln Ile His Asn Leu Pro
    1490                1495                1500
His Arg Ser Leu Arg Ile Leu Lys Pro Thr Phe Lys His Ala Ser
    1505                1510                1515
Val Met Ser Arg Leu Met Ser Ile Asp Pro His Phe Ser Ile Tyr
    1520                1525                1530
Ile Gly Gly Ala Ala Gly Asp Arg Gly Leu Ser Asp Ala Ala Arg
    1535                1540                1545
Leu Phe Leu Arg Thr Ser Ile Ser Ser Phe Leu Thr Phe Val Lys
    1550                1555                1560
Glu Trp Ile Ile Asn Arg Gly Thr Ile Val Pro Leu Trp Ile Val
    1565                1570                1575
Tyr Pro Leu Glu Gly Gln Asn Pro Thr Pro Val Asn Asn Phe Leu
    1580                1585                1590
Tyr Gln Ile Val Glu Leu Leu Val His Asp Ser Ser Arg Gln Gln
    1595                1600                1605
Ala Phe Lys Thr Thr Ile Ser Asp His Val His Pro His Asp Asn
    1610                1615                1620
Leu Val Tyr Thr Cys Lys Ser Thr Ala Ser Asn Phe Phe His Ala
    1625                1630                1635
Ser Leu Ala Tyr Trp Arg Ser Arg His Arg Asn Ser Asn Arg Lys
    1640                1645                1650
Tyr Leu Ala Arg Asp Ser Ser Thr Gly Ser Ser Thr Asn Asn Ser
    1655                1660                1665
Asp Gly His Ile Glu Arg Ser Gln Glu Gln Thr Thr Arg Asp Pro
    1670                1675                1680
His Asp Gly Thr Glu Arg Asn Leu Val Leu Gln Met Ser His Glu
    1685                1690                1695
Ile Lys Arg Thr Thr Ile Pro Gln Glu Asn Thr His Gln Gly Pro
    1700                1705                1710
Ser Phe Gln Ser Phe Leu Ser Asp Ser Ala Cys Gly Thr Ala Asn
    1715                1720                1725
Pro Lys Leu Asn Phe Asp Arg Ser Arg His Asn Val Lys Phe Gln
    1730                1735                1740
Asp His Asn Ser Ala Ser Lys Arg Glu Gly His Gln Ile Ile Ser
```

-continued

```
        1745                1750                1755
His Arg Leu Val Leu Pro Phe Phe Thr Leu Ser Gln Gly Thr Arg
        1760                1765                1770
Gln Leu Thr Ser Ser Asn Glu Ser Gln Thr Gln Asp Glu Ile Ser
        1775                1780                1785
Lys Tyr Leu Arg Gln Leu Arg Ser Val Ile Asp Thr Thr Val Tyr
        1790                1795                1800
Cys Arg Phe Thr Gly Ile Val Ser Ser Met His Tyr Lys Leu Asp
        1805                1810                1815
Glu Val Leu Trp Glu Ile Glu Ser Phe Lys Ser Ala Val Thr Leu
        1820                1825                1830
Ala Glu Gly Glu Gly Ala Gly Ala Leu Leu Leu Ile Gln Lys Tyr
        1835                1840                1845
Gln Val Lys Thr Leu Phe Phe Asn Thr Leu Ala Thr Glu Ser Ser
        1850                1855                1860
Ile Glu Ser Glu Ile Val Ser Gly Met Thr Thr Pro Arg Met Leu
        1865                1870                1875
Leu Pro Val Met Ser Lys Phe His Asn Asp Gln Ile Glu Ile Ile
        1880                1885                1890
Leu Asn Asn Ser Ala Ser Gln Ile Thr Asp Ile Thr Asn Pro Thr
        1895                1900                1905
Trp Phe Lys Asp Gln Arg Ala Arg Leu Pro Lys Gln Val Glu Val
        1910                1915                1920
Ile Thr Met Asp Ala Glu Thr Thr Glu Asn Ile Asn Arg Ser Lys
        1925                1930                1935
Leu Tyr Glu Ala Val Tyr Lys Leu Ile Leu His His Ile Asp Pro
        1940                1945                1950
Ser Val Leu Lys Ala Val Val Leu Lys Val Phe Leu Ser Asp Thr
        1955                1960                1965
Glu Gly Met Leu Trp Leu Asn Asp Asn Leu Ala Pro Phe Phe Ala
        1970                1975                1980
Thr Gly Tyr Leu Ile Lys Pro Ile Thr Ser Ser Ala Arg Ser Ser
        1985                1990                1995
Glu Trp Tyr Leu Cys Leu Thr Asn Phe Leu Ser Thr Thr Arg Lys
        2000                2005                2010
Met Pro His Gln Asn His Leu Ser Cys Lys Gln Val Ile Leu Thr
        2015                2020                2025
Ala Leu Gln Leu Gln Ile Gln Arg Ser Pro Tyr Trp Leu Ser His
        2030                2035                2040
Leu Thr Gln Tyr Ala Asp Cys Glu Leu His Leu Ser Tyr Ile Arg
        2045                2050                2055
Leu Gly Phe Pro Ser Leu Glu Lys Val Leu Tyr His Arg Tyr Asn
        2060                2065                2070
Leu Val Asp Ser Lys Arg Gly Pro Leu Val Ser Ile Thr Gln His
        2075                2080                2085
Leu Ala His Leu Arg Ala Glu Ile Arg Glu Leu Thr Asn Asp Tyr
        2090                2095                2100
Asn Gln Gln Arg Gln Ser Arg Thr Gln Thr Tyr His Phe Ile Arg
        2105                2110                2115
Thr Ala Lys Gly Arg Ile Thr Lys Leu Val Asn Asp Tyr Leu Lys
        2120                2125                2130
Phe Phe Leu Ile Val Gln Ala Leu Lys His Asn Gly Thr Trp Gln
        2135                2140                2145
```

```
Ala Glu Phe Lys Lys Leu Pro Glu Leu Ile Ser Val Cys Asn Arg
2150                2155                2160

Phe Tyr His Ile Arg Asp Cys Asn Cys Glu Glu Arg Phe Leu Val
2165                2170                2175

Gln Thr Leu Tyr Leu His Arg Met Gln Asp Ser Glu Val Lys Leu
2180                2185                2190

Ile Glu Arg Leu Thr Gly Leu Leu Ser Leu Phe Pro Asp Gly Leu
2195                2200                2205

Tyr Arg Phe Asp
2210

<210> SEQ ID NO 13
<211> LENGTH: 738
<212> TYPE: PRT
<213> ORGANISM: Sudan ebolavirus

<400> SEQUENCE: 13

Met Asp Lys Arg Val Arg Gly Ser Trp Ala Leu Gly Gly Gln Ser Glu
1               5                   10                  15

Val Asp Leu Asp Tyr His Lys Ile Leu Thr Ala Gly Leu Ser Val Gln
            20                  25                  30

Gln Gly Ile Val Arg Gln Arg Val Ile Pro Val Tyr Val Val Asn Asp
        35                  40                  45

Leu Glu Gly Ile Cys Gln His Ile Ile Gln Ala Phe Glu Ala Gly Val
    50                  55                  60

Asp Phe Gln Asp Asn Ala Asp Ser Phe Leu Leu Leu Cys Leu His
65                  70                  75                  80

His Ala Tyr Gln Gly Asp His Arg Leu Phe Leu Lys Ser Asp Ala Val
                85                  90                  95

Gln Tyr Leu Glu Gly His Gly Phe Arg Phe Glu Val Arg Glu Lys Glu
            100                 105                 110

Asn Val His Arg Leu Asp Glu Leu Leu Pro Asn Val Thr Gly Gly Lys
        115                 120                 125

Asn Leu Arg Arg Thr Leu Ala Ala Met Pro Glu Glu Glu Thr Thr Glu
    130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ser Trp Gln
            180                 185                 190

Ser Val Gly His Met Met Val Ile Phe Arg Leu Met Arg Thr Asn Phe
        195                 200                 205

Leu Ile Lys Phe Leu Leu Ile His Gln Gly Met His Met Val Ala Gly
    210                 215                 220

His Asp Ala Asn Asp Thr Val Ile Ser Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Asp Leu Gly Val Arg Leu His Pro Leu Ala Arg Thr Ala Lys
            260                 265                 270

Val Lys Asn Glu Val Ser Ser Phe Lys Ala Ala Leu Gly Ser Leu Ala
        275                 280                 285

Lys His Gly Glu Tyr Ala Pro Phe Ala Arg Leu Leu Asn Leu Ser Gly
```

```
            290                 295                 300
Val Asn Asn Leu Glu His Gly Leu Tyr Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
                340                 345                 350

Gln Leu Gln Gln Tyr Ala Glu Thr Arg Glu Leu Asp Asn Leu Gly Leu
                355                 360                 365

Asp Glu Gln Glu Lys Lys Ile Leu Met Ser Phe His Gln Lys Lys Asn
370                 375                 380

Glu Ile Ser Phe Gln Gln Thr Asn Ala Met Val Thr Leu Arg Lys Glu
385                 390                 395                 400

Arg Leu Ala Lys Leu Thr Glu Ala Ile Thr Thr Ala Ser Lys Ile Lys
                405                 410                 415

Val Gly Asp Arg Tyr Pro Asp Asp Asn Asp Ile Pro Phe Pro Gly Pro
                420                 425                 430

Ile Tyr Asp Asp Thr His Pro Asn Pro Ser Asp Asp Asn Pro Asp Asp
                435                 440                 445

Ser Arg Asp Thr Thr Ile Pro Gly Gly Val Val Asp Pro Tyr Asp Asp
                450                 455                 460

Glu Ser Asn Asn Tyr Pro Asp Tyr Glu Asp Ser Ala Glu Gly Thr Thr
465                 470                 475                 480

Gly Asp Leu Asp Leu Phe Asn Leu Asp Asp Asp Asp Asp Asp Ser Arg
                485                 490                 495

Pro Gly Pro Pro Asp Arg Gly Gln Asn Lys Glu Arg Ala Ala Arg Thr
                500                 505                 510

Tyr Gly Leu Gln Asp Pro Thr Leu Asp Gly Ala Lys Lys Val Pro Glu
                515                 520                 525

Leu Thr Pro Gly Ser His Gln Pro Gly Asn Leu His Ile Thr Lys Ser
530                 535                 540

Gly Ser Asn Thr Asn Gln Pro Gln Gly Asn Met Ser Ser Thr Leu His
545                 550                 555                 560

Ser Met Thr Pro Ile Gln Glu Glu Ser Glu Pro Asp Asp Gln Lys Asp
                565                 570                 575

Asn Asp Asp Glu Ser Leu Thr Ser Leu Asp Ser Glu Gly Asp Glu Asp
                580                 585                 590

Gly Glu Ser Ile Ser Glu Glu Asn Thr Pro Thr Val Ala Pro Pro Ala
                595                 600                 605

Pro Val Tyr Lys Asp Thr Gly Val Asp Thr Asn Gln Gln Asn Gly Pro
                610                 615                 620

Ser Ser Thr Val Asp Ser Gln Gly Ser Glu Ser Glu Ala Leu Pro Ile
625                 630                 635                 640

Asn Ser Lys Lys Ser Ser Ala Leu Glu Glu Thr Tyr Tyr His Leu Leu
                645                 650                 655

Lys Thr Gln Gly Pro Phe Glu Ala Ile Asn Tyr Tyr His Leu Met Ser
                660                 665                 670

Asp Glu Pro Ile Ala Phe Ser Thr Glu Ser Gly Lys Glu Tyr Ile Phe
                675                 680                 685

Pro Asp Ser Leu Glu Glu Ala Tyr Pro Pro Trp Leu Ser Glu Lys Glu
                690                 695                 700

Ala Leu Glu Lys Glu Asn Arg Tyr Leu Val Ile Asp Gly Gln Gln Phe
705                 710                 715                 720
```

-continued

Leu Trp Pro Val Met Ser Leu Gln Asp Lys Phe Leu Ala Val Leu Gln
            725                 730                 735

His Asp

<210> SEQ ID NO 14
<211> LENGTH: 251
<212> TYPE: PRT
<213> ORGANISM: Sudan ebolavirus

<400> SEQUENCE: 14

Met Ala Lys Ala Thr Gly Arg Tyr Asn Leu Val Thr Pro Lys Arg Glu
1               5                   10                  15

Leu Glu Gln Gly Val Val Phe Ser Asp Leu Cys Asn Phe Leu Val Thr
            20                  25                  30

Pro Thr Val Gln Gly Trp Lys Val Tyr Trp Ala Gly Leu Glu Phe Asp
        35                  40                  45

Val Asn Gln Lys Gly Ile Thr Leu Leu Asn Arg Leu Lys Val Asn Asp
50                  55                  60

Phe Ala Pro Ala Trp Ala Met Thr Arg Asn Leu Phe Pro His Leu Phe
65                  70                  75                  80

Lys Asn Gln Gln Ser Glu Val Gln Thr Pro Ile Trp Ala Leu Arg Val
                85                  90                  95

Ile Leu Ala Ala Gly Ile Leu Asp Gln Leu Met Asp His Ser Leu Ile
            100                 105                 110

Glu Pro Leu Ser Gly Ala Leu Asn Leu Ile Ala Asp Trp Leu Leu Thr
        115                 120                 125

Thr Ser Thr Asn His Phe Asn Met Arg Thr Gln Arg Val Lys Asp Gln
130                 135                 140

Leu Ser Met Arg Met Leu Ser Leu Ile Arg Ser Asn Ile Ile Asn Phe
145                 150                 155                 160

Ile Asn Lys Leu Glu Thr Leu His Val Val Asn Tyr Lys Gly Leu Leu
                165                 170                 175

Ser Ser Val Glu Ile Gly Thr Pro Ser Tyr Ala Ile Ile Ile Thr Arg
            180                 185                 190

Thr Asn Met Gly Tyr Leu Val Glu Val Gln Glu Pro Asp Lys Ser Ala
        195                 200                 205

Met Asp Ile Arg His Pro Gly Pro Val Lys Phe Ser Leu Leu His Glu
    210                 215                 220

Ser Thr Leu Lys Pro Val Ala Thr Ser Lys Pro Ser Ser Ile Thr Ser
225                 230                 235                 240

Leu Ile Met Glu Phe Asn Ser Ser Leu Ala Ile
                245                 250

<210> SEQ ID NO 15
<211> LENGTH: 288
<212> TYPE: PRT
<213> ORGANISM: Sudan ebolavirus

<400> SEQUENCE: 15

Met Glu Arg Gly Arg Glu Arg Gly Arg Ser Arg Ser Ser Arg Ala Asp
1               5                   10                  15

Gln Gln Asn Ser Thr Gly Pro Gln Phe Arg Thr Arg Ser Ile Ser Arg
            20                  25                  30

Asp Lys Thr Thr Thr Asp Tyr Arg Ser Ser Arg Ser Thr Ser Gln Val
        35                  40                  45

```
Arg Val Pro Thr Val Phe His Lys Lys Gly Thr Gly Thr Leu Thr Val
 50                  55                  60

Pro Pro Ala Pro Lys Asp Ile Cys Pro Thr Leu Arg Lys Gly Phe Leu
 65              70                  75                  80

Cys Asp Ser Asn Phe Cys Lys Lys Asp His Gln Leu Glu Ser Leu Thr
                 85                  90                  95

Asp Arg Glu Leu Leu Leu Ile Ala Arg Lys Thr Cys Gly Ser Thr
            100                 105                 110

Asp Ser Ser Leu Asn Ile Ala Ala Pro Lys Asp Leu Arg Leu Ala Asn
            115                 120                 125

Pro Thr Ala Asp Asp Phe Lys Gln Asp Gly Ser Pro Lys Leu Thr Leu
130                 135                 140

Lys Leu Leu Val Glu Thr Ala Glu Phe Trp Ala Asn Gln Asn Ile Asn
145                 150                 155                 160

Glu Val Asp Asp Ala Lys Leu Arg Ala Leu Leu Thr Leu Ser Ala Val
                165                 170                 175

Leu Val Arg Lys Phe Ser Lys Ser Gln Leu Ser Gln Leu Cys Glu Ser
            180                 185                 190

His Leu Arg Arg Glu Asn Leu Gly Gln Asp Gln Ala Glu Ser Val Leu
            195                 200                 205

Glu Val Tyr Gln Arg Leu His Ser Asp Lys Gly Gly Ala Phe Glu Ala
210                 215                 220

Ala Leu Trp Gln Gln Trp Asp Arg Gln Ser Leu Thr Met Phe Ile Ser
225                 230                 235                 240

Ala Phe Leu His Val Ala Leu Gln Leu Ser Cys Glu Ser Ser Thr Val
                245                 250                 255

Val Ile Ser Gly Leu Arg Leu Leu Ala Pro Pro Ser Val Asn Glu Gly
            260                 265                 270

Leu Pro Pro Ala Pro Gly Glu Tyr Thr Trp Ser Glu Asp Ser Thr Thr
            275                 280                 285

<210> SEQ ID NO 16
<211> LENGTH: 329
<212> TYPE: PRT
<213> ORGANISM: Sudan ebolavirus

<400> SEQUENCE: 16

Met Gln Gln Asp Lys Thr Tyr Arg His His Gly Pro Glu Val Ser Gly
 1               5                  10                  15

Trp Phe Ser Glu Gln Leu Met Thr Gly Lys Ile Pro Leu Thr Glu Val
                 20                  25                  30

Phe Val Asp Val Glu Thr Lys Pro Ser Pro Thr Pro Ile Thr Ile Ile
             35                  40                  45

Ser Lys Asn Pro Lys Thr Thr Arg Lys Ser Asp Lys Gln Val Gln Thr
 50                  55                  60

Asp Asp Ala Ser Ser Leu Leu Thr Glu Glu Val Lys Thr Ala Ile Asn
 65                  70                  75                  80

Ser Val Ile Ser Ala Val Arg Arg Gln Thr Asn Ala Ile Glu Ser Leu
                 85                  90                  95

Glu Ser Arg Ile Ala Asn Leu Glu Ala Ser Leu Lys Pro Val Gln Asp
            100                 105                 110

Met Ala Lys Thr Ile Ser Ser Leu Asn Arg Ser Cys Ala Glu Met Val
            115                 120                 125

Ala Lys Tyr Asp Leu Leu Val Met Thr Thr Gly Arg Ala Thr Ala Thr
            130                 135                 140
```

-continued

Ala Ala Ala Thr Glu Ala Tyr Trp Asn Glu His Gly Gln Ala Pro Pro
145                 150                 155                 160

Gly Pro Ser Leu Tyr Glu Asp Asp Ala Ile Lys Ala Lys Leu Lys Asp
            165                 170                 175

Pro Asn Gly Lys Val Pro Glu Ser Val Lys Gln Ala Tyr Thr Asn Leu
        180                 185                 190

Asp Ser Thr Ser Ala Leu Asn Glu Glu Asn Phe Gly Arg Pro Tyr Ile
            195                 200                 205

Ser Ala Lys Asp Leu Lys Glu Ile Ile Tyr Asp His Leu Pro Gly Phe
210                 215                 220

Gly Thr Ala Phe His Gln Leu Val Gln Val Ile Cys Lys Ile Gly Lys
225                 230                 235                 240

Asp Asn Asn Ile Leu Asp Ile Ile His Ala Glu Phe Gln Ala Ser Leu
                245                 250                 255

Ala Glu Gly Asp Ser Pro Gln Cys Ala Leu Ile Gln Ile Thr Lys Arg
            260                 265                 270

Ile Pro Thr Phe Gln Asp Ala Ser Pro Ile Val His Ile Lys Ser
        275                 280                 285

Arg Gly Asp Ile Pro Lys Ala Cys Gln Lys Ser Leu Arg Pro Val Pro
        290                 295                 300

Pro Ser Pro Lys Ile Asp Arg Gly Trp Val Cys Ile Phe Gln Phe Gln
305                 310                 315                 320

Asp Gly Lys Thr Leu Gly Leu Lys Ile
                325

<210> SEQ ID NO 17
<211> LENGTH: 326
<212> TYPE: PRT
<213> ORGANISM: Sudan ebolavirus

<400> SEQUENCE: 17

Met Arg Arg Val Thr Val Pro Thr Ala Pro Pro Ala Tyr Ala Asp Ile
1               5                   10                  15

Gly Tyr Pro Met Ser Met Leu Pro Ile Lys Ser Ser Arg Ala Val Ser
            20                  25                  30

Gly Ile Gln Gln Lys Gln Glu Val Leu Pro Gly Met Asp Thr Pro Ser
        35                  40                  45

Asn Ser Met Arg Pro Val Ala Asp Asp Asn Ile Asp His Thr Ser His
    50                  55                  60

Thr Pro Asn Gly Val Ala Ser Ala Phe Ile Leu Glu Ala Thr Val Asn
65                  70                  75                  80

Val Ile Ser Gly Pro Lys Val Leu Met Lys Gln Ile Pro Ile Trp Leu
                85                  90                  95

Pro Leu Gly Ile Ala Asp Gln Lys Thr Tyr Ser Phe Asp Ser Thr Thr
            100                 105                 110

Ala Ala Ile Met Leu Ala Ser Tyr Thr Ile Thr His Phe Gly Lys Ala
        115                 120                 125

Asn Asn Pro Leu Val Arg Val Asn Arg Leu Gly Gln Gly Ile Pro Asp
    130                 135                 140

His Pro Leu Arg Leu Leu Arg Met Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Val Thr Gln Pro Leu Pro Ala Ala Thr Trp Thr

```
                180             185             190
Asp Glu Thr Pro Ser Asn Leu Ser Gly Ala Leu Arg Pro Gly Leu Ser
            195                 200             205

Phe His Pro Lys Leu Arg Pro Val Leu Leu Pro Gly Lys Thr Gly Lys
        210                 215                 220

Lys Gly His Val Ser Asp Leu Thr Ala Pro Asp Lys Ile Gln Thr Ile
225                 230                 235                 240

Val Asn Leu Met Gln Asp Phe Lys Ile Val Pro Ile Asp Pro Ala Lys
                245                 250                 255

Ser Ile Ile Gly Ile Glu Val Pro Glu Leu Leu Val His Lys Leu Thr
            260                 265                 270

Gly Lys Lys Met Ser Gln Lys Asn Gly Gln Pro Ile Ile Pro Val Leu
        275                 280                 285

Leu Pro Lys Tyr Ile Gly Leu Asp Pro Ile Ser Pro Gly Asp Leu Thr
            290                 295                 300

Met Val Ile Thr Pro Asp Tyr Asp Asp Cys His Ser Pro Ala Ser Cys
305                 310                 315                 320

Ser Tyr Leu Ser Glu Lys
                325

<210> SEQ ID NO 18
<211> LENGTH: 2210
<212> TYPE: PRT
<213> ORGANISM: Sudan ebolavirus

<400> SEQUENCE: 18

Met Met Ala Thr Gln His Thr Gln Tyr Pro Asp Ala Arg Leu Ser Ser
1               5                   10                  15

Pro Ile Val Leu Asp Gln Cys Asp Leu Val Thr Arg Ala Cys Gly Leu
            20                  25                  30

Tyr Ser Glu Tyr Ser Leu Asn Pro Lys Leu Arg Thr Cys Arg Leu Pro
        35                  40                  45

Lys His Ile Tyr Arg Leu Lys Tyr Asp Ala Ile Val Leu Arg Phe Ile
    50                  55                  60

Ser Asp Val Pro Val Ala Thr Ile Pro Ile Asp Tyr Ile Ala Pro Met
65                  70                  75                  80

Leu Ile Asn Val Leu Ala Asp Ser Lys Asn Ala Pro Leu Glu Pro Pro
                85                  90                  95

Cys Leu Ser Phe Leu Asp Glu Ile Val Asn Tyr Thr Val Gln Asp Ala
            100                 105                 110

Ala Phe Leu Asn Tyr Tyr Met Asn Gln Ile Lys Thr Gln Glu Gly Val
        115                 120                 125

Ile Thr Asp Gln Leu Lys Gln Asn Ile Arg Arg Val Ile His Lys Asn
    130                 135                 140

Arg Tyr Leu Ser Ala Leu Phe Phe Trp His Asp Leu Ser Ile Leu Thr
145                 150                 155                 160

Arg Arg Gly Arg Met Asn Arg Gly Asn Val Arg Ser Thr Trp Phe Val
                165                 170                 175

Thr Asn Glu Val Val Asp Ile Leu Gly Tyr Gly Asp Tyr Ile Phe Trp
            180                 185                 190

Lys Ile Pro Ile Ala Leu Leu Pro Met Asn Thr Ala Asn Val Pro His
        195                 200                 205

Ala Ser Thr Asp Trp Tyr Gln Pro Asn Ile Phe Lys Glu Ala Ile Gln
    210                 215                 220
```

-continued

Gly His Thr His Ile Ile Ser Val Ser Thr Ala Glu Val Leu Ile Met
225                 230                 235                 240

Cys Lys Asp Leu Val Thr Ser Arg Phe Asn Thr Leu Leu Ile Ala Glu
            245                 250                 255

Leu Ala Arg Leu Glu Asp Pro Val Ser Ala Asp Tyr Pro Leu Val Asp
        260                 265                 270

Asp Ile Gln Ser Leu Tyr Asn Ala Gly Asp Tyr Leu Leu Ser Ile Leu
    275                 280                 285

Gly Ser Glu Gly Tyr Lys Ile Ile Lys Tyr Leu Glu Pro Leu Cys Leu
290                 295                 300

Ala Lys Ile Gln Leu Cys Ser Gln Tyr Thr Glu Arg Lys Gly Arg Phe
305                 310                 315                 320

Leu Thr Gln Met His Leu Ala Val Ile Gln Thr Leu Arg Glu Leu Leu
            325                 330                 335

Leu Asn Arg Gly Leu Lys Lys Ser Gln Leu Ser Lys Ile Arg Glu Phe
        340                 345                 350

His Gln Leu Leu Leu Arg Leu Arg Ser Thr Pro Gln Gln Leu Cys Glu
    355                 360                 365

Leu Phe Ser Ile Gln Lys His Trp Gly His Pro Val Leu His Ser Glu
370                 375                 380

Lys Ala Ile Gln Lys Val Lys Asn His Ala Thr Val Leu Lys Ala Leu
385                 390                 395                 400

Arg Pro Ile Ile Ile Ser Glu Thr Tyr Cys Val Phe Lys Tyr Ser Val
            405                 410                 415

Ala Lys His Phe Phe Asp Ser Gln Gly Thr Trp Tyr Ser Val Ile Ser
        420                 425                 430

Asp Arg Cys Leu Thr Pro Gly Leu Asn Ser Tyr Ile Arg Arg Asn Gln
    435                 440                 445

Phe Pro Pro Leu Pro Met Ile Lys Asp Leu Leu Trp Glu Phe Tyr His
450                 455                 460

Leu Asp His Pro Pro Leu Phe Ser Thr Lys Ile Ile Ser Asp Leu Ser
465                 470                 475                 480

Ile Phe Ile Lys Asp Arg Ala Thr Ala Val Glu Gln Thr Cys Trp Asp
            485                 490                 495

Ala Val Phe Glu Pro Asn Val Leu Gly Tyr Ser Pro Tyr Arg Phe
        500                 505                 510

Asn Thr Lys Arg Val Pro Glu Gln Phe Leu Glu Gln Glu Asp Phe Ser
    515                 520                 525

Ile Glu Ser Val Leu Gln Tyr Ala Gln Glu Leu Arg Tyr Leu Leu Pro
530                 535                 540

Gln Asn Arg Asn Phe Ser Phe Ser Leu Lys Glu Lys Glu Leu Asn Val
545                 550                 555                 560

Gly Arg Thr Phe Gly Lys Leu Pro Tyr Leu Thr Arg Asn Val Gln Thr
            565                 570                 575

Leu Cys Glu Ala Leu Leu Ala Asp Gly Leu Ala Lys Ala Phe Pro Ser
        580                 585                 590

Asn Met Met Val Val Thr Glu Arg Glu Gln Lys Glu Ser Leu Leu His
    595                 600                 605

Gln Ala Ser Trp His His Thr Ser Asp Asp Phe Gly Glu His Ala Thr
610                 615                 620

Val Arg Gly Ser Ser Phe Val Thr Asp Leu Glu Lys Tyr Asn Leu Ala
625                 630                 635                 640

Phe Arg Tyr Glu Phe Thr Ala Pro Phe Ile Lys Tyr Cys Asn Gln Cys

```
                    645                 650                 655
Tyr Gly Val Arg Asn Val Phe Asp Trp Met His Phe Leu Ile Pro Gln
                660                 665                 670

Cys Tyr Met His Val Ser Asp Tyr Tyr Asn Pro Pro His Asn Val Thr
                675                 680                 685

Leu Glu Asn Arg Glu Tyr Pro Pro Glu Gly Pro Ser Ala Tyr Arg Gly
                690                 695                 700

His Leu Gly Gly Ile Glu Gly Leu Gln Gln Lys Leu Trp Thr Ser Ile
705                 710                 715                 720

Ser Cys Ala Gln Ile Ser Leu Val Glu Ile Lys Thr Gly Phe Lys Leu
                725                 730                 735

Arg Ser Ala Val Met Gly Asp Asn Gln Cys Ile Thr Val Leu Ser Val
                740                 745                 750

Phe Pro Leu Glu Ser Ser Pro Asn Glu Gln Glu Arg Cys Ala Glu Asp
                755                 760                 765

Asn Ala Ala Arg Val Ala Ala Ser Leu Ala Lys Val Thr Ser Ala Cys
                770                 775                 780

Gly Ile Phe Leu Lys Pro Asp Glu Thr Phe Val His Ser Gly Phe Ile
785                 790                 795                 800

Tyr Phe Gly Lys Lys Gln Tyr Leu Asn Gly Ile Gln Leu Pro Gln Ser
                805                 810                 815

Leu Lys Thr Ala Ala Arg Met Ala Pro Leu Ser Asp Ala Ile Phe Asp
                820                 825                 830

Asp Leu Gln Gly Thr Leu Ala Ser Ile Gly Thr Ala Phe Glu Arg Ser
                835                 840                 845

Ile Ser Glu Thr Arg His Ile Leu Pro Cys Arg Val Ala Ala Ala Phe
850                 855                 860

His Thr Tyr Phe Ser Val Arg Ile Leu Gln His His Leu Gly Phe
865                 870                 875                 880

His Lys Gly Ser Asp Leu Gly Gln Leu Ala Ile Asn Lys Pro Leu Asp
                885                 890                 895

Phe Gly Thr Ile Ala Leu Ser Leu Ala Val Pro Gln Val Leu Gly Gly
                900                 905                 910

Leu Ser Phe Leu Asn Pro Glu Lys Cys Leu Tyr Arg Asn Leu Gly Asp
                915                 920                 925

Pro Val Thr Ser Gly Leu Phe Gln Leu Lys His Tyr Leu Ser Met Val
                930                 935                 940

Gly Met Ser Asp Ile Phe His Ala Leu Val Ala Lys Ser Pro Gly Asn
945                 950                 955                 960

Cys Ser Ala Ile Asp Phe Val Leu Asn Pro Gly Gly Leu Asn Val Pro
                965                 970                 975

Gly Ser Gln Asp Leu Thr Ser Phe Leu Arg Gln Ile Val Arg Arg Ser
                980                 985                 990

Ile Thr Leu Ser Ala Arg Asn Lys Leu Ile Asn Thr Leu Phe His Ala
                995                 1000                1005

Ser Ala Asp Leu Glu Asp Glu Leu Val Cys Lys Trp Leu Leu Ser
                1010                1015                1020

Ser Thr Pro Val Met Ser Arg Phe Ala Ala Asp Ile Phe Ser Arg
                1025                1030                1035

Thr Pro Ser Gly Lys Arg Leu Gln Ile Leu Gly Tyr Leu Glu Gly
                1040                1045                1050

Thr Arg Thr Leu Leu Ala Ser Arg Met Ile Ser Asn Asn Ala Glu
                1055                1060                1065
```

-continued

```
Thr Pro Ile Leu Glu Arg Leu Arg Lys Ile Thr Leu Gln Arg Trp
1070                1075                1080

Asn Leu Trp Phe Ser Tyr Leu Asp His Cys Asp Ser Ala Leu Met
    1085                1090                1095

Glu Ala Ile Gln Pro Ile Arg Cys Thr Val Asp Ile Ala Gln Ile
    1100                1105                1110

Leu Arg Glu Tyr Ser Trp Ala His Ile Leu Asp Gly Arg Gln Leu
    1115                1120                1125

Ile Gly Ala Thr Leu Pro Cys Ile Pro Glu Gln Phe Gln Thr Thr
    1130                1135                1140

Trp Leu Lys Pro Tyr Glu Gln Cys Val Glu Cys Ser Ser Thr Asn
    1145                1150                1155

Asn Ser Ser Pro Tyr Val Ser Val Ala Leu Lys Arg Asn Val Val
    1160                1165                1170

Ser Ala Trp Pro Asp Ala Ser Arg Leu Gly Trp Thr Ile Gly Asp
    1175                1180                1185

Gly Ile Pro Tyr Ile Gly Ser Arg Thr Glu Asp Lys Ile Gly Gln
    1190                1195                1200

Pro Ala Ile Lys Pro Arg Cys Pro Ser Ala Ala Leu Arg Glu Ala
    1205                1210                1215

Ile Glu Leu Thr Ser Arg Leu Thr Trp Val Thr Gln Gly Ser Ala
    1220                1225                1230

Asn Ser Asp Gln Leu Ile Arg Pro Phe Leu Glu Ala Arg Val Asn
    1235                1240                1245

Leu Ser Val Gln Glu Ile Leu Gln Met Thr Pro Ser His Tyr Ser
    1250                1255                1260

Gly Asn Ile Val His Arg Tyr Asn Asp Gln Tyr Ser Pro His Ser
    1265                1270                1275

Phe Met Ala Asn Arg Met Ser Asn Thr Ala Thr Arg Leu Met Val
    1280                1285                1290

Ser Thr Asn Thr Leu Gly Glu Phe Ser Gly Gly Gln Ala Ala
    1295                1300                1305

Arg Asp Ser Asn Ile Ile Phe Gln Asn Val Ile Asn Phe Ala Val
    1310                1315                1320

Ala Leu Tyr Asp Ile Arg Phe Arg Asn Thr Cys Thr Ser Ser Ile
    1325                1330                1335

Gln Tyr His Arg Ala His Ile His Leu Thr Asp Cys Cys Thr Arg
    1340                1345                1350

Glu Val Pro Ala Gln Tyr Leu Thr Tyr Thr Thr Leu Asn Leu
    1355                1360                1365

Asp Leu Ser Lys Tyr Arg Asn Asn Glu Leu Ile Tyr Asp Ser Glu
    1370                1375                1380

Pro Leu Arg Gly Gly Leu Asn Cys Asn Leu Ser Ile Asp Ser Pro
    1385                1390                1395

Leu Met Lys Gly Pro Arg Leu Asn Ile Ile Glu Asp Asp Leu Ile
    1400                1405                1410

Arg Leu Pro His Leu Ser Gly Trp Glu Leu Ala Lys Thr Val Leu
    1415                1420                1425

Gln Ser Ile Ile Ser Asp Ser Ser Asn Ser Ser Thr Asp Pro Ile
    1430                1435                1440

Ser Ser Gly Glu Thr Arg Ser Phe Thr Thr His Phe Leu Thr Tyr
    1445                1450                1455
```

-continued

Pro Lys Ile Gly Leu Leu Tyr Ser Phe Gly Ala Leu Ile Ser Phe
1460                1465                1470

Tyr Leu Gly Asn Thr Ile Leu Cys Thr Lys Lys Ile Gly Leu Thr
1475                1480                1485

Glu Phe Leu Tyr Tyr Leu Gln Asn Gln Ile His Asn Leu Ser His
1490                1495                1500

Arg Ser Leu Arg Ile Phe Lys Pro Thr Phe Arg His Ser Ser Val
1505                1510                1515

Met Ser Arg Leu Met Asp Ile Asp Pro Asn Phe Ser Ile Tyr Ile
1520                1525                1530

Gly Gly Thr Ala Gly Asp Arg Gly Leu Ser Asp Ala Ala Arg Leu
1535                1540                1545

Phe Leu Arg Ile Ala Ile Ser Thr Phe Leu Ser Phe Val Glu Glu
1550                1555                1560

Trp Val Ile Phe Arg Lys Ala Asn Ile Pro Leu Trp Val Val Tyr
1565                1570                1575

Pro Leu Glu Gly Gln Arg Pro Asp Pro Pro Gly Glu Phe Leu Asn
1580                1585                1590

Arg Val Lys Ser Leu Ile Val Gly Ile Glu Asp Asp Lys Asn Lys
1595                1600                1605

Gly Ser Ile Leu Ser Arg Ser Glu Glu Lys Gly Ser Ser Asn Leu
1610                1615                1620

Val Tyr Asn Cys Lys Ser Thr Ala Ser Asn Phe Phe His Ala Ser
1625                1630                1635

Leu Ala Tyr Trp Arg Gly Arg His Arg Pro Lys Lys Thr Ile Gly
1640                1645                1650

Ala Thr Lys Ala Thr Thr Ala Pro His Ile Ile Leu Pro Leu Gly
1655                1660                1665

Asn Ser Asp Arg Pro Pro Gly Leu Asp Leu Asn Gln Ser Asn Asp
1670                1675                1680

Thr Phe Ile Pro Thr Arg Ile Lys Gln Ile Val Gln Gly Asp Ser
1685                1690                1695

Arg Asn Asp Arg Thr Thr Thr Thr Arg Leu Pro Pro Lys Ser Arg
1700                1705                1710

Ser Thr Pro Thr Ser Ala Thr Glu Pro Pro Thr Lys Ile Tyr Glu
1715                1720                1725

Gly Ser Thr Thr Tyr Arg Gly Lys Ser Thr Asp Thr His Leu Asp
1730                1735                1740

Glu Gly His Asn Ala Lys Glu Phe Pro Phe Asn Pro His Arg Leu
1745                1750                1755

Val Val Pro Phe Phe Lys Leu Thr Lys Asp Gly Glu Tyr Ser Ile
1760                1765                1770

Glu Pro Ser Pro Glu Glu Ser Arg Ser Asn Ile Lys Gly Leu Leu
1775                1780                1785

Gln His Leu Arg Thr Met Val Asp Thr Thr Ile Tyr Cys Arg Phe
1790                1795                1800

Thr Gly Ile Val Ser Ser Met His Tyr Lys Leu Asp Glu Val Leu
1805                1810                1815

Trp Glu Tyr Asn Lys Phe Glu Ser Ala Val Thr Leu Ala Glu Gly
1820                1825                1830

Glu Gly Ser Gly Ala Leu Leu Leu Ile Gln Lys Tyr Gly Val Lys
1835                1840                1845

Lys Leu Phe Leu Asn Thr Leu Ala Thr Glu His Ser Ile Glu Ser

```
                    1850                1855                1860
Glu Val Ile Ser Gly Tyr Thr Thr Pro Arg Met Leu Leu Ser Val
    1865                1870                1875

Met Pro Arg Thr His Arg Gly Glu Leu Glu Val Ile Leu Asn Asn
    1880                1885                1890

Ser Ala Ser Gln Ile Thr Asp Ile Thr His Arg Asp Trp Phe Ser
    1895                1900                1905

Asn Gln Lys Asn Arg Ile Pro Asn Asp Val Asp Ile Ile Thr Met
    1910                1915                1920

Asp Ala Glu Thr Thr Glu Asn Leu Asp Arg Ser Arg Leu Tyr Glu
    1925                1930                1935

Ala Val Tyr Thr Ile Ile Cys Asn His Ile Asn Pro Lys Thr Leu
    1940                1945                1950

Lys Val Val Ile Leu Lys Val Phe Leu Ser Asp Leu Asp Gly Met
    1955                1960                1965

Cys Trp Ile Asn Asn Tyr Leu Ala Pro Met Phe Gly Ser Gly Tyr
    1970                1975                1980

Leu Ile Lys Pro Ile Thr Ser Ser Ala Arg Ser Ser Glu Trp Tyr
    1985                1990                1995

Leu Cys Leu Ser Asn Leu Leu Ser Thr Leu Arg Thr Thr Gln His
    2000                2005                2010

Gln Thr Gln Ala Asn Cys Leu His Val Val Gln Cys Ala Leu Gln
    2015                2020                2025

Gln Gln Val Gln Arg Gly Ser Tyr Trp Leu Ser His Leu Thr Lys
    2030                2035                2040

Tyr Thr Thr Ser Arg Leu His Asn Ser Tyr Ile Ala Phe Gly Phe
    2045                2050                2055

Pro Ser Leu Glu Lys Val Leu Tyr His Arg Tyr Asn Leu Val Asp
    2060                2065                2070

Ser Arg Asn Gly Pro Leu Val Ser Ile Thr Arg His Leu Ala Leu
    2075                2080                2085

Leu Gln Thr Glu Ile Arg Glu Leu Val Thr Asp Tyr Asn Gln Leu
    2090                2095                2100

Arg Gln Ser Arg Thr Gln Thr Tyr His Phe Ile Lys Thr Ser Lys
    2105                2110                2115

Gly Arg Ile Thr Lys Leu Val Asn Asp Tyr Leu Arg Phe Glu Leu
    2120                2125                2130

Val Ile Arg Ala Leu Lys Asn Asn Ser Thr Trp His His Glu Leu
    2135                2140                2145

Tyr Leu Leu Pro Glu Leu Ile Gly Val Cys His Arg Phe Asn His
    2150                2155                2160

Thr Arg Asn Cys Thr Cys Ser Glu Arg Phe Leu Val Gln Thr Leu
    2165                2170                2175

Tyr Leu His Arg Met Ser Asp Ala Glu Ile Lys Leu Met Asp Arg
    2180                2185                2190

Leu Thr Ser Leu Val Asn Met Phe Pro Glu Gly Phe Arg Ser Ser
    2195                2200                2205

Ser Val
    2210

<210> SEQ ID NO 19
<211> LENGTH: 739
<212> TYPE: PRT
<213> ORGANISM: Cote d'Ivoire ebolavirus
```

<400> SEQUENCE: 19

```
Met Glu Ser Arg Ala His Lys Ala Trp Met Thr His Thr Ala Ser Gly
1               5                   10                  15

Phe Glu Thr Asp Tyr His Lys Ile Leu Thr Ala Gly Leu Ser Val Gln
            20                  25                  30

Gln Gly Ile Val Arg Gln Arg Val Ile Gln Val His Gln Val Thr Asn
        35                  40                  45

Leu Glu Glu Ile Cys Gln Leu Ile Ile Gln Ala Phe Glu Ala Gly Val
50                  55                  60

Asp Phe Gln Glu Ser Ala Asp Ser Phe Leu Leu Met Leu Cys Leu His
65                  70                  75                  80

His Ala Tyr Gln Gly Asp Tyr Lys Gln Phe Leu Glu Ser Asn Ala Val
                85                  90                  95

Lys Tyr Leu Glu Gly His Gly Phe Arg Phe Glu Val Arg Lys Lys Glu
            100                 105                 110

Gly Val Lys Arg Leu Glu Glu Leu Leu Pro Ala Ala Ser Ser Gly Lys
        115                 120                 125

Ser Ile Arg Arg Thr Leu Ala Ala Met Pro Glu Glu Thr Thr Glu
130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ser Glu Gln Gly Leu Ile Gln Tyr Pro Thr Ala Trp Gln
            180                 185                 190

Ser Val Gly His Met Met Val Ile Phe Arg Leu Met Arg Thr Asn Phe
        195                 200                 205

Leu Ile Lys Phe Leu Leu Ile His Gln Gly Met His Met Val Ala Gly
210                 215                 220

His Asp Ala Asn Asp Ala Val Ile Ala Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu His Gly Val Arg Leu His Pro Leu Ala Arg Thr Ala Lys
            260                 265                 270

Val Lys Asn Glu Val Asn Ser Phe Lys Ala Ala Leu Ser Ser Leu Ala
        275                 280                 285

Gln His Gly Glu Tyr Ala Pro Phe Ala Arg Leu Leu Asn Leu Ser Gly
    290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350

Gln Leu Gln Lys Tyr Ala Glu Ser Arg Glu Leu Asp His Leu Gly Leu
        355                 360                 365

Asp Asp Gln Glu Lys Lys Ile Leu Lys Asp Phe His Gln Lys Lys Asn
    370                 375                 380

Glu Ile Ser Phe Gln Gln Thr Thr Ala Met Val Thr Leu Arg Lys Glu
385                 390                 395                 400

Arg Leu Ala Lys Leu Thr Glu Ala Ile Thr Ser Thr Ser Leu Leu Lys
```

Thr Gly Lys Gln Tyr Asp Asp Asn Asp Ile Pro Phe Pro Gly Pro
            405                 410                 415
        420                 425                 430

Ile Asn Asp Asn Glu Asn Ser Glu Gln Gln Asp Asp Pro Thr Asp
        435                 440                 445

Ser Gln Asp Thr Thr Ile Pro Asp Ile Val Asp Pro Asp Asp Gly
        450                 455                 460

Arg Tyr Asn Asn Tyr Gly Asp Tyr Pro Ser Glu Thr Ala Asn Ala Pro
465                 470                 475                 480

Glu Asp Leu Val Leu Phe Asp Leu Glu Asp Gly Asp Glu Asp His
                485                 490                 495

Arg Pro Ser Ser Ser Glu Asn Asn Asn Lys His Ser Leu Thr Gly
                500                 505                 510

Thr Asp Ser Asn Lys Thr Ser Asn Trp Asn Arg Asn Pro Thr Asn Met
            515                 520                 525

Pro Lys Lys Asp Ser Thr Gln Asn Asn Asp Asn Pro Ala Gln Arg Ala
            530                 535                 540

Gln Glu Tyr Ala Arg Asp Asn Ile Gln Asp Thr Pro Thr Pro His Arg
545                 550                 555                 560

Ala Leu Thr Pro Ile Ser Glu Glu Thr Gly Ser Asn Gly His Asn Glu
                565                 570                 575

Asp Asp Ile Asp Ser Ile Pro Pro Leu Glu Ser Asp Glu Glu Asn Asn
            580                 585                 590

Thr Glu Thr Thr Ile Thr Thr Thr Lys Asn Thr Thr Ala Pro Pro Ala
                595                 600                 605

Pro Val Tyr Arg Ser Asn Ser Glu Lys Glu Pro Leu Pro Gln Glu Lys
            610                 615                 620

Ser Gln Lys Gln Pro Asn Gln Val Ser Gly Ser Glu Asn Thr Asp Asn
625                 630                 635                 640

Lys Pro His Ser Glu Gln Ser Val Glu Glu Met Tyr Arg His Ile Leu
                645                 650                 655

Gln Thr Gln Gly Pro Phe Asp Ala Ile Leu Tyr Tyr Met Met Thr
                660                 665                 670

Glu Glu Pro Ile Val Phe Ser Thr Ser Asp Gly Lys Glu Tyr Val Tyr
            675                 680                 685

Pro Asp Ser Leu Glu Gly Glu His Pro Pro Trp Leu Ser Glu Lys Glu
            690                 695                 700

Ala Leu Asn Glu Asp Asn Arg Phe Ile Thr Met Asp Asp Gln Gln Phe
705                 710                 715                 720

Tyr Trp Pro Val Met Asn His Arg Asn Lys Phe Met Ala Ile Leu Gln
                725                 730                 735

His His Lys

<210> SEQ ID NO 20
<211> LENGTH: 251
<212> TYPE: PRT
<213> ORGANISM: Cote d'Ivoire ebolavirus

<400> SEQUENCE: 20

Met Ala Lys Ala Thr Gly Arg Tyr Asn Leu Ile Ser Pro Lys Lys Asp
1               5                   10                  15

Leu Glu Lys Gly Leu Val Leu Asn Asp Leu Cys Thr Leu Ser Val Ala
            20                  25                  30

Gln Thr Val Gln Gly Trp Lys Val Thr Trp Ala Gly Ile Glu Phe Asp

-continued

```
                35                  40                  45
Val Thr Gln Lys Gly Met Ala Leu Leu His Arg Leu Lys Thr Ser Asp
 50                  55                  60
Phe Ala Pro Ala Trp Ser Met Thr Arg Asn Leu Phe Pro His Leu Phe
 65                  70                  75                  80
Gln Asn Pro Asn Ser Thr Ile Glu Ser Pro Leu Trp Ala Leu Arg Val
                 85                  90                  95
Ile Leu Ala Ala Gly Ile Gln Asp Gln Leu Ile Asp Gln Ser Leu Ile
            100                 105                 110
Glu Pro Leu Ala Gly Ala Leu Gly Leu Ile Ala Asp Trp Leu Leu Thr
        115                 120                 125
Thr Gly Thr Asn His Phe Gln Met Arg Thr Gln Gln Ala Lys Glu Gln
130                 135                 140
Leu Ser Leu Lys Met Leu Ser Leu Val Arg Ser Asn Ile Leu Lys Phe
145                 150                 155                 160
Ile Asn Gln Leu Asp Ala Leu His Val Val Asn Tyr Asn Gly Leu Leu
                165                 170                 175
Ser Ser Ile Glu Ile Gly Thr Lys Ser His Thr Ile Ile Ile Thr Arg
            180                 185                 190
Thr Asn Met Gly Phe Leu Val Glu Leu Gln Glu Pro Asp Lys Ser Ala
        195                 200                 205
Met Asn Thr Arg Lys Pro Gly Pro Val Lys Phe Ser Leu Leu His Glu
210                 215                 220
Ser Thr Leu Lys Thr Leu Ala Lys Lys Pro Ala Thr Gln Met Gln Ala
225                 230                 235                 240
Leu Ile Leu Glu Phe Asn Ser Ser Leu Ala Ile
                245                 250
```

<210> SEQ ID NO 21
<211> LENGTH: 289
<212> TYPE: PRT
<213> ORGANISM: Cote d'Ivoire ebolavirus

<400> SEQUENCE: 21

```
Met Glu Val Val His Glu Arg Gly Arg Ser Arg Ile Ser Arg Gln Asn
 1               5                  10                  15
Thr Arg Asp Gly Pro Ser His Leu Val Arg Ala Arg Ser Ser Ser Arg
                 20                  25                  30
Ala Ser Tyr Arg Ser Glu Tyr His Thr Pro Arg Ser Ala Ser Gln Ile
            35                  40                  45
Arg Val Pro Thr Val Phe His Arg Lys Lys Thr Asp Leu Leu Thr Val
 50                  55                  60
Pro Pro Ala Pro Lys Asp Val Cys Pro Thr Leu Lys Lys Gly Phe Leu
 65                  70                  75                  80
Cys Asp Ser Asn Phe Cys Lys Lys Asp His Gln Leu Glu Ser Leu Thr
                 85                  90                  95
Asp Arg Glu Leu Leu Leu Leu Ile Ala Arg Lys Thr Cys Gly Ser Thr
            100                 105                 110
Glu Gln Gln Leu Ser Ile Val Ala Pro Lys Asp Ser Arg Leu Ala Asn
        115                 120                 125
Pro Ile Ala Glu Asp Phe Gln Gln Lys Asp Gly Pro Lys Val Thr Leu
130                 135                 140
Ser Met Leu Ile Glu Thr Ala Gly Tyr Trp Ser Lys Gln Asp Ile Lys
145                 150                 155                 160
```

```
Asn Ile Asp Asp Ser Arg Leu Arg Ala Leu Leu Thr Leu Cys Ala Val
                165                 170                 175
Met Thr Arg Lys Phe Ser Lys Ser Gln Leu Ser Leu Leu Cys Glu Ser
            180                 185                 190
His Leu Arg Arg Glu Gly Leu Gly Gln Asp Gln Ser Glu Ser Val Leu
        195                 200                 205
Glu Val Tyr Gln Arg Leu His Ser Asp Lys Gly Gly Asn Phe Glu Ala
    210                 215                 220
Ala Leu Trp Gln Gln Trp Asp Arg Gln Ser Leu Ile Met Phe Ile Thr
225                 230                 235                 240
Ala Phe Leu Asn Ile Ala Leu Gln Leu Pro Cys Glu Ser Ser Ser Val
                245                 250                 255
Val Ile Ser Gly Leu Arg Met Leu Ile Pro Gln Ser Glu Ala Thr Glu
            260                 265                 270
Val Val Thr Pro Ser Glu Thr Cys Thr Trp Ser Glu Gly Ser Ser
        275                 280                 285
His
```

<210> SEQ ID NO 22
<211> LENGTH: 341
<212> TYPE: PRT
<213> ORGANISM: Cote d'Ivoire ebolavirus

<400> SEQUENCE: 22

```
Met Ile Ser Thr Arg Ala Ala Ala Ile Asn Asp Pro Ser Leu Pro Ile
1               5                   10                  15
Arg Asn Gln Cys Thr Arg Gly Pro Glu Leu Ser Gly Trp Ile Ser Glu
                20                  25                  30
Gln Leu Met Thr Gly Lys Ile Pro Val His Glu Ile Phe Asn Asp Thr
            35                  40                  45
Glu Pro His Ile Ser Ser Gly Ser Asp Cys Leu Pro Arg Pro Lys Asn
        50                  55                  60
Thr Ala Pro Arg Thr Arg Asn Thr Gln Thr Gln Thr Asp Pro Val Cys
65                  70                  75                  80
Asn His Asn Phe Glu Asp Val Thr Gln Ala Leu Thr Ser Leu Thr Asn
                85                  90                  95
Val Ile Gln Lys Gln Ala Leu Asn Leu Glu Ser Leu Glu Gln Arg Ile
            100                 105                 110
Ile Asp Leu Glu Asn Gly Leu Lys Pro Met Tyr Asp Met Ala Lys Val
        115                 120                 125
Ile Ser Ala Leu Asn Arg Ser Cys Ala Glu Met Val Ala Lys Tyr Asp
    130                 135                 140
Leu Leu Val Met Thr Thr Gly Arg Ala Thr Ala Thr Ala Ala Ala Thr
145                 150                 155                 160
Glu Ala Tyr Trp Glu Glu His Gly Gln Pro Pro Pro Gly Pro Ser Leu
                165                 170                 175
Tyr Glu Glu Ser Ala Ile Arg Gly Lys Ile Asn Lys Gln Glu Asp Lys
            180                 185                 190
Val Pro Lys Glu Val Gln Glu Ala Phe Arg Asn Leu Asp Ser Thr Ser
        195                 200                 205
Ser Leu Thr Glu Glu Asn Phe Gly Lys Pro Asp Ile Ser Ala Lys Asp
    210                 215                 220
Leu Arg Asp Ile Met Tyr Asp His Leu Pro Gly Phe Gly Thr Ala Phe
225                 230                 235                 240
```

```
His Gln Leu Val Gln Val Ile Cys Lys Leu Gly Lys Asp Asn Ser Ala
                245                 250                 255

Leu Asp Ile Ile His Ala Glu Phe Gln Ala Ser Leu Ala Glu Gly Asp
            260                 265                 270

Ser Pro Gln Cys Ala Leu Ile Gln Ile Thr Lys Arg Ile Pro Ile Phe
        275                 280                 285

Gln Asp Ala Thr Pro Pro Thr Ile His Ile Arg Ser Arg Gly Asp Ile
    290                 295                 300

Pro Arg Ala Cys Gln Lys Ser Leu Arg Pro Val Pro Pro Ser Pro Lys
305                 310                 315                 320

Ile Asp Arg Gly Trp Val Cys Ile Phe Gln Leu Gln Asp Gly Lys Thr
                325                 330                 335

Leu Gly Leu Lys Ile
            340

<210> SEQ ID NO 23
<211> LENGTH: 326
<212> TYPE: PRT
<213> ORGANISM: Cote d'Ivoire ebolavirus

<400> SEQUENCE: 23

Met Arg Arg Ile Ile Leu Pro Thr Ala Pro Pro Glu Tyr Met Glu Ala
1               5                   10                  15

Val Tyr Pro Met Arg Thr Met Asn Ser Gly Ala Asp Asn Thr Ala Ser
            20                  25                  30

Gly Pro Asn Tyr Thr Thr Thr Gly Val Met Thr Asn Asp Thr Pro Ser
        35                  40                  45

Asn Ser Leu Arg Pro Val Ala Asp Asp Asn Ile Asp His Pro Ser His
50                  55                  60

Thr Pro Asn Ser Val Ala Ser Ala Phe Ile Leu Glu Ala Met Val Asn
65                  70                  75                  80

Val Ile Ser Gly Pro Lys Val Leu Met Lys Gln Ile Pro Ile Trp Leu
                85                  90                  95

Pro Leu Gly Val Ser Asp Gln Lys Thr Tyr Ser Phe Asp Ser Thr Thr
            100                 105                 110

Ala Ala Ile Met Leu Ala Ser Tyr Thr Ile Thr His Phe Gly Lys Thr
        115                 120                 125

Ser Asn Pro Leu Val Arg Ile Asn Arg Leu Gly Pro Gly Ile Pro Asp
    130                 135                 140

His Pro Leu Arg Leu Leu Arg Ile Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Ile Thr Gln Pro Leu Pro Ala Ala Thr Trp Thr
            180                 185                 190

Asp Glu Thr Pro Ala Val Ser Thr Gly Thr Leu Arg Pro Gly Ile Ser
        195                 200                 205

Phe His Pro Lys Leu Arg Pro Ile Leu Leu Pro Gly Arg Ala Gly Lys
    210                 215                 220

Lys Gly Ser Asn Ser Asp Leu Thr Ser Pro Asp Lys Ile Gln Ala Ile
225                 230                 235                 240

Met Asn Phe Leu Gln Asp Leu Lys Ile Val Pro Ile Asp Pro Thr Lys
                245                 250                 255

Asn Ile Met Gly Ile Glu Val Pro Glu Leu Leu Val His Arg Leu Thr
            260                 265                 270
```

```
Gly Lys Lys Thr Thr Thr Lys Asn Gly Gln Pro Ile Ile Pro Ile Leu
        275                 280                 285

Leu Pro Lys Tyr Ile Gly Leu Asp Pro Leu Ser Gln Gly Asp Leu Thr
    290                 295                 300

Met Val Ile Thr Gln Asp Cys Asp Ser Cys His Ser Pro Ala Ser Leu
305                 310                 315                 320

Pro Pro Val Asn Glu Lys
                325

<210> SEQ ID NO 24
<211> LENGTH: 2210
<212> TYPE: PRT
<213> ORGANISM: Cote d'Ivoire ebolavirus

<400> SEQUENCE: 24

Met Ala Thr Gln His Thr Gln Tyr Pro Asp Ala Arg Leu Ser Ser Pro
1               5                   10                  15

Ile Val Leu Asp Gln Cys Asp Leu Val Thr Arg Ala Cys Gly Leu Tyr
            20                  25                  30

Ser Ala Tyr Ser Leu Asn Pro Gln Leu Lys Asn Cys Arg Leu Pro Lys
        35                  40                  45

His Ile Tyr Arg Leu Lys Tyr Asp Thr Thr Val Thr Glu Phe Leu Ser
    50                  55                  60

Asp Val Pro Val Ala Thr Leu Pro Ala Asp Phe Leu Val Pro Thr Phe
65                  70                  75                  80

Leu Arg Thr Leu Ser Gly Asn Gly Ser Cys Pro Ile Asp Pro Lys Cys
                85                  90                  95

Ser Gln Phe Leu Glu Glu Ile Val Asn Tyr Thr Leu Gln Asp Ile Arg
            100                 105                 110

Phe Leu Asn Tyr Tyr Leu Asn Arg Ala Gly Val His Asn Asp His Val
        115                 120                 125

Asp Arg Asp Phe Gly Gln Lys Ile Arg Asn Leu Ile Cys Asp Asn Glu
    130                 135                 140

Val Leu His Gln Met Phe His Trp Tyr Asp Leu Ala Ile Leu Ala Arg
145                 150                 155                 160

Arg Gly Arg Leu Asn Arg Gly Asn Asn Arg Ser Thr Trp Phe Ala Ser
                165                 170                 175

Asp Asn Leu Val Asp Ile Leu Gly Tyr Gly Asp Tyr Ile Phe Trp Lys
            180                 185                 190

Ile Pro Leu Ser Leu Leu Pro Val Asp Thr Gln Gly Leu Pro His Ala
        195                 200                 205

Ala Lys Asp Trp Tyr His Glu Ser Val Phe Lys Glu Ala Ile Gln Gly
    210                 215                 220

His Thr His Ile Val Ser Ile Ser Thr Ala Asp Val Leu Ile Met Cys
225                 230                 235                 240

Lys Asp Ile Ile Thr Cys Arg Phe Asn Thr Leu Leu Ile Ala Ala Val
                245                 250                 255

Ala Asn Leu Glu Asp Ser Val His Ser Asp Tyr Pro Leu Pro Glu Thr
            260                 265                 270

Val Ser Asp Leu Tyr Lys Ala Gly Asp Tyr Leu Ile Ser Leu Leu Gly
        275                 280                 285

Ser Glu Gly Tyr Lys Val Ile Lys Phe Leu Glu Pro Leu Cys Leu Ala
    290                 295                 300

Lys Ile Gln Leu Cys Ser Asn Tyr Thr Glu Arg Lys Gly Arg Phe Leu
```

-continued

```
            305                 310                 315                 320
        Thr Gln Met His Leu Ala Val Asn His Thr Leu Glu Glu Leu Thr Gly
                        325                 330                 335
        Ser Arg Glu Leu Arg Pro Gln Gln Ile Arg Lys Val Arg Glu Phe His
                        340                 345                 350
        Gln Met Leu Ile Asn Leu Lys Ala Thr Pro Gln Gln Leu Cys Glu Leu
                        355                 360                 365
        Phe Ser Val Gln Lys His Trp Gly His Pro Val Leu His Ser Glu Lys
                        370                 375                 380
        Ala Ile Gln Lys Val Lys Lys His Ala Thr Val Ile Lys Ala Leu Arg
        385                 390                 395                 400
        Pro Ile Ile Ile Phe Glu Thr Tyr Cys Val Phe Lys Tyr Ser Ile Ala
                                405                 410                 415
        Lys His Tyr Phe Asp Ser Gln Gly Thr Trp Tyr Ser Val Thr Ser Asp
                        420                 425                 430
        Arg Cys Leu Thr Pro Gly Leu Ser Ser Tyr Ile Lys Arg Asn Gln Phe
                        435                 440                 445
        Pro Pro Leu Pro Met Ile Lys Glu Leu Leu Trp Glu Phe Tyr His Leu
                        450                 455                 460
        Asp His Pro Pro Leu Phe Ser Thr Lys Val Ile Ser Asp Leu Ser Ile
        465                 470                 475                 480
        Phe Ile Lys Asp Arg Ala Thr Ala Val Glu Lys Thr Cys Trp Asp Ala
                        485                 490                 495
        Val Phe Glu Pro Asn Val Leu Gly Tyr Asn Pro Pro Asn Lys Phe Ala
                        500                 505                 510
        Thr Lys Arg Val Pro Glu Gln Phe Leu Glu Gln Glu Asn Phe Ser Ile
                        515                 520                 525
        Glu Ser Val Leu His Tyr Ala Gln Arg Leu Glu Tyr Leu Leu Pro Glu
                        530                 535                 540
        Tyr Arg Asn Phe Ser Phe Ser Leu Lys Glu Lys Glu Leu Asn Ile Gly
        545                 550                 555                 560
        Arg Ala Phe Gly Lys Leu Pro Tyr Pro Thr Arg Asn Val Gln Thr Leu
                        565                 570                 575
        Cys Glu Ala Leu Leu Ala Asp Gly Leu Ala Lys Ala Phe Pro Ser Asn
                        580                 585                 590
        Met Met Val Val Thr Glu Arg Glu Gln Lys Glu Ser Leu Leu His Gln
                        595                 600                 605
        Ala Ser Trp His His Thr Ser Asp Asp Phe Gly Glu Asn Ala Thr Val
                        610                 615                 620
        Arg Gly Ser Ser Phe Val Thr Asp Leu Glu Lys Tyr Asn Leu Ala Phe
        625                 630                 635                 640
        Arg Tyr Glu Phe Thr Ala Pro Phe Ile Glu Tyr Cys Asn Arg Cys Tyr
                        645                 650                 655
        Gly Val Arg Asn Leu Phe Asn Trp Met His Tyr Thr Ile Pro Gln Cys
                        660                 665                 670
        Tyr Ile His Val Ser Asp Tyr Tyr Asn Pro Pro His Gly Val Ser Leu
                        675                 680                 685
        Glu Asn Arg Glu Asn Pro Pro Glu Gly Pro Ser Tyr Arg Gly His
                        690                 695                 700
        Leu Gly Gly Ile Glu Gly Leu Gln Gln Lys Leu Trp Thr Ser Ile Ser
        705                 710                 715                 720
        Cys Ala Gln Ile Ser Leu Val Glu Ile Lys Thr Gly Phe Lys Leu Arg
                        725                 730                 735
```

```
Ser Ala Val Met Gly Asp Asn Gln Cys Ile Thr Val Leu Ser Val Phe
            740                 745                 750

Pro Leu Glu Thr Glu Ser Ser Glu Gln Glu Leu Ser Ser Glu Asp Asn
            755                 760                 765

Ala Ala Arg Val Ala Ala Ser Leu Ala Lys Val Thr Ser Ala Cys Gly
            770                 775                 780

Ile Phe Leu Lys Pro Asp Glu Thr Phe Val His Ser Gly Phe Ile Tyr
785                 790                 795                 800

Phe Gly Lys Lys Gln Tyr Leu Asn Gly Val Gln Leu Pro Gln Ser Leu
                805                 810                 815

Lys Thr Ala Thr Arg Ile Ala Pro Leu Ser Asp Ala Ile Phe Asp Asp
            820                 825                 830

Leu Gln Gly Thr Leu Ala Ser Ile Gly Thr Ala Phe Glu Arg Ser Ile
            835                 840                 845

Ser Glu Thr Arg His Val Val Pro Cys Arg Val Ala Ala Ala Phe His
            850                 855                 860

Thr Phe Phe Ser Val Arg Ile Leu Gln Tyr His His Leu Gly Phe Asn
865                 870                 875                 880

Lys Gly Thr Asp Leu Gly Gln Leu Ser Leu Ser Lys Pro Leu Asp Phe
                885                 890                 895

Gly Thr Ile Thr Leu Ala Leu Ala Val Pro Gln Val Leu Gly Gly Leu
            900                 905                 910

Ser Phe Leu Asn Pro Glu Lys Cys Phe Tyr Arg Asn Leu Gly Asp Pro
            915                 920                 925

Val Thr Ser Gly Leu Phe Gln Leu Lys Thr Tyr Leu Gln Met Ile His
            930                 935                 940

Met Asp Asp Leu Phe Leu Pro Leu Ile Ala Lys Asn Pro Gly Asn Cys
945                 950                 955                 960

Ser Ala Ile Asp Phe Val Leu Asn Pro Ser Gly Leu Asn Val Pro Gly
                965                 970                 975

Ser Gln Asp Leu Thr Ser Phe Leu Arg Gln Ile Val Arg Arg Thr Ile
            980                 985                 990

Thr Leu Ser Ala Lys Asn Lys Leu  Ile Asn Thr Leu Phe  His Ser Ser
            995                 1000                1005

Ala Asp  Leu Glu Asp Glu Met  Val Cys Lys Trp Leu  Leu Ser Ser
    1010                1015                1020

Thr Pro Val Met Ser Arg Phe  Ala Ala Asp Ile Phe  Ser Arg Thr
    1025                1030                1035

Pro Ser  Gly Lys Arg Leu Gln  Ile Leu Gly Tyr Leu  Glu Gly Thr
    1040                1045                1050

Arg Thr  Leu Leu Ala Ser Lys  Ile Ile Asn His Asn  Thr Glu Thr
    1055                1060                1065

Pro Ile  Leu Asp Arg Leu Arg  Lys Ile Thr Leu Gln  Arg Trp Ser
    1070                1075                1080

Leu Trp  Phe Ser Tyr Leu Asp  His Cys Asp Gln Val  Leu Ala Asp
    1085                1090                1095

Ala Leu  Thr Gln Ile Thr Cys  Thr Val Asp Leu Ala  Gln Ile Leu
    1100                1105                1110

Arg Glu  Tyr Thr Trp Ala His  Ile Leu Glu Gly Arg  Gln Leu Ile
    1115                1120                1125

Gly Ala  Thr Leu Pro Cys Ile  Leu Glu Gln Leu Asn  Val Ile Trp
    1130                1135                1140
```

```
Leu Lys Pro Tyr Glu His Cys Pro Lys Cys Ala Lys Ser Ala Asn
1145                 1150                1155

Pro Lys Gly Glu Pro Phe Val Ser Ile Ala Ile Lys Lys His Val
1160                 1165                1170

Val Ser Ala Trp Pro Asp Gln Ser Arg Leu Ser Trp Thr Ile Gly
1175                 1180                1185

Asp Gly Ile Pro Tyr Ile Gly Ser Arg Thr Glu Asp Lys Ile Gly
1190                 1195                1200

Gln Pro Ala Ile Lys Pro Lys Cys Pro Ser Ala Ala Leu Arg Glu
1205                 1210                1215

Ala Ile Glu Leu Thr Ser Arg Leu Thr Trp Val Thr Gln Gly Gly
1220                 1225                1230

Ala Asn Ser Asp Leu Leu Val Lys Pro Phe Ile Glu Ala Arg Val
1235                 1240                1245

Asn Leu Ser Val Gln Glu Ile Leu Gln Met Thr Pro Ser His Tyr
1250                 1255                1260

Ser Gly Asn Ile Val His Arg Tyr Asn Asp Gln Tyr Ser Pro His
1265                 1270                1275

Ser Phe Met Ala Asn Arg Met Ser Asn Ser Ala Thr Arg Leu Val
1280                 1285                1290

Val Ser Thr Asn Thr Leu Gly Glu Phe Ser Gly Gly Gly Gln Ser
1295                 1300                1305

Ala Arg Asp Ser Asn Ile Ile Phe Gln Asn Val Ile Asn Phe Ala
1310                 1315                1320

Val Ala Leu Phe Asp Leu Arg Phe Arg Asn Val Ala Thr Ser Ser
1325                 1330                1335

Ile Gln His His Arg Ala His Leu His Leu Ser Lys Cys Cys Thr
1340                 1345                1350

Arg Glu Val Pro Ala Gln Tyr Leu Val Tyr Thr Ser Thr Leu Pro
1355                 1360                1365

Leu Asp Leu Thr Arg Tyr Arg Asp Asn Glu Leu Ile Tyr Asp Asp
1370                 1375                1380

Asn Pro Leu Arg Gly Gly Leu Asn Cys Asn Leu Ser Phe Asp Asn
1385                 1390                1395

Pro Leu Phe Lys Gly Gln Arg Leu Asn Ile Ile Glu Glu Asp Leu
1400                 1405                1410

Ile Arg Leu Pro Tyr Leu Ser Gly Trp Glu Leu Ala Lys Thr Val
1415                 1420                1425

Ile Gln Ser Ile Ile Ser Asp Ser Asn Asn Ser Thr Asp Pro
1430                 1435                1440

Ile Ser Ser Gly Glu Thr Arg Ser Phe Thr Thr His Phe Leu Thr
1445                 1450                1455

Tyr Pro Lys Ile Gly Leu Leu Tyr Ser Phe Gly Ala Leu Ile Ser
1460                 1465                1470

Tyr Tyr Leu Gly Asn Thr Ile Ile Arg Thr Lys Lys Leu Thr Leu
1475                 1480                1485

Asn Asn Phe Ile Tyr Tyr Leu Ala Thr Gln Ile His Asn Leu Pro
1490                 1495                1500

His Arg Ser Leu Arg Ile Leu Lys Pro Thr Leu Lys His Ala Ser
1505                 1510                1515

Val Ile Ser Arg Leu Ile Ser Ile Asp Ser His Phe Ser Ile Tyr
1520                 1525                1530

Ile Gly Gly Thr Ala Gly Asp Arg Gly Leu Ser Asp Ala Ala Arg
```

```
              1535                1540                1545

Leu Phe Leu Arg Thr Ala Ile Thr Val Phe Leu Gln Phe Val Arg
    1550                1555                1560

Lys Trp Ile Val Glu Arg Lys Thr Ala Ile Pro Leu Trp Val Ile
    1565                1570                1575

Tyr Pro Leu Glu Gly Gln Ser Pro Ser Pro Ile Asn Ser Phe Leu
    1580                1585                1590

His His Val Ile Ala Leu Leu Gln His Glu Ser Ser His Asp His
    1595                1600                1605

Val Cys Ala Ala Glu Ala His Ser Arg Val Glu Thr Phe Asp Asn
    1610                1615                1620

Leu Val Tyr Met Cys Lys Ser Thr Ala Ser Asn Phe Phe His Ala
    1625                1630                1635

Ser Leu Ala Tyr Trp Arg Ser Arg Ser Lys Asn Gln Asp Lys Arg
    1640                1645                1650

Glu Met Thr Lys Ile Leu Ser Leu Thr Gln Thr Glu Lys Lys Asn
    1655                1660                1665

Ser Phe Gly Tyr Thr Ala His Pro Glu Ser Thr Ala Val Leu Gly
    1670                1675                1680

Ser Leu Gln Thr Ser Leu Ala Pro Pro Ser Ala Asp Glu Ala
    1685                1690                1695

Thr Tyr Asp Arg Lys Asn Lys Val Leu Lys Ala Ser Arg Pro Gly
    1700                1705                1710

Lys Tyr Ser Gln Asn Thr Thr Lys Ala Pro Pro Asn Gln Thr Ser
    1715                1720                1725

Cys Arg Asp Val Ser Pro Asn Ile Thr Gly Thr Asp Gly Cys Pro
    1730                1735                1740

Ser Ala Asn Glu Gly Ser Asn Ser Asn Asn Asn Asn Leu Val Ser
    1745                1750                1755

His Arg Ile Val Leu Pro Phe Phe Thr Leu Ser His Asn Tyr Asn
    1760                1765                1770

Glu Arg Pro Ser Ile Arg Lys Ser Glu Gly Thr Thr Glu Ile Val
    1775                1780                1785

Arg Leu Thr Arg Gln Leu Arg Ala Ile Pro Asp Thr Thr Ile Tyr
    1790                1795                1800

Cys Arg Phe Thr Gly Ile Val Ser Ser Met His Tyr Lys Leu Asp
    1805                1810                1815

Glu Val Leu Trp Glu Phe Asp Asn Phe Lys Ser Ala Ile Thr Leu
    1820                1825                1830

Ala Glu Gly Glu Gly Ser Gly Ala Leu Leu Leu Gln Lys Tyr
    1835                1840                1845

Lys Val Glu Thr Leu Phe Phe Asn Thr Leu Ala Thr Glu His Ser
    1850                1855                1860

Ile Glu Ala Glu Ile Ile Ser Gly Ile Thr Thr Pro Arg Met Leu
    1865                1870                1875

Leu Pro Ile Met Ser Arg Phe His Gly Gly Gln Ile Lys Val Thr
    1880                1885                1890

Leu Asn Asn Ser Ala Ser Gln Ile Thr Asp Ile Thr Asn Pro Ser
    1895                1900                1905

Trp Leu Ala Asp Gln Lys Ser Arg Ile Pro Lys Gln Val Glu Ile
    1910                1915                1920

Ile Thr Met Asp Ala Glu Thr Thr Glu Asn Ile Asn Arg Ser Lys
    1925                1930                1935
```

```
Leu Tyr Glu Ala Val Gln Gln Leu Ile Val Ser His Ile Asp Pro
    1940                1945                1950

Asn Ala Leu Lys Val Val Leu Lys Val Phe Leu Ser Asp Ile
    1955                1960                1965

Asp Gly Ile Leu Trp Leu Asn Asp Asn Leu Thr Pro Leu Phe Gly
    1970                1975                1980

Leu Gly Tyr Leu Ile Lys Pro Ile Thr Ser Ser Pro Lys Ser Ser
    1985                1990                1995

Glu Trp Tyr Leu Cys Leu Ser Asn Leu Leu Ser Thr Ser Arg Arg
    2000                2005                2010

Leu Pro His Gln Ser His Thr Thr Cys Met His Val Ile Gln Thr
    2015                2020                2025

Ala Leu Gln Leu Gln Ile Gln Arg Ser Ser Tyr Trp Leu Ser His
    2030                2035                2040

Leu Val Gln Tyr Ala Asn His Asn Leu His Leu Asp Tyr Ile Asn
    2045                2050                2055

Leu Gly Phe Pro Ser Leu Glu Arg Val Leu Tyr His Arg Tyr Asn
    2060                2065                2070

Leu Val Asp Ser Gln Lys Gly Pro Leu Thr Ser Ile Val Gln His
    2075                2080                2085

Leu Ala His Leu Gln Thr Glu Ile Arg Glu Leu Val Asn Asp Tyr
    2090                2095                2100

Asn Gln Gln Arg Gln Ser Arg Thr Gln Thr Tyr His Phe Ile Lys
    2105                2110                2115

Thr Ile Lys Gly Arg Ile Thr Lys Leu Val Asn Asp Tyr Leu Lys
    2120                2125                2130

Phe Phe Leu Ile Ile Gln Ala Leu Lys His Asn Cys Thr Trp Gln
    2135                2140                2145

Glu Glu Leu Arg Ala Leu Pro Asp Leu Ile Ser Val Cys Thr Arg
    2150                2155                2160

Phe Tyr His Thr Arg Asn Cys Ser Cys Glu Asn Arg Phe Leu Val
    2165                2170                2175

Gln Thr Leu Tyr Leu Ser Arg Met Gln Asp Ser Glu Ile Lys Leu
    2180                2185                2190

Ile Asp Arg Leu Thr Gly Leu Leu Ser Leu Cys Pro Asn Gly Phe
    2195                2200                2205

Phe Arg
    2210

<210> SEQ ID NO 25
<211> LENGTH: 739
<212> TYPE: PRT
<213> ORGANISM: Reston ebolavirus

<400> SEQUENCE: 25

Met Asp Arg Gly Thr Arg Arg Ile Trp Val Ser Gln Asn Gln Gly Asp
1               5                   10                  15

Thr Asp Leu Asp Tyr His Lys Ile Leu Thr Ala Gly Leu Thr Val Gln
                20                  25                  30

Gln Gly Ile Val Arg Gln Lys Ile Ile Ser Val Tyr Leu Val Asp Asn
            35                  40                  45

Leu Glu Ala Met Cys Gln Leu Val Ile Gln Ala Phe Glu Ala Gly Ile
        50                  55                  60

Asp Phe Gln Glu Asn Ala Asp Ser Phe Leu Leu Met Leu Cys Leu His
```

```
            65                  70                  75                  80
His Ala Tyr Gln Gly Asp Tyr Lys Leu Phe Leu Glu Ser Asn Ala Val
                    85                  90                  95
Gln Tyr Leu Glu Gly His Gly Phe Lys Phe Glu Leu Arg Lys Lys Asp
                100                 105                 110
Gly Val Asn Arg Leu Glu Glu Leu Pro Ala Ala Thr Ser Gly Lys
                115                 120                 125
Asn Ile Arg Arg Thr Leu Ala Ala Leu Pro Glu Glu Thr Thr Glu
                130                 135                 140
Ala Asn Ala Gly Gln Phe Leu Ser Phe Ala Ser Leu Phe Leu Pro Lys
145                 150                 155                 160
Leu Val Val Gly Glu Lys Ala Cys Leu Glu Lys Val Gln Arg Gln Ile
                165                 170                 175
Gln Val His Ala Glu Gln Gly Leu Ile Gln Tyr Pro Thr Ala Trp Gln
                180                 185                 190
Ser Val Gly His Met Met Val Ile Phe Arg Leu Met Arg Thr Asn Phe
                195                 200                 205
Leu Ile Lys Tyr Leu Leu Ile His Gln Gly Met His Met Val Ala Gly
    210                 215                 220
His Asp Ala Asn Asp Ala Val Ile Ala Asn Ser Val Ala Gln Ala Arg
225                 230                 235                 240
Phe Ser Gly Leu Leu Ile Val Lys Thr Val Leu Asp His Ile Leu Gln
                245                 250                 255
Lys Thr Asp Gln Gly Val Arg Leu His Pro Leu Ala Arg Thr Ala Lys
                260                 265                 270
Val Arg Asn Glu Val Asn Ala Phe Lys Ala Ala Leu Ser Ser Leu Ala
        275                 280                 285
Lys His Gly Glu Tyr Ala Pro Phe Ala Arg Leu Leu Asn Leu Ser Gly
        290                 295                 300
Val Asn Asn Leu Glu His Gly Leu Tyr Pro Gln Leu Ser Ala Ile Ala
305                 310                 315                 320
Leu Gly Val Ala Thr Ala His Gly Ser Thr Leu Ala Gly Val Asn Val
                325                 330                 335
Gly Glu Gln Tyr Gln Gln Leu Arg Glu Ala Ala Thr Glu Ala Glu Lys
            340                 345                 350
Gln Leu Gln Gln Tyr Ala Glu Ser Arg Glu Leu Asp Ser Leu Gly Leu
            355                 360                 365
Asp Asp Gln Glu Arg Arg Ile Leu Met Asn Phe His Gln Lys Lys Asn
    370                 375                 380
Glu Ile Ser Phe Gln Gln Thr Asn Ala Met Val Thr Leu Arg Lys Glu
385                 390                 395                 400
Arg Leu Ala Lys Leu Thr Glu Ala Ile Thr Leu Ala Ser Arg Pro Asn
                405                 410                 415
Leu Gly Ser Arg Gln Asp Asp Gly Asn Glu Ile Pro Phe Pro Gly Pro
                420                 425                 430
Ile Ser Asn Asn Pro Asp Gln Asp His Leu Glu Asp Asp Pro Arg Asp
                435                 440                 445
Ser Arg Asp Thr Ile Ile Pro Asn Gly Ala Ile Asp Pro Glu Asp Gly
                450                 455                 460
Asp Phe Glu Asn Tyr Asn Gly Tyr His Asp Asp Glu Val Gly Thr Ala
465                 470                 475                 480
Gly Asp Leu Val Leu Phe Asp Leu Asp Asp His Glu Asp Asp Asn Lys
                485                 490                 495
```

```
Ala Phe Glu Pro Gln Asp Ser Ser Pro Gln Ser Gln Arg Glu Ile Glu
            500                 505                 510

Arg Glu Arg Leu Ile His Pro Pro Gly Asn Asn Lys Asp Asp Asn
        515                 520                 525

Arg Ala Ser Asp Asn Asn Gln Gln Ser Ala Asp Ser Glu Glu Gln Gly
530                 535                 540

Gly Gln Tyr Asn Trp His Arg Gly Pro Glu Arg Thr Thr Ala Asn Arg
545                 550                 555                 560

Arg Leu Ser Pro Val His Glu Glu Asp Thr Leu Met Asp Gln Gly Asp
                565                 570                 575

Asp Asp Pro Ser Ser Leu Pro Pro Leu Glu Ser Asp Asp Asp Ala
            580                 585                 590

Ser Ser Ser Gln Gln Asp Pro Asp Tyr Thr Ala Val Ala Pro Pro Ala
        595                 600                 605

Pro Val Tyr Arg Ser Ala Glu Ala His Glu Pro Pro His Lys Ser Ser
    610                 615                 620

Asn Glu Pro Ala Glu Thr Ser Gln Leu Asn Glu Asp Pro Asp Ile Gly
625                 630                 635                 640

Gln Ser Lys Ser Met Gln Lys Leu Glu Glu Thr Tyr His His Leu Leu
                645                 650                 655

Arg Thr Gln Gly Pro Phe Glu Ala Ile Asn Tyr Tyr His Met Met Lys
            660                 665                 670

Asp Glu Pro Val Ile Phe Ser Thr Asp Asp Gly Lys Glu Tyr Thr Tyr
        675                 680                 685

Pro Asp Ser Leu Glu Glu Ala Tyr Pro Pro Trp Leu Thr Glu Lys Glu
    690                 695                 700

Arg Leu Asp Lys Glu Asn Arg Tyr Ile Tyr Ile Asn Asn Gln Gln Phe
705                 710                 715                 720

Phe Trp Pro Val Met Ser Pro Arg Asp Lys Phe Leu Ala Ile Leu Gln
                725                 730                 735

His His Gln

<210> SEQ ID NO 26
<211> LENGTH: 251
<212> TYPE: PRT
<213> ORGANISM: Reston ebolavirus

<400> SEQUENCE: 26

Met Ala Lys Ala Thr Gly Arg Tyr Asn Leu Val Pro Pro Lys Lys Asp
1               5                   10                  15

Met Glu Lys Gly Val Ile Phe Ser Asp Leu Cys Asn Phe Leu Ile Thr
            20                  25                  30

Gln Thr Leu Gln Gly Trp Lys Val Tyr Trp Ala Gly Ile Glu Phe Asp
        35                  40                  45

Val Ser Gln Lys Gly Met Ala Leu Leu Thr Arg Leu Lys Thr Asn Asp
    50                  55                  60

Phe Ala Pro Ala Trp Ala Met Thr Arg Asn Leu Phe Pro His Leu Phe
65                  70                  75                  80

Gln Asn Pro Asn Ser Val Ile Gln Ser Pro Ile Trp Ala Leu Arg Val
                85                  90                  95

Ile Leu Ala Ala Gly Leu Gln Asp Gln Leu Leu Asp His Ser Leu Val
            100                 105                 110

Glu Pro Leu Thr Gly Ala Leu Gly Leu Ile Ser Asp Trp Leu Leu Thr
        115                 120                 125
```

Thr Thr Ser Thr His Phe Asn Leu Arg Thr Arg Ser Val Lys Asp Gln
    130                 135                 140

Leu Ser Leu Arg Met Leu Ser Leu Ile Arg Ser Asn Ile Leu Gln Phe
145                 150                 155                 160

Ile Asn Lys Leu Asp Ala Leu His Val Val Asn Tyr Asn Gly Leu Leu
                165                 170                 175

Ser Ser Ile Glu Ile Gly Thr Ser Thr His Thr Ile Ile Thr Arg
            180                 185                 190

Thr Asn Met Gly Phe Leu Val Glu Val Gln Glu Pro Asp Lys Ser Ala
                195                 200                 205

Met Asn Ser Lys Arg Pro Gly Pro Val Lys Phe Ser Leu Leu His Glu
    210                 215                 220

Ser Ala Phe Lys Pro Phe Thr Arg Val Pro Gln Ser Gly Met Gln Ser
225                 230                 235                 240

Leu Ile Met Glu Phe Asn Ser Leu Leu Ala Ile
                245                 250

<210> SEQ ID NO 27
<211> LENGTH: 287
<212> TYPE: PRT
<213> ORGANISM: Reston ebolavirus

<400> SEQUENCE: 27

Met Glu His Ser Arg Glu Arg Gly Arg Ser Asn Met Arg His Asn
1               5                   10                  15

Ser Arg Glu Pro Tyr Glu Asn Pro Ser Arg Ser Arg Ser Leu Ser Arg
                20                  25                  30

Asp Pro Asn Gln Val Asp Arg Arg Gln Pro Arg Ser Ala Ser Gln Ile
            35                  40                  45

Arg Val Pro Asn Leu Phe His Arg Lys Thr Asp Ala Leu Ile Val
    50                  55                  60

Pro Pro Ala Pro Lys Asp Ile Cys Pro Thr Leu Lys Lys Gly Phe Leu
65                  70                  75                  80

Cys Asp Ser Lys Phe Cys Lys Lys Asp His Gln Leu Asp Ser Leu Asn
                85                  90                  95

Asp His Glu Leu Leu Leu Leu Ile Ala Arg Arg Thr Cys Gly Ile Ile
                100                 105                 110

Glu Ser Asn Ser Gln Ile Thr Ser Pro Lys Asp Met Arg Leu Ala Asn
            115                 120                 125

Pro Thr Ala Glu Asp Phe Ser Gln Gly Asn Ser Pro Lys Leu Thr Leu
    130                 135                 140

Ala Val Leu Leu Gln Ile Ala Glu His Trp Ala Thr Arg Asp Leu Arg
145                 150                 155                 160

Gln Ile Glu Asp Ser Lys Leu Arg Ala Leu Leu Thr Leu Cys Ala Val
                165                 170                 175

Leu Thr Arg Lys Phe Ser Lys Ser Gln Leu Gly Leu Leu Cys Glu Thr
            180                 185                 190

His Leu Arg His Glu Gly Leu Gly Gln Asp Gln Ala Asp Ser Val Leu
    195                 200                 205

Glu Val Tyr Gln Arg Leu His Ser Asp Lys Gly Gly Asn Phe Glu Ala
    210                 215                 220

Ala Leu Trp Gln Gln Trp Asp Arg Gln Ser Leu Ile Met Phe Ile Ser
225                 230                 235                 240

Ala Phe Leu Asn Ile Ala Leu Gln Ile Pro Cys Glu Ser Ser Ser Val

```
                   245                 250                 255
Val Val Ser Gly Leu Ala Thr Leu Tyr Pro Ala Gln Asp Asn Ser Thr
            260                 265                 270

Pro Ser Glu Ala Thr Asn Asp Thr Thr Trp Ser Ser Thr Val Glu
        275                 280                 285

<210> SEQ ID NO 28
<211> LENGTH: 329
<212> TYPE: PRT
<213> ORGANISM: Reston ebolavirus

<400> SEQUENCE: 28

Met Tyr Asn Asn Lys Leu Lys Val Cys Ser Gly Pro Glu Thr Thr Gly
1               5                   10                  15

Trp Ile Ser Glu Gln Leu Met Thr Gly Lys Ile Pro Val Thr Asp Ile
            20                  25                  30

Phe Ile Asp Ile Asp Asn Lys Pro Asp Gln Met Glu Val Arg Leu Lys
        35                  40                  45

Pro Ser Ser Arg Ser Ser Thr Arg Thr Cys Thr Ser Ser Ser Gln Thr
    50                  55                  60

Glu Val Asn Tyr Val Pro Leu Leu Lys Lys Val Glu Asp Thr Leu Thr
65                  70                  75                  80

Met Leu Val Asn Ala Thr Ser Arg Gln Asn Ala Ala Ile Glu Ala Leu
                85                  90                  95

Glu Asn Arg Leu Ser Thr Leu Glu Ser Ser Leu Lys Pro Ile Gln Asp
            100                 105                 110

Met Gly Lys Val Ile Ser Ser Leu Asn Arg Ser Cys Ala Glu Met Val
        115                 120                 125

Ala Lys Tyr Asp Leu Leu Val Met Thr Thr Gly Arg Ala Thr Ser Thr
130                 135                 140

Ala Ala Ala Val Asp Ala Tyr Trp Lys Glu His Lys Gln Pro Pro Pro
145                 150                 155                 160

Gly Pro Ala Leu Tyr Glu Glu Asn Ala Leu Lys Gly Lys Ile Asp Asp
                165                 170                 175

Pro Asn Ser Tyr Val Pro Asp Ala Val Gln Glu Ala Tyr Lys Asn Leu
            180                 185                 190

Asp Ser Thr Ser Thr Leu Thr Glu Glu Asn Phe Gly Lys Pro Tyr Ile
        195                 200                 205

Ser Ala Lys Asp Leu Lys Glu Ile Met Tyr Asp His Leu Pro Gly Phe
    210                 215                 220

Gly Thr Ala Phe His Gln Leu Val Gln Val Ile Cys Lys Ile Gly Lys
225                 230                 235                 240

Asp Asn Asn Leu Leu Asp Thr Ile His Ala Glu Phe Gln Ala Ser Leu
                245                 250                 255

Ala Asp Gly Asp Ser Pro Gln Cys Ala Leu Ile Gln Ile Thr Lys Arg
            260                 265                 270

Val Pro Ile Phe Gln Asp Val Pro Pro Ile Ile His Ile Arg Ser
        275                 280                 285

Arg Gly Asp Ile Pro Arg Ala Cys Gln Lys Ser Leu Arg Pro Ala Pro
    290                 295                 300

Pro Ser Pro Lys Ile Asp Arg Gly Trp Val Cys Leu Phe Lys Met Gln
305                 310                 315                 320

Asp Gly Lys Thr Leu Gly Leu Lys Ile
                325
```

<210> SEQ ID NO 29
<211> LENGTH: 331
<212> TYPE: PRT
<213> ORGANISM: Reston ebolavirus

<400> SEQUENCE: 29

Met Arg Arg Gly Val Leu Pro Thr Ala Pro Ala Tyr Asn Asp Ile
1               5                   10                  15

Ala Tyr Pro Met Ser Ile Leu Pro Thr Arg Pro Ser Val Ile Val Asn
            20                  25                  30

Glu Thr Lys Ser Asp Val Leu Ala Val Pro Gly Ala Asp Val Pro Ser
        35                  40                  45

Asn Ser Met Arg Pro Val Ala Asp Asn Ile Asp His Ser Ser His
    50                  55                  60

Thr Pro Ser Gly Val Ala Ser Ala Phe Ile Leu Glu Ala Thr Val Asn
65                  70                  75                  80

Val Ile Ser Gly Thr Lys Val Leu Met Lys Gln Ile Pro Ile Trp Leu
                85                  90                  95

Pro Leu Gly Val Ala Asp Gln Lys Ile Tyr Ser Phe Asp Ser Thr Thr
            100                 105                 110

Ala Ala Ile Met Leu Ala Ser Tyr Thr Val Thr His Phe Gly Lys Ile
        115                 120                 125

Ser Asn Pro Leu Val Arg Val Asn Arg Leu Gly Pro Gly Ile Pro Asp
    130                 135                 140

His Pro Leu Arg Leu Leu Arg Leu Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Ile Thr Gln Pro Leu Pro Ala Ala Thr Trp Thr
            180                 185                 190

Asp Glu Thr Pro Ala Gly Ala Val Asn Ala Leu Arg Pro Gly Leu Ser
        195                 200                 205

Leu His Pro Lys Leu Arg Pro Ile Leu Leu Pro Gly Lys Thr Gly Lys
    210                 215                 220

Lys Gly His Ala Ser Asp Leu Thr Ser Pro Asp Lys Ile Gln Thr Ile
225                 230                 235                 240

Met Asn Ala Ile Pro Asp Leu Lys Ile Val Pro Ile Asp Pro Thr Lys
                245                 250                 255

Asn Ile Val Gly Ile Glu Val Pro Glu Leu Leu Val Gln Arg Leu Thr
            260                 265                 270

Gly Lys Lys Pro Gln Pro Lys Asn Gly Gln Pro Ile Ile Pro Val Leu
        275                 280                 285

Leu Pro Lys Tyr Val Gly Leu Asp Pro Ile Ser Pro Gly Asp Leu Thr
    290                 295                 300

Met Val Ile Thr Gln Asp Cys Asp Ser Cys His Ser Pro Ala Ser His
305                 310                 315                 320

Pro Tyr His Met Asp Lys Gln Asn Ser Tyr Gln
                325                 330

<210> SEQ ID NO 30
<211> LENGTH: 2212
<212> TYPE: PRT
<213> ORGANISM: Reston ebolavirus

<400> SEQUENCE: 30

Met Ala Thr Gln His Thr Gln Tyr Pro Asp Ala Arg Leu Ser Ser Pro
1               5                   10                  15

Ile Val Leu Asp Gln Cys Asp Leu Val Thr Arg Ala Cys Gly Leu Tyr
            20                  25                  30

Ser Ser Tyr Ser Leu Asn Pro Gln Leu Arg Gln Cys Lys Leu Pro Lys
            35                  40                  45

His Ile Tyr Arg Leu Lys Phe Asp Thr Ile Val Ser Lys Phe Leu Ser
        50                  55                  60

Asp Thr Pro Val Ala Thr Leu Pro Ile Asp Tyr Leu Val Pro Ile Leu
65                  70                  75                  80

Leu Arg Ser Leu Thr Gly His Gly Asp Arg Pro Leu Thr Pro Thr Cys
                85                  90                  95

Asn Gln Phe Leu Asp Glu Ile Ile Asn Tyr Thr Leu His Asp Ala Ala
            100                 105                 110

Phe Leu Asp Tyr Tyr Leu Lys Ala Thr Gly Ala Gln Asp His Leu Thr
            115                 120                 125

Asn Ile Ala Thr Arg Glu Lys Leu Lys Asn Glu Ile Leu Asn Asn Asp
        130                 135                 140

Tyr Val His Gln Leu Phe Phe Trp His Asp Leu Ser Ile Leu Ala Arg
145                 150                 155                 160

Arg Gly Arg Leu Asn Arg Gly Asn Asn Arg Ser Thr Trp Phe Val His
                165                 170                 175

Asp Glu Phe Ile Asp Ile Leu Gly Tyr Gly Asp Tyr Ile Phe Trp Lys
            180                 185                 190

Ile Pro Leu Ser Leu Leu Pro Val Thr Ile Asp Gly Val Pro His Ala
            195                 200                 205

Ala Thr Asp Trp Tyr Gln Pro Thr Leu Phe Lys Glu Ser Ile Leu Gly
        210                 215                 220

His Ser Gln Ile Leu Ser Val Ser Thr Ala Glu Ile Leu Ile Met Cys
225                 230                 235                 240

Lys Asp Ile Ile Thr Cys Arg Phe Asn Thr Ser Leu Ile Ala Ser Ile
                245                 250                 255

Ala Lys Leu Glu Asp Val Asp Val Ser Asp Tyr Pro Asp Pro Ser Asp
            260                 265                 270

Ile Leu Lys Ile Tyr Asn Ala Gly Asp Tyr Val Ile Ser Ile Leu Gly
            275                 280                 285

Ser Glu Gly Tyr Lys Ile Ile Lys Tyr Leu Glu Pro Leu Cys Leu Ala
        290                 295                 300

Lys Ile Gln Leu Cys Ser Lys Phe Thr Glu Arg Lys Gly Arg Phe Leu
305                 310                 315                 320

Thr Gln Met His Leu Ser Val Ile Asn Asp Leu Arg Glu Leu Ile Ser
                325                 330                 335

Asn Arg Arg Leu Lys Asp Tyr Gln Gln Glu Lys Ile Arg Asp Phe His
            340                 345                 350

Lys Ile Leu Leu Gln Leu Gln Leu Ser Pro Gln Phe Cys Glu Leu
            355                 360                 365

Phe Ser Val Gln Lys His Trp Gly His Pro Ile Leu His Ser Glu Lys
            370                 375                 380

Ala Ile Gln Lys Val Lys Arg His Ala Thr Ile Leu Lys Ala Leu Arg
385                 390                 395                 400

Pro Asn Val Ile Phe Glu Thr Tyr Cys Val Phe Lys Tyr Asn Ile Ala
                405                 410                 415

Lys His Tyr Phe Asp Ser Gln Gly Thr Trp Tyr Ser Val Ile Ser Asp

```
                420             425             430
Arg Asn Leu Thr Pro Gly Leu Asn Ser Phe Ile Lys Arg Asn His Phe
            435             440             445
Pro Ser Leu Pro Met Ile Lys Asp Leu Leu Trp Glu Phe Tyr His Leu
            450             455             460
Asn His Pro Pro Leu Phe Ser Thr Lys Val Ile Ser Asp Leu Ser Ile
465             470             475             480
Phe Ile Lys Asp Arg Ala Thr Ala Val Glu Gln Thr Cys Trp Asp Ala
            485             490             495
Val Phe Glu Pro Asn Val Leu Gly Tyr Asn Pro Pro Asn Lys Phe Ser
            500             505             510
Thr Lys Arg Val Pro Glu Gln Phe Leu Glu Gln Asp Phe Ser Ile
            515             520             525
Glu Ser Val Leu Asn Tyr Ala Gln Glu Leu His Tyr Leu Leu Pro Gln
            530             535             540
Asn Arg Asn Phe Ser Phe Ser Leu Lys Glu Lys Glu Leu Asn Ile Gly
545             550             555             560
Arg Thr Phe Gly Lys Leu Pro Tyr Leu Thr Arg Asn Val Gln Thr Leu
            565             570             575
Cys Glu Ala Leu Leu Ala Asp Gly Leu Ala Lys Ala Phe Pro Ser Asn
            580             585             590
Met Met Val Val Thr Glu Arg Glu Gln Lys Glu Ser Leu Leu His Gln
            595             600             605
Ala Ser Trp His His Thr Ser Asp Asp Phe Gly Glu Asn Ala Thr Val
            610             615             620
Arg Gly Ser Ser Phe Val Thr Asp Leu Glu Lys Tyr Asn Leu Ala Phe
625             630             635             640
Arg Tyr Glu Phe Thr Ala Pro Phe Ile Glu Tyr Cys Asn His Cys Tyr
            645             650             655
Gly Val Arg Asn Val Phe Asn Trp Met His Tyr Leu Ile Pro Gln Cys
            660             665             670
Tyr Met His Val Ser Asp Tyr Tyr Asn Pro Pro His Asn Val Asn Leu
            675             680             685
Ser Asn Arg Glu Tyr Pro Pro Glu Gly Pro Ser Ser Tyr Arg Gly His
            690             695             700
Leu Gly Gly Ile Glu Gly Leu Gln Gln Lys Leu Trp Thr Ser Ile Ser
705             710             715             720
Cys Ala Gln Ile Ser Leu Val Glu Ile Lys Thr Gly Phe Lys Leu Arg
            725             730             735
Ser Ala Val Met Gly Asp Asn Gln Cys Ile Thr Val Leu Ser Val Phe
            740             745             750
Pro Leu Lys Thr Asp Pro Glu Glu Gln Glu Gln Ser Ala Glu Asp Asn
            755             760             765
Ala Ala Arg Val Ala Ala Ser Leu Ala Lys Val Thr Ser Ala Cys Gly
            770             775             780
Ile Phe Leu Lys Pro Asp Glu Thr Phe Val His Ser Gly Phe Ile Tyr
785             790             795             800
Phe Gly Lys Lys Gln Tyr Leu Asn Gly Val Gln Leu Pro Gln Ser Leu
            805             810             815
Lys Thr Ala Ala Arg Met Ala Pro Leu Ser Asp Ala Ile Phe Asp Asp
            820             825             830
Leu Gln Gly Thr Leu Ala Ser Ile Gly Thr Ala Phe Glu Arg Ala Ile
            835             840             845
```

```
Ser Glu Thr Arg His Ile Leu Pro Cys Arg Ile Val Ala Ala Phe His
    850                 855                 860

Thr Tyr Phe Ala Val Arg Ile Leu Gln Tyr His His Leu Gly Phe Asn
865                 870                 875                 880

Lys Gly Ile Asp Leu Gly Gln Leu Ser Leu Ser Lys Pro Leu Asp Tyr
                885                 890                 895

Gly Thr Ile Thr Leu Thr Leu Ala Val Pro Gln Val Leu Gly Gly Leu
            900                 905                 910

Ser Phe Leu Asn Pro Glu Lys Cys Phe Tyr Arg Asn Phe Gly Asp Pro
        915                 920                 925

Val Thr Ser Gly Leu Phe Gln Leu Arg Val Tyr Leu Glu Met Val Asn
    930                 935                 940

Met Lys Asp Leu Phe Cys Pro Leu Ile Ser Lys Asn Pro Gly Asn Cys
945                 950                 955                 960

Ser Ala Ile Asp Phe Val Leu Asn Pro Ser Gly Leu Asn Val Pro Gly
                965                 970                 975

Ser Gln Asp Leu Thr Ser Phe Leu Arg Gln Ile Val Arg Arg Ser Ile
            980                 985                 990

Thr Leu Thr Ala Arg Asn Lys Leu Ile Asn Thr Leu Phe His Ala Ser
        995                 1000                1005

Ala Asp Leu Glu Asp Glu Met Val Cys Lys Trp Leu Leu Ser Ser
    1010                1015                1020

Asn Pro Val Met Ser Arg Phe Ala Ala Asp Ile Phe Ser Arg Thr
    1025                1030                1035

Pro Ser Gly Lys Arg Leu Gln Ile Leu Gly Tyr Leu Glu Gly Thr
    1040                1045                1050

Arg Thr Leu Leu Ala Ser Lys Ile Ile Asn Asn Asn Ser Glu Thr
    1055                1060                1065

Pro Val Leu Asp Lys Leu Arg Lys Ile Thr Leu Gln Arg Trp Asn
    1070                1075                1080

Leu Trp Phe Ser Tyr Leu Asp His Cys Asp Gln Leu Leu Ala Asp
    1085                1090                1095

Ala Leu Gln Lys Ile Ser Cys Thr Val Asp Leu Ala Gln Ile Leu
    1100                1105                1110

Arg Glu Tyr Thr Trp Ser His Ile Leu Glu Gly Arg Ser Leu Ile
    1115                1120                1125

Gly Ala Thr Leu Pro Cys Met Val Glu Gln Phe Lys Val Lys Trp
    1130                1135                1140

Leu Gly Gln Tyr Glu Pro Cys Pro Glu Cys Leu Asn Lys Lys Gly
    1145                1150                1155

Ser Asn Ala Tyr Val Ser Val Ala Val Lys Asp Gln Val Val Ser
    1160                1165                1170

Ala Trp Pro Asn Thr Ser Arg Ile Ser Trp Thr Ile Gly Ser Gly
    1175                1180                1185

Val Pro Tyr Ile Gly Ser Arg Thr Glu Asp Lys Ile Gly Gln Pro
    1190                1195                1200

Ala Ile Lys Pro Arg Cys Pro Ser Ser Ala Leu Lys Glu Ala Ile
    1205                1210                1215

Glu Leu Ala Ser Arg Leu Thr Trp Val Thr Gln Gly Gly Ser Asn
    1220                1225                1230

Ser Glu Gln Leu Ile Arg Pro Phe Leu Glu Ala Arg Val Asn Leu
    1235                1240                1245
```

```
Ser Val Ser Glu Val Leu Gln Met Thr Pro Ser His Tyr Ser Gly
1250                1255                1260

Asn Ile Val His Arg Tyr Asn Asp Gln Tyr Ser Pro His Ser Phe
1265                1270                1275

Met Ala Asn Arg Met Ser Asn Thr Ala Thr Arg Leu Ile Val Ser
1280                1285                1290

Thr Asn Thr Leu Gly Glu Phe Ser Gly Gly Gln Ala Ala Arg
1295                1300                1305

Asp Ser Asn Ile Ile Phe Gln Asn Val Ile Asn Leu Ala Val Ala
1310                1315                1320

Leu Tyr Asp Ile Arg Phe Arg Asn Thr Asn Thr Ser Asp Ile Arg
1325                1330                1335

His Asn Arg Ala His Leu His Leu Thr Glu Cys Cys Thr Lys Glu
1340                1345                1350

Val Pro Ala Gln Tyr Leu Thr Tyr Thr Ser Ala Leu Asn Leu Asp
1355                1360                1365

Leu Ser Arg Tyr Arg Asp Asn Glu Leu Ile Tyr Asp Ser Asn Pro
1370                1375                1380

Leu Lys Gly Gly Leu Asn Cys Asn Leu Thr Ile Asp Ser Pro Leu
1385                1390                1395

Val Lys Gly Pro Arg Leu Asn Met Ile Glu Asp Asp Leu Leu Arg
1400                1405                1410

Phe Pro His Leu Ser Gly Trp Glu Leu Ala Lys Thr Val Val Gln
1415                1420                1425

Ser Ile Ile Ser Asp Asn Ser Asn Ser Ser Thr Asp Pro Ile Ser
1430                1435                1440

Ser Gly Glu Thr Arg Ser Phe Thr Thr His Phe Leu Thr Tyr Pro
1445                1450                1455

Gln Ile Gly Leu Leu Tyr Ser Phe Gly Ala Val Leu Cys Phe Tyr
1460                1465                1470

Leu Gly Asn Thr Ile Leu Trp Thr Lys Lys Leu Asp Tyr Glu Gln
1475                1480                1485

Phe Leu Tyr Tyr Leu His Asn Gln Leu His Asn Leu Pro His Arg
1490                1495                1500

Ala Leu Arg Val Phe Lys Pro Thr Phe Lys His Ala Ser Val Met
1505                1510                1515

Ser Arg Leu Met Glu Ile Asp Ser Asn Phe Ser Ile Tyr Ile Gly
1520                1525                1530

Gly Thr Ser Gly Asp Arg Gly Leu Ser Asp Ala Ala Arg Leu Phe
1535                1540                1545

Leu Arg Thr Ala Ile Ala Ser Phe Leu Gln Phe Leu Lys Ser Trp
1550                1555                1560

Ile Ile Asp Arg Gln Lys Thr Ile Pro Leu Trp Ile Val Tyr Pro
1565                1570                1575

Leu Glu Gly Gln Gln Pro Glu Ser Ile Asn Glu Phe Leu His Lys
1580                1585                1590

Ile Leu Gly Leu Leu Lys Gln Gly Pro Lys Ser Ile Pro Lys Glu
1595                1600                1605

Val Ser Ile Gln Asn Asp Gly His Leu Asp Leu Ala Glu Asn Asn
1610                1615                1620

Tyr Val Tyr Asn Ser Lys Ser Thr Ala Ser Asn Phe Phe His Ala
1625                1630                1635

Ser Leu Ala Tyr Trp Arg Ser Arg Lys Ser Arg Lys Thr Gln Asp
```

-continued

```
            1640                1645                1650
His Asn Asp Phe Ser Arg Gly Asp Gly Thr Leu Thr Glu Pro Val
    1655                1660                1665
Arg Lys Phe Ser Ser Asn His Gln Ser Asp Glu Lys Tyr Tyr Asn
    1670                1675                1680
Val Thr Cys Gly Lys Ser Pro Lys Pro Gln Glu Arg Lys Asp Phe
    1685                1690                1695
Ser Gln Tyr Arg Leu Ser Asn Asn Gly Gln Thr Met Ser Asn His
    1700                1705                1710
Arg Lys Lys Gly Lys Phe His Lys Trp Asn Pro Cys Lys Met Leu
    1715                1720                1725
Met Glu Ser Gln Arg Gly Thr Val Leu Thr Glu Gly Asp Tyr Phe
    1730                1735                1740
Gln Asn Asn Thr Pro Pro Thr Asp Asp Val Ser Ser Pro His Arg
    1745                1750                1755
Leu Ile Leu Pro Phe Phe Lys Leu Gly Asn His Asn His Ala His
    1760                1765                1770
Asp Gln Asp Ala Gln Glu Leu Met Asn Gln Asn Ile Lys Gln Tyr
    1775                1780                1785
Leu His Gln Leu Arg Ser Met Leu Asp Thr Thr Ile Tyr Cys Arg
    1790                1795                1800
Phe Thr Gly Ile Val Ser Ser Met His Tyr Lys Leu Asp Glu Val
    1805                1810                1815
Leu Leu Glu Tyr Asn Ser Phe Asp Ser Ala Ile Thr Leu Ala Glu
    1820                1825                1830
Gly Glu Gly Ser Gly Ala Leu Leu Leu Gln Lys Tyr Ser Thr
    1835                1840                1845
Arg Leu Leu Phe Leu Asn Thr Leu Ala Thr Glu His Ser Ile Glu
    1850                1855                1860
Ser Glu Val Val Ser Gly Phe Ser Thr Pro Arg Met Leu Leu Pro
    1865                1870                1875
Ile Met Gln Lys Val His Glu Gly Gln Val Thr Val Ile Leu Asn
    1880                1885                1890
Asn Ser Ala Ser Gln Ile Thr Asp Ile Thr Ser Ser Met Trp Leu
    1895                1900                1905
Ser Asn Gln Lys Tyr Asn Leu Pro Cys Gln Val Glu Ile Ile Met
    1910                1915                1920
Met Asp Ala Glu Thr Thr Glu Asn Leu Asn Arg Ser Gln Leu Tyr
    1925                1930                1935
Arg Ala Val Tyr Asn Leu Ile Leu Asp His Ile Asp Pro Gln Tyr
    1940                1945                1950
Leu Lys Val Val Val Leu Lys Val Phe Leu Ser Asp Ile Glu Gly
    1955                1960                1965
Ile Leu Trp Ile Asn Asp Tyr Leu Ala Pro Leu Phe Gly Ala Gly
    1970                1975                1980
Tyr Leu Ile Lys Pro Ile Thr Ser Ser Ala Arg Ser Ser Glu Trp
    1985                1990                1995
Tyr Leu Cys Leu Ser Asn Leu Ile Ser Thr Asn Arg Arg Ser Ala
    2000                2005                2010
His Gln Thr His Lys Ala Cys Leu Gly Val Ile Arg Asp Ala Leu
    2015                2020                2025
Gln Ala Gln Val Gln Arg Gly Val Tyr Trp Leu Ser His Ile Ala
    2030                2035                2040
```

```
Gln Tyr Ala Thr Lys Asn Leu His Cys Glu Tyr Ile Gly Leu Gly
        2045                2050                2055

Phe Pro Ser Leu Glu Lys Val Leu Tyr His Arg Tyr Asn Leu Val
    2060                2065                2070

Asp Thr Gly Leu Gly Pro Leu Ser Ser Val Ile Arg His Leu Thr
    2075                2080                2085

Asn Leu Gln Ala Glu Ile Arg Asp Leu Val Leu Asp Tyr Asn Leu
    2090                2095                2100

Met Arg Glu Ser Arg Thr Gln Thr Tyr His Phe Ile Lys Thr Ala
    2105                2110                2115

Lys Gly Arg Ile Thr Lys Leu Val Asn Asp Phe Leu Lys Phe Ser
    2120                2125                2130

Leu Ile Val Gln Ala Leu Lys Asn Asn Ser Ser Trp Tyr Thr Glu
    2135                2140                2145

Leu Lys Lys Leu Pro Glu Val Ile Asn Val Cys Asn Arg Phe Tyr
    2150                2155                2160

His Thr His Asn Cys Glu Cys Gln Glu Lys Phe Phe Val Gln Thr
    2165                2170                2175

Leu Tyr Leu Gln Arg Leu Arg Asp Ala Glu Ile Lys Leu Ile Glu
    2180                2185                2190

Arg Leu Thr Gly Leu Met Arg Phe Tyr Pro Glu Gly Leu Ile Tyr
    2195                2200                2205

Ser Asn His Thr
    2210

<210> SEQ ID NO 31
<211> LENGTH: 739
<212> TYPE: PRT
<213> ORGANISM: Bundibugyo ebolavirus

<400> SEQUENCE: 31

Met Asp Pro Arg Pro Ile Arg Thr Trp Met Met His Asn Thr Ser Glu
1               5                   10                  15

Val Glu Ala Asp Tyr His Lys Ile Leu Thr Ala Gly Leu Ser Val Gln
            20                  25                  30

Gln Gly Ile Val Arg Gln Arg Ile Ile Pro Val Tyr Gln Ile Ser Asn
        35                  40                  45

Leu Glu Glu Val Cys Gln Leu Ile Ile Gln Ala Phe Glu Ala Gly Val
    50                  55                  60

Asp Phe Gln Asp Ser Ala Asp Ser Phe Leu Leu Met Leu Cys Leu His
65                  70                  75                  80

His Ala Tyr Gln Gly Asp Tyr Lys Gln Phe Leu Glu Ser Asn Ala Val
                85                  90                  95

Lys Tyr Leu Glu Gly His Gly Phe Arg Phe Glu Met Lys Lys Lys Glu
            100                 105                 110

Gly Val Lys Arg Leu Glu Leu Leu Pro Ala Ala Ser Ser Gly Lys
        115                 120                 125

Asn Ile Lys Arg Thr Leu Ala Ala Met Pro Glu Glu Glu Thr Thr Glu
    130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ser Trp Gln
```

```
            180                 185                 190
Ser Val Gly His Met Met Val Ile Phe Arg Leu Met Arg Thr Asn Phe
            195                 200                 205
Leu Ile Lys Phe Leu Leu Ile His Gln Gly Met His Met Val Ala Gly
            210                 215                 220
His Asp Ala Asn Asp Ala Val Ile Ala Asn Ser Val Ala Gln Ala Arg
225                 230                 235                 240
Phe Ser Gly Leu Leu Ile Val Lys Thr Val Leu Asp His Ile Leu Gln
            245                 250                 255
Lys Thr Glu His Gly Val Arg Leu His Pro Leu Ala Arg Thr Ala Lys
            260                 265                 270
Val Lys Asn Glu Val Ser Ser Phe Lys Ala Ala Leu Ala Ser Leu Ala
            275                 280                 285
Gln His Gly Glu Tyr Ala Pro Phe Ala Arg Leu Leu Asn Leu Ser Gly
            290                 295                 300
Val Asn Asn Leu Glu His Gly Leu Phe Pro Gln Leu Ser Ala Ile Ala
305                 310                 315                 320
Leu Gly Val Ala Thr Ala His Gly Ser Thr Leu Ala Gly Val Asn Val
            325                 330                 335
Gly Glu Gln Tyr Gln Gln Leu Arg Glu Ala Ala Thr Glu Ala Glu Lys
            340                 345                 350
Gln Leu Gln Lys Tyr Ala Glu Ser Arg Glu Leu Asp His Leu Gly Leu
            355                 360                 365
Asp Asp Gln Glu Lys Lys Ile Leu Lys Asp Phe His Gln Lys Lys Asn
            370                 375                 380
Glu Ile Ser Phe Gln Gln Thr Thr Ala Met Val Thr Leu Arg Lys Glu
385                 390                 395                 400
Arg Leu Ala Lys Leu Thr Glu Ala Ile Thr Ser Thr Ser Ile Leu Lys
            405                 410                 415
Thr Gly Arg Arg Tyr Asp Asp Asp Asn Asp Ile Pro Phe Pro Gly Pro
            420                 425                 430
Ile Asn Asp Asn Glu Asn Ser Gly Gln Asn Asp Asp Pro Thr Asp
            435                 440                 445
Ser Gln Asp Thr Thr Ile Pro Asp Val Ile Ile Asp Pro Asn Asp Gly
            450                 455                 460
Gly Tyr Asn Asn Tyr Ser Asp Tyr Ala Asn Asp Ala Ala Ser Ala Pro
465                 470                 475                 480
Asp Asp Leu Val Leu Phe Asp Leu Glu Asp Glu Asp Ala Asp Asn
            485                 490                 495
Pro Ala Gln Asn Thr Pro Glu Lys Asn Asp Arg Pro Ala Thr Thr Lys
            500                 505                 510
Leu Arg Asn Gly Gln Asp Gln Asp Gly Asn Gln Gly Glu Thr Ala Ser
            515                 520                 525
Pro Arg Val Ala Pro Asn Gln Tyr Arg Asp Lys Pro Met Pro Gln Val
            530                 535                 540
Gln Asp Arg Ser Glu Asn His Asp Gln Thr Leu Gln Thr Gln Ser Arg
545                 550                 555                 560
Val Leu Thr Pro Ile Ser Glu Glu Ala Asp Pro Ser Asp His Asn Asp
            565                 570                 575
Gly Asp Asn Glu Ser Ile Pro Pro Leu Glu Ser Asp Asp Glu Gly Ser
            580                 585                 590
Thr Asp Thr Thr Ala Ala Glu Thr Lys Pro Ala Thr Ala Pro Pro Ala
            595                 600                 605
```

```
Pro Val Tyr Arg Ser Ile Ser Val Asp Asp Ser Val Pro Ser Glu Asn
        610                 615                 620

Ile Pro Ala Gln Ser Asn Gln Thr Asn Asn Glu Asp Asn Val Arg Asn
625                 630                 635                 640

Asn Ala Gln Ser Glu Gln Ser Ile Ala Glu Met Tyr Gln His Ile Leu
                645                 650                 655

Lys Thr Gln Gly Pro Phe Asp Ala Ile Leu Tyr Tyr His Met Met Lys
                660                 665                 670

Glu Glu Pro Ile Ile Phe Ser Thr Ser Asp Gly Lys Glu Tyr Thr Tyr
            675                 680                 685

Pro Asp Ser Leu Glu Asp Glu Tyr Pro Pro Trp Leu Ser Glu Lys Glu
        690                 695                 700

Ala Met Asn Glu Asp Asn Arg Phe Ile Thr Met Asp Gly Gln Gln Phe
705                 710                 715                 720

Tyr Trp Pro Val Met Asn His Arg Asn Lys Phe Met Ala Ile Leu Gln
                725                 730                 735

His His Arg

<210> SEQ ID NO 32
<211> LENGTH: 251
<212> TYPE: PRT
<213> ORGANISM: Bundibugyo ebolavirus

<400> SEQUENCE: 32

Met Ala Lys Ala Thr Gly Arg Tyr Asn Leu Val Ser Pro Lys Lys Asp
1               5                   10                  15

Leu Glu Arg Gly Leu Val Leu Ser Asp Leu Cys Thr Phe Leu Val Asp
                20                  25                  30

Gln Thr Ile Gln Gly Trp Arg Val Thr Trp Val Gly Ile Glu Phe Asp
            35                  40                  45

Ile Ala Gln Lys Gly Met Ala Leu Leu His Arg Leu Lys Thr Ala Asp
        50                  55                  60

Phe Ala Pro Ala Trp Ser Met Thr Arg Asn Leu Phe Pro His Leu Phe
65                  70                  75                  80

Gln Asn Ser Asn Ser Thr Ile Glu Ser Pro Leu Trp Ala Leu Arg Val
                85                  90                  95

Ile Leu Ala Ala Gly Ile Gln Asp Gln Leu Ile Asp Gln Ser Leu Val
                100                 105                 110

Glu Pro Leu Ala Gly Ala Leu Ser Leu Val Ser Asp Trp Leu Leu Thr
            115                 120                 125

Thr Asn Thr Asn His Phe Gln Met Arg Thr Gln His Ala Lys Glu Gln
130                 135                 140

Leu Ser Leu Lys Met Leu Ser Leu Val Arg Ser Asn Ile Leu Lys Phe
145                 150                 155                 160

Ile Ser Gln Leu Asp Ala Leu His Val Val Asn Tyr Asn Gly Leu Leu
                165                 170                 175

Ser Ser Ile Glu Ile Gly Thr Arg Asn His Thr Ile Ile Thr Arg
            180                 185                 190

Thr Asn Met Gly Phe Leu Val Glu Leu Gln Pro Asp Lys Ser Ala
        195                 200                 205

Met Asn Gln Lys Lys Pro Gly Pro Val Lys Phe Ser Leu Leu His Glu
        210                 215                 220

Ser Thr Phe Lys Ala Leu Ile Lys Lys Pro Ala Thr Lys Met Gln Ala
225                 230                 235                 240
```

```
Leu Ile Leu Glu Phe Asn Ser Ser Leu Ala Ile
            245                 250

<210> SEQ ID NO 33
<211> LENGTH: 289
<212> TYPE: PRT
<213> ORGANISM: Bundibugyo ebolavirus

<400> SEQUENCE: 33

Met Asp Ser Phe His Glu Arg Gly Arg Ser Arg Thr Ile Arg Gln Ser
1               5                   10                  15

Ala Arg Asp Gly Pro Ser His Gln Val Arg Thr Arg Ser Ser Ser Arg
            20                  25                  30

Asp Ser His Arg Ser Glu Tyr His Thr Pro Arg Ser Ser Ser Gln Val
        35                  40                  45

Arg Val Pro Thr Val Phe His Arg Lys Arg Thr Asp Ser Leu Thr Val
    50                  55                  60

Pro Pro Ala Pro Lys Asp Ile Cys Pro Thr Leu Arg Lys Gly Phe Leu
65                  70                  75                  80

Cys Asp Ser Asn Phe Cys Lys Lys Asp His Gln Leu Glu Ser Leu Thr
                85                  90                  95

Asp Arg Glu Leu Leu Leu Ile Ala Arg Lys Thr Cys Gly Ser Leu
            100                 105                 110

Glu Gln Gln Leu Asn Ile Thr Ala Pro Lys Asp Thr Arg Leu Ala Asn
        115                 120                 125

Pro Ile Ala Asp Asp Phe Gln Gln Lys Asp Gly Pro Lys Ile Thr Leu
    130                 135                 140

Leu Thr Leu Leu Glu Thr Ala Glu Tyr Trp Ser Lys Gln Asp Ile Lys
145                 150                 155                 160

Gly Ile Asp Asp Ser Arg Leu Arg Ala Leu Leu Thr Leu Cys Ala Val
                165                 170                 175

Met Thr Arg Lys Phe Ser Lys Ser Gln Leu Ser Leu Leu Cys Glu Ser
            180                 185                 190

His Leu Arg Arg Glu Gly Leu Gly Gln Asp Gln Ser Glu Ser Val Leu
        195                 200                 205

Glu Val Tyr Gln Arg Leu His Ser Asp Lys Gly Gly Asn Phe Glu Ala
    210                 215                 220

Ala Leu Trp Gln Gln Trp Asp Arg Gln Ser Leu Ile Met Phe Ile Thr
225                 230                 235                 240

Ala Phe Leu Asn Ile Ala Leu Gln Leu Pro Cys Glu Ser Ser Ser Val
                245                 250                 255

Val Ile Ser Gly Leu Arg Leu Leu Val Pro Gln Ser Glu Asp Thr Glu
            260                 265                 270

Thr Ser Thr Tyr Thr Glu Thr Arg Ala Trp Ser Glu Glu Gly Gly Pro
        275                 280                 285

His

<210> SEQ ID NO 34
<211> LENGTH: 341
<212> TYPE: PRT
<213> ORGANISM: Bundibugyo ebolavirus

<400> SEQUENCE: 34

Met Thr Ser Asn Arg Ala Arg Val Thr Tyr Asn Pro Pro Thr Thr
1               5                   10                  15
```

Thr Gly Thr Arg Ser Cys Gly Pro Glu Leu Ser Gly Trp Ile Ser Glu
              20                  25                  30

Gln Leu Met Thr Gly Lys Ile Pro Ile Thr Asp Ile Phe Asn Glu Ile
             35                  40                  45

Glu Thr Leu Pro Ser Ile Ser Pro Ser Ile His Ser Lys Ile Lys Thr
 50                  55                  60

Pro Ser Val Gln Thr Arg Ser Val Gln Thr Gln Thr Asp Pro Asn Cys
 65                  70                  75                  80

Asn His Asp Phe Ala Glu Val Val Lys Met Leu Thr Ser Leu Thr Leu
                 85                  90                  95

Val Val Gln Lys Gln Thr Leu Ala Thr Glu Ser Leu Glu Gln Arg Ile
             100                 105                 110

Thr Asp Leu Glu Gly Ser Leu Lys Pro Val Ser Glu Ile Thr Lys Ile
         115                 120                 125

Val Ser Ala Leu Asn Arg Ser Cys Ala Glu Met Val Ala Lys Tyr Asp
 130                 135                 140

Leu Leu Val Met Thr Thr Gly Arg Ala Thr Ala Thr Ala Ala Ala Thr
145                 150                 155                 160

Glu Ala Tyr Trp Ala Glu His Gly Arg Pro Pro Pro Gly Pro Ser Leu
                 165                 170                 175

Tyr Glu Glu Asp Ala Ile Arg Thr Lys Ile Gly Lys Gln Gly Asp Met
             180                 185                 190

Val Pro Lys Glu Val Gln Glu Ala Phe Arg Asn Leu Asp Ser Thr Ala
         195                 200                 205

Leu Leu Thr Glu Glu Asn Phe Gly Lys Pro Asp Ile Ser Ala Lys Asp
 210                 215                 220

Leu Arg Asn Ile Met Tyr Asp His Leu Pro Gly Phe Gly Thr Ala Phe
225                 230                 235                 240

His Gln Leu Val Gln Val Ile Cys Lys Leu Gly Lys Asp Asn Ser Ser
                 245                 250                 255

Leu Asp Val Ile His Ala Glu Phe Gln Ala Ser Leu Ala Glu Gly Asp
             260                 265                 270

Ser Pro Gln Cys Ala Leu Ile Gln Ile Thr Lys Arg Ile Pro Ile Phe
         275                 280                 285

Gln Asp Ala Ala Pro Val Ile His Ile Arg Ser Arg Gly Asp Ile
 290                 295                 300

Pro Lys Ala Cys Gln Lys Ser Leu Arg Pro Val Pro Pro Ser Pro Lys
305                 310                 315                 320

Ile Asp Arg Gly Trp Val Cys Ile Phe Gln Leu Gln Asp Gly Lys Thr
                 325                 330                 335

Leu Gly Leu Lys Ile
            340

<210> SEQ ID NO 35
<211> LENGTH: 326
<212> TYPE: PRT
<213> ORGANISM: Bundibugyo ebolavirus

<400> SEQUENCE: 35

Met Arg Arg Ala Ile Leu Pro Thr Ala Pro Pro Glu Tyr Ile Glu Ala
 1               5                  10                  15

Val Tyr Pro Met Arg Thr Val Ser Thr Ser Ile Asn Ser Thr Ala Ser
             20                  25                  30

Gly Pro Asn Phe Pro Ala Pro Asp Val Met Met Ser Asp Thr Pro Ser
         35                  40                  45

```
Asn Ser Leu Arg Pro Ile Ala Asp Asp Asn Ile Asp His Pro Ser His
 50                  55                  60

Thr Pro Thr Ser Val Ser Ser Ala Phe Ile Leu Glu Ala Met Val Asn
 65                  70                  75                  80

Val Ile Ser Gly Pro Lys Val Leu Met Lys Gln Ile Pro Ile Trp Leu
                 85                  90                  95

Pro Leu Gly Val Ala Asp Gln Lys Thr Tyr Ser Phe Asp Ser Thr Thr
                100                 105                 110

Ala Ala Ile Met Leu Ala Ser Tyr Thr Ile Thr His Phe Gly Lys Thr
                115                 120                 125

Ser Asn Pro Leu Val Arg Ile Asn Arg Leu Gly Pro Gly Ile Pro Asp
130                 135                 140

His Pro Leu Arg Leu Leu Arg Ile Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Ile Thr Gln Pro Leu Pro Ala Ala Thr Trp Thr
                180                 185                 190

Asp Asp Thr Pro Thr Gly Pro Thr Gly Ile Leu Arg Pro Gly Ile Ser
                195                 200                 205

Phe His Pro Lys Leu Arg Pro Ile Leu Leu Pro Gly Lys Thr Gly Lys
210                 215                 220

Arg Gly Ser Ser Ser Asp Leu Thr Ser Pro Asp Lys Ile Gln Ala Ile
225                 230                 235                 240

Met Asn Phe Leu Gln Asp Leu Lys Leu Val Pro Ile Asp Pro Ala Lys
                245                 250                 255

Asn Ile Met Gly Ile Glu Val Pro Glu Leu Leu Val His Arg Leu Thr
                260                 265                 270

Gly Lys Lys Ile Thr Thr Lys Asn Gly Gln Pro Ile Ile Pro Ile Leu
                275                 280                 285

Leu Pro Lys Tyr Ile Gly Met Asp Pro Ile Ser Gln Gly Asp Leu Thr
290                 295                 300

Met Val Ile Thr Gln Asp Cys Asp Thr Cys His Ser Pro Ala Ser Leu
305                 310                 315                 320

Pro Pro Val Ser Glu Lys
                325

<210> SEQ ID NO 36
<211> LENGTH: 2210
<212> TYPE: PRT
<213> ORGANISM: Bundibugyo ebolavirus

<400> SEQUENCE: 36

Met Ala Thr Gln His Thr Gln Tyr Pro Asp Ala Arg Leu Ser Ser Pro
  1               5                  10                  15

Ile Val Leu Asp Gln Cys Asp Leu Val Thr Arg Ala Cys Gly Leu Tyr
                 20                  25                  30

Ser Ser Tyr Ser Leu Asn Pro Gln Leu Lys Asn Cys Arg Leu Pro Lys
                 35                  40                  45

His Ile Tyr Arg Leu Lys Phe Asp Ala Thr Val Thr Lys Phe Leu Ser
                 50                  55                  60

Asp Val Pro Ile Val Thr Leu Pro Ile Asp Tyr Leu Thr Pro Leu Leu
 65                  70                  75                  80

Leu Arg Thr Leu Ser Gly Glu Gly Leu Cys Pro Val Glu Pro Lys Cys
```

```
                    85                  90                  95
Ser Gln Phe Leu Asp Glu Ile Val Ser Tyr Val Leu Gln Asp Ala Arg
                100                 105                 110

Phe Leu Arg Tyr Tyr Phe Arg His Val Gly Val His Asp Asp Asn Val
            115                 120                 125

Gly Lys Asn Phe Glu Pro Lys Ile Lys Ala Leu Ile Tyr Asp Asn Glu
        130                 135                 140

Phe Leu Gln Gln Leu Phe Tyr Trp Tyr Asp Leu Ala Ile Leu Thr Arg
145                 150                 155                 160

Arg Gly Arg Leu Asn Arg Gly Asn Asn Arg Ser Thr Trp Phe Ala Asn
                165                 170                 175

Asp Asp Leu Ile Asp Ile Leu Gly Tyr Gly Asp Tyr Ile Phe Trp Lys
                180                 185                 190

Ile Pro Leu Ser Leu Leu Ser Leu Asn Thr Glu Gly Ile Pro His Ala
                195                 200                 205

Ala Lys Asp Trp Tyr His Ala Ser Ile Phe Lys Glu Ala Val Gln Gly
            210                 215                 220

His Thr His Ile Val Ser Val Ser Thr Ala Asp Val Leu Ile Met Cys
225                 230                 235                 240

Lys Asp Ile Ile Thr Cys Arg Phe Asn Thr Thr Leu Ile Ala Ala Leu
                245                 250                 255

Ala Asn Leu Glu Asp Ser Ile Cys Ser Asp Tyr Pro Gln Pro Glu Thr
                260                 265                 270

Ile Ser Asn Leu Tyr Lys Ala Gly Asp Tyr Leu Ile Ser Ile Leu Gly
            275                 280                 285

Ser Glu Gly Tyr Lys Val Ile Lys Phe Leu Glu Pro Leu Cys Leu Ala
        290                 295                 300

Lys Ile Gln Leu Cys Ser Asn Tyr Thr Glu Arg Lys Gly Arg Phe Leu
305                 310                 315                 320

Thr Gln Met His Leu Ala Val Asn His Thr Leu Glu Glu Leu Ile Glu
                325                 330                 335

Gly Arg Gly Leu Lys Ser Gln Gln Asp Trp Lys Met Arg Glu Phe His
            340                 345                 350

Arg Ile Leu Val Asn Leu Lys Ser Thr Pro Gln Gln Leu Cys Glu Leu
        355                 360                 365

Phe Ser Val Gln Lys His Trp Gly His Pro Val Leu His Ser Glu Lys
        370                 375                 380

Ala Ile Gln Lys Val Lys Lys His Ala Thr Val Ile Lys Ala Leu Arg
385                 390                 395                 400

Pro Val Ile Ile Phe Glu Thr Tyr Cys Val Phe Lys Tyr Ser Ile Ala
                405                 410                 415

Lys His Tyr Phe Asp Ser Gln Gly Ser Trp Tyr Ser Val Ile Ser Asp
            420                 425                 430

Lys His Leu Thr Pro Gly Leu His Ser Tyr Ile Lys Arg Asn Gln Phe
        435                 440                 445

Pro Pro Leu Pro Met Ile Lys Asp Leu Leu Trp Glu Phe Tyr His Leu
        450                 455                 460

Asp His Pro Pro Leu Phe Ser Thr Lys Ile Ile Ser Asp Leu Ser Ile
465                 470                 475                 480

Phe Ile Lys Asp Arg Ala Thr Ala Val Glu Lys Thr Cys Trp Asp Ala
                485                 490                 495

Val Phe Glu Pro Asn Val Leu Gly Tyr Ser Pro Asn Lys Phe Ser
                500                 505                 510
```

```
Thr Lys Arg Val Pro Glu Gln Phe Leu Glu Gln Asn Phe Ser Ile
    515                 520                 525

Asp Ser Val Leu Thr Tyr Ala Gln Arg Leu Asp Tyr Leu Leu Pro Gln
    530                 535                 540

Tyr Arg Asn Phe Ser Phe Ser Leu Lys Glu Lys Glu Leu Asn Val Gly
545                 550                 555                 560

Arg Ala Phe Gly Lys Leu Pro Tyr Pro Thr Arg Asn Val Gln Thr Leu
                565                 570                 575

Cys Glu Ala Leu Leu Ala Asp Gly Leu Ala Lys Ala Phe Pro Ser Asn
                580                 585                 590

Met Met Val Val Thr Glu Arg Gln Lys Glu Ser Leu Leu His Gln
    595                 600                 605

Ala Ser Trp His His Thr Ser Asp Asp Phe Gly Glu Asn Ala Thr Val
    610                 615                 620

Arg Gly Ser Ser Phe Val Thr Asp Leu Glu Lys Tyr Asn Leu Ala Phe
625                 630                 635                 640

Arg Tyr Glu Phe Thr Ala Pro Phe Ile Glu Tyr Cys Asn Arg Cys Tyr
                645                 650                 655

Gly Val Lys Asn Leu Phe Asn Trp Met His Tyr Thr Ile Pro Gln Cys
                660                 665                 670

Tyr Ile His Val Ser Asp Tyr Tyr Asn Pro His Gly Val Ser Leu
    675                 680                 685

Glu Asn Arg Glu Asp Pro Pro Glu Gly Pro Ser Ser Tyr Arg Gly His
    690                 695                 700

Leu Gly Gly Ile Glu Gly Leu Gln Lys Leu Trp Thr Ser Ile Ser
705                 710                 715                 720

Cys Ala Gln Ile Ser Leu Val Glu Ile Lys Thr Gly Phe Lys Leu Arg
                725                 730                 735

Ser Ala Val Met Gly Asp Asn Gln Cys Ile Thr Val Leu Ser Val Phe
                740                 745                 750

Pro Leu Glu Thr Asp Ser Asn Glu Gln Glu His Ser Ser Glu Asp Asn
    755                 760                 765

Ala Ala Arg Val Ala Ala Ser Leu Ala Lys Val Thr Ser Ala Cys Gly
    770                 775                 780

Ile Phe Leu Lys Pro Asp Glu Thr Phe Val His Ser Gly Phe Ile Tyr
785                 790                 795                 800

Phe Gly Lys Lys Gln Tyr Leu Asn Gly Val Gln Leu Pro Gln Ser Leu
                805                 810                 815

Lys Thr Ala Thr Arg Ile Ala Pro Leu Ser Asp Ala Ile Phe Asp Asp
                820                 825                 830

Leu Gln Gly Thr Leu Ala Ser Ile Gly Thr Ala Phe Glu Arg Ser Ile
    835                 840                 845

Ser Glu Thr Arg His Val Tyr Pro Cys Arg Val Val Ala Ala Phe His
    850                 855                 860

Thr Phe Phe Ser Val Arg Ile Leu Gln Tyr His His Leu Gly Phe Asn
865                 870                 875                 880

Lys Gly Thr Asp Leu Gly Gln Leu Ser Leu Ser Lys Pro Leu Asp Phe
                885                 890                 895

Gly Thr Ile Thr Leu Ala Leu Ala Val Pro Gln Val Leu Gly Gly Leu
                900                 905                 910

Ser Phe Leu Asn Pro Glu Lys Cys Phe Tyr Arg Asn Leu Gly Asp Pro
    915                 920                 925
```

Val Thr Ser Gly Leu Phe Gln Leu Arg Thr Tyr Leu Gln Met Ile Asn
930                935                940

Met Asp Asp Leu Phe Leu Pro Leu Ile Ala Lys Asn Pro Gly Asn Cys
945                950                955                960

Ser Ala Ile Asp Phe Val Leu Asn Pro Ser Gly Leu Asn Val Pro Gly
        965                970                975

Ser Gln Asp Leu Thr Ser Phe Leu Arg Gln Ile Val Arg Arg Thr Ile
            980                985                990

Thr Leu Ser Ala Lys Asn Lys Leu Ile Asn Thr Leu Phe His Ser Ser
            995                1000               1005

Ala Asp Leu Glu Asp Glu Met Val Cys Lys Trp Leu Leu Ser Ser
1010                1015                1020

Thr Pro Val Met Ser Arg Phe Ala Ala Asp Ile Phe Ser Arg Thr
1025                1030                1035

Pro Ser Gly Lys Arg Leu Gln Ile Leu Gly Tyr Leu Glu Gly Thr
1040                1045                1050

Arg Thr Leu Leu Ala Ser Lys Val Ile Asn Asn Asn Ala Glu Thr
1055                1060                1065

Pro Ile Leu Asp Arg Leu Arg Lys Ile Thr Leu Gln Arg Trp Ser
1070                1075                1080

Leu Trp Phe Ser Tyr Leu Asp His Cys Asp Gln Val Leu Ala Asp
1085                1090                1095

Ala Leu Ile Lys Val Ser Cys Thr Val Asp Leu Ala Gln Ile Leu
1100                1105                1110

Arg Glu Tyr Thr Trp Ala His Ile Leu Glu Gly Arg Gln Leu Ile
1115                1120                1125

Gly Ala Thr Leu Pro Cys Met Leu Glu Gln Phe Asn Val Phe Trp
1130                1135                1140

Leu Lys Ser Tyr Glu Gln Cys Pro Lys Cys Ala Lys Ser Arg Asn
1145                1150                1155

Pro Lys Gly Glu Pro Phe Val Ser Ile Ala Ile Lys Lys Gln Val
1160                1165                1170

Val Ser Ala Trp Pro Asn Gln Ser Arg Leu Asn Trp Thr Ile Gly
1175                1180                1185

Asp Gly Val Pro Tyr Ile Gly Ser Arg Thr Glu Asp Lys Ile Gly
1190                1195                1200

Gln Pro Ala Ile Lys Pro Lys Cys Pro Ser Ala Ala Leu Arg Glu
1205                1210                1215

Ala Ile Glu Leu Thr Ser Arg Leu Thr Trp Val Thr Gln Gly Gly
1220                1225                1230

Ala Asn Ser Asp Leu Leu Val Lys Pro Phe Val Glu Ala Arg Val
1235                1240                1245

Asn Leu Ser Val Gln Glu Ile Leu Gln Met Thr Pro Ser His Tyr
1250                1255                1260

Ser Gly Asn Ile Val His Arg Tyr Asn Asp Gln Tyr Ser Pro His
1265                1270                1275

Ser Phe Met Ala Asn Arg Met Ser Asn Ser Ala Thr Arg Leu Val
1280                1285                1290

Val Ser Thr Asn Thr Leu Gly Glu Phe Ser Gly Gly Gly Gln Ser
1295                1300                1305

Ala Arg Asp Ser Asn Ile Ile Phe Gln Asn Val Ile Asn Phe Ser
1310                1315                1320

Val Ala Leu Phe Asp Leu Arg Phe Arg Asn Thr Glu Thr Ser Ser

```
               1325                1330                1335

Ile Gln His Asn Arg Ala His Leu His Leu Ser Gln Cys Cys Thr
    1340                1345                1350

Arg Glu Val Pro Ala Gln Tyr Leu Thr Tyr Thr Ser Thr Leu Ser
    1355                1360                1365

Leu Asp Leu Thr Arg Tyr Arg Glu Asn Glu Leu Ile Tyr Asp Asn
    1370                1375                1380

Asn Pro Leu Lys Gly Gly Leu Asn Cys Asn Leu Ser Phe Asp Asn
    1385                1390                1395

Pro Leu Phe Lys Gly Gln Arg Leu Asn Ile Ile Glu Glu Asp Leu
    1400                1405                1410

Ile Arg Phe Pro His Leu Ser Gly Trp Glu Leu Ala Lys Thr Ile
    1415                1420                1425

Ile Gln Ser Ile Ile Ser Asp Ser Asn Asn Ser Ser Thr Asp Pro
    1430                1435                1440

Ile Ser Ser Gly Glu Thr Arg Ser Phe Thr Thr His Phe Leu Thr
    1445                1450                1455

Tyr Pro Lys Val Gly Leu Leu Tyr Ser Phe Gly Ala Ile Val Ser
    1460                1465                1470

Tyr Tyr Leu Gly Asn Thr Ile Ile Arg Thr Lys Lys Leu Asp Leu
    1475                1480                1485

Ser His Phe Met Tyr Tyr Leu Thr Thr Gln Ile His Asn Leu Pro
    1490                1495                1500

His Arg Ser Leu Arg Ile Leu Lys Pro Thr Phe Lys His Val Ser
    1505                1510                1515

Val Ile Ser Arg Leu Met Ser Ile Asp Pro His Phe Ser Ile Tyr
    1520                1525                1530

Ile Gly Gly Thr Ala Gly Asp Arg Gly Leu Ser Asp Ala Thr Arg
    1535                1540                1545

Leu Phe Leu Arg Val Ala Ile Ser Ser Phe Leu Gln Phe Ile Lys
    1550                1555                1560

Lys Trp Ile Val Glu Tyr Lys Thr Ala Ile Pro Leu Trp Val Ile
    1565                1570                1575

Tyr Pro Leu Glu Gly Gln Asn Pro Asp Pro Ile Asn Ser Phe Leu
    1580                1585                1590

His Leu Ile Ile Ala Leu Leu Gln Asn Glu Ser Pro Gln Asn Asn
    1595                1600                1605

Ile Gln Phe Gln Glu Asp Arg Asn Asn Gln Gln Leu Ser Asp Asn
    1610                1615                1620

Leu Val Tyr Met Cys Lys Ser Thr Ala Ser Asn Phe Phe His Ala
    1625                1630                1635

Ser Leu Ala Tyr Trp Arg Ser Arg His Lys Gly Arg Pro Lys Asn
    1640                1645                1650

Arg Ser Thr Glu Glu Gln Thr Val Lys Pro Ile Pro Tyr Asp Asn
    1655                1660                1665

Phe His Ser Val Lys Cys Ala Ser Asn Pro Pro Ser Ile Pro Lys
    1670                1675                1680

Ser Lys Ser Gly Thr Gln Gly Ser Ser Ala Phe Phe Glu Lys Leu
    1685                1690                1695

Glu Tyr Asp Lys Glu Arg Glu Leu Pro Thr Ala Ser Thr Pro Ala
    1700                1705                1710

Glu Gln Ser Lys Thr Tyr Ile Lys Ala Leu Ser Ser Arg Ile Tyr
    1715                1720                1725
```

```
His Gly Lys Thr Pro Ser Asn Ala Ala Lys Asp Asp Ser Thr Thr
    1730            1735            1740

Ser Lys Gly Cys Asp Ser Lys Glu Glu Asn Ala Val Gln Ala Ser
    1745            1750            1755

His Arg Ile Val Leu Pro Phe Phe Thr Leu Ser Gln Asn Asp Tyr
    1760            1765            1770

Arg Thr Pro Ser Ala Lys Lys Ser Glu Tyr Ile Thr Glu Ile Thr
    1775            1780            1785

Lys Leu Ile Arg Gln Leu Lys Ala Ile Pro Asp Thr Thr Val Tyr
    1790            1795            1800

Cys Arg Phe Thr Gly Val Val Ser Ser Met His Tyr Lys Leu Asp
    1805            1810            1815

Glu Val Leu Trp Glu Phe Asp Ser Phe Lys Thr Ala Val Thr Leu
    1820            1825            1830

Ala Glu Gly Glu Gly Ser Gly Ala Leu Leu Leu Gln Lys Tyr
    1835            1840            1845

Lys Val Arg Thr Ile Phe Phe Asn Thr Leu Ala Thr Glu His Ser
    1850            1855            1860

Ile Glu Ala Glu Ile Val Ser Gly Thr Thr Thr Pro Arg Met Leu
    1865            1870            1875

Leu Pro Val Met Ala Lys Leu His Asp Asp Gln Ile Asn Val Ile
    1880            1885            1890

Leu Asn Asn Ser Ala Ser Gln Val Thr Asp Ile Thr Asn Pro Ala
    1895            1900            1905

Trp Phe Thr Asp Gln Lys Ser Arg Ile Pro Thr Gln Val Glu Ile
    1910            1915            1920

Met Thr Met Asp Ala Glu Thr Thr Glu Asn Ile Asn Arg Ser Lys
    1925            1930            1935

Leu Tyr Glu Ala Ile Gln Gln Leu Ile Val Ser His Ile Asp Thr
    1940            1945            1950

Arg Val Leu Lys Ile Val Ile Ile Lys Val Phe Leu Ser Asp Ile
    1955            1960            1965

Glu Gly Leu Leu Trp Leu Asn Asp His Leu Ala Pro Leu Phe Gly
    1970            1975            1980

Ser Gly Tyr Leu Ile Lys Pro Ile Thr Ser Ser Pro Lys Ser Ser
    1985            1990            1995

Glu Trp Tyr Leu Cys Leu Ser Asn Phe Leu Ser Ala Ser Arg Arg
    2000            2005            2010

Arg Pro His Gln Gly His Ala Thr Cys Met Gln Val Ile Gln Thr
    2015            2020            2025

Ala Leu Arg Leu Gln Val Gln Arg Ser Ser Tyr Trp Leu Ser His
    2030            2035            2040

Leu Val Gln Tyr Ala Asp Ile Asn Leu His Leu Ser Tyr Val Asn
    2045            2050            2055

Leu Gly Phe Pro Ser Leu Glu Lys Val Leu Tyr His Arg Tyr Asn
    2060            2065            2070

Leu Val Asp Ser Arg Lys Gly Pro Leu Val Ser Ile Leu Tyr His
    2075            2080            2085

Leu Thr His Leu Gln Ala Glu Ile Arg Glu Leu Val Cys Asp Tyr
    2090            2095            2100

Asn Gln Gln Arg Gln Ser Arg Thr Gln Thr Tyr His Phe Ile Lys
    2105            2110            2115
```

```
Thr Thr Lys Gly Arg Ile Thr Lys Leu Val Asn Asp Tyr Leu Lys
    2120                2125                2130

Phe Tyr Leu Val Val Gln Ala Leu Lys His Asn Cys Leu Trp Gln
    2135                2140                2145

Glu Glu Leu Arg Thr Leu Pro Asp Leu Ile Asn Val Cys Asn Arg
    2150                2155                2160

Phe Tyr His Ile Arg Asp Cys Ser Cys Glu Asp Arg Phe Leu Ile
    2165                2170                2175

Gln Thr Leu Tyr Leu Thr Arg Met Gln Asp Ser Glu Ala Lys Leu
    2180                2185                2190

Met Glu Arg Leu Thr Gly Phe Leu Gly Leu Tyr Pro Asn Gly Ile
    2195                2200                2205

Asn Ala
    2210

<210> SEQ ID NO 37
<211> LENGTH: 695
<212> TYPE: PRT
<213> ORGANISM: Lake Victoria marburgvirus

<400> SEQUENCE: 37

Met Asp Leu His Ser Leu Leu Glu Leu Gly Thr Lys Pro Thr Ala Pro
1               5                   10                  15

His Val Arg Asn Lys Lys Val Ile Leu Phe Asp Thr Asn His Gln Val
                20                  25                  30

Ser Ile Cys Asn Gln Ile Ile Asp Ala Ile Asn Ser Gly Ile Asp Leu
            35                  40                  45

Gly Asp Leu Leu Glu Gly Gly Leu Leu Thr Leu Cys Val Glu His Tyr
        50                  55                  60

Tyr Asn Ser Asp Lys Asp Lys Phe Asn Thr Ser Pro Ile Ala Lys Tyr
65                  70                  75                  80

Leu Arg Asp Ala Gly Tyr Glu Phe Asp Val Ile Lys Asn Ala Asp Ala
                85                  90                  95

Thr Arg Phe Leu Asp Val Ile Pro Asn Glu Pro His Tyr Ser Pro Leu
            100                 105                 110

Ile Leu Ala Leu Lys Thr Leu Glu Ser Thr Glu Ser Gln Arg Gly Arg
        115                 120                 125

Ile Gly Leu Phe Leu Ser Phe Cys Ser Leu Phe Leu Pro Lys Leu Val
    130                 135                 140

Val Gly Asp Arg Ala Ser Ile Glu Lys Ala Leu Arg Gln Val Thr Val
145                 150                 155                 160

His Gln Glu Gln Gly Ile Val Thr Tyr Pro Asn His Trp Leu Thr Thr
                165                 170                 175

Gly His Met Lys Val Ile Phe Gly Ile Leu Arg Ser Ser Phe Ile Leu
            180                 185                 190

Lys Phe Val Leu Ile His Gln Gly Val Asn Leu Val Thr Gly His Asp
        195                 200                 205

Ala Tyr Asp Ser Ile Ile Ser Asn Ser Val Gly Gln Thr Arg Phe Ser
    210                 215                 220

Gly Leu Leu Ile Val Lys Thr Val Leu Glu Phe Ile Leu Gln Lys Thr
225                 230                 235                 240

Asp Ser Gly Val Thr Leu His Pro Leu Val Arg Thr Ser Lys Val Lys
                245                 250                 255

Asn Glu Val Ala Ser Phe Lys Gln Ala Leu Ser Asn Leu Ala Arg His
            260                 265                 270
```

Gly Glu Tyr Ala Pro Phe Ala Arg Val Leu Asn Leu Ser Gly Ile Asn
            275                 280                 285

Asn Leu Glu His Gly Leu Tyr Pro Gln Leu Ser Ala Ile Ala Leu Gly
        290                 295                 300

Val Ala Thr Ala His Gly Ser Thr Leu Ala Gly Val Asn Val Gly Glu
305                 310                 315                 320

Gln Tyr Gln Gln Leu Arg Glu Ala Ala His Asp Ala Glu Val Lys Leu
                325                 330                 335

Gln Arg Arg His Glu His Gln Glu Ile Gln Ala Ile Ala Glu Asp Asp
            340                 345                 350

Glu Glu Arg Lys Ile Leu Glu Gln Phe His Leu Gln Lys Thr Glu Ile
        355                 360                 365

Thr His Ser Gln Thr Leu Ala Val Leu Ser Gln Lys Arg Glu Lys Leu
        370                 375                 380

Ala Arg Leu Ala Ala Glu Ile Glu Asn Asn Ile Val Glu Asp Gln Gly
385                 390                 395                 400

Phe Lys Gln Ser Gln Asn Arg Val Ser Gln Ser Phe Leu Asn Asp Pro
                405                 410                 415

Thr Pro Val Glu Val Thr Val Gln Ala Arg Pro Met Asn Arg Pro Thr
            420                 425                 430

Ala Leu Pro Pro Pro Val Asp Asp Lys Ile Glu His Glu Ser Thr Glu
385                 440                 445

Asp Ser Ser Ser Ser Ser Phe Val Asp Leu Asn Asp Pro Phe Ala
450                 455                 460

Leu Leu Asn Glu Asp Glu Asp Thr Leu Asp Asp Ser Val Met Ile Pro
465                 470                 475                 480

Gly Thr Thr Ser Arg Glu Phe Gln Gly Ile Pro Glu Pro Pro Arg Gln
                485                 490                 495

Ser Gln Asp Leu Asn Asn Ser Gln Gly Lys Gln Glu Asp Glu Ser Thr
            500                 505                 510

Asn Pro Ile Lys Lys Gln Phe Leu Arg Tyr Gln Glu Leu Pro Pro Val
        515                 520                 525

Gln Glu Asp Asp Glu Ser Glu Tyr Thr Thr Asp Ser Gln Glu Ser Ile
530                 535                 540

Asp Gln Pro Gly Ser Asp Asn Glu Gln Gly Val Asp Leu Pro Pro Pro
545                 550                 555                 560

Pro Leu Tyr Ala Gln Glu Lys Arg Gln Asp Pro Ile Gln His Pro Ala
                565                 570                 575

Ala Asn Pro Gln Asp Pro Phe Gly Ser Ile Gly Asp Val Asn Gly Asp
            580                 585                 590

Ile Leu Glu Pro Ile Arg Ser Pro Ser Ser Pro Ser Ala Pro Gln Glu
        595                 600                 605

Asp Thr Arg Met Arg Glu Ala Tyr Glu Leu Ser Pro Asp Phe Thr Asn
        610                 615                 620

Asp Glu Asp Asn Gln Gln Asn Trp Pro Gln Arg Val Val Thr Lys Lys
625                 630                 635                 640

Gly Arg Thr Phe Leu Tyr Pro Asn Asp Leu Leu Gln Thr Asn Pro Pro
                645                 650                 655

Glu Ser Leu Ile Thr Ala Leu Val Glu Glu Tyr Gln Asn Pro Val Ser
            660                 665                 670

Ala Lys Glu Leu Gln Ala Asp Trp Pro Asp Met Ser Phe Asp Glu Arg
        675                 680                 685

```
Arg His Val Ala Met Asn Leu
    690             695

<210> SEQ ID NO 38
<211> LENGTH: 253
<212> TYPE: PRT
<213> ORGANISM: Lake Victoria marburgvirus

<400> SEQUENCE: 38

Met Ala Glu Leu Ser Thr Arg Tyr Asn Leu Pro Ala Asn Val Thr Glu
1               5                   10                  15

Asn Ser Ile Asn Leu Asp Leu Asn Ser Thr Ala Arg Trp Ile Lys Glu
            20                  25                  30

Pro Ser Val Gly Gly Trp Thr Val Lys Trp Gly Asn Phe Val Phe His
        35                  40                  45

Ile Pro Asn Thr Gly Met Thr Leu Leu His His Leu Lys Ser Asn Phe
50                  55                  60

Val Val Pro Glu Trp Gln Gln Thr Arg Asn Leu Phe Ser His Leu Phe
65                  70                  75                  80

Lys Asn Pro Lys Ser Thr Ile Ile Glu Pro Phe Leu Ala Leu Arg Ile
                85                  90                  95

Leu Leu Gly Val Ala Leu Lys Asp Gln Glu Leu Gln Gln Ser Leu Ile
            100                 105                 110

Pro Gly Phe Arg Ser Ile Val His Met Leu Ser Glu Trp Leu Leu Leu
        115                 120                 125

Glu Val Thr Ser Ala Ile His Ile Ser Pro Asn Leu Leu Gly Ile Tyr
    130                 135                 140

Leu Thr Ser Asp Met Phe Lys Ile Leu Met Ala Gly Val Lys Asn Phe
145                 150                 155                 160

Phe Asn Lys Met Phe Thr Leu His Val Val Asn Asp His Gly Lys Pro
                165                 170                 175

Ser Ser Ile Glu Ile Lys Leu Thr Gly Gln Gln Ile Ile Ile Thr Arg
            180                 185                 190

Val Asn Met Gly Phe Leu Val Glu Val Arg Arg Ile Asp Ile Glu Pro
        195                 200                 205

Cys Cys Gly Glu Thr Val Leu Ser Glu Ser Val Val Phe Gly Leu Val
    210                 215                 220

Ala Glu Ala Val Leu Arg Glu His Ser Gln Met Glu Lys Gly Gln Pro
225                 230                 235                 240

Leu Asn Leu Thr Gln Tyr Met Asn Ser Lys Ile Ala Ile
                245                 250

<210> SEQ ID NO 39
<211> LENGTH: 281
<212> TYPE: PRT
<213> ORGANISM: Lake Victoria marburgvirus

<400> SEQUENCE: 39

Met Gln Gln Pro Arg Gly Arg Ser Arg Thr Arg Asn His Gln Val Thr
1               5                   10                  15

Pro Thr Ile Tyr His Glu Thr Gln Leu Pro Ser Lys Pro His Tyr Thr
            20                  25                  30

Asn Tyr His Pro Arg Ala Arg Ser Met Ser Ser Thr Arg Ser Ser Ala
        35                  40                  45

Glu Ser Ser Pro Thr Asn His Ile Pro Arg Ala Arg Pro Pro Ser Thr
50                  55                  60
```

```
Phe Asn Leu Ser Lys Pro Pro Pro Pro Lys Asp Met Cys Arg Asn
 65              70                  75                  80

Met Lys Ile Gly Leu Pro Cys Ala Asp Pro Thr Cys Asn Arg Asp His
                 85                  90                  95

Asp Leu Asp Asn Leu Thr Asn Arg Glu Leu Leu Leu Met Ala Arg
            100                 105                 110

Lys Met Leu Pro Asn Thr Asp Lys Thr Phe Arg Ser Pro Gln Asp Cys
            115                 120                 125

Gly Ser Pro Ser Leu Ser Lys Gly Leu Ser Lys Asp Lys Gln Glu Gln
        130                 135                 140

Thr Lys Asp Val Leu Thr Leu Glu Asn Leu Gly His Ile Leu Ser Tyr
145                 150                 155                 160

Leu His Arg Ser Glu Ile Gly Lys Leu Asp Glu Thr Ser Leu Arg Ala
                165                 170                 175

Ala Leu Ser Leu Thr Cys Ala Gly Ile Arg Lys Thr Asn Arg Ser Leu
            180                 185                 190

Ile Asn Thr Met Thr Glu Leu His Met Asn His Glu Asn Leu Pro Gln
            195                 200                 205

Asp Gln Asn Gly Val Ile Lys Gln Thr Tyr Thr Gly Ile His Leu Asp
        210                 215                 220

Lys Gly Gly Gln Phe Glu Ala Ala Leu Trp Gln Gly Trp Asp Lys Arg
225                 230                 235                 240

Ser Ile Ser Leu Phe Val Gln Ala Ala Leu Tyr Val Met Asn Asn Ile
                245                 250                 255

Pro Cys Glu Ser Ser Ile Ser Val Gln Ala Ser Tyr Asp His Phe Ile
            260                 265                 270

Leu Pro Gln Ser Gln Gly Lys Gly Gln
            275                 280

<210> SEQ ID NO 40
<211> LENGTH: 329
<212> TYPE: PRT
<213> ORGANISM: Lake Victoria marburgvirus

<400> SEQUENCE: 40

Met Trp Asp Ser Ser Tyr Met Gln Gln Val Ser Glu Gly Leu Met Thr
  1               5                  10                  15

Gly Lys Val Pro Ile Asp Gln Val Phe Gly Ala Asn Pro Leu Glu Lys
             20                  25                  30

Leu Tyr Lys Arg Arg Lys Pro Lys Gly Thr Val Gly Leu Gln Cys Ser
         35                  40                  45

Pro Cys Leu Met Ser Lys Ala Thr Ser Thr Asp Ile Ile Trp Asp
 50                  55                  60

Gln Leu Ile Val Lys Arg Thr Leu Ala Asp Leu Leu Ile Pro Ile Asn
 65                  70                  75                  80

Arg Gln Ile Ser Asp Ile Gln Ser Thr Leu Ser Glu Val Thr Thr Arg
                 85                  90                  95

Val His Glu Ile Glu Arg Gln Leu His Glu Ile Thr Pro Val Leu Lys
            100                 105                 110

Met Gly Arg Thr Leu Glu Ala Ile Ser Lys Gly Met Ser Glu Met Leu
            115                 120                 125

Ala Lys Tyr Asp His Leu Val Ile Ser Thr Gly Arg Thr Thr Ala Pro
        130                 135                 140

Ala Ala Ala Phe Asp Ala Tyr Leu Asn Glu His Gly Val Pro Pro Pro
145                 150                 155                 160
```

-continued

```
Gln Pro Ala Ile Phe Lys Asp Leu Gly Val Ala Gln Ala Cys Ser
            165                 170                 175

Lys Gly Thr Met Val Lys Asn Ala Thr Thr Asp Ala Ala Asp Lys Met
        180                 185                 190

Ser Lys Val Leu Glu Leu Ser Glu Glu Thr Phe Ser Lys Pro Asn Leu
        195                 200                 205

Ser Ala Lys Asp Leu Ala Leu Leu Leu Phe Thr His Leu Pro Gly Asn
    210                 215                 220

Asn Thr Pro Phe His Ile Leu Ala Gln Val Leu Ser Lys Ile Ala Tyr
225                 230                 235                 240

Lys Ser Gly Lys Ser Gly Ala Phe Leu Asp Ala Phe His Gln Ile Leu
                245                 250                 255

Ser Glu Gly Glu Asn Ala Gln Ala Ala Leu Thr Arg Leu Ser Arg Thr
            260                 265                 270

Phe Asp Ala Phe Leu Gly Val Val Pro Val Ile Arg Val Lys Asn
        275                 280                 285

Phe Gln Thr Val Pro Arg Pro Cys Gln Lys Ser Leu Arg Ala Val Pro
    290                 295                 300

Pro Asn Pro Thr Ile Asp Lys Gly Trp Val Cys Val Tyr Ser Ser Glu
305                 310                 315                 320

Gln Gly Glu Thr Arg Ala Leu Lys Ile
                325
```

<210> SEQ ID NO 41
<211> LENGTH: 303
<212> TYPE: PRT
<213> ORGANISM: Lake Victoria marburgvirus

<400> SEQUENCE: 41

```
Met Ala Ser Ser Asn Tyr Asn Thr Tyr Met Gln Tyr Leu Asn Pro
1               5                   10                  15

Pro Pro Tyr Ala Asp His Gly Ala Asn Gln Leu Ile Pro Ala Asp Gln
            20                  25                  30

Leu Ser Asn Gln Gln Gly Ile Thr Pro Asn Tyr Val Gly Asp Leu Asn
        35                  40                  45

Leu Asp Asp Gln Phe Lys Gly Asn Val Cys His Ala Phe Thr Leu Glu
    50                  55                  60

Ala Ile Ile Asp Ile Ser Ala Tyr Asn Glu Arg Thr Val Lys Gly Val
65                  70                  75                  80

Pro Ala Trp Leu Pro Leu Gly Ile Met Ser Asn Phe Glu Tyr Pro Leu
                85                  90                  95

Ala His Thr Val Ala Ala Leu Leu Thr Gly Ser Tyr Thr Ile Thr Gln
            100                 105                 110

Phe Thr His Asn Gly Gln Lys Phe Val Arg Val Asn Arg Leu Gly Thr
        115                 120                 125

Gly Ile Pro Ala His Pro Leu Arg Met Leu Arg Glu Gly Asn Gln Ala
    130                 135                 140

Phe Ile Gln Asn Met Val Ile Pro Arg Asn Phe Ser Thr Asn Gln Phe
145                 150                 155                 160

Thr Tyr Asn Leu Thr Asn Leu Val Leu Ser Val Gln Lys Leu Pro Asp
                165                 170                 175

Asp Ala Trp Arg Pro Ser Lys Asp Lys Leu Ile Gly Asn Thr Met His
            180                 185                 190

Pro Ala Val Ser Ile His Pro Asn Leu Pro Pro Ile Val Leu Pro Thr
```

```
                195                 200                 205
Val Lys Lys Gln Ala Tyr Arg Gln His Lys Asn Pro Asn Asn Gly Pro
210                 215                 220

Leu Leu Ala Ile Ser Gly Ile Leu His Gln Leu Arg Val Glu Lys Val
225                 230                 235                 240

Pro Glu Lys Thr Ser Leu Phe Arg Ile Ser Leu Pro Ala Asp Met Phe
                245                 250                 255

Ser Val Lys Glu Gly Met Met Lys Lys Arg Gly Glu Asn Ser Pro Val
                260                 265                 270

Val Tyr Phe Gln Ala Pro Glu Asn Phe Pro Leu Asn Gly Phe Asn Asn
            275                 280                 285

Arg Gln Val Val Leu Ala Tyr Ala Asn Pro Thr Leu Ser Ala Val
            290                 295                 300

<210> SEQ ID NO 42
<211> LENGTH: 2331
<212> TYPE: PRT
<213> ORGANISM: Lake Victoria marburgvirus

<400> SEQUENCE: 42

Met Gln His Pro Thr Gln Tyr Pro Asp Ala Arg Leu Ser Ser Pro Ile
1               5                   10                  15

Ile Leu Asp Gln Cys Asp Leu Leu Ala Arg Ser Leu Gly Leu Tyr Ser
                20                  25                  30

His Tyr Ser His Asn Pro Lys Leu Arg Asn Cys Arg Ile Pro His His
            35                  40                  45

Ile Tyr Arg Leu Arg Asn Ser Thr Ala Leu Lys Thr Phe Leu Gln Asn
50                  55                  60

Cys Ser Ile Leu Thr Val Pro Phe His Ser Ile Trp Asp His Ile Leu
65                  70                  75                  80

Thr Ser Ile Gln Tyr Asp Ala Ile Asn His Val Asp Asp Phe Lys Tyr
                85                  90                  95

Leu Leu Pro Ser Glu Leu Val Lys Tyr Ala Asn Trp Asp Asn Glu Phe
            100                 105                 110

Leu Lys Ala Tyr Leu Asn Lys Ile Leu Gly Leu Asp His Val Phe Ser
            115                 120                 125

Ala Ser Ala Arg Ser Gln Cys Glu Asp Phe Ser Pro Lys Glu Asn Pro
130                 135                 140

Tyr Tyr Trp Gly Met Leu Leu Leu Val His Leu Ser Gln Leu Ala Arg
145                 150                 155                 160

Arg Ile Lys Gly Gln Arg Gly Ser Leu Arg Ser Asn Trp Lys Phe Ile
                165                 170                 175

Gly Thr Asp Leu Glu Leu Phe Gly Ile Ala Asp Phe Val Ile Phe Lys
            180                 185                 190

Val Pro Val Lys Thr Ile Ile Arg Asn Ala Val Ser Leu Gln Ala Ser
            195                 200                 205

Lys Pro Gly Leu Arg Ile Trp Tyr Arg Asp Gln Asn Leu Thr Pro Tyr
210                 215                 220

Leu Cys Asp Asp Glu Phe Ile Val Ser Val Ala Ser Tyr Glu Cys Phe
225                 230                 235                 240

Ile Met Ile Lys Asp Val Phe Ile Glu Arg Tyr Asn Thr Trp Glu Ile
                245                 250                 255

Cys Ala Arg Ala Trp Leu Glu Asp Ser Asp Gly Ala Asp Tyr Pro Pro
            260                 265                 270
```

-continued

```
Leu Asp Val Leu Gly Glu Leu Tyr Asn Gln Gly Asp Gln Ile Ile Ala
            275                 280                 285

Met Tyr Leu Glu Asp Gly Phe Lys Leu Ile Lys His Leu Glu Pro Leu
            290                 295                 300

Cys Val Ser Cys Ile Gln Thr His Gly Ile Phe Thr Pro Arg Lys Tyr
305                 310                 315                 320

Trp Phe Gln Ser Gln Met Ile Lys Ser Tyr Tyr Asp Glu Leu His Asp
                    325                 330                 335

Leu Asn Leu Lys Leu Gln Ile Ser Asp Asn Lys Ala Glu Cys Ala Gln
                340                 345                 350

Asn Phe Ile Lys Thr Ile Val Gln Ala Lys Leu Thr Pro Gln Gln Tyr
            355                 360                 365

Cys Glu Leu Phe Ser Leu Gln Lys His Trp Gly His Pro Val Leu Tyr
            370                 375                 380

Asn Asp Val Ala Leu Asp Lys Val Lys Lys His Ala Gln Ser Thr Lys
385                 390                 395                 400

Ile Leu Lys Pro Lys Val Met Phe Glu Thr Phe Cys Val Phe Lys Phe
                    405                 410                 415

Ile Val Ala Lys Asn His Tyr His Ser Gln Gly Ser Trp Tyr Lys Thr
                420                 425                 430

Thr His Asp Leu His Leu Thr Pro Tyr Leu Arg Gln His Ile Val Ser
            435                 440                 445

Asn Ser Phe Pro Ser Gln Ala Glu Ile Tyr Gln His Leu Trp Glu Trp
            450                 455                 460

Tyr Phe Val Glu His Glu Pro Leu Phe Ser Thr Lys Ile Ile Ser Asp
465                 470                 475                 480

Leu Ser Ile Phe Ile Lys Asp Arg Ala Thr Ala Val Asn Gln Glu Cys
                    485                 490                 495

Trp Asp Ser Val Phe Asp Arg Ser Val Leu Gly Tyr Asn Pro Pro Val
                500                 505                 510

Arg Phe Gln Ser Lys Arg Val Pro Glu Gln Phe Leu Gly Gln Ala Asp
            515                 520                 525

Phe Ser Leu Asn Gln Ile Leu Glu Phe Ala Glu Lys Leu Glu Tyr Leu
            530                 535                 540

Ala Pro Ser Tyr Arg Asn Phe Ser Phe Ser Leu Lys Glu Lys Glu Leu
545                 550                 555                 560

Asn Ile Gly Arg Thr Phe Gly Lys Leu Pro Tyr Arg Val Arg Asn Val
                    565                 570                 575

Gln Thr Leu Ala Glu Ala Leu Leu Ala Asp Gly Leu Ala Lys Ala Phe
                580                 585                 590

Pro Ser Asn Met Met Val Val Thr Glu Arg Glu Gln Lys Glu Ala Leu
            595                 600                 605

Leu His Gln Ala Ser Trp His His Asn Ser Ala Ser Ile Gly Glu Asn
            610                 615                 620

Ala Ile Val Arg Gly Ala Ser Phe Val Thr Asp Leu Glu Lys Tyr Asn
625                 630                 635                 640

Leu Ala Phe Arg Tyr Glu Phe Thr Arg His Phe Ile Asp Tyr Cys Asn
                    645                 650                 655

Arg Cys Tyr Gly Val Lys Asn Leu Phe Asp Trp Met His Phe Leu Ile
                660                 665                 670

Pro Leu Cys Tyr Met His Val Ser Asp Phe Tyr Ser Pro Pro His Cys
            675                 680                 685

Val Thr Glu Asp Asn Arg Asn Asn Pro Pro Asp Cys Ala Asn Ala Tyr
```

```
            690                 695                 700
His Tyr His Leu Gly Gly Ile Glu Gly Leu Gln Gln Lys Leu Trp Thr
705                 710                 715                 720

Cys Ile Ser Cys Ala Gln Ile Thr Leu Val Glu Leu Lys Thr Lys Leu
                725                 730                 735

Lys Leu Lys Ser Ser Val Met Gly Asp Asn Gln Cys Ile Thr Thr Leu
                740                 745                 750

Ser Leu Phe Pro Ile Asp Ala Pro Asn Asp Tyr Gln Glu Asn Glu Ala
        755                 760                 765

Glu Leu Asn Ala Ala Arg Val Ala Val Glu Leu Ala Ile Thr Thr Gly
        770                 775                 780

Tyr Ser Gly Ile Phe Leu Lys Pro Glu Glu Thr Phe Val His Ser Gly
785                 790                 795                 800

Phe Ile Tyr Phe Gly Lys Lys Gln Tyr Leu Asn Gly Val Gln Leu Pro
                805                 810                 815

Gln Ser Leu Lys Thr Met Ala Arg Cys Gly Pro Leu Ser Asp Ser Ile
                820                 825                 830

Phe Asp Asp Leu Gln Gly Ser Leu Ala Ser Ile Gly Thr Ser Phe Glu
        835                 840                 845

Arg Gly Thr Ser Glu Thr Arg His Ile Phe Pro Ser Arg Trp Ile Ala
        850                 855                 860

Ser Phe His Ser Met Leu Ala Ile Asn Leu Leu Asn Gln Asn His Leu
865                 870                 875                 880

Gly Phe Pro Leu Gly Phe Asn Ile Asp Ile Ser Cys Phe Lys Lys Pro
                885                 890                 895

Leu Thr Phe Ser Glu Lys Leu Ile Ala Leu Ile Thr Pro Gln Val Leu
                900                 905                 910

Gly Gly Leu Ser Phe Leu Asn Pro Glu Lys Leu Phe Tyr Arg Asn Ile
        915                 920                 925

Ser Asp Pro Leu Thr Ser Gly Leu Phe Gln Leu Lys Asn Ala Leu Glu
        930                 935                 940

Phe Leu Glu Lys Glu Glu Leu Phe Tyr Ile Leu Ile Ser Lys Lys Pro
945                 950                 955                 960

Gly Leu Ala Asp Ala Ser Asp Phe Val Met Asn Pro Leu Gly Leu Asn
                965                 970                 975

Val Pro Gly Ser Lys Glu Ile Ile Thr Phe Leu Arg Gln Thr Val Arg
                980                 985                 990

Glu Asn Ile Thr Ile Thr Ser Gln Asn Arg Ile Ile Asn Ser Leu Phe
        995                 1000                1005

His Ile Gly Ser Asp Leu Glu Asp Gln Arg Val Cys Glu Trp Leu
        1010                1015                1020

Leu Ser Ser Asn Pro Val Met Ser Arg Phe Ala Ala Asp Ile Phe
        1025                1030                1035

Ser Arg Thr Pro Ser Gly Lys Arg Leu Gln Val Leu Gly Tyr Leu
        1040                1045                1050

Glu Gly Thr Arg Thr Leu Leu Ala Ser Arg Thr Ile Ser Leu Thr
        1055                1060                1065

Thr Glu Gly Thr Met Leu Met Lys Leu Arg Glu Leu Thr Arg Asn
        1070                1075                1080

Arg Trp Lys Ser Trp Phe Ser Tyr Ile Asp Ala Leu Asp Asp Asp
        1085                1090                1095

Leu Ser Glu Ser Leu Glu Lys Phe Thr Cys Thr Val Asp Val Ala
        1100                1105                1110
```

```
Asn Phe Leu Arg Ala Tyr Ser Trp Ser Asp Val Leu Lys Gly Lys
    1115                1120                1125

Arg Leu Ile Gly Ala Thr Leu Pro Cys Leu Leu Glu Gln Phe Glu
    1130                1135                1140

Val Lys Trp Ile Asn Leu Ser Glu Asp Leu Arg Glu Gln Phe Asn
    1145                1150                1155

Leu Ser Ser Asp Ser Lys Ser Thr Ile Asn Leu Leu Pro Tyr Asp
    1160                1165                1170

Cys Lys Glu Leu Arg Leu Glu Gly Ser Asn Asp Thr Glu Leu Asn
    1175                1180                1185

Tyr Val Ser Cys Ala Leu Asp Arg Lys Val Val Gln Lys His Pro
    1190                1195                1200

Ser Val Asn Arg Leu Ala Trp Thr Ile Gly Asn Arg Ala Pro Tyr
    1205                1210                1215

Ile Gly Ser Arg Thr Glu Asp Lys Ile Gly Tyr Pro Pro Leu Arg
    1220                1225                1230

Val Asn Cys Pro Ser Ala Ala Leu Lys Glu Ala Ile Glu Met Val
    1235                1240                1245

Ser Arg Leu Leu Trp Val Thr Gln Gly Thr Ala Asp Arg Glu Lys
    1250                1255                1260

Leu Leu Ile Pro Leu Leu Asn Ser Arg Val Asn Leu Asp Tyr Gln
    1265                1270                1275

Thr Val Leu Asn Phe Leu Pro Thr His Tyr Ser Gly Asn Ile Val
    1280                1285                1290

His Arg Tyr Asn Asp Gln Tyr Gly Gln His Ser Phe Met Ala Asn
    1295                1300                1305

Arg Met Ser Asn Thr Ser Thr Arg Ala Ile Ile Ser Thr Asn Thr
    1310                1315                1320

Leu Gly Lys Tyr Ala Gly Gly Gly Gln Ala Ala Ile Asp Ser Asn
    1325                1330                1335

Ile Ile Phe Gln Asn Thr Ile Asn Leu Gly Val Ala Val Leu Asp
    1340                1345                1350

Ile Ala Leu Ser Leu Ala Lys Leu Ser Ser Ala Ser Asn Val Thr
    1355                1360                1365

Phe Arg Leu Met Leu Asn Lys Cys Cys Thr Arg His Val Pro Ser
    1370                1375                1380

Glu Tyr Leu Tyr Phe Asp Lys Pro Leu Asp Val Asp Leu Asn Lys
    1385                1390                1395

Tyr Met Asp Asn Glu Leu Val Tyr Asp Asn Asp Pro Leu Cys Ser
    1400                1405                1410

Gly Ile Lys Gly Arg Leu Gly Arg Val Ser Arg Ser Thr Leu Thr
    1415                1420                1425

Leu Ser Leu Asn Val Ser Asp Ile Gly Ser Tyr Asp Phe Pro Thr
    1430                1435                1440

Ile Ala Ala Trp Thr Leu Gly Glu Thr Ile Val Gly Ser Ile Phe
    1445                1450                1455

Ser Asp Glu Ser Ser Gln Ser Thr Asp Pro Ile Ser Ser Gly Cys
    1460                1465                1470

Thr Lys Thr Phe Val Thr His Phe Leu Val Tyr Pro Val Glu Ser
    1475                1480                1485

Ile Phe Tyr Ala Phe Gly Ala Asn Leu Ile Val Glu Ser Leu Ser
    1490                1495                1500
```

Leu Ser Arg Ile Lys Ser Ile Lys Asn Leu Ser Asp Leu Thr Phe
1505                1510                1515

Leu Ile Ser Ser Thr Ile Arg Asn Leu Ser His Arg Ser Leu Arg
1520                1525                1530

Ile Leu Gln Ser Thr Phe Arg His Glu Leu Val Leu Thr Arg Leu
1535                1540                1545

Ala His His Ile Pro Leu Ile Ser Leu Met Leu Gly Gly Ser Ala
1550                1555                1560

Gly Glu Lys Ser Ser Ser Asp Ala Val Arg Leu Phe Leu Thr Ala
1565                1570                1575

Ser Tyr Gln Asn Phe Ile Asn Asn Phe Ser Cys Leu Met Lys Lys
1580                1585                1590

Gly Gln Ser Ser Leu Pro Val Trp Leu Tyr Phe Pro Ser Glu Gly
1595                1600                1605

Gln Gln Leu Lys Pro Ile Leu Lys Ile Leu Gln Arg Leu Ser Asp
1610                1615                1620

Leu Leu Ser Pro Asp Lys Ile Gln Lys Arg Lys Ile Leu Ala Asp
1625                1630                1635

Thr Cys Cys Pro Ile Gly Ser Phe Trp Val Tyr Pro Ser Lys Ser
1640                1645                1650

Thr Arg Thr Asn His Tyr Tyr Ala Ser Leu Asn Tyr Trp Arg Asp
1655                1660                1665

Lys Ala Asn Lys Val Lys Asn Thr Pro Phe Ser His Leu Ile Asn
1670                1675                1680

Cys Ser Phe Pro Glu Phe Ser Ser His Thr Ser Ser Val Ser Ser
1685                1690                1695

Asn Gln Gln Val Thr Asn Ser Lys Tyr Ile Val Tyr Pro Glu Asn
1700                1705                1710

Ile Thr Glu Ile Asn Ala Arg Thr Arg Leu Ile Asn Tyr Gly Ser
1715                1720                1725

Thr Ala Leu Gln Gly Met Asp Thr Lys Met Pro Leu Ser Glu Gln
1730                1735                1740

Asn Leu Val Glu Asn Cys Arg Pro Ser Glu Gly Ile Arg Phe Lys
1745                1750                1755

Asp Asn Gln Lys Ile Thr Lys His Asp Gln Arg Cys Glu Arg Glu
1760                1765                1770

Glu Ser Ser Pro Gln Gln Met Phe Pro Glu Asp Asn Met Gln Thr
1775                1780                1785

Pro Ala His Ile His Ser Ser Ser Pro Phe Gln Ile Leu Ile Lys
1790                1795                1800

Ser Leu Asp Ala His Glu Asp Phe Asp Ala Ser Lys Ile Ile Leu
1805                1810                1815

Asn Ser Glu Ile Asn Asn Leu Asn Leu Thr Glu Tyr Thr Leu Asn
1820                1825                1830

Thr Lys Leu Leu Thr Thr Pro Thr Arg Thr Glu Ile Leu Asp Thr
1835                1840                1845

Ser Pro Leu Gln Ser Ser Arg Tyr Ser Ser Thr Ser Arg Glu Arg
1850                1855                1860

Ser Leu Leu Ser Arg Glu Gln Ala Ser Tyr Leu Tyr Val Asp Cys
1865                1870                1875

Ser Asn Ile Pro Ser Ile Ser Leu Asp Pro Gly Phe Arg Ser Met
1880                1885                1890

Ser Asp Gln Asn Gln Val Gln Met Leu Ile Asn Thr Tyr Lys Arg

-continued

```
            1895                1900                1905
Asp Leu His Ala Cys Phe Asp Ser Asn Gln Phe Cys Arg Phe Thr
        1910                1915                1920
Gly Val Val Ser Ser Met His Tyr Lys Leu Tyr Asp Leu Leu Pro
        1925                1930                1935
Pro Gly Lys Leu Lys Lys Ala Ile Cys Leu Ala Glu Gly Glu Gly
        1940                1945                1950
Ser Gly Ala Arg Leu Leu Leu Lys Trp Lys Glu Thr Asp Tyr Leu
        1955                1960                1965
Phe Phe Asn Thr Leu Ala Thr Asp Ser Gln Gln Glu Ala Glu Ile
        1970                1975                1980
Leu Ser Gly Arg Val Ile Pro Arg Met Leu Tyr Asn Ile Asp Arg
        1985                1990                1995
Leu Ser Ala Leu Leu Glu Ser Arg Arg Leu Ile Leu Asn Asn Leu
        2000                2005                2010
Thr Ile Gln Ile Thr Asp Ile Thr Asn Pro Leu Trp Leu Asp Ser
        2015                2020                2025
Val Ile Gln Tyr Leu Pro Glu Asp Ser Asp Ile Leu Thr Met Asp
        2030                2035                2040
Ala Glu Thr Thr Lys Asp Glu Thr Arg Glu Gln Leu Tyr Lys Thr
        2045                2050                2055
Ile Val Asn Ile Trp Thr Arg Thr Ser Pro Asn Ile Pro Lys Ile
        2060                2065                2070
Ser Ile Ile Lys Val Phe Leu Leu Asp Tyr Glu Gly Thr Leu Phe
        2075                2080                2085
Leu Met Lys Asn Ala Ile Gln Tyr Tyr Gly Gln Val Gln Leu Lys
        2090                2095                2100
Lys Pro Tyr Ser Ser Asn Ala Lys Asn Ser Glu Trp Tyr Leu Cys
        2105                2110                2115
Cys Gly Lys Arg Arg Ile Gln Arg Leu Gln Ile Asp Phe Ser Asp
        2120                2125                2130
Gln Val Gly Ile Phe Leu Ile Cys Lys Ala Met Ser Arg Gln Arg
        2135                2140                2145
Gln Ala Ile Pro Tyr Trp Leu Lys His Ile Glu Lys Asn Tyr Pro
        2150                2155                2160
Ala Ser Leu His Glu Phe Phe Leu Thr Leu Gly Phe Pro Ser Leu
        2165                2170                2175
Glu Ser Ser Phe Cys His Arg Tyr Thr Ile Pro Phe Ser Glu Gly
        2180                2185                2190
Lys Ala Leu Phe His Lys Val Gln Ser Tyr Val Arg Gln Gly Lys
        2195                2200                2205
Gln His Leu His Ser Leu Met Leu Asp Tyr Glu Asn Asn Ser Pro
        2210                2215                2220
Leu Leu Asp Leu Arg Asn His Phe Ile Cys Ser Leu Arg Gly Lys
        2225                2230                2235
Ile Thr Lys Tyr Tyr Asn Asp Ile Leu Lys Leu Asn Leu Val Ile
        2240                2245                2250
Lys Ala Val Glu Lys Gly Lys Asn Trp Ser Gln Leu Val Glu Ile
        2255                2260                2265
Leu Pro Asn Met His Ser Val Cys Ile Val His Val Asp His Glu
        2270                2275                2280
Cys Ser Gly Cys Glu Lys Arg Leu Leu Leu Lys Leu Asp Phe Ile
        2285                2290                2295
```

```
Arg Asn Thr Lys Ile Ala Glu Gln Lys Leu Leu Asn Arg Val Ile
    2300            2305                2310
Gly Tyr Ile Leu Phe Phe Pro Phe Gly Leu Phe Lys Ser Gly Ser
    2315            2320                2325
Leu Arg Ala
    2330
```

<210> SEQ ID NO 43
<211> LENGTH: 13597
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 43

| | | | | | |
|---|---|---|---|---|---|
| acgcttaaca | accagatcaa | agaaaaaaca | gacattgtca | attgcaaagc | aaaaatgtaa | 60 |
| caccccctaca | atggatgccg | acaagattgt | attcaaagtc | aataatcagg | tggtctcttt | 120 |
| gaagcctgag | attatcgtgg | atcaatatga | gtacaagtac | cctgccatca | agatttgaa | 180 |
| aaagccctgt | ataaccctag | gaaaggctcc | cgatttaaat | aaagcataca | agtcagtttt | 240 |
| gtcaggcatg | agcgccgcca | aacttaatcc | tgacgatgta | tgttcctatt | tggcagcggc | 300 |
| aatgcagttt | tttgagggga | catgtccgga | agactggacc | agctatgaa | ttgtgattgc | 360 |
| acgaaaagga | gataagatca | ccccaggttc | tctggtggag | ataaaacgta | ctgatgtaga | 420 |
| agggaattgg | gctctgacag | gaggcatgga | actgacaaga | gaccccactg | tccctgagca | 480 |
| tgcgtcctta | gtcggtcttc | tcttgagtct | gtataggttg | agcaaaatat | ccgggcaaaa | 540 |
| cactggtaac | tataagacaa | acattgcaga | caggatagag | cagattttg | agacagcccc | 600 |
| ttttgttaaa | atcgtggaac | accatactct | aatgacaact | cacaaaatgt | gtgctaattg | 660 |
| gagtactata | ccaaacttca | gattttttggc | cggaacctat | gacatgtttt | tctcccggat | 720 |
| tgagcatcta | tattcagcaa | tcagagtggg | cacagttgtc | actgcttatg | aagactgttc | 780 |
| aggactggta | tcatttactg | ggttcataaa | acaaatcaat | ctcaccgcta | gagaggcaat | 840 |
| actatatttc | ttccacaaga | actttgagga | agagataaga | agaatgtttg | agccagggca | 900 |
| ggagacagct | gttcctcact | cttatttcat | ccacttccgt | tcactaggct | tgagtgggaa | 960 |
| atctccttat | tcatcaaatg | ctgttggtca | cgtgttcaat | ctcattcact | ttgtaggatg | 1020 |
| ctatatgggt | caagtcagat | ccctaaatgc | aacggttatt | gctgcatgtg | ctcctcatga | 1080 |
| aatgtctgtt | ctaggggct | atctgggaga | ggaattcttc | gggaaaggga | catttgaaag | 1140 |
| aagattcttc | agagatgaga | agaacttca | agaatacgag | gcggctgaac | tgacaaagac | 1200 |
| tgacgtagca | ctggcagatg | atggaactgt | caactctgac | gacgaggact | acttttcagg | 1260 |
| tgaaaccaga | agtccggagg | ctgtttatac | tcgaatcatg | atgaatggag | tcgactaaa | 1320 |
| gagatctcac | atacggagat | atgtctcagt | cagttccaat | catcaagccc | gtccaaactc | 1380 |
| attcgccgag | tttctaaaca | agacatattc | gagtgactca | taacatgaaa | aaaactaaca | 1440 |
| cccctcccgt | acgccgccac | catgggtgtt | acaggaaatt | tgcagttacc | tcgtgatcga | 1500 |
| ttcaagagga | catcattctt | tctttgggta | attatccttt | tccaaagaac | attttccatc | 1560 |
| ccacttggag | tcatccacaa | tagcacatta | caggttagtg | atgtcgacaa | actagtttgt | 1620 |
| cgtgacaaac | tgtcatccac | aaatcaattg | agatcagttg | gactgaatct | cgaagggaat | 1680 |
| ggagtggcaa | ctgacgtgcc | atctgcaact | aaaagatggg | gcttcaggtc | cggtgtccca | 1740 |

```
ccaaaggtgg tcaattatga agctggtgaa tgggctgaaa actgctacaa tcttgaaatc    1800
aaaaaacctg acgggagtga gtgtctacca gcagcgccag acgggattcg ggcttcccc     1860 cggtgccggt atgtgcacaa agtatcagga acgggaccgt gtgccggaga ctttgccttc    1920
cataaagagg gtgctttctt cctgtatgat cgacttgctt ccacagttat ctaccgagga    1980
acgactttcg ctgaaggtgt cgttgcattt ctgatactgc cccaagctaa aaggacttc     2040 ttcagctcac accccttgag agagccggtc aatgcaacgg aggacccgtc tagtggctac    2100
tattctacca caattagata tcaggctacc ggttttggaa ccaatgagac agagtacttg    2160
ttcgaggttg acaatttgac ctacgtccaa cttgaatcaa gattcacacc acagtttctg    2220
ctccagctga atgagacaat atatacaagt gggaaaagga gcaataccac gggaaaacta    2280
atttggaagg tcaaccccga aattgataca acaatcgggg agtgggcctt ctgggaaact    2340
aaaaaaaacc tcactagaaa aattcgcagt gaagagttgt ctttcacagt tgtatcaaac    2400
agagccaaaa acatcagtgg tcagagtccg gcgcgaactt cttccgaccc agggaccaac    2460
acaacaactg aagaccacaa aatcatggct tcagaaaatt cctctgcaat ggttcaagtg    2520
cacagtcaag gaagggaagc tgcagtgtcg catctgacaa cccctgccac aatctccacg    2580
agtcttcaac cccccacaac caaaccaggt ccggacaaca gcacccacaa tacacccgtg    2640
tataaacttg acatctctga ggcaactcaa gttgaacaac atcaccgcag aacagacaac    2700
gacagcacag cctccgacac tccctctgcc acgaccgcag ccggaccccc aaaagcagag    2760
aacaccaaca cgagcaagag cactgacttc ctggaccccg ccaccacaac aagtccccaa    2820
aaccacagcg agaccgctgg caacaacaac actcatcacc aagataccgg agaagagagt    2880
gccagcagcg ggaagctagg cttaattacc aatactattg ctggagtcgc aggactgatc    2940
acaggcggga gaagaactcg aagagaagca attgtcaatg ctcaacccaa atgcaaccct    3000
aatttacatt actggactac tcaggatgaa ggtgctgcaa tcggactggc ctggatacca    3060
tatttcgggc cagcagccga gggaatttac atagaggggc taatgcacaa tcaagatggt    3120
ttaatctgtg ggttgagaca gctggccaac gagacgactc aagctcttca actgttcctg    3180
agagccacaa ctgagctacg caccttttca atcctcaacc gtaaggcaat tgatttcttg    3240
ctgcagcgat ggggcggcac atgccacatt ctgggaccgg actgctgtat cgaaccacat    3300
gattggacca agaacataac agacaaaatt gatcagatta ttcatgattt tgttgataaa    3360
acccttccgg accaggggga caatgacaat tggtggacag gatggagaca atggataccg    3420
gcaggtattg gagttacagg cgttgtaatt gcagttatcg ctttattctg tatatgcaaa    3480
tttgtctttt aggagctagc catgaaaaaa actaacaccc ctccttttcga accatcccaa    3540 acatgagcaa gatctttgtc aatcctagtg ctattagagc cggtctggcc gatcttgaga    3600
tggctgaaga aactgttgat ctgatcaata gaaatatcga agacaatcag gctcatctcc    3660
aaggggaacc catagaggtg acaatctccc tgaggatat ggggcgactt cacctggatg     3720
atggaaaatc gcccaaccat ggtgagatag ccaaggtggg agaaggcaag tatcgagagg    3780
actttcagat ggatgaagga gaggatccta gcttcctgtt ccagtcatac ctggaaaatg    3840
ttggagtcca aatagtcaga caaatgaggt caggagagag atttctcaag atatggtcac    3900
agaccgtaga agagattata tcctatgtcg cggtcaactt tcccaaccct ccaggaaagt    3960
cttcagagga taaatcaacc cagactactg gccgagagct caagaaggag acaacaccca    4020
ctccttctca gagagaaagc caatcatcga aagccaggat ggcggctcaa attgcttctg    4080
```

```
gccctccagc ccttgaatgg tcggctacca atgaagagga tgatctatca gtggaggctg    4140
agatcgctca ccagattgca gaaagtttct ccaaaaaata taagtttccc tctcgatcct    4200
cagggatact cttgtataat tttgagcaat tgaaaatgaa ccttgatgat atagttaaag    4260
aggcaaaaaa tgtaccaggt gtgacccgtt tagcccatga cgggtccaaa ctcccccctaa   4320 gatgtgtact gggatgggtc gctttggcca actctaagaa attccagttg ttagtcgaat    4380
ccgacaagct gagtaaaatc atgcaagatg acttgaatcg ctatacatct tgctaaccga    4440
acctctcccc tcagtccctc tagacaataa aatccgagat gtcccaaagt caacatgaaa    4500
aaaacaggca acaccactga taaaatgaac ctcctacgta agatagtgaa aaaccgcagg    4560
gacgaggaca ctcaaaaatc ctctcccgcg tcagcccctc tggatgacga tgacttgtgg    4620
cttccacccc ctgaatacgt cccgctgaaa gaacttacag gcaagaagaa catgaggaac    4680
ttttgtatca acggaagggt taaagtgtgt agcccgaatg gttactcgtt caggatcctg    4740
cggcacattc tgaaatcatt cgacgagata tattctggga atcataggat gatcgggtta    4800
gtcaaagtgg ttattggact ggctttgtca ggatctccag tccctgaggg cctgaactgg    4860
gtatacaaat tgaggagaac ctttatcttc cagtgggctg attccagggg ccctcttgaa    4920
ggggaggagt tggaatactc tcaggagatc acttgggatg atgatactga gttcgtcgga    4980
ttgcaaataa gagtgattgc aaaacagtgt catatccagg gcagagtctg gtgtatcaac    5040
atgaacccga gagcatgtca actatggtct gacatgtctc ttcagacaca aaggtccgaa    5100
gaggacaaag attcctctct gcttctagaa taatcagatt atatcccgca aatttatcac    5160
ttgtttacct ctggaggaga gaacatatgg gctcaactcc aacccttggg agcaatataa    5220
caaaaaacat gttatggtgc cattaaaccg ctgcatttca tcaaagtcaa gttgattacc    5280
tttacatttt gatcctcttg gatgtgaaaa aaactattaa catccctcaa aagaccccgg    5340
gaaagatggt tcctcaggct ctcctgtttg tacccttct ggttttttca ttgtgttttg     5400
ggaaattccc tatttacacg ataccagaca agcttggtcc ctggagtccg attgacatac    5460
atcacctcag ctgcccaaac aatttggtag tggaggacga aggatgcacc aacctgtcag    5520
ggttctccta catggaactt aaagttggat acatcttagc cataaaagtg aacgggttca    5580
cttgcacagg cgttgtgacg gaggctgaaa cctacactaa cttcgttggt tatgtcacaa    5640
ccacgttcaa aagaaagcat ttccgcccaa caccagatgc atgtagagcc gcgtacaact    5700
ggaagatggc cggtgacccc agatatgaag agtctctaca caatccgtac cctgactacc    5760
gctggcttcg aactgtaaaa accaccaagg agtctctcgt tatcatatct ccaagtgtgg    5820
cagatttgga cccatatgac agatcccttc actcgagggt cttccctagc gggaagtgct    5880
caggagtagc ggtgtcttct acctactgct ccactaacca cgattacacc atttggatgc    5940
ccgagaatcc gagactaggg atgtcttgtg acattttac caatagtaga gggaagagag     6000
catccaaagg gagtgagact tgcggctttg tagatgaaag aggcctatat aagtctttaa    6060
aaggagcatg caaactcaag ttatgtggag ttctaggact tagacttatg gatggaacat    6120
gggtctcgat gcaaacatca aatgaaacca atggtgccc tcccgataag ttggtgaacc     6180
tgcacgactt tcgctcagac gaaattgagc accttgttgt agaggagttg gtcaggaaga    6240
gagaggagtg tctggatgca ctagagtcca tcatgacaac caagtcagtg agtttcagac    6300
gtctcagtca tttaagaaaa cttgtccctg ggttggaaa agcatatacc atattcaaca     6360
agaccttgat ggaagccgat gctcactaca agtcagtcga gacttggaat gagatcctcc    6420
cttcaaaagg gtgtttaaga gttgggggga ggtgtcatcc tcatgtgaac ggggtgtttt    6480
```

```
tcaatggtat aatattagga cctgacggca atgtcttaat cccagagatg caatcatccc    6540
tcctccagca acatatggag ttgttggaat cctcggttat cccccttgtg cacccctgg    6600 cagacccgtc taccgttttc aaggacggtg acgaggctga ggattttgtt gaagttcacc    6660
ttcccgatgt gcacaatcag gtctcaggag ttgacttggg tctcccgaac tgggggaagt    6720
atgtattact gagtgcaggg gccctgactg ccttgatgtt gataattttc ctgatgacat    6780
gttgtagaag agtcaatcga tcagaaccta cgcaacacaa tctcagaggg acagggaggg    6840
aggtgtcagt cactccccaa agcgggaaga tcatatcttc atgggaatca cacaagagtg    6900
ggggtgagac cagactgtaa ttaattaacg tcctttcaac gatccaagtc catgaaaaaa    6960
actaacaccc ctcccgtacc tagcttataa agtgctgggt catctaagct tttcagtcga    7020
gaaaaaaaca ttagatcaga agaacaactg gcaacacttc tcaacctgag acttacttca    7080
agatgctcga tcctggagag gtctatgatg accctattga cccaatcgag ttagaggctg    7140
aacccagagg aaccccatt gtccccaaca tcttgaggaa ctctgactac aatctcaact    7200
ctcctttgat agaagatcct gctagactaa tgttagaatg gttaaaaaca gggaatagac    7260
cttatcggat gactctaaca gacaattgct ccaggtcttt cagagttttg aaagattatt    7320
tcaagaaggt agatttgggt tctctcaagg tgggcggaat ggctgcacag tcaatgattt    7380
ctctctggtt atatggtgcc cactctgaat ccaacaggag ccggagatgt ataacagact    7440
tggcccattt ctattccaag tcgtccccca tagagaagct gttgaatctc acgctaggaa    7500
atagagggct gagaatcccc ccagagggag tgttaagttg ccttgagagg gttgattatg    7560
ataatgcatt tggaaggtat cttgccaaca cgtattcctc ttacttgttc ttccatgtaa    7620
tcaccttata catgaacgcc ctagactggg atgaagaaaa gaccatccta gcattatgga    7680
aagatttaac ctcagtggac atcgggaagg acttggtaaa gttcaaagac caaatatggg    7740
gactgctgat cgtgacaaag gactttgttt actcccaaag ttccaattgt cttttgaca    7800 gaaactacac acttatgcta aagatctttt cttgtctcg cttcaactcc ttaatggtct    7860
tgctctctcc cccagagccc cgatactcag atgacttgat atctcaacta tgccagctgt    7920
acattgctgg ggatcaagtc ttgtctatgt gtggaaactc cggctatgaa gtcatcaaaa    7980
tattggagcc atatgtcgtg aatagtttag tccagagagc agaaaagttt aggcctctca    8040
ttcattcctt gggagacttt cctgtattta taaaagacaa ggtaagtcaa cttgaagaga    8100
cgttcggtcc ctgtgcaaga aggttcttta gggctctgga tcaattcgac aacatacatg    8160
acttggtttt tgtgtttggc tgttacaggc attgggggca cccatatata gattatcgaa    8220
agggtctgtc aaaactatat gatcaggttc accttaaaaa aatgatagat aagtcctacc    8280
aggagtgctt agcaagcgac ctagccagga ggatccttag atggggtttt gataagtact    8340
ccaagtggta tctggattca agattcctag cccgagacca cccccttgact ccttatatca    8400 aaacccaaac atggccaccc aaacatattg tagacttggt gggggataca tggcacaagc    8460
tcccgatcac gcagatcttt gagattcctg aatcaatgga tccgtcagaa atattggatg    8520
acaaatcaca ttcttttcacc agaacgagac tagcttcttg gctgtcagaa aaccgagggg    8580
ggcctgttcc tagcgaaaaa gttattatca cggccctgtc taagccgcct gtcaatcccc    8640
gagagtttct gaggtctata gacctcggag gattgccaga tgaagacttg ataattggcc    8700
tcaagccaaa ggaacgggaa ttgaagattg aaggtcgatt ctttgctcta atgtcatgga    8760
atctaagatt gtattttgtc atcactgaaa aactcttggc caactacatc ttgccacttt    8820
```

```
ttgacgcgct gactatgaca gacaacctga acaaggtgtt taaaaagctg atcgacaggg    8880
tcaccgggca agggcttttg gactattcaa gggtcacata tgcatttcac ctggactatg    8940
aaaagtggaa caaccatcaa agattagagt caacagagga tgtattttct gtcctagatc    9000
aagtgtttgg attgaagaga gtgttttcta gaacacacga gttttttcaa aaggcctgga    9060
tctattattc agacagatca gacctcatcg ggttacggga ggatcaaata tactgcttag    9120
atgcgtccaa cggcccaacc tgttggaatg gccaggatgg cgggctagaa ggcttacggc    9180
agaagggctg gagtctagtc agcttattga tgatagatag agaatctcaa atcaggaaca    9240
caagaaccaa aatactagct caaggagaca accaggtttt atgtccgaca tacatgttgt    9300
cgccagggct atctcaagag gggctcctct atgaattgga gagaatatca aggaatgcac    9360
tttcgatata cagagccgtc gaggaagggg catctaagct agggctgatc atcaagaaag    9420
aagagaccat gtgtagttat gacttcctca tctatggaaa aaccccttttg tttagaggta    9480
acatattggt gcctgagtcc aaaagatggg ccagagtctc ttgcgtctct aatgaccaaa    9540
tagtcaacct cgccaatata atgtcgacag tgtccaccaa tgcgctaaca gtggcacaac    9600
actctcaatc tttgatcaaa ccgatgaggg attttctgct catgtcagta caggcagtct    9660
ttcactacct gctatttagc ccaatcttaa agggaagagt ttacaagatt ctgagcgctg    9720
aaggggagag ctttctccta gccatgtcaa ggataatcta tctagatcct tctttgggag    9780
ggatatctgg aatgtccctc ggaagattcc atatacgaca gttctcagac cctgtctctg    9840
aagggttatc cttctggaga gagatctggt taagctccca agagtcctgg attcacgcgt    9900
tgtgtcaaga ggctggaaac ccagatcttg gagagagaac actcgagagc ttcactcgcc    9960
ttctagaaga tccgaccacc ttaaatatca gaggagggc cagtcctacc attctactca   10020
aggatgcaat cagaaaggct ttatatgacg aggtggacaa ggtggaaaat tcagagtttc   10080
gagaggcaat cctgttgtcc aagacccata gagataattt tatactcttc ttaatatctg   10140
ttgagcctct gttcctcga tttcagtg agctattcag ttcgtctttt ttgggaatcc   10200
ccgagtcaat cattggattg atacaaaact cccgaacgat aagaaggcag tttagaaaga   10260
gtctctcaaa aactttagaa gaatccttct acaactcaga gatccacggg attagtcgga   10320
tgacccagac acctcagagg gttggggggg tgtggccttg ctcttcagag agggcagatc   10380
tacttaggga gatctcttgg ggaagaaaag tggtaggcac gacagttcct cacccttctg   10440
agatgttggg attacttccc aagtcctcta tttcttgcac ttgtggagca acaggaggag   10500
gcaatcctag agtttctgta tcagtactcc cgtcctttga tcagtcattt ttttcacgag   10560
gcccctaaa gggatacttg ggctcgtcca cctctatgtc gacccagcta ttccatgcat   10620
gggaaaaagt cactaatgtt catgtggtga agagagctct atcgttaaaa gaatctataa   10680
actggttcat tactagagat tccaacttgg ctcaagctct aattaggaac attatgtctc   10740
tgacaggccc tgatttccct ctagaggagg cccctgtctt caaaaggacg gggtcagcct   10800
tgcataggtt caagtctgcc agatacagcg aaggagggta ttcttctgtc tgcccgaacc   10860
tcctctctca tatttctgtt agtacagaca ccatgtctga tttgacccaa gacgggaaga   10920
actacgattt catgttccag ccattgatgc tttatgcaca gacatggaca tcagagctgg   10980
tacagagaga cacaaggcta agagactcta cgtttcattg gcacctccga tgcaacaggt   11040
gtgtgagacc cattgacgac gtgacccctg gacctctca gatcttcgag tttccggatg   11100
tgtcgaaaag aatatcccaga atggtttctg gggctgtgcc tcacttccag aggcttcccg   11160
atatccgtct gagaccagga gattttgaat ctctaagcgg tagagaaaag tctccaccata   11220
```

```
tcggatcagc tcaggggctc ttatactcaa tcttagtggc aattcacgac tcaggataca   11280
atgatggaac catcttccct gtcaacatat acggcaaggt ttcccctaga gactatttga   11340
gagggctcgc aagggagta ttgataggat cctcgatttg cttcttgaca agaatgacaa    11400
atatcaatat taatagacct cttgaattgg tctcaggggt aatctcatat attctcctga   11460
ggctagataa ccatccctcc ttgtacataa tgctcagaga accgtctctt agaggagaga   11520
tattttctat ccctcagaaa atccccgccg cttatccaac cactatgaaa gaaggcaaca   11580
gatcaatctt gtgttatctc caacatgtgc tacgctatga gcgagagata atcacggcgt   11640
ctccagagaa tgactggcta tggatctttt cagactttag aagtgccaaa atgacgtacc   11700
tatccctcat tacttaccag tctcatcttc tactccagag ggttgagaga aacctatcta   11760
agagtatgag agataacctg cgacaattga gttctttgat gaggcaggtg ctgggcgggc   11820
acggagaaga taccttagag tcagacgaca acattcaacg actgctaaaa gactctttac   11880
gaaggacaag atgggtggat caagaggtgc gccatgcagc tagaaccatg actggagatt   11940
acagccccaa caagaaggtg tcccgtaagg taggatgttc agaatgggtc tgctctgctc   12000
aacaggttgc agtctctacc tcagcaaacc cggcccctgt ctcggagctt gacataaggg   12060
ccctctctaa gaggttccag aacccttgga tctcgggctt gagagtggtt cagtgggcaa   12120
ccggtgctca ttataagctt aagcctattc tagatgatct caatgttttc ccatctctct   12180
gccttgtagt tggggacggg tcagggggga tatcaagggc agtcctcaac atgtttccag   12240
atgccaagct tgtgttcaac agtcttttag aggtgaatga cctgatggct tccggaacac   12300
atccactgcc tccttcagca atcatgaggg gaggaaatga tatcgtctcc agagtgatag   12360
atcttgactc aatctgggaa aaaccgtccg acttgagaaa cttggcaacc tggaaatact   12420
tccagtcagt ccaaaagcag gtcaacatgt cctatgacct cattatttgc gatgcagaag   12480
ttactgacat tgcatctatc aaccggatca ccctgttaat gtccgatttt gcattgtcta   12540
tagatggacc actctatttg gtcttcaaaa cttatgggac tatgctagta aatccaaact   12600
acaaggctat tcaacacctg tcaagagcgt tcccctcggt cacagggttt atcacccaag   12660
taacttcgtc ttttttcatct gagctctacc tccgattctc caaacgaggg aagttttca   12720 gagatgctga gtacttgacc tcttccaccc ttcgagaaat gagccttgtg ttattcaatt   12780
gtagcagccc caagagtgag atgcagagag ctcgttcctt gaactatcag gatcttgtga   12840
gaggatttcc tgaagaaatc atatcaaatc cttacaatga gatgatcata actctgattg   12900
acagtgatgt agaatctttt ctagtccaca agatggttga tgatcttgag ttacagaggg   12960
gaactctgtc taaagtggct atcattatag ccatcatgat agttttctcc aacagagtct   13020
tcaacgtttc caaacccta actgaccct cgttctatcc accgtctgat cccaaaatcc     13080
tgaggcactt caacatatgt tgcagtacta tgatgtatct atctactgct ttaggtgacg   13140
tccctagctt cgcaagactt cacgacctgt ataacagacc tataacttat tacttcagaa   13200
agcaagtcat tcgagggaac gtttatctat cttggagttg gtccaacgac acctcagtgt   13260 tcaaagggt agcctgtaat tctagcctga gtctgtcatc tcactggatc aggttgattt    13320
acaagatagt gaagactacc agactcgttg gcagcatcaa ggatctatcc agagaagtgg   13380
aaagacacct tcataggtac aacaggtgga tcaccctaga ggatatcaga tctagatcat   13440
ccctactaga ctacagttgc ctgtgaaccg gatactcctg gaagcctgcc catgctaaga   13500
ctcttgtgtg atgtatcttg aaaaaaacaa gatcctaaat ctgaacctttt ggttgtttga   13560
```
ttgtttttct catttttgtt gtttatttgt taagcgt                                13597

<210> SEQ ID NO 44
<211> LENGTH: 13721
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44

```
acgcttaaca accagatcaa agaaaaaaca gacattgtca attgcaaagc aaaaatgtaa       60
caccccctaca atggatgccg acaagattgt attcaaagtc aataatcagg tggtctcttt     120
gaagcctgag attatcgtgg atcaatatga gtacaagtac cctgccatca agatttgaa      180
aaagccctgt ataaccctag aaaggctcc cgatttaaat aaagcataca agtcagtttt     240
gtcaggcatg agcgccgcca aacttaatcc tgacgatgta tgttcctatt tggcagcggc     300
aatgcagttt tttgagggga catgtccgga agactggacc agctatggaa ttgtgattgc     360
acgaaaagga gataagatca ccccaggttc tctggtggag ataaaacgta ctgatgtaga     420
agggaattgg gctctgacag gaggcatgga actgacaaga gaccccactg tccctgagca     480
tgcgtcctta gtcggtcttc tcttgagtct gtataggttg agcaaaatat ccgggcaaaa     540
cactggtaac tataagacaa acattgcaga caggatagag cagattttg agacagcccc     600
ttttgttaaa atcgtggaac accatactct aatgacaact cacaaaatgt gtgctaattg     660
gagtactata ccaaacttca gattttggc cggaacctat gacatgtttt tctcccggat     720
tgagcatcta tattcagcaa tcagagtggg cacagttgtc actgcttatg aagactgttc     780
aggactggta tcatttactg ggttcataaa acaaatcaat ctcaccgcta gagaggcaat     840
actatatttc ttccacaaga actttgagga agagataaga agaatgtttg agccagggca     900
ggagacagct gttcctcact cttatttcat ccacttccgt tcactaggct tgagtgggaa     960
atctccttat tcatcaaatg ctgttggtca cgtgttcaat ctcattcact tgtaggatg     1020
ctatatgggt caagtcagat ccctaaatgc aacggttatt gctgcatgtg ctcctcatga    1080
aatgtctgtt ctagggggct atctgggaga ggaattcttc gggaaaggga catttgaaag    1140
aagattcttc agagatgaga agaacttca agaatacgag gcggctgaac tgacaaagac    1200
tgacgtagca ctggcagatg atggaactgt caactctgac gacgaggact acttttcagg    1260
tgaaaccaga agtccggagg ctgtttatac tcgaatcatg atgaatggag tcgactaaa    1320
gagatctcac atacggagat atgtctcagt cagttccaat catcaagccc gtccaaactc    1380
attcgccgag tttctaaaca agacatattc gagtgactca taacatgaaa aaaactaaca    1440
cccctcccgt acgccgccac catgggtgtt acaggaatat tgcagttacc tcgtgatcga    1500
ttcaagagga catcattctt tctttgggta attatccttt tccaaagaac attttccatc    1560
ccacttggag tcatccacaa tagcacatta caggttagtg atgtcgacaa actagtttgt    1620
cgtgacaaac tgtcatccac aaatcaattg agatcagttg gactgaatct cgaagggaat    1680
ggagtggcaa ctgacgtgcc atctgcaact aaaagatggg gcttcaggtc cggtgtccca    1740
ccaaaggtgg tcaattatga agctggtgaa tgggctgaaa actgctacaa tcttgaaatc    1800
aaaaaacctg acgggagtga gtgtctacca gcagcgccag acgggattcg ggcttcccc    1860
cggtgccggt atgtgcacaa agtatcagga acggaccgt gtgccggaga ctttgccttc    1920
cataaagagg gtgctttctt cctgtatgat cgacttgctt ccacagttat ctaccgagga    1980
```

```
acgactttcg ctgaaggtgt cgttgcattt ctgatactgc cccaagctaa gaaggacttc    2040
ttcagctcac accccttgag agagccggtc aatgcaacgg aggacccgtc tagtggctac    2100
tattctacca caattagata tcaggctacc ggttttggaa ccaatgagac agagtacttg    2160
ttcgaggttg acaatttgac ctacgtccaa cttgaatcaa gattcacacc acagtttctg    2220
ctccagctga atgagacaat atatacaagt gggaaaagga gcaataccac gggaaaacta    2280
atttggaagg tcaaccccga aattgataca acaatcgggg agtgggcctt ctgggaaact    2340
aaaaaaaacc tcactagaaa aattcgcagt gaagagttgt ctttcacagt tgtatcaaac    2400
agagccaaaa acatcagtgg tcagagtccg gcgcgaactt cttccgaccc agggaccaac    2460
acaacaactg aagaccacaa aatcatggct tcagaaaatt cctctgcaat ggttcaagtg    2520
cacagtcaag gaagggaagc tgcagtgtcg catctgacaa cccctgccac aatctccacg    2580
agtcttcaac cccccacaac caaaccaggt ccggacaaca gcacccacaa tacacccgtg    2640
tataaacttg acatctctga ggcaactcaa gttgaacaac atcaccgcag aacagacaac    2700
gacagcacag cctccgacac tccctctgcc acgaccgcag ccggaccccc aaaagcagag    2760
aacaccaaca cgagcaagag cactgacttc ctggaccccg ccaccacaac aagtccccaa    2820
aaccacagcg agaccgctgg caacaacaac actcatcacc aagataccgg agaagagagt    2880
gccagcagcg ggaagctagg cttaattacc aatactattg ctggagtcgc aggactgatc    2940
acaggcggga gaagaactcg aagagaagca attgtcaatg ctcaacccaa atgcaaccct    3000
aatttacatt actggactac tcaggatgaa ggtgctgcaa tcggactggc ctggatacca    3060
tatttcgggc cagcagccga gggaatttac atagaggggc taatgcacaa tcaagatggt    3120
ttaatctgtg ggttgagaca gctggccaac gagacgactc aagctcttca actgttcctg    3180
agagccacaa ctgagctacg caccttttca atcctcaacc gtaaggcaat tgatttcttg    3240
ctgcagcgat ggggcggcac atgccacatt ctgggaccgg actgctgtat cgaaccacat    3300
gattggacca agaacataac agacaaaatt gatcagatta ttcatgattt tgttgataaa    3360
acccttccgg accaggggga caatgacaat tggtggacag gatggagaca atggataccg    3420
gcaggtattg gagttacagg cgttgtaatt gcagttatcg ctttattctg tatatgcgtt    3480
aacagaagag tcaatcgatc agaacctacg caacacaatc tcagagggac agggagggag    3540
gtgtcagtca ctccccaaag cgggaagatc atatcttcat gggaatcaca caagagtggg    3600
ggtgagacca gactgtaagc tagccatgaa aaaaactaac acccctcctt tcgaaccatc    3660
ccaaacatga gcaagatctt tgtcaatcct agtgctatta gagccggtct ggccgatctt    3720
gagatggctg aagaaactgt tgatctgatc aatagaaata tcgaagacaa tcaggctcat    3780
ctccaagggg aacccataga ggtggacaat ctccctgagg atatggggcg acttcacctg    3840
gatgatggaa atcgcccaa ccatggtgag atagccaagg tgggagaagg caagtatcga    3900
gaggactttc agatggatga aggagaggat cctagcttcc tgttccagtc atacctggaa    3960
aatgttggag tccaaatagt cagacaaatg aggtcaggag agagatttct caagatatgg    4020
tcacagaccg tagaagagat tatatcctat gtcgcggtca actttcccaa ccctccagga    4080
aagtcttcag aggataaatc aacccagact actggccgag agctcaagaa ggagacaaca    4140
cccactcctt ctcagagaga aagccaatca tcgaaagcca ggatggcggc tcaaattgct    4200
tctggccctc cagcccttga atggtcggct accaatgaag aggatgatct atcagtggag    4260
gctgagatcg ctcaccagat tgcagaaagt ttctccaaaa aatataagtt tcccctctcga    4320
```

-continued

| | | | | | |
|---|---|---|---|---|---|
| tcctcaggga | tactcttgta | taattttgag | caattgaaaa | tgaaccttga | tgatatagtt | 4380 |
| aaagaggcaa | aaaatgtacc | aggtgtgacc | cgtttagccc | atgacgggtc | caaactcccc | 4440 |
| ctaagatgtg | tactgggatg | ggtcgctttg | gccaactcta | agaaattcca | gttgttagtc | 4500 |
| gaatccgaca | agctgagtaa | aatcatgcaa | gatgacttga | atcgctatac | atcttgctaa | 4560 |
| ccgaacctct | cccctcagtc | cctctagaca | ataaaatccg | agatgtccca | aagtcaacat | 4620 |
| gaaaaaaaca | ggcaacacca | ctgataaaat | gaacctccta | cgtaagatag | tgaaaaaccg | 4680 |
| cagggacgag | gacactcaaa | atcctctcc | cgcgtcagcc | cctctggatg | acgatgactt | 4740 |
| gtggcttcca | cccctgaat | acgtcccgct | gaaagaactt | acaggcaaga | agaacatgag | 4800 |
| gaacttttgt | atcaacggaa | gggttaaagt | gtgtagcccg | aatggttact | cgttcaggat | 4860 |
| cctgcggcac | attctgaaat | cattcgacga | gatatattct | gggaatcata | ggatgatcgg | 4920 |
| gttagtcaaa | gtggttattg | gactggcttt | gtcaggatct | ccagtccctg | agggctgaa | 4980 |
| ctgggtatac | aaattgagga | gaaccttat | cttccagtgg | gctgattcca | ggggccctct | 5040 |
| tgaaggggag | gagttggaat | actctcagga | gatcacttgg | gatgatgata | ctgagttcgt | 5100 |
| cggattgcaa | ataagagtga | ttgcaaaaca | gtgtcatatc | cagggcagag | tctggtgtat | 5160 |
| caacatgaac | ccgagagcat | gtcaactatg | gtctgacatg | tctcttcaga | cacaaaggtc | 5220 |
| cgaagaggac | aaagattcct | ctctgcttct | agaataatca | gattatatcc | cgcaaattta | 5280 |
| tcacttgttt | acctctggag | gagagaacat | atgggctcaa | ctccaaccct | tgggagcaat | 5340 |
| ataacaaaaa | acatgttatg | gtgccattaa | accgctgcat | ttcatcaaag | tcaagttgat | 5400 |
| taccttaca | ttttgatcct | cttggatgtg | aaaaaaacta | ttaacatccc | tcaaaagacc | 5460 |
| ccgggaaaga | tggttcctca | ggctctcctg | tttgtacccc | ttctggtttt | tccattgtgt | 5520 |
| tttgggaaat | tccctattta | cacgatacca | gacaagcttg | gtccctggag | tccgattgac | 5580 |
| atacatcacc | tcagctgccc | aaacaatttg | gtagtggagg | acgaaggatg | caccaacctg | 5640 |
| tcagggttct | cctacatgga | acttaaagtt | ggatacatct | tagccataaa | agtgaacggg | 5700 |
| ttcacttgca | caggcgttgt | gacggaggct | gaaacctaca | ctaacttcgt | tggttatgtc | 5760 |
| acaaccacgt | tcaaaagaaa | gcatttccgc | ccaacaccag | atgcatgtag | agccgcgtac | 5820 |
| aactggaaga | tggccggtga | ccccagatat | gaagagtctc | tacacaatcc | gtaccctgac | 5880 |
| taccgctggc | ttcgaactgt | aaaaaccacc | aaggagtctc | tcgttatcat | atctccaagt | 5940 |
| gtggcagatt | tggacccata | tgacagatcc | cttcactcga | gggtcttccc | tagcgggaag | 6000 |
| tgctcaggag | tagcggtgtc | ttctacctac | tgctccacta | accacgatta | caccatttgg | 6060 |
| atgcccgaga | atccgagact | agggatgtct | tgtgacattt | ttaccaatag | tagagggaag | 6120 |
| agagcatcca | aagggagtga | gacttgcggc | tttgtagatg | aaagaggcct | atataagtct | 6180 |
| ttaaaaggag | catgcaaact | caagttatgt | ggagttctag | gacttagact | tatggatgga | 6240 |
| acatgggtct | cgatgcaaac | atcaaatgaa | accaaatggt | gccctcccga | taagttggtg | 6300 |
| aacctgcacg | actttcgctc | agacgaaatt | gagcaccttg | ttgtagagga | gttggtcagg | 6360 |
| aagagagagg | agtgtctgga | tgcactagag | tccatcatga | caaccaagtc | agtgagtttc | 6420 |
| agacgtctca | gtcatttaag | aaaacttgtc | cctgggtttg | gaaaagcata | taccatattc | 6480 |
| aacaagacct | tgatggaagc | cgatgctcac | tacaagtcag | tcgagacttg | gaatgagatc | 6540 |
| ctcccttcaa | aagggtgttt | aagagttggg | gggaggtgtc | atcctcatgt | gaacggggtg | 6600 |
| tttttcaatg | gtataatatt | aggacctgac | ggcaatgtct | taatcccaga | gatgcaatca | 6660 |
| tccctcctcc | agcaacatat | ggagttgttg | gaatcctcgg | ttatccccct | tgtgcacccc | 6720 |

```
ctggcagacc cgtctaccgt tttcaaggac ggtgacgagg ctgaggattt tgttgaagtt    6780
caccttcccg atgtgcacaa tcaggtctca ggagttgact tgggtctccc gaactggggg    6840
aagtatgtat tactgagtgc aggggccctg actgccttga tgttgataat tttcctgatg    6900
acatgttgta gaagagtcaa tcgatcagaa cctacgcaac acaatctcag agggacaggg    6960
agggaggtgt cagtcactcc ccaaagcggg aagatcatat cttcatggga atcacacaag    7020
agtgggggtg agaccagact gtaattaatt aacgtccttt caacgatcca agtccatgaa    7080
aaaaactaac acccctcccg tacctagctt ataaagtgct gggtcatcta agcttttcag    7140
tcgagaaaaa aacattagat cagaagaaca actggcaaca cttctcaacc tgagacttac    7200
ttcaagatgc tcgatcctgg agaggtctat gatgacccta ttgacccaat cgagttagag    7260
gctgaaccca gaggaacccc cattgtcccc aacatcttga ggaactctga ctacaatctc    7320
aactctcctt tgatagaaga tcctgctaga ctaatgttag aatggttaaa aacagggaat    7380
agaccttatc ggatgactct aacagacaat tgctccaggt cttcagagt tttgaaagat    7440 tatttcaaga aggtagattt gggttctctc aaggtgggcg aatggctgc acagtcaatg    7500 atttctctct ggttatatgg tgcccactct gaatccaaca ggagccggag atgtataaca    7560
gacttggccc atttctattc caagtcgtcc cccatagaga agctgttgaa tctcacgcta    7620
ggaaatagag ggctgagaat ccccccagag ggagtgttaa gttgccttga gagggttgat    7680
tatgataatg catttggaag gtatcttgcc aacacgtatt cctcttactt gttcttccat    7740
gtaatcacct tatacatgaa cgccctagac tgggatgaag aaaagaccat cctagcatta    7800
tggaaagatt taacctcagt ggacatcggg aaggacttgg taaagttcaa agaccaaata    7860
tggggactgc tgatcgtgac aaaggacttt gtttactccc aaagttccaa ttgtcttttt    7920
gacagaaact acacacttat gctaaaagat cttttcttgt ctcgcttcaa ctccttaatg    7980
gtcttgctct ctcccccaga gccccgatac tcagatgact tgatatctca actatgccag    8040
ctgtacattg ctgggatca gtcttgtct atgtgtggaa actccggcta tgaagtcatc    8100
aaaatattgg agccatatgt cgtgaatagt ttagtccaga gagcagaaaa gtttaggcct    8160
ctcattcatt ccttgggaga cttttcctgta tttataaaag acaaggtaag tcaacttgaa    8220
gagacgttcg gtccctgtgc aagaaggttc tttagggctc tggatcaatt cgacaacata    8280
catgacttgg tttttgtgtt tggctgttac aggcattggg ggcacccata tagagattat    8340
cgaaagggtc tgtcaaaact atatgatcag gttcaccta aaaaaatgat agataagtcc    8400
taccaggagt gcttagcaag cgacctagcc aggaggatcc ttagatgggg ttttgataag    8460
tactccaagt ggtatctgga ttcaagattc ctagcccgag accacccctt gactccttat    8520
atcaaaaccc aaacatggcc acccaaacat attgtagact tggtggggga tacatggcac    8580
aagctcccga tcacgcagat ctttgagatt cctgaatcaa tggatccgtc agaaatattg    8640
gatgacaaat cacattcttt caccagaacg agactagctt cttggctgtc agaaaaccga    8700 gggggggcctg ttcctagcga aaaagttatt atcacggccc tgtctaagcc gcctgtcaat    8760
ccccgagagt ttctgaggtc tatagacctc ggaggattgc cagatgaaga cttgataatt    8820
ggcctcaagc caaaggaacg ggaattgaag attgaaggtc gattctttgc tctaatgtca    8880
tggaatctaa gattgtattt tgtcatcact gaaaaactct ggccaactaa catcttgcca    8940 cttttttgacg cgctgactat gacagacaac ctgaacaagg tgtttaaaaa gctgatcgac    9000
agggtcaccg ggcaagggct tttggactat tcaagggtca catatgcatt tcacctggac    9060
```

```
tatgaaaagt ggaacaacca tcaaagatta gagtcaacag aggatgtatt ttctgtccta   9120
gatcaagtgt ttggattgaa gagagtgttt tctagaacac acgagttttt tcaaaaggcc   9180
tggatctatt attcagacag atcagacctc atcgggttac gggaggatca aatatactgc   9240
ttagatgcgt ccaacggccc aacctgttgg aatggccagg atggcgggct agaaggctta   9300
cggcagaagg gctggagtct agtcagctta ttgatgatag atagagaatc tcaaatcagg   9360
aacacaagaa ccaaaatact agctcaagga gacaaccagg ttttatgtcc gacatacatg   9420
ttgtcgccag ggctatctca agaggggctc ctctatgaat tggagagaat atcaaggaat   9480
gcactttcga tatacagagc cgtcgaggaa ggggcatcta agctagggct gatcatcaag   9540
aaagaagaga ccatgtgtag ttatgacttc ctcatctatg aaaaacccc tttgtttaga    9600 ggtaacatat tggtgcctga gtccaaaaga tgggccagag tctcttgcgt ctctaatgac   9660
caaatagtca acctcgccaa tataatgtcg acagtgtcca ccaatgcgct aacagtggca   9720
caacactctc aatctttgat caaaccgatg agggattttc tgctcatgtc agtacaggca   9780
gtctttcact acctgctatt tagcccaatc ttaaagggaa gagtttacaa gattctgagc   9840
gctgaagggg agagctttct cctagccatg tcaaggataa tctatctaga tccttctttg   9900
ggagggatat ctggaatgtc cctcggaaga ttccatatac gacagttctc agaccctgtc   9960
tctgaagggt tatccttctg gagagagatc tggttaagct cccaagagtc ctggattcac  10020
gcgttgtgtc aagaggctgg aaacccagat cttggagaga gaacactcga gagcttcact  10080
cgccttctag aagatccgac caccttaaat atcagaggag gggccagtcc taccattcta  10140
ctcaaggatg caatcagaaa ggctttatat gacgaggtgg acaaggtgga aaattcagag  10200
tttcgagagg caatcctgtt gtccaagacc catagagata attttatact cttcttaata  10260
tctgttgagc ctctgtttcc tcgatttctc agtgagctat tcagttcgtc ttttttggga  10320
atccccgagt caatcattgg attgatacaa aactcccgaa cgataagaag gcagtttaga  10380
aagagtctct caaaaacttt agaagaatcc ttctacaact cagagatcca cgggattagt  10440
cggatgaccc agacacctca gagggttggg ggggtgtggc cttgctcttc agagagggca  10500
gatctactta gggagatctc ttggggaaga aaagtggtag gcacgacagt tcctcaccct  10560
tctgagatgt tgggattact tcccaagtcc tctatttctt gcacttgtgg agcaacagga  10620
ggaggcaatc ctagagtttc tgtatcagta ctcccgtcct ttgatcagtc attttttttca  10680 cgaggccccc taagggata cttgggctcg tccacctcta tgtcgaccca gctattccat   10740
gcatgggaaa aagtcactaa tgttcatgtg gtgaagagag ctctatcgtt aaaagaatct  10800
ataaactggt tcattactag agattccaac ttggctcaag ctctaattag gaacattatg  10860
tctctgacag gccctgattt ccctctagag gaggcccctg tcttcaaaag gacgggtca   10920 gccttgcata ggttcaagtc tgccagatac agcgaaggag ggtattcttc tgtctgcccg  10980
aacctcctct ctcatatttc tgttagtaca gacaccatgt ctgatttgac ccaagacggg  11040
aagaactacg atttcatgtt ccagccattg atgcttatg cacagacatg gacatcagag   11100
ctggtacaga gagacacaag gctaagagac tctacgtttc attggcacct ccgatgcaac  11160
aggtgtgtga gacccattga cgacgtgacc ctggagacct ctcagatctt cgagtttccg  11220
gatgtgtcga aaagaatatc cagaatggtt tctggggctg tgcctcactt ccagaggctt  11280
cccgatatcc gtctgagacc aggagatttt gaatctctaa gcggtagaga aaagtctcac  11340
catatcggat cagctcaggg gctcttatac tcaatcttag tggcaattca cgactcagga  11400
tacaatgatg gaaccatctt ccctgtcaac atatacggca aggtttcccc tagagactat  11460
```

```
ttgagagggc tcgcaagggg agtattgata ggatcctcga tttgcttctt gacaagaatg    11520
acaaatatca atattaatag acctcttgaa ttggtctcag gggtaatctc atatattctc    11580
ctgaggctag ataaccatcc ctccttgtac ataatgctca gagaaccgtc tcttagagga    11640
gagatatttt ctatccctca gaaaatcccc gccgcttatc caaccactat gaagaaggc    11700 aacagatcaa tcttgtgtta tctccaacat gtgctacgct atgagcgaga gataatcacg    11760
gcgtctccag agaatgactg gctatggatc ttttcagact ttagaagtgc caaaatgacg    11820
tacctatccc tcattactta ccagtctcat cttctactcc agagggttga gagaaaccta    11880
tctaagagta tgagagataa cctgcgacaa ttgagttctt tgatgaggca ggtgctgggc    11940
gggcacggag aagatacctt agagtcagac gacaacattc aacgactgct aaaagactct    12000
ttacgaagga caagatgggt ggatcaagag gtgcgccatg cagctagaac catgactgga    12060
gattacagcc ccaacaagaa ggtgtcccgt aaggtaggat gttcagaatg ggtctgctct    12120
gctcaacagg ttgcagtctc tacctcagca aacccggccc ctgtctcgga gcttgacata    12180
agggccctct ctaagaggtt ccagaaccct ttgatctcgg gcttgagagt ggttcagtgg    12240
gcaaccggtg ctcattataa gcttaagcct attctagatg atctcaatgt tttcccatct    12300
ctctgccttg tagttgggga cgggtcaggg gggatatcaa gggcagtcct caacatgttt    12360
ccagatgcca agcttgtgtt caacagtctt ttagaggtga atgacctgat ggcttccgga    12420
acacatccac tgcctccttc agcaatcatg aggggaggaa atgatatcgt ctccagagtg    12480
atagatcttg actcaatctg ggaaaaaccg tccgacttga gaaacttggc aacctggaaa    12540
tacttccagt cagtccaaaa gcaggtcaac atgtcctatg acctcattat tgcgatgca    12600 gaagttactg acattgcatc tatcaaccgg atcaccctgt taatgtccga ttttgcattg    12660
tctatagatg gaccactcta tttggtcttc aaaacttatg ggactatgct agtaaatcca    12720
aactacaagg ctattcaaca cctgtcaaga gcgttcccct cggtcacagg gtttatcacc    12780
caagtaactt cgtctttttc atctgagctc tacctccgat tctccaaacg agggaagttt    12840
ttcagagatg ctgagtactt gacctcttcc acccttcgag aaatgagcct tgtgttattc    12900
aattgtagca gccccaagag tgagatgcag agagctcgtt ccttgaacta tcaggatctt    12960
gtgagaggat ttcctgaaga aatcatatca aatccttaca atgagatgat cataactctg    13020
attgacagtg atgtagaatc ttttctagtc cacaagatgg ttgatgatct tgagttacag    13080
aggggaactc tgtctaaagt ggctatcatt atagccatca tgatagtttt ctccaacaga    13140
gtcttcaacg tttccaaacc cctaactgac ccctcgttct atccaccgtc tgatcccaaa    13200
atcctgaggc acttcaacat atgttgcagt actatgatgt atctatctac tgctttaggt    13260
gacgtcccta gcttcgcaag acttcacgac ctgtataaca gacctataac ttattacttc    13320
agaaagcaag tcattcgagg gaacgtttat ctatcttgga gttggtccaa cgacacctca    13380
gtgttcaaaa gggtagcctg taattctagc ctgagtctgt catctcactg gatcaggttg    13440
atttacaaga tagtgaagac taccagactc gttggcagca tcaaggatct atccagagaa    13500
gtggaaagac accttcatag gtacaacagg tggatcaccc tagaggatat cagatctaga    13560
tcatccctac tagactacag ttgcctgtga accggatact cctggaagcc tgcccatgct    13620
aagactcttg tgtgatgtat cttgaaaaaa acaagatcct aaatctgaac ctttggttgt    13680
ttgattgttt ttctcatttt tgttgtttat ttgttaagcg t                        13721
```

<210> SEQ ID NO 45

<211> LENGTH: 12010
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 45

| | | | | | |
|---|---|---|---|---|---|
| acgcttaaca | accagatcaa | agaaaaaaca | gacattgtca | attgcaaagc | aaaaatgtaa | 60 |
| caccccctaca | atggatgccg | acaagattgt | attcaaagtc | aataatcagg | tggtctcttt | 120 |
| gaagcctgag | attatcgtgg | atcaatatga | gtacaagtac | cctgccatca | aagatttgaa | 180 |
| aaagccctgt | ataaccctag | gaaaggctcc | cgatttaaat | aaagcataca | agtcagtttt | 240 |
| gtcaggcatg | agcgccgcca | aacttaatcc | tgacgatgta | tgttcctatt | tggcagcggc | 300 |
| aatgcagttt | tttgagggga | catgtccgga | agactggacc | agctatggaa | ttgtgattgc | 360 |
| acgaaaagga | gataagatca | ccccaggttc | tctggtggag | ataaaacgta | ctgatgtaga | 420 |
| agggaattgg | gctctgacag | gaggcatgga | actgacaaga | gaccccactg | tccctgagca | 480 |
| tgcgtcctta | gtcggtcttc | tcttgagtct | gtataggttg | agcaaaatat | ccgggcaaaa | 540 |
| cactggtaac | tataagacaa | acattgcaga | caggatagag | cagattttg | agacagcccc | 600 |
| ttttgttaaa | atcgtggaac | accatactct | aatgacaact | cacaaaatgt | gtgctaattg | 660 |
| gagtactata | ccaaacttca | gattttggc | cggaacctat | gacatgtttt | tctcccggat | 720 |
| tgagcatcta | tattcagcaa | tcagagtggg | cacagttgtc | actgcttatg | aagactgttc | 780 |
| aggactggta | tcatttactg | ggttcataaa | acaaatcaat | ctcaccgcta | gagaggcaat | 840 |
| actatatttc | ttccacaaga | actttgagga | agagataaga | agaatgtttg | agccagggca | 900 |
| ggagacagct | gttcctcact | cttatttcat | ccacttccgt | tcactaggct | tgagtgggaa | 960 |
| atctccttat | tcatcaaatg | ctgttggtca | cgtgttcaat | ctcattcact | ttgtaggatg | 1020 |
| ctatatgggt | caagtcagat | ccctaaatgc | aacggttatt | gctgcatgtg | ctcctcatga | 1080 |
| aatgtctgtt | ctaggggct | atctgggaga | ggaattcttc | gggaaaggga | catttgaaag | 1140 |
| aagattcttc | agagatgaga | agaacttca | agaatacgag | gcggctgaac | tgacaaagac | 1200 |
| tgacgtagca | ctggcagatg | atggaactgt | caactctgac | gacgaggact | acttttcagg | 1260 |
| tgaaaccaga | agtccggagg | ctgtttatac | tcgaatcatg | atgaatggag | tcgactaaa | 1320 |
| gagatctcac | atacggagat | atgtctcagt | cagttccaat | catcaagccc | gtccaaactc | 1380 |
| attcgccgag | tttctaaaca | agacatattc | gagtgactca | taacatgaaa | aaaactaaca | 1440 |
| ccccctcccgt | acgccgccac | catgggtgtt | acaggaatat | tgcagttacc | tcgtgatcga | 1500 |
| ttcaagagga | catcattctt | tctttgggta | attatccttt | tccaaagaac | attttccatc | 1560 |
| ccacttggag | tcatccacaa | tagcacatta | caggttagtg | atgtcgacaa | actagtttgt | 1620 |
| cgtgacaaac | tgtcatccac | aaatcaattg | agatcagttg | gactgaatct | cgaagggaat | 1680 |
| ggagtggcaa | ctgacgtgcc | atctgcaact | aaaagatggg | gcttcaggtc | cggtgtccca | 1740 |
| ccaaaggtgg | tcaattatga | agctggtgaa | tgggctgaaa | actgctacaa | tcttgaaatc | 1800 |
| aaaaaacctg | acgggagtga | gtgtctacca | gcagcgccag | acgggattcg | ggcttcccc | 1860 |
| cggtgccggt | atgtgcacaa | agtatcagga | acgggaccgt | gtgccggaga | ctttgccttc | 1920 |
| cataaagagg | gtgctttctt | cctgtatgat | cgacttgctt | ccacagttat | ctaccgagga | 1980 |
| acgactttcg | ctgaaggtgt | cgttgcattt | ctgatactgc | cccaagctaa | gaaggacttc | 2040 |
| ttcagctcac | accccttgag | agagccggtc | aatgcaacgg | aggacccgtc | tagtggctac | 2100 |

```
tattctacca caattagata tcaggctacc ggttttggaa ccaatgagac agagtacttg    2160
ttcgaggttg acaatttgac ctacgtccaa cttgaatcaa gattcacacc acagtttctg    2220
ctccagctga atgagacaat atatacaagt gggaaaagga gcaataccac gggaaaacta    2280
atttggaagg tcaaccccga aattgataca acaatcgggg agtgggcctt ctgggaaact    2340
aaaaaaaacc tcactagaaa aattcgcagt gaagagttgt ctttcacagt tgtatcaaac    2400
agagccaaaa acatcagtgg tcagagtccg gcgcgaactt cttccgaccc agggaccaac    2460
acaacaactg aagaccacaa aatcatggct tcagaaaatt cctctgcaat ggttcaagtg    2520
cacagtcaag gaagggaagc tgcagtgtcg catctgacaa cccctgccac aatctccacg    2580
agtcttcaac cccccacaac caaaccaggt ccggacaaca gcacccacaa tacacccgtg    2640
tataaacttg acatctctga ggcaactcaa gttgaacaac atcaccgcag aacagacaac    2700
gacagcacag cctccgacac tccctctgcc acgaccgcag ccggaccccc aaaagcagag    2760
aacaccaaca cgagcaagag cactgacttc ctggaccccg ccaccacaac aagtccccaa    2820
aaccacagcg agaccgctgg caacaacaac actcatcacc aagataccgg agaagagagt    2880
gccagcagcg ggaagctagg cttaattacc aatactattg ctggagtcgc aggactgatc    2940
acaggcggga gaagaactcg aagagaagca attgtcaatg ctcaacccaa atgcaaccct    3000
aatttacatt actggactac tcaggatgaa ggtgctgcaa tcggactggc ctggatacca    3060
tatttcgggc cagcagccga gggaatttac atagaggggc taatgcacaa tcaagatggt    3120
ttaatctgtg ggttgagaca gctggccaac gagacgactc aagctcttca actgttcctg    3180
agagccacaa ctgagctacg caccttttca atcctcaacc gtaaggcaat tgatttcttg    3240
ctgcagcgat ggggcggcac atgccacatt ctgggaccgg actgctgtat cgaaccacat    3300
gattggacca agaacataac agacaaaatt gatcagatta ttcatgattt tgttgataaa    3360
acccttccgg accaggggga caatgacaat tggtggacag gatggagaca atggataccg    3420
gcaggtattg gagttacagg cgttgtaatt gcagttatcg ctttattctg tatatgcaaa    3480
tttgtctttt aggagctagc catgaaaaaa actaacaccc ctcctttcga accatcccaa    3540
acatgagcaa gatctttgtc aatcctagtg ctattagagc cggtctggcc gatcttgaga    3600
tggctgaaga aactgttgat ctgatcaata gaaatatcga agacaatcag gctcatctcc    3660
aaggggaacc catagaggtg gacaatctcc ctgaggatat ggggcgactt cacctggatg    3720
atggaaaatc gcccaaccat ggtgagatag ccaaggtggg agaaggcaag tatcgagagg    3780
actttcagat ggatgaagga gaggatccta gcttcctgtt ccagtcatac ctggaaaatg    3840
ttggagtcca aatagtcaga caaatgaggt caggagagag atttctcaag atatggtcac    3900
agaccgtaga agagattata tcctatgtcg cggtcaactt tcccaaccct ccaggaaagt    3960
cttcagagga taaatcaacc cagactactg gccgagagct caagaaggag acaacaccca    4020
ctccttctca gagagaaagc caatcatcga aagccaggat ggcggctcaa attgcttctg    4080
gccctccagc ccttgaatgg tcggctacca atgaagagga tgatctatca gtggaggctg    4140
agatcgctca ccagattgca gaaagtttct ccaaaaaata taagtttccc tctcgatcct    4200
cagggatact cttgtataat tttgagcaat tgaaaatgaa ccttgatgat atagttaaag    4260
aggcaaaaaa tgtaccaggt gtgacccgtt tagcccatga cgggtccaaa ctccccctaa    4320
gatgtgtact gggatgggtc gctttggcca actctaagaa attccagttg ttagtcgaat    4380
ccgacaagct gagtaaaatc atgcaagatg acttgaatcg ctatacatct tgctaaccga    4440
```

```
acctctcccc tcagtccctc tagacaataa aatccgagat gtcccaaagt caacatgaaa    4500
aaaacaggca acaccactga taaaatgaac ctcctacgta agatagtgaa aaaccgcagg    4560
gacgaggaca ctcaaaaatc ctctcccgcg tcagcccctc tggatgacga tgacttgtgg    4620
cttccacccc ctgaatacgt cccgctgaaa gaacttacag gcaagaagaa catgaggaac    4680
ttttgtatca acggaagggt taaagtgtgt agcccgaatg gttactcgtt caggatcctg    4740
cggcacattc tgaaatcatt cgacgagata tattctggga atcataggat gatcgggtta    4800
gtcaaagtgg ttattggact ggctttgtca ggatctccag tccctgaggg cctgaactgg    4860
gtatacaaat tgaggagaac ctttatcttc cagtgggctg attccagggg ccctcttgaa    4920
ggggaggagt tggaatactc tcaggagatc acttgggatg atgatactga gttcgtcgga    4980
ttgcaaataa gagtgattgc aaaacagtgt catatccagg gcagagtctg tgtgtatcaac   5040
atgaacccga gagcatgtca actatggtct gacatgtctc ttcagacaca aaggtccgaa    5100
gaggacaaag attcctctct gcttctagaa taatcagatt atatcccgca aatttatcac    5160
ttgtttacct ctggaggaga gaacatatgg gctcaactcc aacccttggg agcaatataa    5220
caaaaaacat gttatggtgc cattaaaccg ctgcatttca tcaaagtcaa gttgattacc    5280
tttacatttt gatcctcttg gatgtgaaaa aaactattaa catccctcaa aagacccta    5340
acgtcctttc aacgatccaa gtccatgaaa aaaactaaca cccctcccgt acctagctta    5400
taaagtgctg ggtcatctaa gcttttcagt cgagaaaaaa acattagatc agaagaacaa    5460
ctggcaacac ttctcaacct gagacttact tcaagatgct cgatcctgga gaggtctatg    5520
atgaccctat tgacccaatc gagttagagg ctgaacccag aggaaccccc attgtcccca    5580
acatcttgag gaactctgac tacaatctca actctccttt gatagaagat cctgctagac    5640
taatgttaga atggttaaaa acagggaata gaccttatcg gatgactcta acagacaatt    5700
gctccaggtc tttcagagtt ttgaaagatt atttcaagaa ggtagatttg ggttctctca    5760
aggtgggcgg aatggctgca cagtcaatga tttctctctg gttatatggt gcccactctg    5820
aatccaacag gagccggaga tgtataacag acttggccca tttctattcc aagtcgtccc    5880
ccatagagaa gctgttgaat ctcacgctag gaaatagagg gctgagaatc cccccagagg    5940
gagtgttaag ttgccttgag agggttgatt atgataatgc atttggaagg tatcttgcca    6000
acacgtattc ctcttacttg ttcttccatg taatcaccctt atacatgaac gccctagact   6060
gggatgaaga aaagaccatc ctagcattat ggaaagattt aacctcagtg gacatcggga    6120
aggacttggt aaagttcaaa gaccaaatat ggggactgct gatcgtgaca aaggactttg    6180
tttactccca aagttccaat tgtctttttg acagaaacta cacacttatg ctaaaagatc    6240
ttttcttgtc tcgcttcaac tccttaatgg tcttgctctc tccccagag ccccgatact    6300
cagatgactt gatatctcaa ctatgccagc tgtacattgc tggggatcaa gtcttgtcta    6360
tgtgtggaaa ctccggctat gaagtcatca aaatattgga gccatatgtc gtgaatagtt    6420
tagtccagag agcagaaaag tttaggcctc tcattcattc cttgggagac tttcctgtat    6480
ttataaaaga caaggtaagt caacttgaag agacgttcgg tccctgtgca agaaggttct    6540
ttagggctct ggatcaattc gacaacatac atgacttggt ttttgtgttt ggctgttaca    6600
ggcattgggg gcacccatat atagattatc gaaagggtct gtcaaaacta tatgatcagg    6660
ttcaccttaa aaaaatgata gataagtcct accaggagtg cttagcaagc gacctagcca    6720
ggaggatcct tagatgggt tttgataagt actccaagtg gtatctggat tcaagattcc    6780
tagcccgaga ccaccccttg actccttata tcaaaaccca aacatggcca cccaaacata    6840
```

```
ttgtagactt ggtggggat acatggcaca agctcccgat cacgcagatc tttgagattc      6900
ctgaatcaat ggatccgtca gaaatattgg atgacaaatc acattctttc accagaacga      6960
gactagcttc ttggctgtca gaaaccgag gggggcctgt tcctagcgaa aaagttatta      7020
tcacggccct gtctaagccg cctgtcaatc cccgagagt tctgaggtct atagacctcg       7080
gaggattgcc agatgaagac ttgataattg gcctcaagcc aaaggaacgg gaattgaaga      7140
ttgaaggtcg attctttgct ctaatgtcat ggaatctaag attgtatttt gtcatcactg      7200
aaaaactctt ggccaactac atcttgccac ttttgacgc gctgactatg acagacaacc       7260
tgaacaaggt gtttaaaaag ctgatcgaca gggtcaccgg gcaagggctt ttggactatt      7320
caagggtcac atatgcattt cacctggact atgaaaagtg gaacaaccat caaagattag      7380
agtcaacaga ggatgtattt tctgtcctag atcaagtgtt tggattgaag agagtgtttt      7440
ctagaacaca cgagtttttt caaaaggcct ggatctatta ttcagacaga tcagacctca      7500
tcgggttacg ggaggatcaa atatactgct tagatgcgtc caacggccca acctgttgga      7560
atggccagga tggcgggcta gaaggcttac ggcagaaggg ctggagtcta gtcagcttat      7620
tgatgataga tagagaatct caaatcagga acacaagaac caaaatacta gctcaaggag      7680
acaaccaggt tttatgtccg acatacatgt tgtcgccagg gctatctcaa gagggctcc       7740
tctatgaatt ggagagaata tcaaggaatg cactttcgat atacagagcc gtcgaggaag      7800
gggcatctaa gctagggctg atcatcaaga agaagagac catgtgtagt tatgacttcc       7860
tcatctatgg aaaaaccct tgtttagag gtaacatatt ggtgcctgag tccaaaagat        7920
gggccagagt ctcttgcgtc tctaatgacc aaatagtcaa cctcgccaat ataatgtcga      7980
cagtgtccac caatgcgcta acagtggcac aacactctca atctttgatc aaaccgatga      8040
gggatttttct gctcatgtca gtacaggcag tctttcacta cctgctatt agcccaatct      8100
taaagggaag agtttacaag attctgagcg ctgaagggga gagctttctc ctagccatgt      8160
caaggataat ctatctagat ccttcttgg gagggatatc tggaatgtcc ctcggaagat       8220
tccatatacg acagttctca gaccctgtct ctgaagggt atccttctgg agagagatct      8280
ggttaagctc ccaagagtcc tggattcacg cgttgtgtca agaggctgga aacccagatc      8340
ttggagagag aacactcgag agcttcactc gccttctaga agatccgacc accttaaata     8400
tcagaggagg ggccagtcct accattctac tcaaggatgc aatcagaaag gctttatatg      8460
acgaggtgga caaggtggaa aattcagagt ttcgagaggc aatcctgttg tccaagaccc      8520
atagagataa tttatactc ttcttaatat ctgttgagcc tctgtttcct cgatttctca      8580
gtgagctatt cagttcgtct tttttgggaa tccccgagtc aatcattgga ttgatacaaa      8640
actcccgaac gataagaagg cagtttagaa agagtctctc aaaaacttta gaagaatcct      8700
tctacaactc agagatccac gggattagtc ggatgaccca gacacctcag agggttgggg      8760
gggtgtggcc ttgctcttca gagagggcag atctacttag ggagatctct tggggaagaa      8820
aagtggtagg cacgacagtt cctcaccctt ctgagatgtt gggattactt cccaagtcct      8880
ctatttcttg cacttgtgga gcaacaggag gaggcaatcc tagagttct gtatcagtac       8940
tcccgtcctt tgatcagtca tttttttcac gaggcccccct aaagggatac ttgggctcgt     9000
ccacctctat gtcgacccag ctattccatg catgggaaaa agtcactaat gttcatgtgg      9060
tgaagagagc tctatcgtta aaagaatcta taaactggtt cattactaga gattccaact      9120
tggctcaagc tctaattagg aacattatgt ctctgacagg ccctgattc cctctagagg      9180
```

```
aggcccctgt cttcaaaagg acggggtcag ccttgcatag gttcaagtct gccagataca   9240
gcgaaggagg gtattcttct gtctgcccga acctcctctc tcatatttct gttagtacag   9300
acaccatgtc tgatttgacc caagacggga agaactacga tttcatgttc cagccattga   9360
tgctttatgc acagacatgg acatcagagc tggtacagag agacacaagg ctaagagact   9420
ctacgtttca ttggcacctc cgatgcaaca ggtgtgtgag acccattgac gacgtgaccc   9480
tggagacctc tcagatcttc gagttttccgg atgtgtcgaa aagaatatcc agaatggttt   9540
ctggggctgt gcctcacttc cagaggcttc ccgatatccg tctgagacca ggagattttg   9600
aatctctaag cggtagagaa aagtctcacc atatcggatc agctcagggg ctcttatact   9660
caatcttagt ggcaattcac gactcaggat acaatgatgg aaccatcttc cctgtcaaca   9720
tatacggcaa ggtttcccct agagactatt tgagagggct cgcaagggga gtattgatag   9780
gatcctcgat ttgcttcttg acaagaatga caaatatcaa tattaataga cctcttgaat   9840
tggtctcagg ggtaatctca tatattctcc tgaggctaga taaccatccc tccttgtaca   9900
taatgctcag agaaccgtct cttagaggag agatattttc tatccctcag aaaatccccg   9960
ccgcttatcc aaccactatg aaagaaggca acagatcaat cttgtgttat ctccaacatg  10020
tgctacgcta tgagcgagag ataatcacgg cgtctccaga gaatgactgg ctatggatct  10080
tttcagactt tagaagtgcc aaaatgacgt acctatccct cattacttac cagtctcatc  10140
ttctactcca gagggttgag agaaacctat ctaagagtat gagagataac ctgcgacaat  10200
tgagttcttt gatgaggcag gtgctgggcg ggcacggaga agataccttta gagtcagacg  10260 acaacattca acgactgcta aaagactctt tacgaaggac aagatgggtg gatcaagagg  10320
tgcgccatgc agctagaacc atgactggag attacagccc caacaagaag gtgtcccgta  10380
aggtaggatg ttcagaatgg gtctgctctg ctcaacaggt tgcagtctct acctcagcaa  10440
acccggcccc tgtctcggag cttgacataa gggccctctc taagaggttc cagaaccctt  10500
tgatctcggg cttgagagtg gttcagtggg caaccggtgc tcattataag cttaagccta  10560
ttctagatga tctcaatgtt ttcccatctc tctgccttgt agttggggac gggtcagggg  10620
ggatatcaag gcagtcctc aacatgtttc cagatgccaa gcttgtgttc aacagtcttt  10680
tagaggtgaa tgacctgatg gcttccggaa cacatccact gcctccttca gcaatcatga  10740
ggggaggaaa tgatatcgtc tccagagtga tagatcttga ctcaatctgg gaaaaaccgt  10800
ccgacttgag aaacttggca acctggaaat acttccagtc agtccaaaag caggtcaaca  10860
tgtcctatga cctcattatt tgcgatgcag aagttactga cattgcatct atcaaccgga  10920
tcaccctgtt aatgtccgat tttgcattgt ctatagatgg accactctat ttggtcttca  10980
aaacttatgg gactatgcta gtaaatccaa actacaaggc tattcaacac ctgtcaagag  11040
cgttcccctc ggtcacaggg tttatcaccc aagtaacttc gtctttttca tctgagctct  11100
acctccgatt ctccaaacga gggaagtttt tcagagatgc tgagtacttg acctcttcca  11160
cccttcgaga aatgagcctt gtgttattca attgtagcag ccccaagagt gagatgcaga  11220
gagctcgttc cttgaactat caggatcttg tgagaggatt tcctgaagaa atcatatcaa  11280
atccttacaa tgagatgatc ataactctga ttgacagtga tgtagaatct tttctagtcc  11340
acaagatggt tgatgatctt gagttacaga ggggaactct gtctaaagtg gctatcatta  11400
tagccatcat gatagttttc tccaacagag tcttcaacgt ttccaaaccc ctaactgacc  11460
cctcgttcta tccaccgtct gatcccaaaa tcctgaggca cttcaacata tgttgcagta  11520
ctatgatgta tctatctact gctttaggtg acgtccctag cttcgcaaga cttcacgacc  11580
```

```
tgtataacag acctataact tattacttca gaaagcaagt cattcgaggg aacgtttatc    11640
tatcttggag ttggtccaac gacacctcag tgttcaaaag ggtagcctgt aattctagcc    11700
tgagtctgtc atctcactgg atcaggttga tttacaagat agtgaagact accagactcg    11760
ttggcagcat caaggatcta tccagagaag tggaaagaca ccttcatagg tacaacaggt    11820
ggatcaccct agaggatatc agatctagat catccctact agactacagt tgcctgtgaa    11880
ccggatactc ctggaagcct gcccatgcta agactcttgt gtgatgtatc ttgaaaaaaa    11940
caagatccta aatctgaacc tttggttgtt tgattgtttt tctcattttt gttgtttatt    12000
tgttaagcgt                                                           12010
```

<210> SEQ ID NO 46
<211> LENGTH: 12134
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 46

```
acgcttaaca accagatcaa agaaaaaaca gacattgtca attgcaaagc aaaaatgtaa      60 caccccctaca atggatgccg acaagattgt attcaaagtc aataatcagg tggtctcttt     120
gaagcctgag attatcgtgg atcaatatga gtacaagtac cctgccatca agatttgaa      180 aaagccctgt ataaccctag gaaaggctcc cgatttaaat aaagcataca agtcagtttt     240
gtcaggcatg agcgccgcca aacttaatcc tgacgatgta tgttcctatt tggcagcggc     300
aatgcagttt tttgagggga catgtccgga agactggacc agctatgaa ttgtgattgc      360 acgaaaagga gataagatca ccccaggttc tctggtggag ataaaacgta ctgatgtaga     420
agggaattgg gctctgacag gaggcatgga actgacaaga gacccccactg tccctgagca     480 tgcgtcctta gtcggtcttc tcttgagtct gtataggttg agcaaaatat ccgggcaaaa     540
cactggtaac tataagacaa acattgcaga caggatagag cagatttttg agacagcccc     600
ttttgttaaa atcgtggaac accatactct aatgacaact cacaaaatgt gtgctaattg     660
gagtactata ccaaacttca gattttttggc cggaacctat gacatgtttt tctcccggat     720
tgagcatcta tattcagcaa tcagagtggg cacagttgtc actgcttatg aagactgttc     780
aggactggta tcatttactg ggttcataaa acaaatcaat ctcaccgcta gagaggcaat     840
actatatttc ttccacaaga actttgagga agagataaga agaatgtttg agccagggca     900
ggagacagct gttcctcact cttatttcat ccacttccgt tcactaggct tgagtgggaa     960
atctccttat tcatcaaatg ctgttggtca cgtgttcaat ctcattcact tgtaggatg    1020 ctatatgggt caagtcagat ccctaaatgc aacggttatt gctgcatgtg ctcctcatga    1080
aatgtctgtt ctaggggct atctgggaga ggaattcttc gggaaaggga catttgaaag    1140
aagattcttc agagatgaga aagaacttca agaatacgag gcggctgaac tgacaaagac    1200
tgacgtagca ctggcagatg atggaactgt caactctgac gacgaggact actttttcagg   1260 tgaaaccaga agtccggagg ctgttttatac tcgaatcatg atgaatggag gtcgactaaa    1320
gagatctcac atacggagat atgtctcagt cagttccaat catcaagccc gtccaaactc    1380
attcgccgag tttctaaaca agacatattc gagtgactca taacatgaaa aaaactaaca    1440
cccctcccgt acgccgccac catgggtgtt acaggaatat tgcagttacc tcgtgatcga    1500
```

```
ttcaagagga catcattctt tctttgggta attatccttt tccaaagaac attttccatc    1560
ccacttggag tcatccacaa tagcacatta caggttagtg atgtcgacaa actagtttgt    1620
cgtgacaaac tgtcatccac aaatcaattg agatcagttg gactgaatct cgaagggaat    1680
ggagtggcaa ctgacgtgcc atctgcaact aaaagatggg gcttcaggtc cggtgtccca    1740
ccaaaggtgg tcaattatga agctggtgaa tgggctgaaa actgctacaa tcttgaaatc    1800
aaaaaacctg acgggagtga gtgtctacca gcagcgccag acgggattcg ggcttcccc    1860 cggtgccggt atgtgcacaa agtatcagga acgggaccgt gtgccggaga ctttgccttc    1920
cataaagagg gtgctttctt cctgtatgat cgacttgctt ccacagttat ctaccgagga    1980
acgactttcg ctgaaggtgt cgttgcattt ctgatactgc cccaagctaa gaaggacttc    2040
ttcagctcac accccttgag agagccggtc aatgcaacgg aggacccgtc tagtggctac    2100
tattctacca caattagata tcaggctacc ggttttggaa ccaatgagac agagtacttg    2160
ttcgaggttg acaatttgac ctacgtccaa cttgaatcaa gattcacacc acagtttctg    2220
ctccagctga atgagacaat atatacaagt gggaaaagga gcaataccac gggaaaacta    2280
atttggaagg tcaaccccga aattgataca acaatcgggg agtgggcctt ctgggaaact    2340
aaaaaaaacc tcactagaaa aattcgcagt gaagagttgt cttttcacagt tgtatcaaac    2400 agagccaaaa acatcagtgg tcagagtccg gcgcgaactt cttccgaccc agggaccaac    2460
acaacaactg aagaccacaa aatcatggct tcagaaaatt cctctgcaat ggttcaagtg    2520
cacagtcaag gaagggaagc tgcagtgtcg catctgacaa cccctgccac aatctccacg    2580
agtcttcaac cccccacaac caaaccaggt ccggacaaca gcacccacaa tacacccgtg    2640
tataaacttg acatctctga ggcaactcaa gttgaacaac atcaccgcag aacagacaac    2700
gacagcacag cctccgacac tccctctgcc acgaccgcag ccggaccccc aaaagcagag    2760
aacaccaaca cgagcaagag cactgacttc ctggaccccg ccaccacaac aagtccccaa    2820
aaccacagcg agaccgctgg caacaacaac actcatcacc aagataccgg agaagagagt    2880
gccagcagcg ggaagctagg cttaattacc aatactattg ctggagtcgc aggactgatc    2940
acaggcggga gaagaactcg aagagaagca attgtcaatg ctcaacccaa atgcaaccct    3000
aatttacatt actggactac tcaggatgaa ggtgctgcaa tcggactggc ctggatacca    3060
tatttcgggc cagcagccga gggaatttac atagaggggc taatgcacaa tcaagatggt    3120
ttaatctgtg ggttgagaca gctggccaac gagacgactc aagctcttca actgttcctg    3180
agagccacaa ctgagctacg cacctttcta atcctcaacc gtaaggcaat tgatttcttg    3240
ctgcagcgat ggggcggcac atgccacatt ctgggaccgg actgctgtat cgaaccacat    3300
gattggacca agaacataac agacaaaatt gatcagatta ttcatgattt tgttgataaa    3360 accettccgg accaggggga caatgacaat tggtggacag gatggagaca atggatacgg    3420
gcaggtattg gagttacagg cgttgtaatt gcagttatcg ctttattctg tatatgcgtt    3480
aacagaagag tcaatcgatc agaacctacg caacacaatc tcagagggac agggagggag    3540
gtgtcagtca ctccccaaag cgggaagatc atatcttcat gggaatcaca caagagtggg    3600
ggtgagacca gactgtaagc tagccatgaa aaaaactaac ccctccctt cgaaccatc    3660 ccaaacatga gcaagatctt tgtcaatcct agtgctatta gagccggtct ggccgatctt    3720
gagatggctg aagaaactgt tgatctgatc aatagaaata tcgaagacaa tcaggctcat    3780
ctccaagggg aacccataga ggtggacaat ctccctgagg atatgggcg acttcacctg    3840 gatgatggaa aatcgcccaa ccatggtgag atagccaagg tgggagaagg caagtatcga    3900
```

```
gaggactttc agatggatga aggagaggat cctagcttcc tgttccagtc atacctggaa    3960
aatgttggag tccaaatagt cagacaaatg aggtcaggag agagatttct caagatatgg    4020
tcacagaccg tagaagagat tatatcctat gtcgcggtca actttcccaa ccctccagga    4080
aagtcttcag aggataaatc aacccagact actggccgag agctcaagaa ggagacaaca    4140
cccactcctt ctcagagaga aagccaatca tcgaaagcca ggatggcggc tcaaattgct    4200
tctggccctc cagcccttga atggtcggct accaatgaag aggatgatct atcagtggag    4260
gctgagatcg ctcaccagat tgcagaaagt ttctccaaaa aatataagtt ccctctcga    4320 tcctcaggga tactcttgta taattttgag caattgaaaa tgaaccttga tgatatagtt    4380
aaagaggcaa aaaatgtacc aggtgtgacc cgtttagccc atgacgggtc caaactcccc    4440
ctaagatgtg tactgggatg ggtcgctttg gccaactcta agaaattcca gttgttagtc    4500
gaatccgaca agctgagtaa aatcatgcaa gatgacttga atcgctatac atcttgctaa    4560
ccgaacctct cccctcagtc cctctagaca ataaaatccg agatgtccca aagtcaacat    4620
gaaaaaaaca ggcaacacca ctgataaaat gaacctccta cgtaagatag tgaaaaaccg    4680
cagggacgag gacactcaaa aatcctctcc cgcgtcagcc cctctggatg acgatgactt    4740
gtggcttcca cccctgaat acgtcccgct gaaagaactt acaggcaaga gaacatgag    4800 gaactttgt atcaacggaa gggttaaagt gtgtagcccg aatggttact cgttcaggat    4860
cctgcggcac attctgaaat cattcgacga gatatattct gggaatcata ggatgatcgg    4920
gttagtcaaa gtggttattg gactggcttt gtcaggatct ccagtccctg agggcctgaa    4980
ctgggtatac aaattgagga gaacctttat cttccagtgg gctgattcca ggggccctct    5040
tgaaggggag gagttggaat actctcagga gatcacttgg gatgatgata ctgagttcgt    5100
cggattgcaa ataagagtga ttgcaaaaca gtgtcatatc cagggcagag tctggtgtat    5160
caacatgaac ccgagagcat gtcaactatg gtctgacatg tctcttcaga cacaaaggtc    5220
cgaagaggac aaagattcct ctctgcttct agaataatca gattatatcc cgcaaattta    5280
tcacttgttt acctctggag gagagaacat atgggctcaa ctccaaccct tgggagcaat    5340
ataacaaaaa acatgttatg gtgccattaa accgctgcat ttcatcaaag tcaagttgat    5400
tacctttaca ttttgatcct cttggatgtg aaaaaaacta ttaacatccc tcaaaagacc    5460
cctaacgtcc tttcaacgat ccaagtccat gaaaaaaact aacaccctc ccgtacctag    5520 cttataaagt gctgggtcat ctaagctttt cagtcgagaa aaaaacatta gatcagaaga    5580
acaactggca acacttctca acctgagact tacttcaaga tgctcgatcc tggagaggtc    5640
tatgatgacc ctattgaccc aatcgagtta gaggctgaac ccagaggaac ccccattgtc    5700
cccaacatct tgaggaactc tgactacaat ctcaactctc ctttgataga agatcctgct    5760
agactaatgt tagaatggtt aaaaacaggg aatagacctt atcggatgac tctaacagac    5820
aattgctcca ggtctttcag agttttgaaa gattatttca agaaggtaga tttgggttct    5880
ctcaaggtgg gcggaatggc tgcacagtca atgatttctc tctggttata tggtgcccac    5940
tctgaatcca acaggagccg gagatgtata acagacttgg cccatttcta ttccaagtcg    6000
tcccccatag agaagctgtt gaatctcacg ctaggaaata gagggctgag aatcccccca    6060
gagggagtgt taagttgcct tgagagggtt gattatgata atgcatttgg aaggtatctt    6120
gccaacacgt attcctctta cttgttcttc catgtaatca cctttatacat gaacgcccta    6180 gactgggatg aagaaaagac catcctagca ttatggaaag atttaacctc agtggacatc    6240
```

```
gggaaggact tggtaaagtt caaagaccaa atatgggac tgctgatcgt gacaaaggac    6300
tttgtttact cccaaagttc caattgtctt tttgacagaa actacacact tatgctaaaa    6360
gatcttttct tgtctcgctt caactcctta atggtcttgc tctctccccc agagccccga    6420
tactcagatg acttgatatc tcaactatgc cagctgtaca ttgctgggga tcaagtcttg    6480
tctatgtgtg gaaactccgg ctatgaagtc atcaaaatat tggagccata tgtcgtgaat    6540
agtttagtcc agagagcaga aaagtttagg cctctcattc attccttggg agactttcct    6600
gtatttataa aagacaaggt aagtcaactt gaagagacgt tcggtccctg tgcaagaagg    6660
ttctttaggg ctctggatca attcgacaac atacatgact tggttttgt gtttggctgt     6720
tacaggcatt gggggcaccc atatatagat tatcgaaagg gtctgtcaaa actatatgat    6780
caggttcacc ttaaaaaaat gatagataag tcctaccagg agtgcttagc aagcgaccta    6840
gccaggagga tccttagatg gggttttgat aagtactcca agtggtatct ggattcaaga    6900
ttcctagccc gagaccaccc cttgactcct tatatcaaaa cccaaacatg gccacccaaa    6960
catattgtag acttggtggg ggatacatgg cacaagctcc cgatcacgca gatctttgag    7020
attcctgaat caatggatcc gtcagaaata ttggatgaca aatcacattc tttcaccaga    7080
acgagactag cttcttggct gtcagaaaac cgagggggc ctgttcctag cgaaaaagtt      7140
attatcacgg ccctgtctaa gccgcctgtc aatccccgag agtttctgag gtctatagac    7200
ctcggaggat tgccagatga agacttgata attggcctca agccaaagga acgggaattg    7260
aagattgaag gtcgattctt tgctctaatg tcatggaatc taagattgta ttttgtcatc    7320
actgaaaaac tcttggccaa ctacatcttg ccactttttg acgcgctgac tatgacagac    7380
aacctgaaca aggtgtttaa aaagctgatc gacagggtca ccgggcaagg gcttttggac    7440
tattcaaggg tcacatatgc atttcacctg gactatgaaa agtggaacaa ccatcaaaga    7500
ttagagtcaa cagaggatgt attttctgtc ctagatcaag tgtttggatt gaagagagtg    7560
ttttctagaa cacacgagtt ttttcaaaag gcctggatct attattcaga cagatcagac    7620
ctcatcgggt tacgggagga tcaaatatac tgcttagatg cgtccaacgg cccaacctgt    7680
tggaatggcc aggatggcgg gctagaaggc ttacggcaga agggctggag tctagtcagc    7740
ttattgatga tagatagaga atctcaaatc aggaacacaa gaaccaaaat actagctcaa    7800
ggagacaacc aggttttatg tccgacatac atgttgtcgc cagggctatc tcaagagggg    7860
ctcctctatg aattggagag aatatcaagg aatgcacttt cgatatacag agccgtcgag    7920
gaaggggcat ctaagctagg gctgatcatc aagaaagaag agaccatgtg tagttatgac    7980
ttcctcatct atggaaaaac ccctttgttt agaggtaaca tattggtgcc tgagtccaaa    8040
agatgggcca gagtctcttg cgtctctaat gaccaaatag tcaacctcgc caatataatg    8100
tcgacagtgt ccaccaatgc gctaacagtg gcacaacact ctcaatcttt gatcaaaccg    8160
atgagggatt ttctgctcat gtcagtacag gcagtctttc actacctgct atttagccca    8220
atcttaaagg gaagagttta caagattctg agcgctgaag gggagagctt tctcctagcc    8280
atgtcaagga taatctatct agatccttct ttgggaggga tatctggaat gtccctcgga    8340
agattccata tacgacagtt ctcagaccct gtctctgaag ggttatcctt ctggagagag    8400
atctggttaa gctcccaaga gtcctggatt cacgcgttgt gtcaagaggc tggaaaccca    8460
gatcttggag agagaacact cgagagcttc actcgccttc tagaagatcc gaccaccta    8520
aatatcagag gaggggccag tcctaccatt ctactcaagg atgcaatcag aaaggcttta    8580
tatgacgagg tggacaaggt ggaaaattca gagtttcgag aggcaatcct gttgtccaag    8640
```

```
acccatagag ataattttat actcttctta atatctgttg agcctctgtt tcctcgattt    8700
ctcagtgagc tattcagttc gtcttttttg ggaatccccg agtcaatcat tggattgata    8760
caaaactccc gaacgataag aaggcagttt agaaagagtc tctcaaaaac tttagaagaa    8820
tccttctaca actcagagat ccacgggatt agtcggatga cccagacacc tcagagggtt    8880
gggggggtgt ggccttgctc ttcagagagg gcagatctac ttagggagat ctcttgggga    8940
agaaaagtgg taggcacgac agttcctcac ccttctgaga tgttgggatt acttcccaag    9000 tcctctatt cttgcacttg tggagcaaca ggaggaggca atcctagagt ttctgtatca    9060
gtactcccgt cctttgatca gtcattttt tcacgaggcc ccctaaaggg atacttgggc    9120
tcgtccacct ctatgtcgac ccagctattc catgcatggg aaaaagtcac taatgttcat    9180
gtggtgaaga gagctctatc gttaaaagaa tctataaact ggttcattac tagagattcc    9240
aacttggctc aagctctaat taggaacatt atgtctctga caggccctga tttccctcta    9300
gaggaggccc ctgtcttcaa aaggacgggg tcagccttgc ataggttcaa gtctgccaga    9360
tacagcgaag gagggtattc ttctgtctgc ccgaacctcc tctctcatat ttctgttagt    9420
acagacacca tgtctgattt gacccaagac gggaagaact acgatttcat gttccagcca    9480
ttgatgcttt atgcacagac atggacatca gagctggtac agagagacac aaggctaaga    9540
gactctacgt ttcattggca cctccgatgc aacaggtgtg tgagacccat tgacgacgtg    9600
accctggaga cctctcagat cttcgagttt ccggatgtgt cgaaaagaat atccagaatg    9660
gtttctgggg ctgtgcctca cttccagagg cttcccgata tccgtctgag accaggagat    9720
tttgaatctc taagcggtag agaaaagtct caccatatcg gatcagctca ggggctctta    9780
tactcaatct tagtggcaat tcacgactca ggatacaatg atggaaccat cttccctgtc    9840
aacatatacg gcaaggtttc ccctagagac tatttgagag ggctcgcaag gggagtattg    9900
ataggatcct cgatttgctt cttgacaaga atgacaaata tcaatattaa tagacctctt    9960
gaattggtct caggggtaat ctcatatatt ctcctgaggc tagataacca tccctccttg   10020
tacataatgc tcagagaacc gtctcttaga ggagagatat tttctatccc tcagaaaatc   10080
cccgccgctt atccaaccac tatgaaagaa ggcaacagat caatcttgtg ttatctccaa   10140
catgtgctac gctatgagcg agagataatc acggcgtctc cagagaatga ctggctatgg   10200
atcttttcag actttagaag tgccaaaatg acgtacctat ccctcattac ttaccagtct   10260
catcttctac tccagagggt tgagagaaac ctatctaaga gtatgagaga taacctgcga   10320
caattgagtt ctttgatgag gcaggtgctg gcgggcacg gagaagatac cttagagtca   10380
gacgacaaca ttcaacgact gctaaaagac tctttacgaa ggacaagatg ggtggatcaa   10440
gaggtgcgcc atgcagctag aaccatgact ggagattaca gccccaacaa gaaggtgtcc   10500
cgtaaggtag gatgttcaga atgggtctgc tctgctcaac aggttgcagt ctctacctca   10560
gcaaacccgg cccctgtctc ggagcttgac ataaggggcc tctctaagag gttccagaac   10620
cctttgatct cgggcttgag agtggttcag tgggcaaccg gtgctcatta taagcttaag   10680
cctattctag atgatctcaa tgttttccca tctctctgcc ttgtagttgg ggacgggtca   10740 gggggatat caagggcagt cctcaacatg tttccagatg ccaagcttgt gttcaacagt   10800
cttttagagg tgaatgacct gatggcttcc ggaacacatc cactgcctcc ttcagcaatc   10860 atgagggag gaaatgatat cgtctcccaga gtgatagatc ttgactcaat ctgggaaaaa   10920
ccgtccgact tgagaaactt ggcaacctgg aaatacttcc agtcagtcca aaagcaggtc   10980
```

-continued

```
aacatgtcct atgacctcat tatttgcgat gcagaagtta ctgacattgc atctatcaac  11040
cggatcaccc tgttaatgtc cgattttgca ttgtctatag atggaccact ctatttggtc  11100
ttcaaaactt atgggactat gctagtaaat ccaaactaca aggctattca acacctgtca  11160
agagcgttcc cctcggtcac agggtttatc acccaagtaa cttcgtcttt ttcatctgag  11220
ctctacctcc gattctccaa acgagggaag ttttcagag atgctgagta cttgacctct   11280
tccacccttc gagaaatgag ccttgtgtta ttcaattgta gcagcccaa gagtgagatg    11340 cagagagctc gttccttgaa ctatcaggat cttgtgagag gatttcctga agaaatcata  11400
tcaaatcctt acaatgagat gatcataact ctgattgaca gtgatgtaga atcttttcta  11460
gtccacaaga tggttgatga tcttgagtta cagagggaa ctctgtctaa agtggctatc    11520
attatagcca tcatgatagt tttctccaac agagtcttca acgtttccaa acccctaact  11580 gaccctcgt tctatccacc gtctgatccc aaaatcctga ggcacttcaa catatgttgc    11640
agtactatga tgtatctatc tactgcttta ggtgacgtcc ctagcttcgc aagacttcac  11700
gacctgtata acagacctat aacttattac ttcagaaagc aagtcattcg agggaacgtt  11760
tatctatctt ggagttggtc caacgacacc tcagtgttca aaagggtagc ctgtaattct  11820
agcctgagtc tgtcatctca ctggatcagg ttgatttaca agatagtgaa gactaccaga  11880
ctcgttggca gcatcaagga tctatccaga gaagtggaaa gacaccttca taggtacaac  11940
aggtggatca ccctagagga tatcagatct agatcatccc tactagacta cagttgcctg  12000
tgaaccggat actcctggaa gcctgcccat gctaagactc ttgtgtgatg tatcttgaaa  12060
aaaacaagat cctaaatctg aacctttggt tgtttgattg ttttctcat ttttgttgtt     12120 tatttgttaa gcgt                                                                                                       12134
```

<210> SEQ ID NO 47
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 47
gtgtgaattc cggaacgtac gccgccacca tgggtgttac aggaatattg cagttacctc    60
gt                                                                                                                                    62

<210> SEQ ID NO 48
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 48
ggaagctagc tcactaaaag acaaatttgc atatacagaa taaagc                                46

<210> SEQ ID NO 49
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

```
<400> SEQUENCE: 49
ggaagctagc ctagttaacg catatacaga ataaagcgat aactgcaa                48
```